(12) United States Patent
Van Rooijen et al.

(10) Patent No.: US 12,416,009 B2
(45) Date of Patent: Sep. 16, 2025

(54) METHODS AND COMPOSITIONS FOR THE MODIFICATION OF PLANTS

(71) Applicant: Flagship Pioneering Innovations VI, LLC, Cambridge, MA (US)

(72) Inventors: Maria Helena Christine Van Rooijen, Cambridge, MA (US); Hok Hei Tam, Newton, MA (US); Maier Steve Avendaño Amado, Cambridge, MA (US); Barry Andrew Martin, Boston, MA (US); Ignacio Martinez, Lexington, MA (US); Piotr Stanislaw Kowalski, Cork (IE); Nataliya Vladimirovna Nukolova, Cambridge, MA (US); Yajie Niu, Lexington, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 0 days.

(21) Appl. No.: 17/270,134

(22) PCT Filed: Aug. 24, 2019

(86) PCT No.: PCT/US2019/048045
§ 371 (c)(1),
(2) Date: Feb. 22, 2021

(87) PCT Pub. No.: WO2020/041782
PCT Pub. Date: Feb. 27, 2020

(65) Prior Publication Data
US 2021/0254085 A1 Aug. 19, 2021

Related U.S. Application Data

(60) Provisional application No. 62/848,470, filed on May 15, 2019, provisional application No. 62/722,694, filed on Aug. 24, 2018.

(51) Int. Cl.
C12N 15/82 (2006.01)

(52) U.S. Cl.
CPC ....... C12N 15/8213 (2013.01); C12N 15/827 (2013.01)

(58) Field of Classification Search
None
See application file for complete search history.

(56) References Cited

U.S. PATENT DOCUMENTS

| | | | |
|---|---|---|---|
| 9,988,634 B2 * | 6/2018 | Sammons | C12N 15/8218 |
| 10,799,457 B2 | 10/2020 | Zhang | |
| 11,827,897 B2 | 11/2023 | Van Rooijen et al. | |
| 12,163,142 B2 | 12/2024 | Van Rooijen et al. | |
| 2014/0057789 A1 * | 2/2014 | Sammons | C12N 15/8206 |
| | | | 504/206 |
| 2014/0308212 A1 | 10/2014 | Zhang | |
| 2016/0208243 A1 * | 7/2016 | Zhang | C12N 9/22 |
| 2018/0362974 A1 | 12/2018 | Zhang | |
| 2019/0380962 A1 | 12/2019 | Zhang | |
| 2021/0180081 A1 | 6/2021 | Van Rooijen et al. | |
| 2021/0196632 A1 | 7/2021 | Van Rooijen et al. | |
| 2021/0219550 A1 | 7/2021 | Van Rooijen et al. | |
| 2021/0228736 A1 | 7/2021 | Van Rooijen et al. | |
| 2022/0064661 A1 | 3/2022 | Van Rooijen et al. | |
| 2022/0152139 A1 | 5/2022 | Van Rooijen et al. | |
| 2022/0192201 A1 | 6/2022 | Van Rooijen et al. | |
| 2022/0273565 A1 | 9/2022 | Van Rooijen et al. | |
| 2022/0288150 A1 | 9/2022 | Van Rooijen et al. | |
| 2022/0304930 A1 | 9/2022 | Van Rooijen et al. | |
| 2023/0248649 A1 | 8/2023 | Zhang | |
| 2023/0355525 A1 | 11/2023 | Zhang | |
| 2024/0141370 A1 | 5/2024 | Van Rooijen et al. | |
| 2024/0298649 A1 | 9/2024 | Bogorad et al. | |
| 2024/0398884 A1 | 12/2024 | Van Rooijen et al. | |

FOREIGN PATENT DOCUMENTS

| | | |
|---|---|---|
| CN | 110402085 A | 11/2019 |
| EP | 3836779 A1 | 6/2021 |
| JP | 2018-518183 A | 7/2018 |
| JP | 2018-522546 A | 8/2018 |
| WO | WO-2011097480 A1 | 8/2011 |
| WO | WO-2016/205613 A1 | 12/2016 |
| WO | WO-2016/205711 A1 | 12/2016 |
| WO | WO-2017/004526 A1 | 1/2017 |
| WO | WO-2017004523 A1 | 1/2017 |
| WO | WO-2017153993 A1 | 9/2017 |
| WO | WO-2017/189308 A1 | 11/2017 |
| WO | WO-2018/005873 A1 | 1/2018 |
| WO | WO-2018106847 A1 | 6/2018 |
| WO | WO-2019222379 A1 | 11/2019 |
| WO | WO-2019222390 A1 | 11/2019 |
| WO | WO-2020/041783 A1 | 2/2020 |
| WO | WO-2020041784 A1 | 2/2020 |
| WO | WO-2020214542 A1 | 10/2020 |
| WO | WO-2020219927 A1 | 10/2020 |
| WO | WO-2021041301 A1 | 3/2021 |
| WO | WO-2022266096 A1 | 12/2022 |

OTHER PUBLICATIONS

Wang et al 1992 (Journal of Phytopathology 135: p. 233-244) (Year: 1992).*
Chen et al 2018 (Cancer Metastasis Rev. 37:1, p. 107-124) (Year: 2018).*
Zhang et al 2010 (International Journal of Pharmaceutics 390: p. 198-207) (Year: 2010).*
Du et al 2014 (Scientific Reports 4: p. 7107-7113) (Year: 2014).*
Matthews et al 1981 (Planta 153: p. 90-94) (Year: 1981).*

(Continued)

*Primary Examiner* — Matthew R Keogh
(74) *Attorney, Agent, or Firm* — Clark & Elbing LLP

(57) ABSTRACT

Disclosed herein are plant-modifying compositions including a plurality of plant messenger packs (PMPs) (e.g., including a plant extracellular vesicle (EV), or segment, portion, or extract thereof), wherein the PMPs include a plant-modifying agent, and wherein the plant-modifying agent comprising the heterologous RNA. The compositions herein are useful in methods for modifying plants such as to increase plant fitness, wherein the increase in plant fitness comprising an increase in development, growth, yield, resistance to abiotic stressors, or resistance to biotic stressors.

11 Claims, 22 Drawing Sheets

Specification includes a Sequence Listing.

(56) References Cited

OTHER PUBLICATIONS

Wang et al 2013 (Nature Communications 4:1867 p. 1-11) (Year: 2013).*
Buckhout et al., "Iron-Stress Induced Redox Activity in Tomato (*Lycopersicum esculentum Mill.*) Is Localized on the Plasma Membrane," Plant Physiol. 90(1):151-6 (1989).
Holden et al., "Fe-Chelate Reductase Activity of Plasma Membranes Isolated from Tomato *Lycopersicon esculentum Mill.*) Roots : Comparison of Enzymes from Fe-Deficient and Fe-Sufficient Roots," Plant Physiol. 97(2):537-44 (1991).
Rutter et al., "Extracellular Vesicles Isolated from the Leaf Apoplast Carry Stress-Response Proteins," Plant Physiol. 173(1):728-741 (2017).
García-Manrique et al., "Therapeutic biomaterials based on extracellular vesicles: classification of bio-engineering and mimetic preparation routes," J Extracell Vesicles. 7(1):1422676 (2018) (19 pages).
International Preliminary Report on Patentability for International Patent Application No. PCT/US2019/048045 issued Mar. 2, 2021 (8 pages).
International Search Report and Written Opinion for International Application No. PCT/US2019/048045, mailed Jan. 15, 2020 (22 pages).
Invitation to Pay Additional Fees for International Application No. PCT/US2019/048045, mailed Nov. 6, 2019 (3 pages).
Luan et al., "Engineering Exosomes as Refined Biological Nanoplatforms for Drug Delivery," Acta Pharmacol Sin. 38(6):754-63 (2017).
Samuel et al., "Extracellular Vesicles Including Exosomes in Cross Kingdom Regulation: A Viewpoint From Plant-Fungal Interactions," Front Plant Sci. 6:766 (2015) (5 pages).
Zhang et al., "Exosome-Mediated Small RNA Delivery: A Novel Therapeutic Approach for Inflammatory Lung Responses," Mol Ther. 26(9):2119-2130 (2018).
Sato et al., "Engineering hybrid exosomes by membrane fusion with liposomes," Sci Rep. 6:21933 (2016) (11 pages).
Wang et al., "Delivery of therapeutic agents by nanoparticles made of grapefruit-derived lipids," Nature Communications, 4(1867) (May 2013) (14 pages).
"Advances in mechanism and application for plant microRNA in cross-kingdom regulation," ScienceChina. Abstract 06, published Apr. 24, 2020 (2 pages).

* cited by examiner

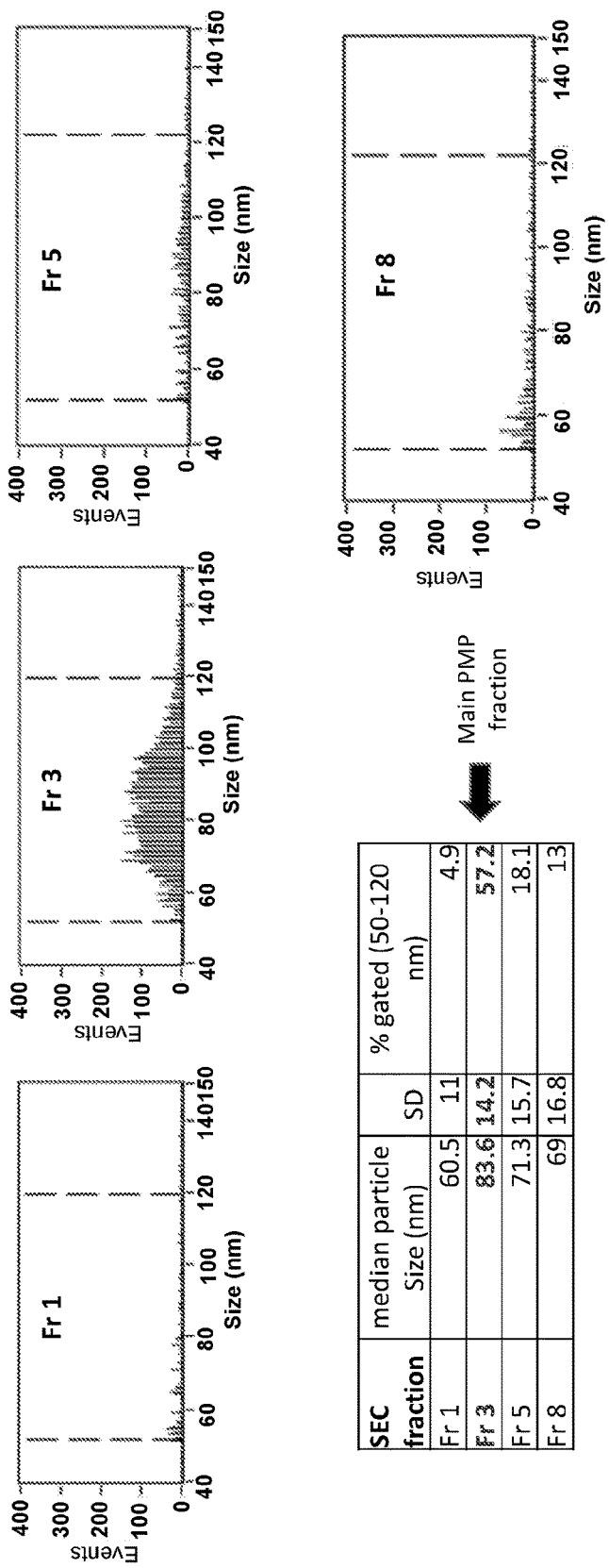

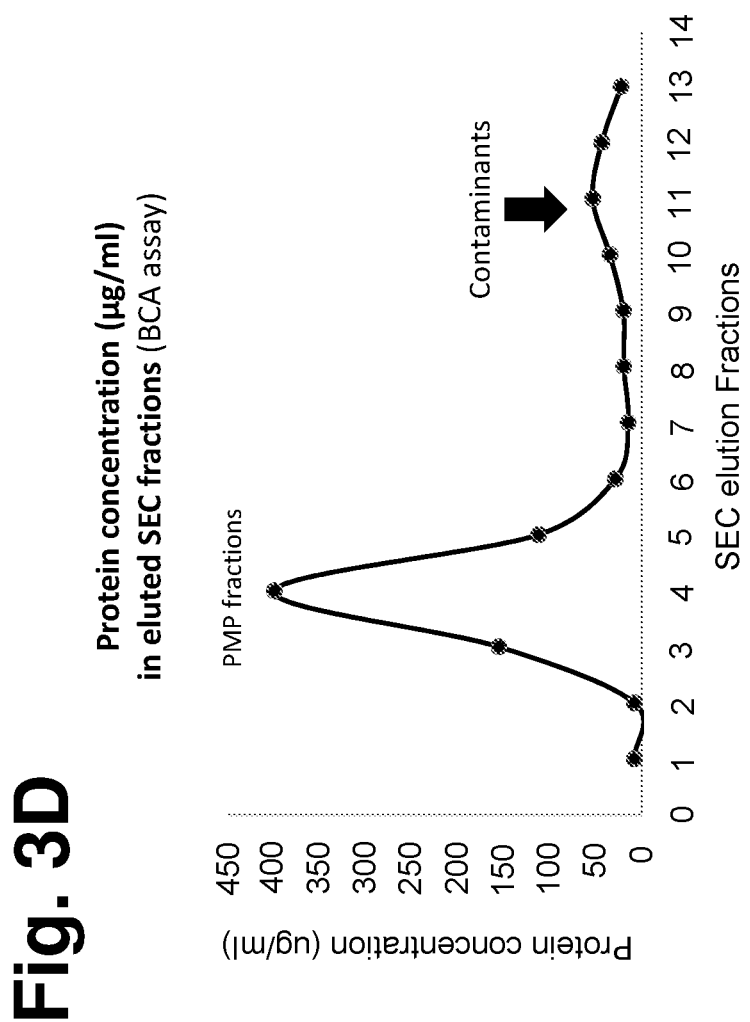

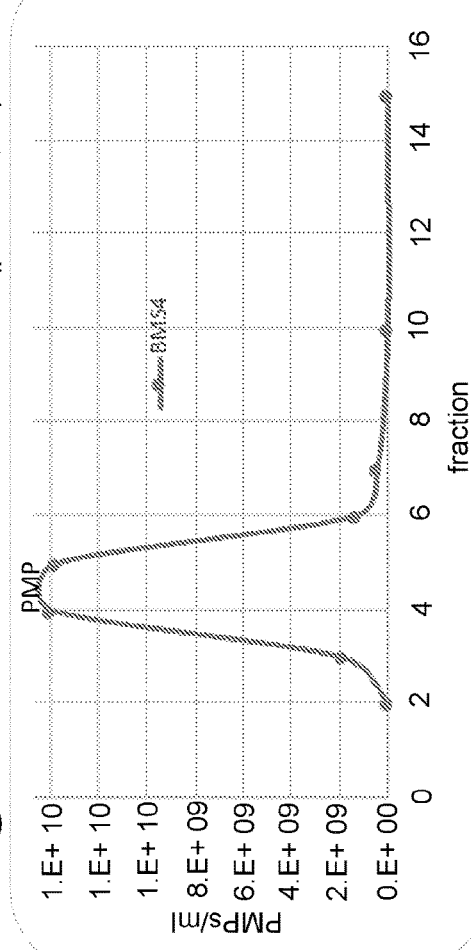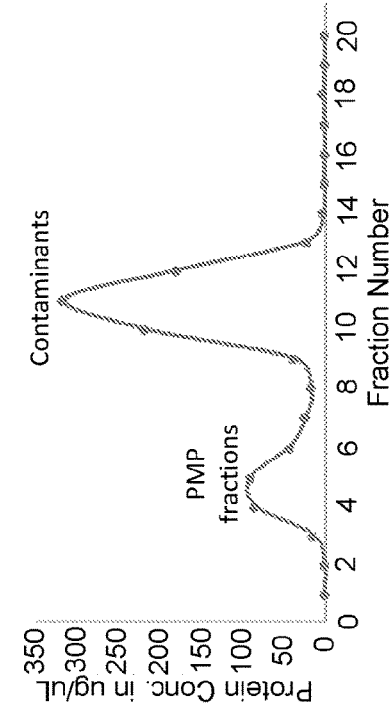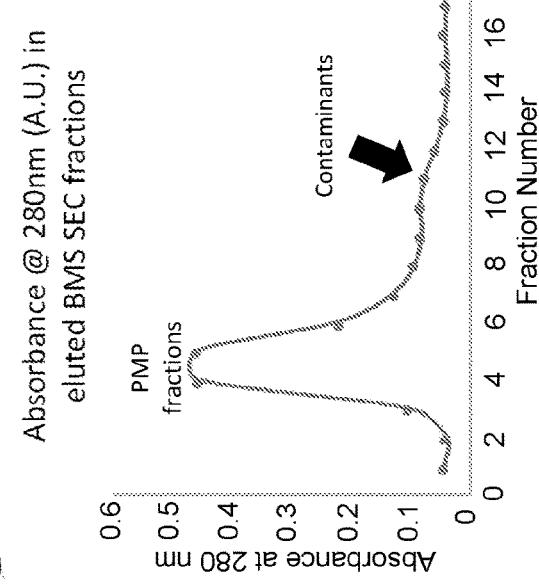

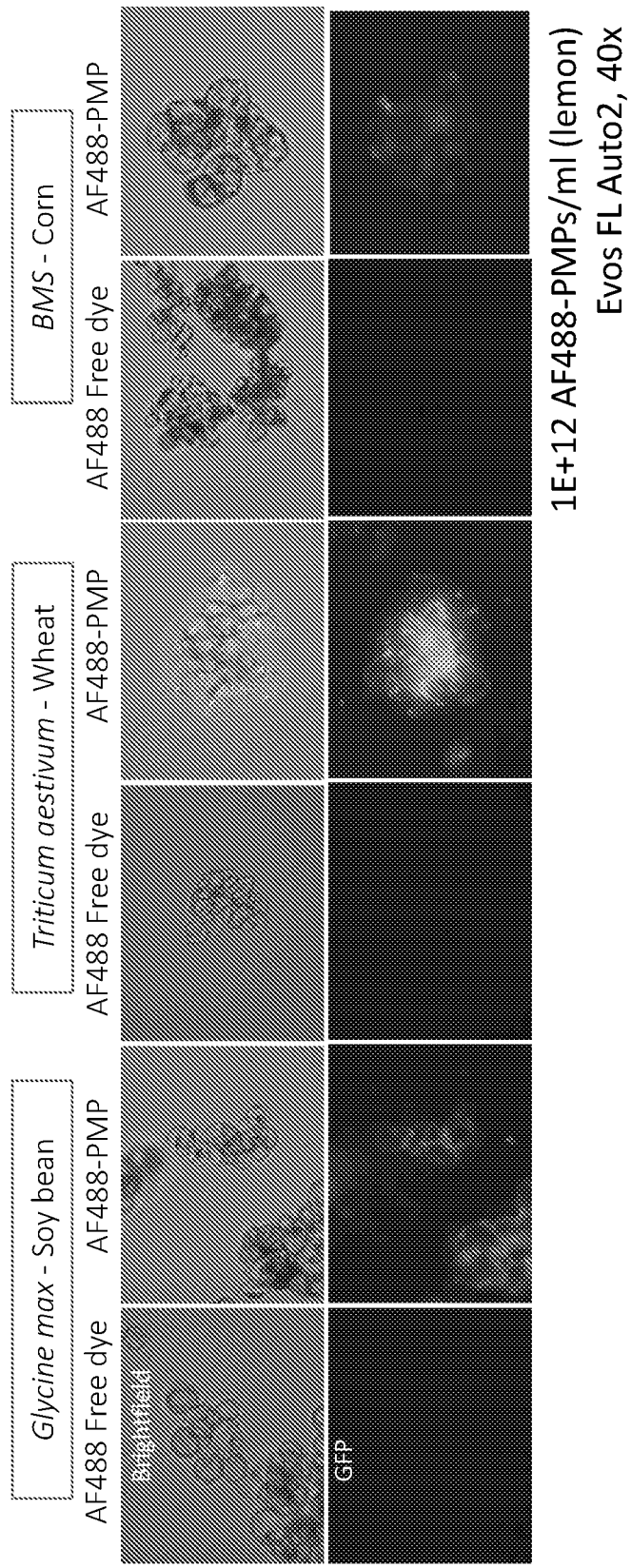

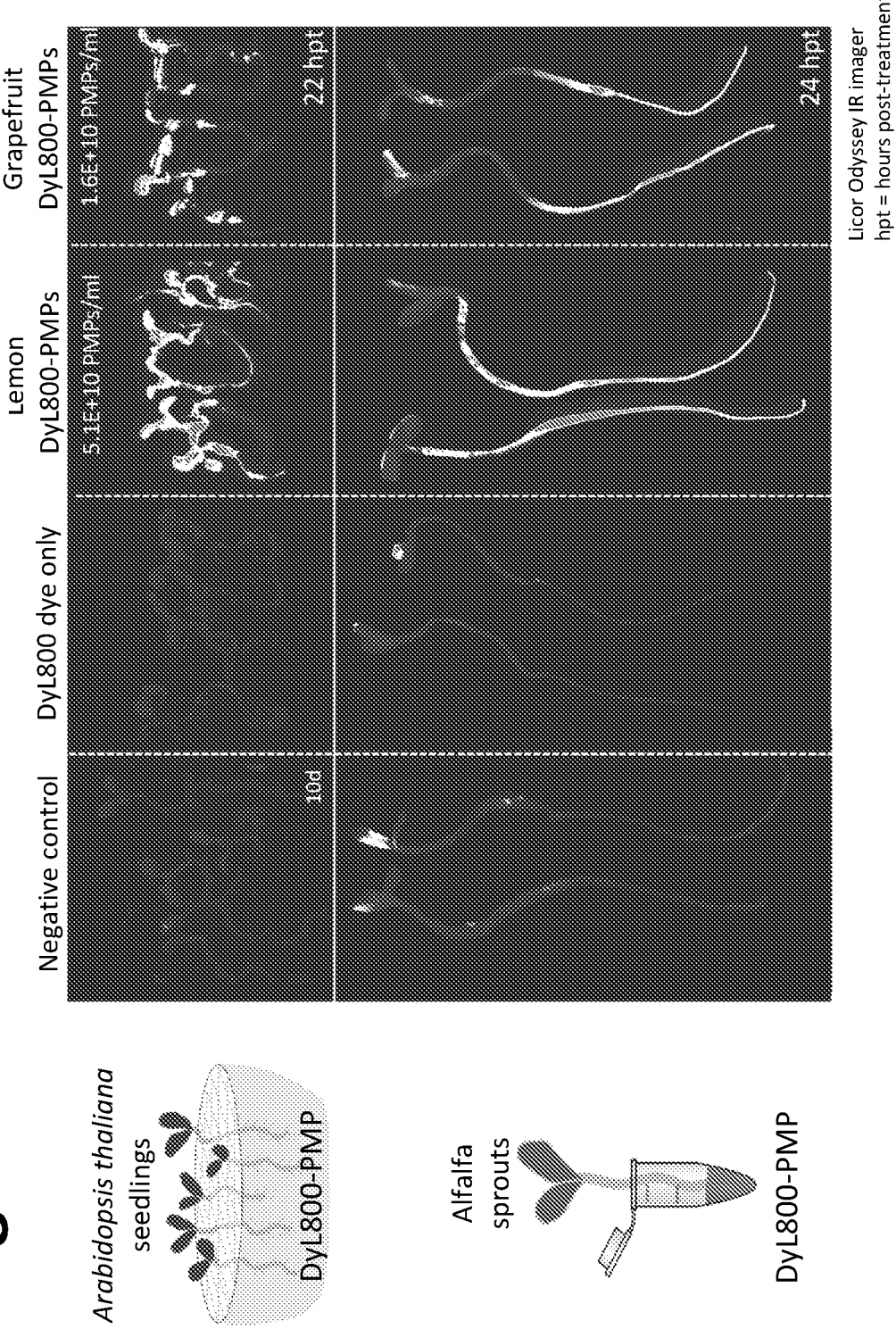

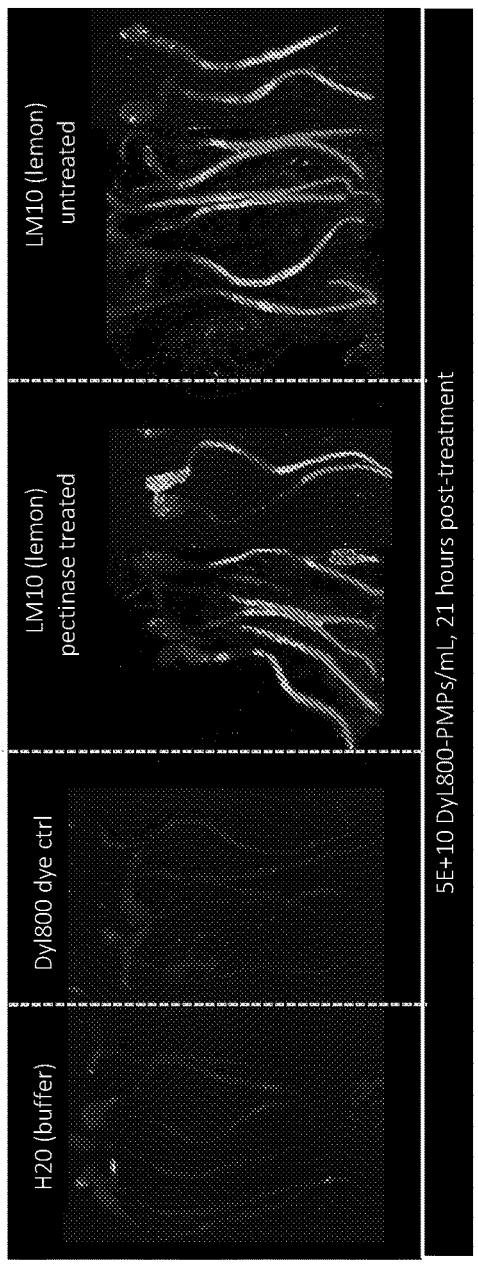
Fig. 8A
Fig. 8B

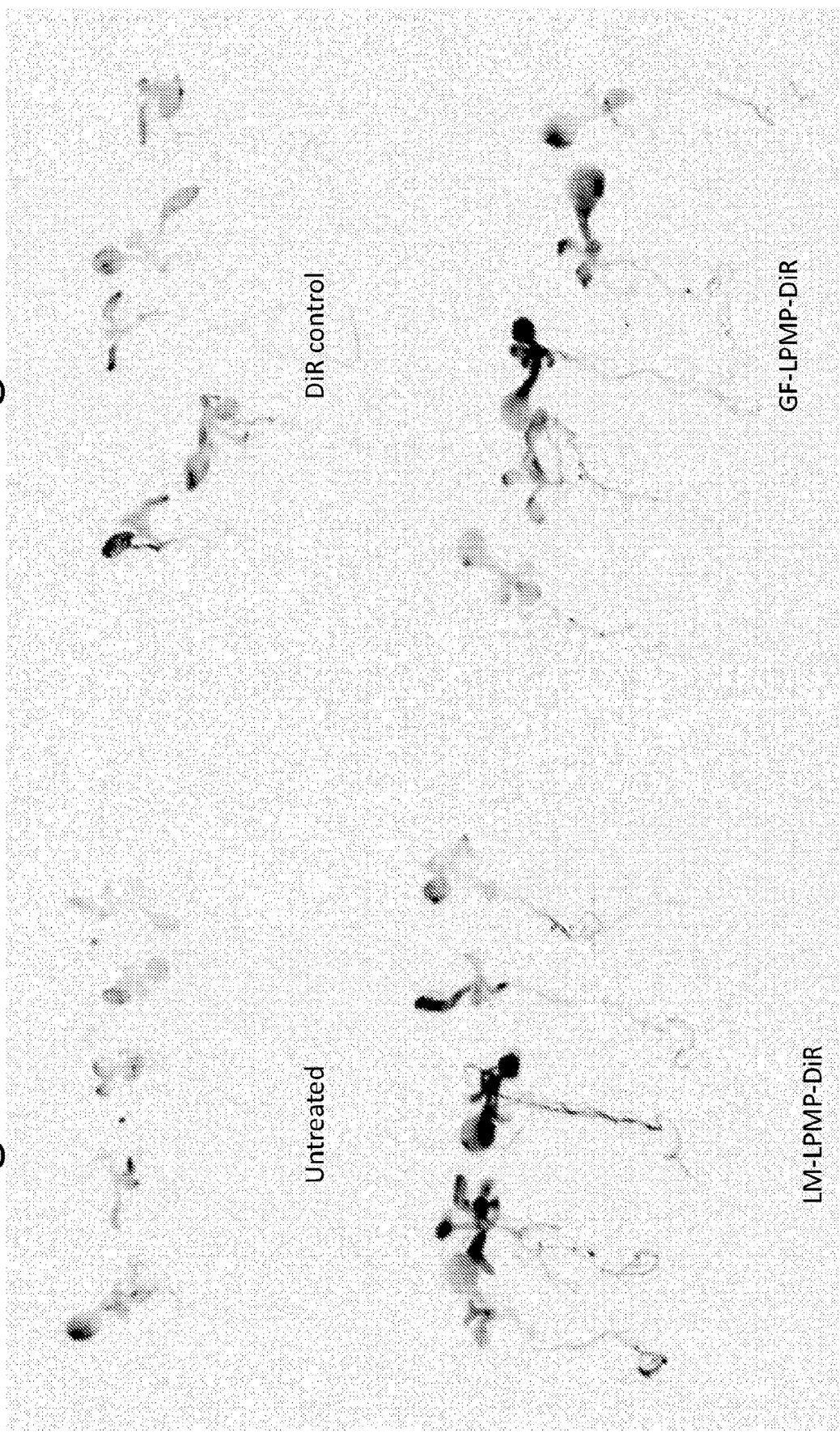

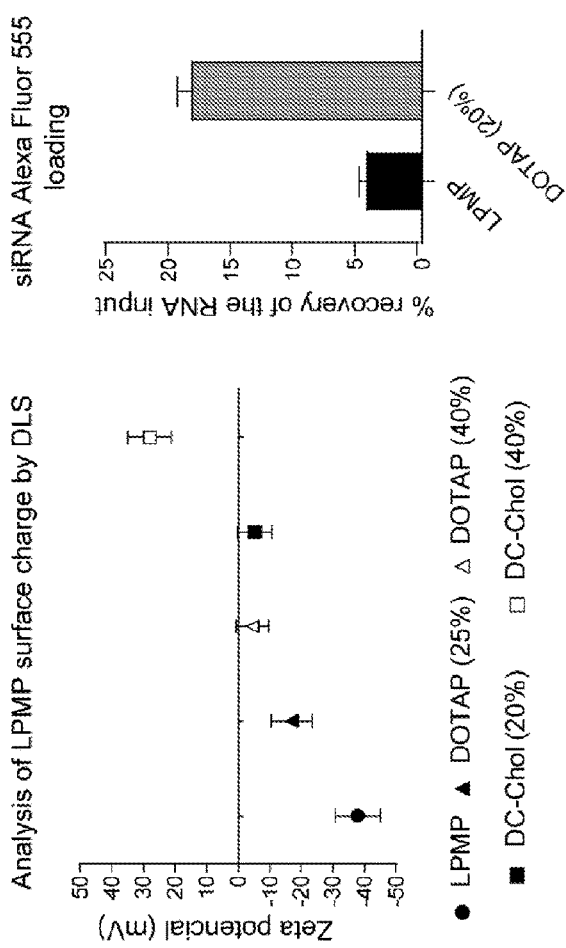
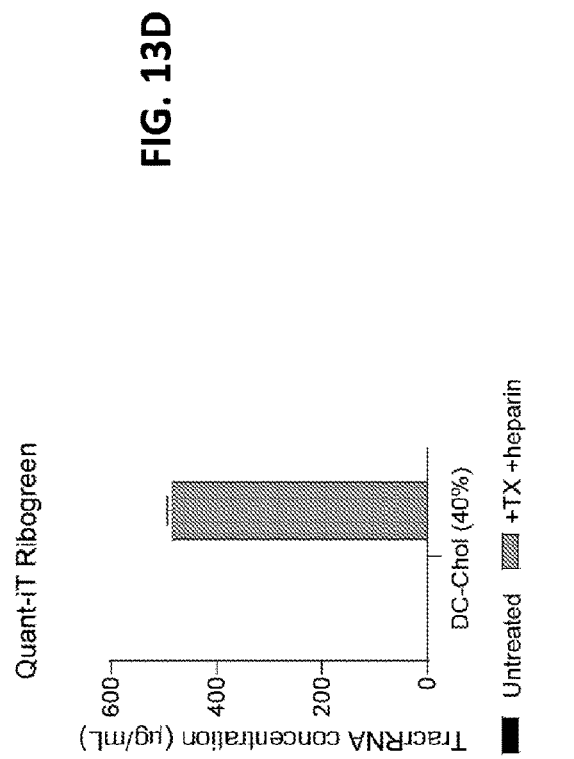
FIG. 13A  FIG. 13B  FIG. 13C  FIG. 13D

SEQUENCE LISTING

<160> NUMBER OF SEQ ID NOS: 60

<210> SEQ ID NO 1
<211> LENGTH: 3
<212> TYPE: DNA
<213> ORGANISM: Streptococcus pyogenes
<220> FEATURE:
<221> NAME/KEY: misc_feature
<222> LOCATION: (1)..(1)
<223> OTHER INFORMATION: n is a, c, g, or t

<400> SEQUENCE: 1 ngg                                                                        3

<210> SEQ ID NO 2
<211> LENGTH: 6
<212> TYPE: DNA
<213> ORGANISM: Streptococcus thermophilus
<220> FEATURE:
<221> NAME/KEY: misc_feature
<222> LOCATION: (1)..(2)
<223> OTHER INFORMATION: n is a, c, g, or t

<400> SEQUENCE: 2 nnagaa                                                                     6

<210> SEQ ID NO 3
<211> LENGTH: 5
<212> TYPE: DNA
<213> ORGANISM: Streptococcus thermophilus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 3 nggng                                                                      5

<210> SEQ ID NO 4
<211> LENGTH: 7
<212> TYPE: DNA
<213> ORGANISM: Neisseria meningitidis
<220> FEATURE:
<221> NAME/KEY: misc_feature
<222> LOCATION: (1)..(3)
<223> OTHER INFORMATION: n is a, c, g, or t

<400> SEQUENCE: 4 nnngatt                                                                    7

<210> SEQ ID NO 5
<211> LENGTH: 3
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: n is a, c, g, or t

<400> SEQUENCE: 5 ttn                                                                        3

```
<210> SEQ ID NO 6
<211> LENGTH: 3
<212> TYPE: DNA
<213> ORGANISM: Artificial Sequence
<220> FEATURE:
<223> OTHER INFORMATION: Synthetic Construct

<400> SEQUENCE: 6 cta                                                                        3

<210> SEQ ID NO 7
<211> LENGTH: 24
<212> TYPE: DNA
<213> ORGANISM: Artificial Sequence
<220> FEATURE:
<223> OTHER INFORMATION: Synthetic Construct

<400> SEQUENCE: 7
aaggagaaga acttttcact ggag                                                24

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
agttcatcca tgccatgtgt a                                                   21

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
ccaggtgggg cttatgcatc                                                     20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
ccacaccaag gcttgaaccc                                                     20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
ggccggattc acgaaacggt                                                     20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 12
cgtcgagatt ggcagttggc                                                  20

<210> SEQ ID NO 13
<211> LENGTH: 25
<212> TYPE: DNA
<213> ORGANISM: Artificial Sequence
<220> FEATURE:
<223> OTHER INFORMATION: Synthetic Construct

<400> SEQUENCE: 13
tctgccctat caactttcga tggta                                            25

<210> SEQ ID NO 14
<211> LENGTH: 25
<212> TYPE: DNA
<213> ORGANISM: Artificial Sequence
<220> FEATURE:
<223> OTHER INFORMATION: Synthetic Construct

<400> SEQUENCE: 14
aatttgcgcg cctgctgcct tcctt                                            25

<210> SEQ ID NO 15
<211> LENGTH: 21
<212> TYPE: RNA
<213> ORGANISM: Artificial Sequence
<220> FEATURE:
<223> OTHER INFORMATION: Synthetic Construct

<400> SEQUENCE: 15
uggcaacaau auuuugucu c                                                 21

<210> SEQ ID NO 16
<211> LENGTH: 21
<212> TYPE: RNA
<213> ORGANISM: Artificial Sequence
<220> FEATURE:
<223> OTHER INFORMATION: Synthetic Construct

<400> SEQUENCE: 16
gacaaaaaga uuguugccac a                                                21

<210> SEQ ID NO 17
<211> LENGTH: 21
<212> TYPE: RNA
<213> ORGANISM: Artificial Sequence
<220> FEATURE:
<223> OTHER INFORMATION: Synthetic Construct

<400> SEQUENCE: 17
uuaguacccu gccuuugcca u                                                21

<210> SEQ ID NO 18
<211> LENGTH: 21
<212> TYPE: RNA
<213> ORGANISM: Artificial Sequence
<220> FEATURE:
<223> OTHER INFORMATION: Synthetic Construct

<400> SEQUENCE: 18
ggcaaaggaa ggguacuaac a                                                21

<210> SEQ ID NO 19
<211> LENGTH: 21
```

```
<212> TYPE: RNA
<213> ORGANISM: Artificial Sequence
<220> FEATURE:
<223> OTHER INFORMATION: Synthetic Construct

<400> SEQUENCE: 19
uacuucgugu gacuuugcca c                                              21

<210> SEQ ID NO 20
<211> LENGTH: 21
<212> TYPE: RNA
<213> ORGANISM: Artificial Sequence
<220> FEATURE:
<223> OTHER INFORMATION: Synthetic Construct

<400> SEQUENCE: 20
ggcaaaguaa cacgaaguac a                                              21

<210> SEQ ID NO 21
<211> LENGTH: 21
<212> TYPE: RNA
<213> ORGANISM: Artificial Sequence
<220> FEATURE:
<223> OTHER INFORMATION: Synthetic Construct

<400> SEQUENCE: 21
uggcaacaau auuuuugucu c                                              21

<210> SEQ ID NO 22
<211> LENGTH: 21
<212> TYPE: RNA
<213> ORGANISM: Artificial Sequence
<220> FEATURE:
<223> OTHER INFORMATION: Synthetic Construct

<400> SEQUENCE: 22
gacaaaaaga uuguugccac a                                              21

<210> SEQ ID NO 23
<211> LENGTH: 21
<212> TYPE: RNA
<213> ORGANISM: Artificial Sequence
<220> FEATURE:
<223> OTHER INFORMATION: Synthetic Construct

<400> SEQUENCE: 23
ucaguacccu gccuuugcca u                                              21

<210> SEQ ID NO 24
<211> LENGTH: 21
<212> TYPE: RNA
<213> ORGANISM: Artificial Sequence
<220> FEATURE:
<223> OTHER INFORMATION: Synthetic Construct

<400> SEQUENCE: 24
ggcaaaggaa ggguacugac a                                              21

<210> SEQ ID NO 25
<211> LENGTH: 21
<212> TYPE: RNA
<213> ORGANISM: Artificial Sequence
<220> FEATURE:
<223> OTHER INFORMATION: Synthetic Construct

<400> SEQUENCE: 25
```
uacuucgugu gacuuugcca c                                                21

<210> SEQ ID NO 26
<211> LENGTH: 21
<212> TYPE: RNA
<213> ORGANISM: Artificial Sequence
<220> FEATURE:
<223> OTHER INFORMATION: Synthetic Construct

<400> SEQUENCE: 26
ggcaaaguaa cacgaaguac a                                                21

<210> SEQ ID NO 27
<211> LENGTH: 21
<212> TYPE: RNA
<213> ORGANISM: Artificial Sequence
<220> FEATURE:
<223> OTHER INFORMATION: Synthetic Construct

<400> SEQUENCE: 27
uuaguggcca ucaacaggcc g                                                21

<210> SEQ ID NO 28
<211> LENGTH: 21
<212> TYPE: RNA
<213> ORGANISM: Artificial Sequence
<220> FEATURE:
<223> OTHER INFORMATION: Synthetic Construct

<400> SEQUENCE: 28
gccuguugcu ggccacuaac a                                                21

<210> SEQ ID NO 29
<211> LENGTH: 21
<212> TYPE: RNA
<213> ORGANISM: Artificial Sequence
<220> FEATURE:
<223> OTHER INFORMATION: Synthetic Construct

<400> SEQUENCE: 29
uaucgauguu aguggccacc u                                                21

<210> SEQ ID NO 30
<211> LENGTH: 21
<212> TYPE: RNA
<213> ORGANISM: Artificial Sequence
<220> FEATURE:
<223> OTHER INFORMATION: Synthetic Construct

<400> SEQUENCE: 30
guggccacga acaucgauac a                                                21

<210> SEQ ID NO 31
<211> LENGTH: 21
<212> TYPE: RNA
<213> ORGANISM: Artificial Sequence
<220> FEATURE:
<223> OTHER INFORMATION: Synthetic Construct

<400> SEQUENCE: 31
uaccgguacc cguuguuuca c                                                21

<210> SEQ ID NO 32
<211> LENGTH: 21
<212> TYPE: RNA
<213> ORGANISM: Artificial Sequence

```
<220> FEATURE:
<223> OTHER INFORMATION: Synthetic Construct

<400> SEQUENCE: 32
gaaacaacug guaccgguac a                                              21

<210> SEQ ID NO 33
<211> LENGTH: 25
<212> TYPE: RNA
<213> ORGANISM: Artificial Sequence
<220> FEATURE:
<223> OTHER INFORMATION: Synthetic Construct

<400> SEQUENCE: 33
caguccacuu aguaucauca ucaag                                          25

<210> SEQ ID NO 34
<211> LENGTH: 27
<212> TYPE: RNA
<213> ORGANISM: Artificial Sequence
<220> FEATURE:
<223> OTHER INFORMATION: Synthetic Construct

<400> SEQUENCE: 34
cuugaugaug auacuaagug gacugug                                        27

<210> SEQ ID NO 35
<211> LENGTH: 25
<212> TYPE: RNA
<213> ORGANISM: Artificial Sequence
<220> FEATURE:
<223> OTHER INFORMATION: Synthetic Construct

<400> SEQUENCE: 35
guccacuuag uaucaucauc aagca                                          25

<210> SEQ ID NO 36
<211> LENGTH: 27
<212> TYPE: RNA
<213> ORGANISM: Artificial Sequence
<220> FEATURE:
<223> OTHER INFORMATION: Synthetic Construct

<400> SEQUENCE: 36
ugcuugauga ugauacuaag uggacug                                        27

<210> SEQ ID NO 37
<211> LENGTH: 25
<212> TYPE: RNA
<213> ORGANISM: Artificial Sequence
<220> FEATURE:
<223> OTHER INFORMATION: Synthetic Construct

<400> SEQUENCE: 37
aguccacuua guaucaucau caagc                                          25

<210> SEQ ID NO 38
<211> LENGTH: 27
<212> TYPE: RNA
<213> ORGANISM: Artificial Sequence
<220> FEATURE:
<223> OTHER INFORMATION: Synthetic Construct

<400> SEQUENCE: 38
gcuugaugau gauacuaagu ggacugu                                        27
```

```
<210> SEQ ID NO 39
<211> LENGTH: 25
<212> TYPE: RNA
<213> ORGANISM: Artificial Sequence
<220> FEATURE:
<223> OTHER INFORMATION: Synthetic Construct

<400> SEQUENCE: 39
aaucuuucau ugauuggaua gcctt                                              25

<210> SEQ ID NO 40
<211> LENGTH: 27
<212> TYPE: RNA
<213> ORGANISM: Artificial Sequence
<220> FEATURE:
<223> OTHER INFORMATION: Synthetic Construct

<400> SEQUENCE: 40
aaggcuaucc aaucaaugaa agauuua                                            27

<210> SEQ ID NO 41
<211> LENGTH: 25
<212> TYPE: RNA
<213> ORGANISM: Artificial Sequence
<220> FEATURE:
<223> OTHER INFORMATION: Synthetic Construct

<400> SEQUENCE: 41
caacaaccuu acgaguaaua ucaca                                              25

<210> SEQ ID NO 42
<211> LENGTH: 27
<212> TYPE: RNA
<213> ORGANISM: Artificial Sequence
<220> FEATURE:
<223> OTHER INFORMATION: Synthetic Construct

<400> SEQUENCE: 42
ugugauauua cucguaaggu uguuggg                                            27

<210> SEQ ID NO 43
<211> LENGTH: 25
<212> TYPE: RNA
<213> ORGANISM: Artificial Sequence
<220> FEATURE:
<223> OTHER INFORMATION: Synthetic Construct

<400> SEQUENCE: 43
caucgaugau uuaguuucua uuctc                                              25

<210> SEQ ID NO 44
<211> LENGTH: 27
<212> TYPE: RNA
<213> ORGANISM: Artificial Sequence
<220> FEATURE:
<223> OTHER INFORMATION: Synthetic Construct

<400> SEQUENCE: 44
gagaauagaa acuaaaucau cgauguu                                            27

<210> SEQ ID NO 45
<211> LENGTH: 25
<212> TYPE: RNA
<213> ORGANISM: Artificial Sequence
<220> FEATURE:
<223> OTHER INFORMATION: Synthetic Construct
```

-continued

```
<400> SEQUENCE: 45
ucgaugauuu aguuucuauu cucaa                                          25

<210> SEQ ID NO 46
<211> LENGTH: 27
<212> TYPE: RNA
<213> ORGANISM: Artificial Sequence
<220> FEATURE:
<223> OTHER INFORMATION: Synthetic Construct

<400> SEQUENCE: 46
uugagaauag aaacuaaauc aucgaug                                        27

<210> SEQ ID NO 47
<211> LENGTH: 25
<212> TYPE: RNA
<213> ORGANISM: Artificial Sequence
<220> FEATURE:
<223> OTHER INFORMATION: Synthetic Construct

<400> SEQUENCE: 47
aucgaugauu uaguuucuau ucuca                                          25

<210> SEQ ID NO 48
<211> LENGTH: 27
<212> TYPE: RNA
<213> ORGANISM: Artificial Sequence
<220> FEATURE:
<223> OTHER INFORMATION: Synthetic Construct

<400> SEQUENCE: 48
ugagaauaga acuaaauca ucgaugu                                         27

<210> SEQ ID NO 49
<211> LENGTH: 25
<212> TYPE: RNA
<213> ORGANISM: Artificial Sequence
<220> FEATURE:
<223> OTHER INFORMATION: Synthetic Construct

<400> SEQUENCE: 49
cgaugauuua guuucuauuc ucaaa                                          25

<210> SEQ ID NO 50
<211> LENGTH: 27
<212> TYPE: RNA
<213> ORGANISM: Artificial Sequence
<220> FEATURE:
<223> OTHER INFORMATION: Synthetic Construct

<400> SEQUENCE: 50
uuugagaaua gaaacuaaau caucgau                                        27

<210> SEQ ID NO 51
<211> LENGTH: 25
<212> TYPE: RNA
<213> ORGANISM: Artificial Sequence
<220> FEATURE:
<223> OTHER INFORMATION: Synthetic Construct

<400> SEQUENCE: 51
gauaugauug uuauucuuaa ugaca                                          25

<210> SEQ ID NO 52
```

```
<211> LENGTH: 27
<212> TYPE: RNA
<213> ORGANISM: Artificial Sequence
<220> FEATURE:
<223> OTHER INFORMATION: Synthetic Construct

<400> SEQUENCE: 52
ugucauuaag aauaacaauc auaucag                                              27

<210> SEQ ID NO 53
<211> LENGTH: 20
<212> TYPE: DNA
<213> ORGANISM: Artificial Sequence
<220> FEATURE:
<223> OTHER INFORMATION: Synthetic Construct

<400> SEQUENCE: 53
acggaaagat gtatgggctt                                                      20

<210> SEQ ID NO 54
<211> LENGTH: 20
<212> TYPE: DNA
<213> ORGANISM: Artificial Sequence
<220> FEATURE:
<223> OTHER INFORMATION: Synthetic Construct

<400> SEQUENCE: 54
aaaactaggc catccatgga                                                      20

<210> SEQ ID NO 55
<211> LENGTH: 23
<212> TYPE: DNA
<213> ORGANISM: Artificial Sequence
<220> FEATURE:
<223> OTHER INFORMATION: Synthetic Construct

<400> SEQUENCE: 55
ttagatccaa aggagtatca aag                                                  23

<210> SEQ ID NO 56
<211> LENGTH: 18
<212> TYPE: DNA
<213> ORGANISM: Artificial Sequence
<220> FEATURE:
<223> OTHER INFORMATION: Synthetic Construct

<400> SEQUENCE: 56
ctttggtacc agcggaga                                                        18

<210> SEQ ID NO 57
<211> LENGTH: 24
<212> TYPE: DNA
<213> ORGANISM: Artificial Sequence
<220> FEATURE:
<223> OTHER INFORMATION: Synthetic Construct

<400> SEQUENCE: 57
gtatgagttg cttctccagc aaag                                                 24

<210> SEQ ID NO 58
<211> LENGTH: 21
<212> TYPE: DNA
<213> ORGANISM: Artificial Sequence
<220> FEATURE:
<223> OTHER INFORMATION: Synthetic Construct

<400> SEQUENCE: 58
```

```
gaggatggct gcaacaagtg t                                              21

<210> SEQ ID NO 59
<211> LENGTH: 20
<212> TYPE: DNA
<213> ORGANISM: Artificial Sequence
<220> FEATURE:
<223> OTHER INFORMATION: Synthetic Construct

<400> SEQUENCE: 59
cctacctttg aggggcttct                                                20

<210> SEQ ID NO 60
<211> LENGTH: 20
<212> TYPE: DNA
<213> ORGANISM: Artificial Sequence
<220> FEATURE:
<223> OTHER INFORMATION: Synthetic Construct

<400> SEQUENCE: 60
gaagtcgtga gacagcgttg                                                20
```

METHODS AND COMPOSITIONS FOR THE MODIFICATION OF PLANTS

SEQUENCE LISTING

The instant application contains a Sequence Listing which has been submitted electronically in ASCII format and is hereby incorporated by reference in its entirety. Said ASCII copy, created on Aug. 23, 2019, is named 51296-004WO3_Sequence_Listing_08.23.19_ST25 and is 12,136 bytes in size.

BACKGROUND

In agriculture, delivery of biologically active agents to plants to induce desirable plant modifications can be hindered in a number of ways. For example, plant-modifying agents, such as nucleic acids or peptides, can be susceptible to degradation during delivery. Further, the plant-modifying agent needs to infiltrate various plant parts, tissues, vascular system, and/or cells to modify the plant. Thus, there is need in the art for methods and composition to effectively deliver plant-modifying agents to plants.

SUMMARY OF THE INVENTION

Disclosed herein are plant-modifying compositions including a plurality of plant messenger packs (PMPs) that carry a plant-modifying agent. The compositions herein are useful in methods for delivering agents that modify plants in a manner that introduces a desirable plant trait, such as an increase in the fitness of the plant.

In a first aspect, provided herein is a method of administering a heterologous RNA to a plant, the method comprising delivering to the plant a composition comprising a plurality of plant messenger packs (PMPs), each of the plurality comprising the heterologous RNA, wherein the composition is delivered at an effective concentration to increase plant fitness.

In some embodiments, the heterologous RNA is a guide RNA (gRNA). In some embodiments, the gRNA is a component of a ribonucleoprotein complex (RNP), and each of the plurality of PMPs comprises the RNP.

In some embodiments, the PMPs are lipid reconstituted PMPs (LPMPs).

In some embodiments, the heterologous RNA is encapsulated by the PMPs.

In some embodiments, each of the PMPs comprises a purified plant extracellular vesicle (EV).

In some embodiments, the PMPs in the composition are at a concentration effective to modify a plant trait, wherein the modification increases the fitness of the plant, e.g., increase development, growth, yield, resistance to abiotic stressors, or resistance to biotic stressors. In some embodiments, the increase in plant fitness is a modification to flowering time, an increase in plant fitness is an increase in the quality of products harvested from the plant, an improvement in taste, appearance, or shelf life of a product harvested from the plant, or a decrease in production of an allergen that stimulates an immune response in an animal.

In another aspect, provided herein is a plant-modifying composition including a plurality of PMPs, wherein the PMPs include a plant-modifying agent. In some embodiments, the PMPs in the composition are at a concentration effective to modify a plant trait, such as plant fitness. In some embodiments, the PMPs in the composition are at a concentration effective to increase the fitness of a plant.

In another aspect, provided herein is a plant-modifying composition including a plurality of plant messenger packs (PMPs), wherein the PMPs include a plant-modifying agent and the PMPs in the composition are at a concentration effective to modify a plant trait, wherein the modification increases the fitness of the plant.

In some embodiments of the compositions described herein, the increase in fitness is an increase in development, growth, yield, resistance to abiotic stressors, or resistance to biotic stressors. In some embodiments, the increase in plant fitness is an increase in disease resistance, drought tolerance, heat tolerance, cold tolerance, salt tolerance, metal tolerance, herbicide tolerance, chemical tolerance, water use efficiency, nitrogen utilization, resistance to nitrogen stress, nitrogen fixation, pest resistance, herbivore resistance, pathogen resistance, yield, yield under water-limited conditions, vigor, growth, photosynthetic capability, nutrition, protein content, carbohydrate content, oil content, biomass, shoot length, root length, root architecture, seed set, seed weight, fruit set, or amount of harvestable produce. In some embodiments, the increase in fitness is earlier flowering. In some embodiments, the increase in plant fitness is an increase in the quality of products harvested from the plant. In some embodiments, the increase in plant fitness is an improvement in taste, appearance, or shelf-life of a product harvested from the plant. In some embodiments, the increase in fitness is a decrease in production of an allergen that stimulates an immune response in an animal.

In some embodiments of the compositions described herein, the plant-modifying agent is a heterologous nucleic acid.

In another aspect, provided herein is a plant-modifying composition including a plurality of plant messenger packs (PMPs), wherein the PMPs include a heterologous nucleic acid and the PMPs in the composition are at a concentration effective to modify a plant, wherein the modification increases the fitness of the plant.

In another aspect, provided herein is a plant-modifying composition including a plurality of plant messenger packs (PMPs), wherein the PMPs include a heterologous nucleic acid and the PMPs in the composition are at a concentration effective to increase plant fitness.

In some embodiments where the plant-modifying agent is a heterologous nucleic acid, the heterologous nucleic acid is a DNA, an RNA, a PNA, or a hybrid DNA-RNA molecule. In some embodiments, the RNA is a messenger RNA (mRNA), a guide RNA (gRNA), or an inhibitory RNA. In some embodiments, the inhibitory RNA is RNAi, shRNA, or miRNA. In some embodiments, the inhibitory RNA inhibits expression of a gene in a plant.

In some embodiments where the plant-modifying agent is a heterologous nucleic acid, the nucleic acid is an mRNA, a modified mRNA, or a DNA molecule that, in the plant, increases expression of an enzyme, a pore-forming protein, a signaling ligand, a cell penetrating peptide, a transcription factor, a receptor, an antibody, a nanobody, a gene editing protein, a riboprotein, a protein aptamer, or a chaperone. In some embodiments, the increase in expression in the plant is an increase in expression of about 5%, 10%, 15%, 20%, 30%, 40%, 50%, 60%, 70%, 80%, 90%, 100%, or more than 100% relative to a reference level (e.g., the expression in an untreated plant). In some embodiments, the increase in expression in the plant is an increase in expression of about 2× fold, about 4× fold, about 5× fold, about 10× fold, about 20× fold, about 25× fold, about 50× fold, about 75× fold, or about 100× fold or more, relative to a reference level (e.g., the expression in an untreated plant).

In some embodiments, the nucleic acid is an antisense a RNA, a siRNA, a shRNA, a miRNA, an aiRNA, a PNA, a morpholino, a LNA, a piRNA, a ribozyme, a DNAzyme, an aptamer, a circRNA, a gRNA, or a DNA molecule that, in the plant, decreases expression of an enzyme, a transcription factor, a secretory protein, a structural factor, a riboprotein, a protein aptamer, a chaperone, a receptor, a signaling ligand, or a transporter. In some embodiments, the decrease in expression in the plant is a decrease in expression of about 5%, 10%, 15%, 20%, 30%, 40%, 50%, 60%, 70%, 80%, 90%, 100%, or more than 100% relative to a reference level (e.g., the expression in an untreated plant). In some embodiments, the decrease in expression in the plant is a decrease in expression of about 2× fold, about 4× fold, about 5× fold, about 10× fold, about 20× fold, about 25× fold, about 50× fold, about 75× fold, or about 100× fold or more, relative to a reference level (e.g., the expression in an untreated plant).

In some embodiments where the plant-modifying agent is a heterologous nucleic acid, the heterologous nucleic acid is a construct that does not integrate into the plant genome. In other embodiments, the heterologous nucleic acid is a construct that integrates (e.g., stably integrates) into the plant genome.

In some embodiments of the compositions described herein, the plant-modifying agent is a heterologous peptide. In some embodiments, the peptide is an enzyme, pore-forming protein, signaling ligand, cell penetrating peptide, transcription factor, receptor, antibody, nanobody, gene editing protein, riboprotein, a protein aptamer, or chaperone. In some embodiments, the peptide decreases expression of a gene in the plant. In some embodiments, the peptide increases expression of a gene in the plant.

In yet another aspect, provided herein is a plant-modifying composition including a plurality of plant messenger packs (PMPs), wherein the PMPs include a heterologous peptide and the PMPs in the composition are at a concentration effective to increase plant fitness. In some embodiments, the peptide is an enzyme, pore-forming protein, signaling ligand, cell penetrating peptide, transcription factor, receptor, antibody, nanobody, gene editing protein, riboprotein, a protein aptamer, or chaperone. In some embodiments, the peptide decreases expression of a gene in the plant. In some embodiments, the peptide increases expression of a gene in the plant.

In some embodiments of the compositions described herein, the PMPs include two or more (e.g., 2, 3, 4, 5, 6, 7, 8, 9, 10, or more than 10) different plant-modifying agents. In some embodiments, the two or more different plant-modifying agents include a heterologous nucleic acid and a heterologous peptide.

In certain embodiments, the heterologous plant-modifying agent is one listed in the section entitled "Heterologous Plant-Modifying Agents" of the Detailed Description herein.

In some embodiments of the compositions described herein, the plant-modifying agent is encapsulated by the PMPs.

In some embodiments of the compositions described herein, the plant-modifying agent is embedded on the surface of the PMPs.

In some embodiments of the compositions described herein, the plant-modifying agent is conjugated to the surface of the PMPs.

In some embodiments, the composition is stable for at least 24 hours (e.g., at least 24 hours, 30 hours, or 40 hours), at least 48 hours (e.g., at least 48 hours (=2 days), 3 days, 4 days, 5 days, or 6 days), at least seven days (e.g., at least seven days (=1 week), at least 2 weeks, at least 3 weeks, or at least 4 weeks), or at least 30 days (e.g., at least 30 days, at least 60 days, or at least 90 days). In some embodiments, the composition is stable at a temperature of at least 24° C. (e.g., at least 24° C., 25° C., 26° C., 27° C., 28° C., 29° C., 30° C., 37° C., 42° C., or more than 42° C.), at least 20° C. (e.g., at least 20° C., 21° C., 22° C., or 23° C.), at least 4° C. (e.g., at least 5° C., 10° C., or 15° C.), at least −20° C. (e.g., at least −20° C., −15° C., −10° C., −5° C., or 0° C.), or at least −80° C. (e.g., at least −80° C., −70° C., −60° C., −50° C., −40° C., or −30° C.). In some embodiments, the PMPs are stable in liquid nitrogen (about −195.8° C.). In some embodiments, the composition is stable for at least one day at room temperature and/or stable for at least one week at 4° C.

In some embodiments, the composition is stable under UV radiation. In some embodiments, the composition is stable for a period defined herein under the temperature in the natural habitat of a plant.

In some embodiments of the compositions described herein, the PMPs may include a plurality of proteins (i.e., PMP proteins), and the concentration of PMPs may be measured as the concentration of PMP proteins therein. In some embodiments, the plurality of PMPs in the composition is at a concentration of at least 0.025 µg PMP protein/ml (e.g., at least 0.025, 0.05, 0.1, or 0.5 µg PMP protein/ml), at least 1 µg PMP protein/ml (e.g., at least 1, 2, 3, 4, 5, 6, 7, 8, or 9 µg PMP protein/ml), at least 10 µg PMP protein/ml (e.g., at least 10, 15, 20, 25, 30, 35, 40, or 45 µg PMP protein/ml), at least 50 µg PMP protein/ml (e.g., at least 50, 55, 60, 65, 70, 75, 80, 85, 90, or 95 µg PMP protein/ml), at least 100 µg PMP protein/ml (e.g., at least 100, 125, 150, 175, 200, or 225 µg PMP protein/ml), at least 250 µg PMP protein/ml (e.g., at least 250, 300, 350, 400, 450, or 500 µg PMP protein/ml), or at least 500 µg PMP protein/ml (e.g., at least 500, 600, 700, 800, or 900 µg PMP protein/ml). In some embodiments, the plurality of PMPs in the composition is a at a concentration of at least 1 mg PMP protein/ml (e.g., at least 1, 2, 3, 4, 5, 6, 7, 8, or 9 PMP protein/ml) or at least 10 mg PMP protein/ml (e.g., at least 10, 20, 30, 40, 50, 60, 70, 80, 90, or 100 mg PMP protein/ml).

In some embodiments of the compositions described herein, the PMPs include a purified plant extracellular vesicle (EV), or a segment or extract thereof. In some embodiments, the plant EV is a modified plant extracellular vesicle (EV). In certain embodiments, the plant EV is a plant exosome or a plant microvesicle. In some embodiments, the PMPs include a plant EV marker, such as those outlined in the Appendix.

In some embodiments of the compositions described herein, the plurality of PMPs may be pure. For example, the composition may be substantially free (e.g., has less than 25%, 20%, 15%, 10%, 5%, 2%) of plant organelles such as chloroplasts, mitochondria, or nuclei).

In some embodiments of the compositions described herein, the plant is an agricultural or horticultural plant. In some embodiments, the agricultural plant is a soybean plant, a wheat plant, a corn plant, a tomato plant, or an alfalfa plant.

In some embodiments of the compositions described herein, the composition is formulated for delivery to a plant. In some embodiments, the composition is formulated for delivery to a leaf, pollen, seed, root, fruit, shoot, or flower of the plant. In some embodiments, the composition includes an agriculturally acceptable carrier.

In some embodiments of the compositions described herein, the composition is formulated to stabilize the PMPs.

In some embodiments of the compositions described herein, the plant-modifying composition is non-pesticidal.

In some embodiments of the compositions described herein, the composition is formulated as a liquid, a solid, an aerosol, a paste, a gel, or a gas composition.

In another aspect, provided herein is a plant-modifying composition including a plurality of PMPs, wherein the PMPs are produced by a process which includes the steps of: (a) providing an initial sample from a plant, or a part thereof, wherein the plant or part thereof comprises EVs; (b) isolating a crude PMP fraction from the initial sample, wherein the crude PMP fraction has a decreased level of at least one contaminant or undesired component from the plant or part thereof relative to the level in the initial sample; (c) purifying the crude PMP fraction, thereby producing a plurality of pure PMPs, wherein the plurality of pure PMPs have a decreased level of at least one contaminant or undesired component from the plant or part thereof relative to the level in the crude EV fraction; (d) loading the plurality of pure PMPs with a plant-modifying agent; and, optionally, (e) formulating the PMPs of step (d) for delivery to a plant. In another aspect, provided herein is a plant including any of the plant-modifying compositions provided herein.

In yet another aspect, provided herein is a method of delivering a plant-modifying composition to a plant including contacting the plant with the composition of any of the plant-modifying compositions provided herein.

In another aspect, provided herein is a method of modifying a plant, the method including delivering to the plant an effective amount of any of the plant-modifying compositions provided herein, wherein the method modifies the plant and thereby introduces or increases a beneficial trait in the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method of increasing the fitness of a plant, the method including delivering to the plant an effective amount of any of the plant-modifying compositions provided herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In some embodiments of the methods described herein, the plant-modifying composition is delivered to a leaf, seed, pollen, root, fruit, shoot, flower, or portion thereof. In some embodiments, the plant-modifying composition is delivered to a cell of the plant. In some embodiments, the plant-modifying composition is delivered to a plant protoplast. In some embodiments, the plant-modifying composition is delivered to a tissue of the plant. For example, the composition may be delivered to meristematic tissue of the plant (e.g., apical meristem, lateral meristem, or intercalary meristem). In some instances, the composition is delivered to permanent tissue of the plant (e.g., simple tissues (e.g., parenchyma, collenchyma, or sclerenchyma) or complex permanent tissue (e.g., xylem or phloem)). In some instances, the composition is delivered to a plant embryo.

In another aspect, provided herein is a method of increasing the fitness of a plant, the method including contacting pollen of the plant with an effective amount of any of the plant-modifying compositions herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method of increasing the fitness of a plant, the method including contacting a seed of the plant with an effective amount of any of the plant-modifying compositions disclosed herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method including contacting a protoplast of the plant with an effective amount of any of the plant-modifying compositions herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method of increasing the fitness of a plant, the method including contacting a plant cell of the plant with an effective amount of any of the plant-modifying compositions herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method of increasing the fitness of a plant, the method including contacting meristematic tissue of the plant with an effective amount of any of the plant-modifying compositions herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method of increasing the fitness of a plant, the method including contacting an embryo of the plant with an effective amount of any of the plant-modifying compositions herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In some embodiments of the methods described herein, the increase in fitness is an increase (e.g., by about 1%, 2%, 5%, 10%, 20%, 30%, 40%, 50%, 60%, 70%, 80%, 90%, 100%, or more than 100%) in development, growth, yield, resistance to abiotic stressors, or resistance to biotic stressors.

In some embodiments of the methods described herein, the increase in plant fitness is an increase (e.g., by about 1%, 2%, 5%, 10%, 20%, 30%, 40%, 50%, 60%, 70%, 80%, 90%, 100%, or more than 100%) in disease resistance, drought tolerance, heat tolerance, cold tolerance, salt tolerance, metal tolerance, herbicide tolerance, chemical tolerance, water use efficiency, nitrogen utilization, resistance to nitrogen stress, nitrogen fixation, pest resistance, herbivore resistance, pathogen resistance, yield, yield under water-limited conditions, vigor, growth, photosynthetic capability, nutrition, protein content, carbohydrate content, oil content, biomass, shoot length, root length, root architecture, seed set, seed weight, fruit set, or amount of harvestable produce. In some embodiments, the increase in fitness is earlier flowering. In some embodiments of the methods described herein, the increase in plant fitness is an increase (e.g., by about 1%, 2%, 5%, 10%, 20%, 30%, 40%, 50%, 60%, 70%, 80%, 90%, 100%, or more than 100%) in quality of products harvested from the plant.

In some embodiments of the methods described herein, the increase in plant fitness is an improvement in taste or appearance of a product harvested from the plant.

In some embodiments of the methods described herein, the increase in plant fitness is an increase in shelf-life of a product harvested from the plant (e.g., by about 1%, 2%, 5%, 10%, 20%, 30%, 40%, 50%, 60%, 70%, 80%, 90%, 100%, or more than 100%).

In some embodiments of the methods described herein, the increase in fitness is a decrease (e.g., by about 1%, 2%, 5%, 10%, 20%, 30%, 40%, 50%, 60%, 70%, 80%, 90%, 100%, or more than 100%) in production of an allergen (e.g., pollen) that stimulates an immune response in an animal (e.g., human).

In some embodiments of the methods herein, the plant is an agricultural or horticultural plant. In some embodiments, the plant is a soybean plant, a wheat plant, a corn plant, a tomato plant, or an alfalfa plant.

In some embodiments of the methods herein, the plant-modifying composition is delivered as a liquid, a solid, an aerosol, a paste, a gel, or a gas.

In another aspect, provided herein is an agricultural formulation including any composition described herein and a carrier or excipient suitable for agricultural use. The formulation may be in a liquid, solid (e.g., granule, pellet, powder, dry flowable, or wettable powder), aerosol, paste, gel, or gas form. The formulation may be configured (and/or combined with instructions) to be diluted (e.g., the composition is a soluble solid, or water dispersible solid), sprayed on, painted on, injected, or applied to, a plant, soil, or seeds.

In another aspect, provided herein are kits including any composition described herein and instructions for use as a plant-modifying composition. In some embodiments of any of the above aspects, the PMPs are lipid reconstituted PMPs (LPMPs). In some embodiments, the LPMPs comprise an exogenous cationic lipid. In some embodiments, each of the modified PMPs comprises at least 1%, 5%, 10%, 20%, 30%, 40%, 50%, 60%, 70%, 80%, 90%, or more than 90% cationic lipid. In some embodiments, the cationic lipid is DOTAP or DC-cholesterol.

Other features and advantages of the invention will be apparent from the following Detailed Description and the Claims.

Definitions

As used herein, the term "plant-modifying composition" refers to a composition including a plurality of PMPs, wherein the PMPs include a plant-modifying agent.

As used herein, "delivering" or "contacting" refers to applying to a plant, a plant-modifying composition either directly on the plant, or adjacent to the plant, in a region where the composition is effective to alter the fitness of the plant. In methods where the composition is directly contacted with a plant, the composition may be contacted with the entire plant or with only a portion of the plant.

As used herein, the term "effective amount," "effective concentration," or "concentration effective to" refers to an amount of a PMP, or a heterologous plant-modifying agent therein (e.g., a polynucleotide or a peptide), sufficient to effect the recited result, e.g., to modify a plant (e.g., increase plant fitness) or to reach a target level (e.g., a predetermined or threshold level) in or on a target plant.

As used herein, the term "formulated for delivery to a plant" refers to a plant-modifying composition that includes an agriculturally acceptable carrier. As used herein, an "agriculturally acceptable" carrier or excipient is one that is suitable for use in agriculture, e.g., for use on plants. In certain embodiments, the agriculturally acceptable carrier or excipient does not have undue adverse side effects to the plants, the environment, or to humans or animals who consume the resulting agricultural products derived therefrom commensurate with a reasonable benefit/risk ratio.

As used herein, "increase the fitness of a plant" refers to an increase in the fitness of the plant directly resulting from contact with a plant-modifying composition described herein and includes, for example, an improved yield, improved vigor of the plant, or improved quality or amount of a harvested product from the plant, an improvement in pre- or post-harvest traits deemed desirable for agriculture or horticulture (e.g., taste, appearance, shelf life), or for an improvement of traits that otherwise benefit humans (e.g., decreased allergen production). An improved yield of a plant relates to an increase in the yield of a product (e.g., as measured by plant biomass, grain, seed or fruit yield, protein content, carbohydrate or oil content or leaf area) of the plant by a measurable amount over the yield of the same product of the plant produced under the same conditions, but without the application of the instant compositions or compared with application of conventional plant-modifying agents (e.g., plant-modifying agents delivered without a PMP). For example, yield can be increased by at least about 0.5%, about 1%, about 2%, about 3%, about 4%, about 5%, about 10%, about 20%, about 30%, about 40%, about 50%, about 60%, about 70%, about 80%, about 90%, about 100%, or more than 100%. Yield can be expressed in terms of an amount by weight or volume of the plant or a product of the plant on some basis. The basis can be expressed in terms of time, growing area, weight of plants produced, or amount of a raw material used. An increase in the fitness of plant can also be measured by other means, such as an increase or improvement of the vigor rating, increase in the stand (the number of plants per unit of area), increase in plant height, increase in stalk circumference, increase in plant canopy, improvement in appearance (such as greener leaf color as measured visually), improvement in root rating, increase in seedling emergence, protein content, increase in leaf size, increase in leaf number, fewer dead basal leaves, increase in tiller strength, decrease in nutrient or fertilizer requirements, increase in seed germination, increase in tiller productivity, increase in flowering, increase in seed or grain maturation or seed maturity, less plant verse (lodging), increased shoot growth, or any combination of these factors, by a measurable or noticeable amount over the same factor of the plant produced under the same conditions, but without the administration of the instant compositions or with application of conventional agricultural agents.

As used herein, the term "heterologous" refers to an agent (e.g., a plant-modifying agent) that is either (1) exogenous to the plant (e.g., originating from a source that is not the plant or plant part from which the PMP is produced) (e.g., added the PMP using loading approaches described herein) or (2) endogenous to the plant cell or tissue from which the PMP is produced, but present in the PMP (e.g., added to the PMP using loading approaches described herein, genetic engineering, in vitro or in vivo approaches) at a concentration that is higher than that found in nature (e.g., higher than a concentration found in a naturally-occurring plant extracellular vesicle).

As used herein, the term "functional agent" refers to an agent (e.g., a peptide or nucleic acid) that is or can be associated with PMPs (e.g., loaded into or onto PMPs (e.g., encapsulated by, embedded in, or conjugated to PMPs) using in vivo or in vitro methods and is capable of effecting the recited result (e.g., modifying a plant) in accordance with the present compositions or methods.

As used herein, the term "nucleic acid" and "polynucleotide" are interchangeable and refer to RNA or DNA that is linear or branched, single or double stranded, or a hybrid thereof, regardless of length (e.g., at least 2, 3, 4, 5, 6, 7, 8, 9, 10, 20, 30, 40, 50, 100, 150, 200, 250, 500, 1000, or more nucleic acids). The term also encompasses RNA/DNA hybrids. Nucleotides are typically linked in a nucleic acid by phosphodiester bonds, although the term "nucleic acid" also encompasses nucleic acid analogs having other types of linkages or backbones (e.g., phosphoramide, phosphorothioate, phosphorodithioate, O-methylphosphoroamidate, morpholino, locked nucleic acid (LNA), glycerol nucleic acid (GNA), threose nucleic acid (TNA), and peptide nucleic acid (PNA) linkages or backbones, among others). The nucleic acids may be single-stranded, double-stranded, or contain portions of both single-stranded and double-stranded sequence. A nucleic acid can contain any combination of deoxyribonucleotides and ribonucleotides, as well as any combination of bases, including, for example, adenine, thymine, cytosine, guanine, uracil, and modified or non-canonical bases (including, e.g., hypoxanthine, xanthine, 7-methylguanine, 5,6-dihydrouracil, 5-methylcytosine, and 5 hydroxymethylcytosine).

As used herein, the term "peptide," "protein," or "polypeptide" encompasses any chain of naturally or non-naturally occurring amino acids (either D- or L-amino acids), regardless of length (e.g., at least 2, 3, 4, 5, 6, 7, 10, 12, 14, 16, 18, 20, 25, 30, 40, 50, 100, or more amino acids), the presence or absence of post-translational modifications (e.g., glycosylation or phosphorylation), or the presence of, e.g., one or more non-amino acyl groups (for example, sugar, lipid, etc.) covalently linked to the peptide, and includes, for example, natural proteins, synthetic, or recombinant polypeptides and peptides, hybrid molecules, peptoids, or peptidomimetics.

As used herein, "percent identity" between two sequences is determined by the BLAST 2.0 algorithm, which is described in Altschul et al., (1990) *J. Mol. Biol.* 215:403-410. Software for performing BLAST analyses is publicly available through the National Center for Biotechnology Information.

As used herein, the term "plant" refers to whole plants, plant organs, plant tissues, seeds, plant cells, seeds, and progeny of the same. Plant cells include, without limitation, cells from seeds, suspension cultures, embryos, meristematic regions, callus tissue, leaves, roots, shoots, gametophytes, sporophytes, pollen, and microspores. Plant parts include differentiated and undifferentiated tissues including, but not limited to the following: roots, stems, shoots, leaves, pollen, seeds, fruit, harvested produce, tumor tissue, sap (e.g., xylem sap and phloem sap), and various forms of cells and culture (e.g., single cells, protoplasts, embryos, and callus tissue). The plant tissue may be in a plant or in a plant organ, tissue, or cell culture. In addition, a plant may be genetically engineered to produce a heterologous protein or RNA, for example, of any of the plant-modifying compositions in the methods or compositions described herein.

As used herein, the term "plant extracellular vesicle", "plant EV", or "EV" refers to an enclosed lipid-bilayer structure naturally occurring in a plant. Optionally, the plant EV includes one or more plant EV markers. As used herein, the term "plant EV marker" refers to a component that is naturally associated with a plant, such as a plant protein, a plant nucleic acid, a plant small molecule, a plant lipid, or a combination thereof, including but not limited to any of the plant EV markers listed in the Appendix. In some instances, the plant EV marker is an identifying marker of a plant EV but is not a pesticidal agent. In some instances, the plant EV marker is an identifying marker of a plant EV and also a pesticidal agent (e.g., either associated with or encapsulated by the plurality of PMPs, or not directly associated with or encapsulated by the plurality of PMPs).

As used herein, the term "plant messenger pack" or "PMP" refers to a lipid structure (e.g., a lipid bilayer, unilamellar, multilamellar structure; e.g., a vesicular lipid structure), that is about 5-2000 nm (e.g., at least 5-1000 nm, at least 5-500 nm, at least 400-500 nm, at least 25-250 nm, at least 50-150 nm, or at least 70-120 nm) in diameter that is derived from (e.g., enriched, isolated or purified from) a plant source or segment, portion, or extract thereof, including lipid or non-lipid components (e.g., peptides, nucleic acids, or small molecules) associated therewith and that has been enriched, isolated or purified from a plant, a plant part, or a plant cell, the enrichment or isolation removing one or more contaminants or undesired components from the source plant. PMPs may be highly purified preparations of naturally occurring EVs. Preferably, at least 1% of contaminants or undesired components from the source plant are removed (e.g., at least 2%, 5%, 10%, 15%, 20%, 25%, 30%, 40%, 45%, 50%, 55%, 60%, 70%, 80%, 90%, 95%, 96%, 98%, 99%, or 100%) of one or more contaminants or undesired components from the source plant, e.g., plant cell wall components; pectin; plant organelles (e.g., mitochondria; plastids such as chloroplasts, leucoplasts or amyloplasts; and nuclei); plant chromatin (e.g., a plant chromosome); or plant molecular aggregates (e.g., protein aggregates, protein-nucleic acid aggregates, lipoprotein aggregates, or lipido-proteic structures). Preferably, a PMP is at least 30% pure (e.g., at least 40% pure, at least 50% pure, at least 60% pure, at least 70% pure, at least 80% pure, at least 90% pure, at least 99% pure, or 100% pure) relative to the one or more contaminants or undesired components from the source plant as measured by weight (w/w), spectral imaging (% transmittance), or conductivity (S/m).

In some instances, the PMP is a lipid extracted PMP (LPMP). As used herein, the terms "lipid extracted PMP" and "LPMP" refer to a PMP that has been derived from a lipid structure (e.g., a lipid bilayer, unilamellar, multilamellar structure; e.g., a vesicular lipid structure) derived from (e.g., enriched, isolated or purified from) a plant source, wherein the lipid structure is disrupted (e.g., disrupted by lipid extraction) and reassembled or reconstituted in a liquid phase (e.g., a liquid phase containing a cargo) using standard methods, e.g., reconstituted by a method comprising lipid film hydration and/or solvent injection, to produce the LPMP, as is described herein. The method may, if desired, further comprise sonication, freeze/thaw treatment, and/or lipid extrusion, e.g., to reduce the size of the reconstituted PMPs. A PMP (e.g., a LPMP) may comprise between 10% and 100% lipids derived from the lipid structure from the plant source, e.g., may contain at least 10%, at least 20%, at least 30%, at least 40%, at least 50%, at least 60%, at least 70%, at least 80%, at least 90%, at least 95%, or 100% lipids derived from the lipid structure from the plant source. A PMP (e.g., a LPMP) may comprise all or a fraction of the lipid species present in the lipid structure from the plant source, e.g., it may contain at least 10%, at least 20%, at least 30%, at least 40%, at least 50%, at least 60%, at least 70%, at least 80%, at least 90%, or 100% of the lipid species present in the lipid structure from the plant source. A PMP (e.g., a LPMP) may comprise none, a fraction, or all of the protein species present in the lipid structure from the plant source, e.g., may contain 0%, less than 1%, less than 5%, less than 10%, less than 15%, less than 20%, less than 30%, less than 40%, less than 50%, less than 60%, less than 70%, less than 80%, less than 90%, less than 100%, or 100% of the protein species present in the lipid structure from the plant source. In some instances, the lipid bilayer of the PMP (e.g., LPMP) does not contain proteins. In some instances, the lipid structure of the PMP (e.g., LPMP) contains a reduced amount of proteins relative to the lipid structure from the plant source.

PMPs (e.g., LPMPs) may optionally include exogenous lipids, e.g., lipids that are either (1) exogenous to the plant (e.g., originating from a source that is not the plant or plant part from which the PMP is produced) (e.g., added the PMP using methods described herein) or (2) endogenous to the plant cell or tissue from which the PMP is produced, but present in the PMP (e.g., added to the PMP using methods described herein, genetic engineering, in vitro or in vivo approaches) at a concentration that is higher than that found in nature (e.g., higher than a concentration found in a naturally-occurring plant extracellular vesicle). The lipid composition of the PMP may include 0%, less than 1%, or at least 1%, 2%, 5%, 10%, 15%, 20%, 25%, 30%, 40%, 50%, 60%, 70%, 80%, 90%, 95%, or more than 95% exogenous lipid. Exemplary exogenous lipids include cationic lipids, ionizable lipids, zwitterionic lipids, and lipidoids.

PMPs may optionally include additional agents, such as heterologous functional agents, e.g., plant-modifying agents, pesticidal agents, fertilizing agents, therapeutic agents, polynucleotides, polypeptides, or small molecules. The PMPs can carry or associate with additional agents (e.g., plant-modifying agents) in a variety of ways to enable delivery of the agent to a target plant, e.g., by encapsulating the agent, incorporation of the agent in the lipid bilayer structure, or association of the agent (e.g., by conjugation) with the surface of the lipid bilayer structure. Heterologous functional agents can be incorporated into the PMPs either in vivo (e.g., in planta) or in vitro (e.g., in tissue culture, in cell culture, or synthetically incorporated).

As used herein, the term "cationic lipid" refers to an amphiphilic molecule (e.g., a lipid or a lipidoid) containing a cationic group (e.g., a cationic head group).

As used herein, the term "lipidoid" refers to a molecule having one or more characteristics of a lipid.

As used herein, the term "plant-modifying agent" refers to an agent that can alter the genetic properties (e.g., increase gene expression, decrease gene expression, or otherwise alter the nucleotide sequence of DNA or RNA) or biochemical properties of a plant in a manner the results in an increase in plant fitness.

As used herein, the term "stable PMP composition" (e.g., a composition including loaded or non-loaded PMPs) refers to a PMP composition that over a period of time (e.g., at least 24 hours, at least 48 hours, at least 1 week, at least 2 weeks, at least 3 weeks, at least 4 weeks, at least 30 days, at least 60 days, or at least 90 days) retains at least 5% (e.g., at least 5%, 10%, 15%, 20%, 25%, 30%, 35%, 40%, 45%, 50%, 55%, 60%, 65%, 70%, 75%, 80%, 85%, 90%, 95%, or 100%) of the initial number of PMPs (e.g., PMPs per mL of solution) relative to the number of PMPs in the PMP composition (e.g., at the time of production or formulation) optionally at a defined temperature range (e.g., a temperature of at least 24° C. (e.g., at least 24° C., 25° C., 26° C., 27° C., 28° C., 29° C., or 30° C.), at least 20° C. (e.g., at least 20° C., 21° C., 22° C., or 23° C.), at least 4° C. (e.g., at least 5° C., 10° C., or 15° C.), at least −20° C. (e.g., at least −20° C., −15° C., −10° C., −5° C., or 0° C.), or −80° C. (e.g., at least −80° C., −70° C., −60° C., −50° C., −40° C., or −30° C.)); or retains at least 5% (e.g., at least 5%, 10%, 15%, 20%, 25%, 30%, 35%, 40%, 45%, 50%, 55%, 60%, 65%, 70%, 75%, 80%, 85%, 90%, 95%, or 100%) of its activity (e.g., pesticidal and/or repellent activity) relative to the initial activity of the PMP (e.g., at the time of production or formulation) optionally at a defined temperature range (e.g., a temperature of at least 24° C. (e.g., at least 24° C., 25° C., 26° C., 27° C., 28° C., 29° C., or 30° C.), at least 20° C. (e.g., at least 20° C., 21° C., 22° C., or 23° C.), at least 4° C. (e.g., at least 5° C., 10° C., or 15° C.), at least −20° C. (e.g., at least −20° C., −15° C., −10° C., −5° C., or 0° C.), or −80° C. (e.g., at least −80° C., −70° C., −60° C., −50° C., −40° C., or −30° C.)).

As used herein, the term "untreated" refers to a plant that has not been contacted with or delivered a plant-modifying composition, including a separate plant that has not been delivered the plant-modifying composition, the same plant undergoing treatment assessed at a time point prior to delivery of the plant-modifying compositions, or the same plant undergoing treatment assessed at an untreated part of the plant.

As used herein, the term "juice sac" or "juice vesicle" refers to a juice-containing membrane-bound component of the endocarp (carpel) of a hesperidium, e.g., a citrus fruit. In some aspects, the juice sacs are separated from other portions of the fruit, e.g., the rind (exocarp or flavedo), the inner rind (mesocarp, albedo, or pith), the central column (placenta), the segment walls, or the seeds. In some aspects, the juice sacs are juice sacs of a grapefruit, a lemon, a lime, or an orange.

BRIEF DESCRIPTION OF THE DRAWINGS

FIG. 3C is a set of graphs and a table showing particle size in nm for selected SEC fractions, as measured using NanoFCM. The graphs show PMP size distribution in fractions 1, 3, 5, and 8.

FIG. 3D is a graph showing protein concentration in µg/mL in SEC fractions, as measured using a BCA assay. The fraction containing the majority of PMPs ("PMP fraction") is labeled, and an arrow indicates a fraction containing contaminants.

FIG. 5A is a graph showing particle concentration (particles/ml) in eluted BMS plant cell culture SEC fractions, as measured by nano-flow cytometry (NanoFCM). PMPs were eluted in SEC fractions 4-6.

FIG. 5B is a graph showing absorbance at 280 nm (A.U.) in eluted BMS SEC fractions, measured on a SpectraMax® spectrophotometer. PMPs were eluted in fractions 4-6; fractions 9-13 contained contaminants.

FIG. 5C is a graph showing protein concentration (µg/ml) in eluted BMS SEC fractions, as determined by BCA analysis. PMPs were eluted in fractions 4-6; fractions 9-13 contained contaminants.

FIG. 6B is a set of photomicrographs showing uptake of lemon (LM) PMPs labeled with Alexa Fluor® 488 (AF488) by the plant cell lines *Glycine max* (soy bean), *Tritium aestivum* (wheat), and maize BMS cell culture. Brightfield panels show the position of cells; panels labeled "GFP" show fluorescence of AF488. Uptake of PMPs by a cell is indicated by the presence of the AF488 signal in the cell. Free AF488 ("Free dye") is shown as a control.

FIG. 7 is a pair of diagrams and a set of photomicrographs showing uptake of lemon (LM) and grapefruit (GF) PMPs labeled with DL800 by *Arabidopsis thaliana* seedlings and alfalfa sprouts. Intensity of fluorescence of DL800 dye is displayed. Intensity of fluorescence was measured at 22 hpt (hours post-treatment) for *Arabidopsis thaliana* seedlings and at 24 hpt for alfalfa sprouts. Seedlings incubated with no dye ("negative control") and with free DL800 dye ("DL800 dye only") are shown as controls.

FIG. 8A is an experimental overview of the treatment of Alfalfa sprouts with DyLight800 nm-labeled PMPs that were produced with or without pectinase treatment.

FIG. 8B is an infrared heat map showing uptake of purified lemon PMPs in alfalfa sprouts, showing that pectinase treatment during lemon PMP production, followed by DL800 nm labeling of the purified PMPs, does not affect uptake or transport of PMPs. Infrared images are taken on an Odyssey scanner.

FIG. 9A is a pair of photomicrographs showing fluorescence of DiR dye at 750 nm in two week-old *Arabidopsis thaliana* seedlings that were not treated (untreated) or were treated with lemon (LM) lipid reconstituted PMPs (LPMPs) stained with DiR (LM-LPMP-DiR). Images were acquired on an Bright 1500 fluorescent imager.

FIG. 9B is a pair of photomicrographs showing fluorescence of DiR dye at 750 nm in two week-old *Arabidopsis thaliana* seedlings that were treated with a DiR control or were treated with grapefruit (GF) LPMPs stained with DiR (GF-LPMP-DiR). Images were acquired on an iBright 1500 fluorescent imager.

FIG. 13A is a graph showing the zeta potential (mV) of LPMPs not comprising added lipids (LPMPs) and LPMPs comprising 25% or 40% DOTAP or DC-cholesterol as measured using dynamic light scattering (DLS). Data are presented as Mean±SD.

FIG. 13B is a bar graph showing the percent of Alexa Fluor 555-labeled siRNA input that was recovered from LPMPs following loading of LPMPs from grapefruit lipids not comprising added lipids (LPMPs) and LPMPs from grapefruit lipids comprising 20% DOTAP.

FIG. 13C is a bar graph showing the percent of ATTO-labeled TracrRNA input that was recovered from LPMPs following loading of LPMPs from lemon lipids not comprising added lipids (LPMPs) and LPMPs from lemon lipids comprising 40% DC-cholesterol (DC-Chol).

FIG. 13D is a bar graph showing TracrRNA concentration (μg/mL) in LPMPs comprising 40% DC-cholesterol that have not been treated or have been lysed using Triton-X100 and heparin (+TX +heparin), as measured using a Quant-iT™ RiboGreen® analysis.

DETAILED DESCRIPTION

Figure 1A:
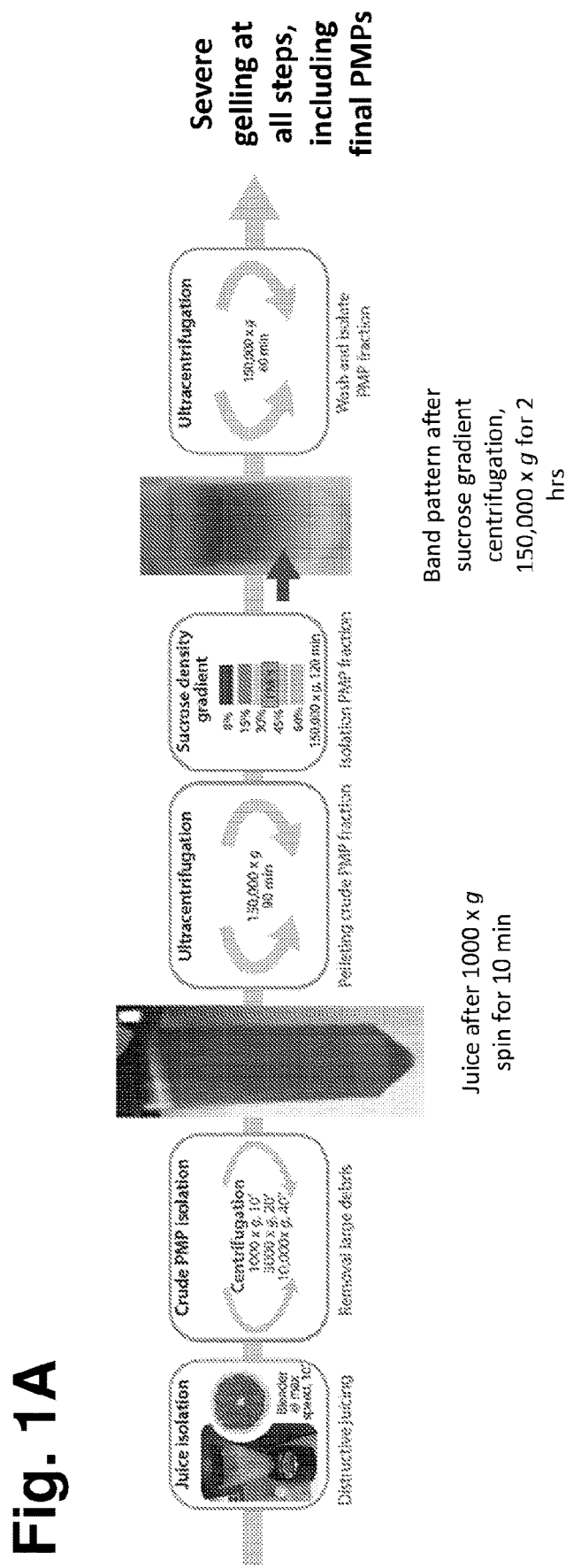
FIG. 1A is a schematic diagram showing a protocol for grapefruit PMP production using a destructive juicing step involving the use of a blender, followed by ultracentrifugation and sucrose gradient purification. Images are included of the grapefruit juice after centrifugation at 1000×g for 10 min and the sucrose gradient band pattern after ultracentrifugation at 150,000×g for 2 hours.

Featured herein are compositions and related methods for modifying plants (e.g., increasing plant fitness) using plant-modifying compositions that include plant messenger packs (PMPs), lipid assemblies produced wholly or in part from plant extracellular vesicles (EVs), or segments, portions, or extracts thereof. The PMPs provided herein include plant-modifying agents. Also included are plant-modifying formulations in which the PMPs are provided in substantially pure form or concentrated forms. The plant-modifying compositions and formulations described herein can be delivered directly to a plant to modify plants in a manner to introduce desirable plant traits in a plant (e.g., to increase the fitness of the plant), such as an agricultural or horticultural plant.

I. Plant-Modifying Compositions

The plant-modifying compositions described herein include a plurality of plant messenger packs (PMP). A PMP is a lipid (e.g., lipid bilayer, unilamellar, or multilamellar structure) structure that includes a plant EV, or segment, portion, or extract (e.g., lipid extract) thereof. Plant EVs refer to an enclosed lipid-bilayer structure that naturally occurs in a plant and that is about 5-2000 nm in diameter. Plant EVs can originate from a variety of plant biogenesis pathways. In nature, plant EVs can be found in the intracellular and extracellular compartments of plants, such as the plant apoplast, the compartment located outside the plasma membrane and formed by a continuum of cell walls and the extracellular space. Alternatively, PMPs can be enriched plant EVs found in cell culture media upon secretion from plant cells. Plant EVs can be separated from plants (e.g., from the apoplastic fluid), thereby producing PMPs, by a variety of methods, further described herein. The PMPs herein further include a heterologous plant-modifying agent, which can be introduced using a variety of in vivo or in vitro methods, such as those further described herein.

PMPs can include plant EVs, or segments, portions, or extracts, thereof. Optionally, PMPs can also include exogenous lipids in addition to lipids derived from plant EVs. In some embodiments, the plant EVs are about 5-2000 nm in diameter. For example, the PMP can include a plant EV, or segment, portion, or extract thereof, that has a mean diameter of about 5-50 nm, about 50-100 nm, about 100-150 nm, about 150-200 nm, about 200-250 nm, about 250-300 nm, about 300-350 nm, about 350-400 nm, about 400-450 nm, about 450-500 nm, about 500-550 nm, about 550-600 nm, about 600-650 nm, about 650-700 nm, about 700-750 nm, about 750-800 nm, about 800-850 nm, about 850-900 nm, about 900-950 nm, about 950-1000 nm, about 1000-1250 nm, about 1250-1500 nm, about 1500-1750 nm, or about 1750-2000 nm. In some instances, the PMP includes a plant EV, or segment, portion, or extract thereof, that has a mean diameter of about 5-950 nm, about 5-900 nm, about 5-850 nm, about 5-800 nm, about 5-750 nm, about 5-700 nm, about 5-650 nm, about 5-600 nm, about 5-550 nm, about 5-500 nm, about 5-450 nm, about 5-400 nm, about 5-350 nm, about 5-300 nm, about 5-250 nm, about 5-200 nm, about 5-150 nm, about 5-100 nm, about 5-50 nm, or about 5-25 nm. In certain instances, the plant EV, or segment, portion, or extract thereof, has a mean diameter of about 50-200 nm. In certain instances, the plant EV, or segment, portion, or extract thereof, has a mean diameter of about 50-300 nm. In certain instances, the plant EV, or segment, portion, or extract thereof, has a mean diameter of about 200-500 nm. In certain instances, the plant EV, or segment, portion, or extract thereof, has a mean diameter of about 30-150 nm.

In some instances, the PMP may include a plant EV, or segment, portion, or extract thereof, that has a mean diameter of at least 5 nm, at least 50 nm, at least 100 nm, at least 150 nm, at least 200 nm, at least 250 nm, at least 300 nm, at least 350 nm, at least 400 nm, at least 450 nm, at least 500 nm, at least 550 nm, at least 600 nm, at least 650 nm, at least 700 nm, at least 750 nm, at least 800 nm, at least 850 nm, at least 900 nm, at least 950 nm, or at least 1000 nm. In some instances, the PMP includes a plant EV, or segment, portion, or extract thereof, that has a mean diameter less than 1000 nm, less than 950 nm, less than 900 nm, less than 850 nm, less than 800 nm, less than 750 nm, less than 700 nm, less than 650 nm, less than 600 nm, less than 550 nm, less than 500 nm, less than 450 nm, less than 400 nm, less than 350 nm, less than 300 nm, less than 250 nm, less than 200 nm, less than 150 nm, less than 100 nm, or less than 50 nm. A variety of methods (e.g., a dynamic light scattering method)

standard in the art can be used to measure the particle diameter of the plant EV, or segment, portion, or extract thereof.

In some instances, the PMP may include a plant EV, or segment, portion, or extract thereof, that has a mean surface area of 77 nm$^2$ to 3.2×10$^6$ nm$^2$ (e.g., 77-100 nm$^2$, 100-1000 nm$^2$, 1000-1×10$^4$ nm$^2$, 1×10$^4$-1×10$^5$ nm$^2$, 1×10$^5$-1×10$^6$ nm$^2$, or 1×10$^6$-3.2×10$^6$ nm$^2$). In some instances, the PMP may include a plant EV, or segment, portion, or extract thereof, that has a mean volume of 65 nm$^3$ to 5.3×10$^8$ nm$^3$ (e.g., 65-100 nm$^3$, 100-1000 nm$^3$, 1000-1×10$^4$ nm$^3$, 1×10$^4$-1×10$^5$ nm$^3$, 1×10$^5$-1×10$^6$ nm$^3$, 1×10$^6$-1×10$^7$ nm$^3$, 1×10$^7$-1×10$^8$ nm$^3$, 1×10$^8$-5.3×10$^8$ nm$^3$). In some instances, the PMP may include a plant EV, or segment, portion, or extract thereof, that has a mean surface area of at least 77 nm$^2$, (e.g., at least 77 nm$^2$, at least 100 nm$^2$, at least 1000 nm$^2$, at least 1×10$^4$ nm$^2$, at least 1×10$^5$ nm$^2$, at least 1×10$^6$ nm$^2$, or at least 2×10$^6$ nm$^2$). In some instances, the PMP may include a plant EV, or segment, portion, or extract thereof, that has a mean volume of at least 65 nm$^3$ (e.g., at least 65 nm$^3$, at least 100 nm$^3$, at least 1000 nm$^3$, at least 1×10$^4$ nm$^3$, at least 1×10$^5$ nm$^3$, at least 1×10$^6$ nm$^3$, at least 1×10$^7$ nm$^3$, at least 1×10$^8$ nm$^3$, at least 2×10$^8$ nm$^3$, at least 3×10$^8$ nm$^3$, at least 4×10$^8$ nm$^3$, or at least 5×10$^8$ nm$^3$.

In some instances, the PMP can have the same size as the plant EV or segment, extract, or portion thereof. Alternatively, the PMP may have a different size than the initial plant EV from which the PMP is produced. For example, the PMP may have a diameter of about 5-2000 nm in diameter. For example, the PMP can have a mean diameter of about 5-50 nm, about 50-100 nm, about 100-150 nm, about 150-200 nm, about 200-250 nm, about 250-300 nm, about 300-350 nm, about 350-400 nm, about 400-450 nm, about 450-500 nm, about 500-550 nm, about 550-600 nm, about 600-650 nm, about 650-700 nm, about 700-750 nm, about 750-800 nm, about 800-850 nm, about 850-900 nm, about 900-950 nm, about 950-1000 nm, about 1000-1200 nm, about 1200-1400 nm, about 1400-1600 nm, about 1600-1800 nm, or about 1800-2000 nm. In some instances, the PMP may have a mean diameter of at least 5 nm, at least 50 nm, at least 100 nm, at least 150 nm, at least 200 nm, at least 250 nm, at least 300 nm, at least 350 nm, at least 400 nm, at least 450 nm, at least 500 nm, at least 550 nm, at least 600 nm, at least 650 nm, at least 700 nm, at least 750 nm, at least 800 nm, at least 850 nm, at least 900 nm, at least 950 nm, at least 1000 nm, at least 1200 nm, at least 1400 nm, at least 1600 nm, at least 1800 nm, or about 2000 nm. A variety of methods (e.g., a dynamic light scattering method) standard in the art can be used to measure the particle diameter of the PMPs. In some instances, the size of the PMP is determined following loading of heterologous plant-modifying agents, or following other modifications to the PMP.

In some instances, the PMP may have a mean surface area of 77 nm$^2$ to 1.3×10$^7$ nm$^2$ (e.g., 77-100 nm$^2$, 100-1000 nm$^2$, 1000-1×10$^4$ nm$^2$, 1×10$^4$-1×10$^5$ nm$^2$, 1×10$^5$-1×10$^6$ nm$^2$, or 1×10$^6$-1.3×10$^7$ nm$^2$).

In some instances, the PMP may have a mean volume of 65 nm$^3$ to 4.2×10$^9$ nm$^3$ (e.g., 65-100 nm$^3$, 100-1000 nm$^3$, 1000-1×10$^4$ nm$^3$, 1×10$^4$-1×10$^5$ nm$^3$, 1×10$^5$-1×10$^6$ nm$^3$, 1×10$^6$-1×10$^7$ nm$^3$, 1×10$^7$-1×10$^8$ nm$^3$, 1×10$^8$-1×10$^9$ nm$^3$, or 1×10$^9$-4.2×10$^9$ nm$^3$). In some instances, the PMP has a mean surface area of at least 77 nm$^2$, (e.g., at least 77 nm$^2$, at least 100 nm$^2$, at least 1000 nm$^2$, at least 1×10$^4$ nm$^2$, at least 1×10$^5$ nm$^2$, at least 1×10$^6$ nm$^2$, or at least 1×10$^7$ nm$^2$). In some instances, the PMP has a mean volume of at least 65 nm$^3$ (e.g., at least 65 nm$^3$, at least 100 nm$^3$, at least 1000 nm$^3$, at least 1×10$^4$ nm$^3$, at least 1×10$^5$ nm$^3$, at least 1×10$^6$ nm$^3$, at least 1×10$^7$ nm$^3$, at least 1×10$^8$ nm$^3$, at least 1×10$^9$ nm$^3$, at least 2×10$^9$ nm$^3$, at least 3×10$^9$ nm$^3$, or at least 4×10$^9$ nm$^3$).

In some instances, the PMP may include an intact plant EV. Alternatively, the PMP may include a segment, portion, or extract of the full surface area of the vesicle (e.g., a segment, portion, or extract including less than 100% (e.g., less than 90%, less than 80%, less than 70%, less than 60%, less than 50%, less than 40%, less than 30%, less than 20%, less than 10%, less than 10%, less than 5%, or less than 1%) of the full surface area of the vesicle) of a plant EV. The segment, portion, or extract may be any shape, such as a circumferential segment, spherical segment (e.g., hemisphere), curvilinear segment, linear segment, or flat segment. In instances where the segment is a spherical segment of the vesicle, the spherical segment may represent one that arises from the splitting of a spherical vesicle along a pair of parallel lines, or one that arises from the splitting of a spherical vesicle along a pair of non-parallel lines. Accordingly, the plurality of PMPs can include a plurality of intact plant EVs, a plurality of plant EV segments, portions, or extracts, or a mixture of intact and segments of plant EVs. One skilled in the art will appreciate that the ratio of intact to segmented plant EVs will depend on the particular isolation method used. For example, grinding or blending a plant, or part thereof, may produce PMPs that contain a higher percentage of plant EV segments, portions, or extracts than a non-destructive extraction method, such as vacuum-infiltration.

In instances where the PMP includes a segment, portion, or extract of a plant EV, the EV segment, portion, or extract may have a mean surface area less than that of an intact vesicle, e.g., a mean surface area less than 77 nm$^2$, 100 nm$^2$, 1000 nm$^2$, 1×10$^4$ nm$^2$, 1×10$^5$ nm$^2$, 1×10$^6$ nm$^2$, or 3.2×10$^6$ nm$^2$). In some instances, the EV segment, portion, or extract has a surface area of less than 70 nm$^2$, 60 nm$^2$, 50 nm$^2$, 40 nm$^2$, 30 nm$^2$, 20 nm$^2$, or 10 nm$^2$). In some instances, the PMP may include a plant EV, or segment, portion, or extract thereof, that has a mean volume less than that of an intact vesicle, e.g., a mean volume of less than 65 nm$^3$, 100 nm$^3$, 1000 nm$^3$, 1×10$^4$ nm$^3$, 1×10$^5$ nm$^3$, 1×10$^6$ nm$^3$, 1×10$^7$ nm$^3$, 1×10$^8$ nm$^3$, or 5.3×10$^8$ nm$^3$).

In instances where the PMP includes an extract of a plant EV, e.g., in instances where the PMP includes lipids extracted (e.g., with chloroform) from a plant EV, the PMP may include at least 1%, 2%, 5%, 10%, 20%, 30%, 40%, 50%, 60%, 70%, 80%, 90%, 95%, 99%, or more than 99% of lipids extracted (e.g., with chloroform) from a plant EV. The PMPs in the plurality may include plant EV segments and/or plant EV-extracted lipids or a mixture thereof.

Further outlined herein are details regarding methods of producing PMPs, plant EV markers that can be associated with PMPs, and formulations for compositions including PMPs.

A. Production Methods

PMPs may be produced from plant EVs, or a segment, portion or extract (e.g., lipid extract) thereof, that occur naturally in plants, or parts thereof, including plant tissues or plant cells. An exemplary method for producing PMPs includes (a) providing an initial sample from a plant, or a part thereof, wherein the plant or part thereof comprises EVs; and (b) isolating a crude PMP fraction from the initial sample, wherein the crude PMP fraction has a decreased level of at least one contaminant or undesired component from the plant or part thereof relative to the level in the initial sample. The method can further include an additional step (c) comprising purifying the crude PMP fraction, thereby producing a plurality of pure PMPs, wherein the plurality of pure PMPs have a decreased level of at least one contaminant or undesired component from the plant or part thereof relative to the level in the crude EV fraction. Each production step is discussed in further detail, below. Exemplary methods regarding the isolation and purification of PMPs is found, for example, in Rutter and Innes, *Plant Physiol.* 173(1): 728-741, 2017; Rutter et al, *Bio. Protoc.* 7(17): e2533, 2017; Regente et al, *J of Exp. Biol.* 68(20): 5485-5496, 2017; Mu et al, *Mol. Nutr. Food Res.,* 58, 1561-1573, 2014, and Regente et al, *FEBS Letters.* 583: 3363-3366, 2009, each of which is herein incorporated by reference.

In some instances, a plurality of PMPs may be isolated from a plant by a process which includes the steps of: (a) providing an initial sample from a plant, or a part thereof, wherein the plant or part thereof comprises EVs; (b) isolating a crude PMP fraction from the initial sample, wherein the crude PMP fraction has a decreased level of at least one contaminant or undesired component from the plant or part thereof relative to the level in the initial sample (e.g., a level that is decreased by at least 1%, 2%, 5%, 10%, 15%, 20%, 25%, 30%, 40%, 45%, 50%, 55%, 60%, 70%, 80%, 90%, 95%, 96%, 98%, 99%, or 100%); and (c) purifying the crude PMP fraction, thereby producing a plurality of pure PMPs, wherein the plurality of pure PMPs have a decreased level of at least one contaminant or undesired component from the plant or part thereof relative to the level in the crude EV fraction (e.g., a level that is decreased by at least 1%, 2%, 5%, 10%, 15%, 20%, 25%, 30%, 40%, 45%, 50%, 55%, 60%, 70%, 80%, 90%, 95%, 96%, 98%, 99%, or 100%).

The PMPs provided herein can include a plant EV, or segment, portion, or extract thereof, produced from a variety of plants. PMPs may be produced from any genera of plants (vascular or nonvascular), including but not limited to angiosperms (monocotyledonous and dicotyledonous plants), gymnosperms, ferns, selaginellas, horsetails, psilophytes, lycophytes, algae (e.g., unicellular or multicellular, e.g., archaeplastida), or bryophytes. In certain instances, PMPs can be produced using a vascular plant, for example monocotyledons or dicotyledons or gymnosperms. For example, PMPs can be produced using alfalfa, apple, *Arabidopsis*, banana, barley, canola, castor bean, chicory, chrysanthemum, clover, cocoa, coffee, cotton, cottonseed, corn, crambe, cranberry, cucumber, dendrobium, dioscorea, eucalyptus, fescue, flax, gladiolus, liliacea, linseed, millet, muskmelon, mustard, oat, oil palm, oilseed rape, papaya, peanut, pineapple, ornamental plants, *Phaseolus*, potato, rapeseed, rice, rye, ryegrass, safflower, sesame, *Ssorghum*, soybean, sugarbeet, sugarcane, sunflower, strawberry, tobacco, tomato, turfgrass, wheat or vegetable crops such as lettuce, celery, broccoli, cauliflower, cucurbits; fruit and nut trees, such as apple, pear, peach, orange, grapefruit, lemon, lime, almond, pecan, walnut, hazel; vines, such as grapes, kiwi, hops; fruit shrubs and brambles, such as raspberry, blackberry, gooseberry; forest trees, such as ash, pine, fir, maple, oak, chestnut, popular; with alfalfa, canola, castor bean, corn, cotton, crambe, flax, linseed, mustard, oil palm, oilseed rape, peanut, potato, rice, safflower, sesame, soybean, sugarbeet, sunflower, tobacco, tomato, or wheat.

PMPs may be produced using a whole plant (e.g., a whole rosettes or seedlings) or alternatively from one or more plant parts (e.g., leaf, seed, root, fruit, vegetable, pollen, phloem sap, or xylem sap). For example, PMPs can be produced using shoot vegetative organs/structures (e.g., leaves, stems, or tubers), roots, flowers and floral organs/structures (e.g., pollen, bracts, sepals, petals, stamens, carpels, anthers, or ovules), seed (including embryo, endosperm, or seed coat), fruit (the mature ovary), sap (e.g., phloem or xylem sap), plant tissue (e.g., vascular tissue, ground tissue, tumor tissue, or the like), and cells (e.g., single cells, protoplasts, embryos, callus tissue, guard cells, egg cells, or the like), or progeny of same. For instance, the isolation step may involve (a) providing a plant, or a part thereof, wherein the plant part is an *Arabidopsis* leaf. The plant may be at any stage of development. For example, the PMP can be produced using seedlings, e.g., 1 week, 2 week, 3 week, 4 week, 5 week, 6 week, 7 week, or 8 week old seedlings (e.g., *Arabidopsis* seedlings). Other exemplary PMPs can include PMPs produced using roots (e.g., ginger roots), fruit juice (e.g., grapefruit juice), vegetables (e.g., broccoli), pollen (e.g., olive pollen), phloem sap (e.g., *Arabidopsis* phloem sap), or xylem sap (e.g., tomato plant xylem sap).

PMPs can be produced using a plant, or part thereof, by a variety of methods. Any method that allows release of the EV-containing apoplastic fraction of a plant, or an otherwise extracellular fraction that contains PMPs comprising secreted EVs (e.g., cell culture media) is suitable in the present methods. EVs can be separated from the plant or plant part by either destructive (e.g., grinding or blending of a plant, or any plant part) or non-destructive (washing or vacuum infiltration of a plant or any plant part) methods. For instance, the plant, or part thereof, can be vacuum-infiltrated, ground, blended, or a combination thereof to isolate EVs from the plant or plant part, thereby producing PMPs. For instance, the isolating step may involve (b) isolating a crude PMP fraction from the initial sample (e.g., a plant, a plant part, or a sample derived from a plant or a plant part), wherein the crude PMP fraction has a decreased level of at least one contaminant or undesired component from the plant or part thereof relative to the level in the initial sample; wherein the isolating step involves vacuum infiltrating the plant (e.g., with a vesicle isolation buffer) to release and collect the apoplastic fraction. Alternatively, the isolating step may involve grinding or blending the plant to release the EVs, thereby producing PMPs.

Upon isolating the plant EVs, thereby producing PMPs, the PMPs can be separated or collected into a crude PMP fraction (e.g., an apoplastic fraction). For instance, the separating step may involve separating the plurality of PMPs into a crude PMP fraction using centrifugation (e.g., differential centrifugation or ultracentrifugation) and/or filtration to separate the plant PMP-containing fraction from large contaminants, including plant tissue debris, plant cells, or plant cell organelles (e.g., nuclei or chloroplast). As such, the crude PMP fraction will have a decreased number of large contaminants, including plant tissue debris or plant cells, as compared to the initial sample from the source plant or plant part. Depending on the method used, the crude PMP fraction may additionally comprise a decreased level of plant cell organelles (e.g., nuclei, mitochondria or chloroplasts), as compared to the initial sample from the source plant or plant part.

In some instances, the isolating step may involve separating the plurality of PMPs into a crude PMP fraction using centrifugation (e.g., differential centrifugation or ultracentrifugation) and/or filtration to separate the plant EV-containing fraction from plant cells or cellular debris. In such instances, the crude PMP fraction will have a decreased number of plant cells or cellular debris, as compared to the initial sample from the source plant or plant part.

The crude PMP fraction can be further purified by additional purification methods to produce a plurality of pure PMPs. For example, the crude PMP fraction can be separated from other plant components by ultracentrifugation, e.g., using a density gradient (iodixanol or sucrose) and/or use of other approaches to remove aggregated components (e.g., precipitation or size-exclusion chromatography). The resulting pure PMPs may have a decreased level of contaminants or undesired components from the source plant (e.g., one or more non-PMP components, such as protein aggregates, nucleic acid aggregates, protein-nucleic acid aggregates, free lipoproteins, lipido-proteic structures), nuclei, cell wall components, cell organelles, or a combination thereof) relative to one or more fractions generated during the earlier separation steps, or relative to a pre-established threshold level, e.g., a commercial release specification. For example, the pure PMPs may have a decreased level (e.g., by about 5%, 10%, 15%, 20%, 30%, 40%, 50%, 60%, 70%, 80%, 90%, 100%, or more than 100%; or by about 2× fold, 4× fold, 5× fold, 10× fold, 20× fold, 25× fold, 50× fold, 75× fold, 100× fold, or more than 100× fold) of plant organelles or cell wall components relative to the level in the initial sample. In some instances, the pure PMPs are substantially free (e.g., have undetectable levels) of one or more non-PMP components, such as protein aggregates, nucleic acid aggregates, protein-nucleic acid aggregates, free lipoproteins, lipido-proteic structures), nuclei, cell wall components, cell organelles, or a combination thereof. Further examples of the releasing and separation steps can be found in Example 1. The PMPs may be at a concentration of, e.g., $1\times10^9$, $5\times10^9$, $1\times10^{10}$, $5\times10^{10}$, $5\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, or more than $1\times10^{13}$ PMPs/mL.

For example, protein aggregates may be removed from PMPs. For example, the PMPs can be taken through a range of pHs (e.g., as measured using a pH probe) to precipitate out protein aggregates in solution. The pH can be adjusted to, e.g., pH 3, pH 5, pH 7, pH 9, or pH 11 with the addition of, e.g., sodium hydroxide or hydrochloric acid. Once the solution is at the specified pH, it can be filtered to remove particulates. Alternatively, the PMPs can be flocculated using the addition of charged polymers, such as Polymin-P or Praestol 2640. Briefly, Polymin-P or Praestol 2640 is added to the solution and mixed with an impeller. The solution can then be filtered to remove particulates. Alternatively, aggregates can be solubilized by increasing salt concentration. For example NaCl can be added to the PMPs until it is at, e.g., 1 mol/L. The solution can then be filtered to isolate the PMPs. Alternatively, aggregates are solubilized by increasing the temperature. For example, the PMPs can be heated under mixing until the solution has reached a uniform temperature of, e.g., 50° C. for 5 minutes. The PMP mixture can then be filtered to isolate the PMPs. Alternatively, soluble contaminants from PMP solutions can be separated by size-exclusion chromatography column according to standard procedures, where PMPs elute in the first fractions, whereas proteins and ribonucleoproteins and some lipoproteins are eluted later. The efficiency of protein aggregate removal can be determined by measuring and comparing the protein concentration before and after removal of protein aggregates via BCA/Bradford protein quantification.

Any of the production methods described herein can be supplemented with any quantitative or qualitative methods known in the art to characterize or identify the PMPs at any step of the production process. PMPs may be characterized by a variety of analysis methods to estimate PMP yield, PMP concentration, PMP purity, PMP composition, or PMP sizes. PMPs can be evaluated by a number of methods known in the art that enable visualization, quantitation, or qualitative characterization (e.g., identification of the composition) of the PMPs, such as microscopy (e.g., transmission electron microscopy), dynamic light scattering, nanoparticle tracking, spectroscopy (e.g., Fourier transform infrared analysis), or mass spectrometry (protein and lipid analysis). In certain instances, methods (e.g., mass spectroscopy) may be used to identify plant EV markers present on the PMP, such as markers disclosed in the Appendix. To aid in analysis and characterization, of the PMP fraction, the PMPs can additionally be labelled or stained. For example, the PMPs can be stained with 3,3'-dihexyloxacarbocyanine iodide ($DIOC_6$), a fluorescent lipophilic dye, PKH67 (Sigma Aldrich); Alexa Fluor® 488 (Thermo Fisher Scientific), or DyLight™ 800 (Thermo Fisher). In the absence of sophisticated forms of nanoparticle tracking, this relatively simple approach quantifies the total membrane content and can be used to indirectly measure the concentration of PMPs (Rutter and Innes, *Plant Physiol.* 173(1): 728-741, 2017; Rutter et al, *Bio. Protoc.* 7(17): e2533, 2017). For more precise measurements, and to assess the size distributions of PMPs, nanoparticle tracking can be used.

During the production process, the PMPs can optionally be prepared such that the PMPs are at an increased concentration (e.g., by about 5%, 10%, 15%, 20%, 30%, 40%, 50%, 60%, 70%, 80%, 90%, 100%, or more than 100%; or by about 2× fold, 4× fold, 5× fold, 10× fold, 20× fold, 25× fold, 50× fold, 75× fold, 100× fold, or more than 100× fold) relative to the EV level in a control or initial sample. The PMPs may make up about 0.1% to about 100% of the plant-modifying composition, such as any one of about 0.01% to about 100%, about 1% to about 99.9%, about 0.1% to about 10%, about 1% to about 25%, about 10% to about 50%, or about 50% to about 99%. In some instances, the composition includes at least any of 0.1%, 0.5%, 1%, 5%, 10%, 20%, 30%, 40%, 50%, 60%, 70%, 80%, 90%, 95%, or more PMPs, e.g., as measured by wt/vol, percent PMP protein composition, and/or percent lipid composition (e.g., by measuring fluorescently labelled lipids); See, e.g., Example 3). In some instances, the concentrated agents are used as concentrated commercial products, e.g., the final user may dilute the commercial product, which have a substantially lower concentration of active ingredient. In some embodiments, the composition is formulated as a plant-modifying concentrate formulation, e.g., an ultra-low-volume concentrate formulation.

As illustrated by Example 1, PMPs can be produced using a variety of plants, or parts thereof (e.g., the leaf apoplast, seed apoplast, root, fruit, vegetable, pollen, phloem, or xylem sap). For example, PMPs can be isolated from the apoplastic fraction of a plant, such as the apoplast of a leaf (e.g., apoplast *Arabidopsis thaliana* leaves) or the apoplast of seeds (e.g., apoplast of sunflower seeds). Other exemplary PMPs are produced using roots (e.g., ginger roots), fruit juice (e.g., grapefruit juice), vegetables (e.g., broccoli), pollen (e.g., olive pollen), phloem sap (e.g., *Arabidopsis* phloem sap), xylem sap (e.g., tomato plant xylem sap), or cell culture supernatant (e.g. BY2 tobacco cell culture supernatant). This example further demonstrates the production of PMPs from these various plant sources.

As illustrated by Example 2, PMPs can be purified by a variety of methods, for example, by using a density gradient (iodixanol or sucrose) in conjunction with ultracentrifugation and/or methods to remove aggregated contaminants, e.g., precipitation or size-exclusion chromatography. For instance, Example 2 illustrates purification of PMPs that have been obtained via the separation steps outlined in Example 1. Further, PMPs can be characterized in accordance with the methods illustrated in Example 3.

In some instances, the PMPs of the present compositions and methods can be produced from a plant, or part thereof, and used without further modification to the PMP. In other instances, the PMP can be modified prior to use, as outlined further herein.

B. Plant EV-Markers

The PMPs of the present compositions and methods may have a range of markers that identify the PMP as being produced using a plant EV, and/or including a segment, portion, or extract thereof. As used herein, the term "plant EV-marker" refers to a component that is naturally associated with a plant and incorporated into or onto the plant EV in planta, such as a plant protein, a plant nucleic acid, a plant small molecule, a plant lipid, or a combination thereof. Examples of plant EV-markers can be found, for example, in Rutter and Innes, *Plant Physiol.* 173(1): 728-741, 2017; Raimondo et al., *Oncotarget.* 6(23): 19514, 2015; Ju et al., *Mol. Therapy.* 21(7):1345-1357, 2013; Wang et al., *Molecular Therapy.* 22(3): 522-534, 2014; and Regente et al, *J of Exp. Biol.* 68(20): 5485-5496, 2017; each of which is incorporated herein by reference. Additional examples of plant EV-markers are listed in the Appendix, and are further outlined herein.

In some instances, the plant EV marker can include a plant lipid. Examples of plant lipid markers that may be found in the PMP include phytosterol, campesterol, β-sitosterol, stigmasterol, avenasterol, glycosyl inositol phosphoryl ceramides (GIPCs), glycolipids (e.g., monogalactosyldiacylglycerol (MGDG) or digalactosyldiacylglycerol (DGDG)), or a combination thereof. For instance, the PMP may include GIPCs, which represent the main sphingolipid class in plants and are one of the most abundant membrane lipids in plants. Other plant EV markers may include lipids that accumulate in plants in response to abiotic or biotic stressors (e.g., bacterial or fungal infection), such as phosphatidic acid (PA) or phosphatidylinositol-4-phosphate (PI4P).

Alternatively, the plant EV marker may include a plant protein. In some instances, the protein plant EV marker may be an antimicrobial protein naturally produced by plants, including defense proteins that plants secrete in response to abiotic or biotic stressors (e.g., bacterial or fungal infection). Plant pathogen defense proteins include soluble N-ethylmaleimide-sensitive factor association protein receptor protein (SNARE) proteins (e.g., Syntaxin-121 (SYP121; GenBank Accession No.: NP_187788.1 or NP_974288.1), Penetration1 (PEN1; GenBank Accession No: NP_567462.1)) or ABC transporter Penetration3 (PEN3; GenBank Accession No: NP_191283.2). Other examples of plant EV markers includes proteins that facilitate the long-distance transport of RNA in plants, including phloem proteins (e.g., Phloem protein2-A1 (PP2-A1), GenBank Accession No: NP_193719.1), calcium-dependent lipid-binding proteins, or lectins (e.g., Jacalin-related lectins, e.g., *Helianthus annuus* jacalin (Helja; GenBank: AHZ86978.1). For example, the RNA binding protein may be Glycine-Rich RNA Binding Protein-7 (GRP7; GenBank Accession Number: NP_179760.1). Additionally, proteins that regulate plasmodesmata function can in some instances be found in plant EVs, including proteins such as Synap-Totgamin A A (GenBank Accession No: NP_565495.1). In some instances, the plant EV marker can include a protein involved in lipid metabolism, such as phospholipase C or phospholipase D. In some instances, the plant protein EV marker is a cellular trafficking protein in plants. In certain instances where the plant EV marker is a protein, the protein marker may lack a signal peptide that is typically associated with secreted proteins. Unconventional secretory proteins seem to share several common features like (i) lack of a leader sequence, (ii) absence of post-translational modifications (PTMs) specific for ER or Golgi apparatus, and/or (iii) secretion not affected by brefeldin A which blocks the classical ER/Golgi-dependent secretion pathway. One skilled in the art can use a variety of tools freely accessible to the public (e.g., SecretomeP Database; SUBA3 (SUBcellular localization database for *Arabidopsis* proteins)) to evaluate a protein for a signal sequence, or lack thereof.

In instances where the plant EV marker is a protein, the protein may have an amino acid sequence having at least 35%, 40%, 45%, 50%, 55%, 60%, 65%, 70%, 75%, 80%, 85%, 90%, 95%, 98%, 99%, or 100% sequence identity to a plant EV marker, such as any of the plant EV markers listed in the Appendix. For example, the protein may have an amino acid sequence having at least 35%, 40%, 45%, 50%, 55%, 60%, 65%, 70%, 75%, 80%, 85%, 90%, 95%, 98%, 99%, or 100% sequence identity to PEN1 from *Arabidopsis thaliana* (GenBank Accession Number: NP_567462.1).

In some instances, the plant EV marker includes a nucleic acid encoded in plants, e.g., a plant RNA, a plant DNA, or a plant PNA. For example, the PMP may include dsRNA, mRNA, a viral RNA, a microRNA (miRNA), or a small interfering RNA (siRNA) encoded by a plant. In some instances, the nucleic acid may be one that is associated with a protein that facilitates the long-distance transport of RNA in plants, as discussed herein. In some instances, the nucleic acid plant EV marker may be one involved in host-induced gene silencing (HIGS), which is the process by which plants silence foreign transcripts of plant pests (e.g., pathogens such as fungi). For example, the nucleic acid may be one that silences bacterial or fungal genes. In some instances, the nucleic acid may be a microRNA, such as miR159 or miR166, which target genes in a fungal pathogen (e.g., *Verticillium dahliae*). In some instances, the protein may be one involved in carrying plant defense compounds, such as proteins involved in glucosinolate (GSL) transport and metabolism, including Glucosinolate Transporter-1-1 (GTR1; GenBank Accession No: NP_566896.2), Glucosinolate Transporter-2 (GTR2; NP_201074.1), or Epithiospecific Modifier 1 (ESM1; NP_188037.1).

In instances where the plant EV marker is a nucleic acid, the nucleic acid may have a nucleotide sequence having at least 35%, 40%, 45%, 50%, 55%, 60%, 65%, 70%, 75%, 80%, 85%, 90%, 95%, 98%, 99%, or 100% sequence identity to a plant EV marker, e.g., such as those encoding the plant EV markers listed in the Appendix. For example, the nucleic acid may have a polynucleotide sequence having at least 35%, 40%, 45%, 50%, 55%, 60%, 65%, 70%, 75%, 80%, 85%, 90%, 95%, 98%, 99%, or 100% sequence identity to miR159 or miR166.

In some instances, the plant EV marker includes a compound produced by plants. For example, the compound may be a defense compound produced in response to abiotic or biotic stressors, such as secondary metabolites. One such secondary metabolite that be found in PMPs are glucosinolates (GSLs), which are nitrogen and sulfur-containing secondary metabolites found mainly in Brassicaceae plants. Other secondary metabolites may include allelochemicals.

In some instances, the PMP may also be identified as being produced using a plant EV based on the lack of certain markers (e.g., lipids, polypeptides, or polynucleotides) that are not typically produced by plants, but are generally associated with other organisms (e.g., markers of animal EVs, bacterial EVs, or fungal EVs). For example, in some instances, the PMP lacks lipids typically found in animal EVs, bacterial EVs, or fungal EVs. In some instances, the PMP lacks lipids typical of animal EVs (e.g., sphingomyelin). In some instances, the PMP does not contain lipids typical of bacterial EVs or bacterial membranes (e.g., LPS). In some instances, the PMP lacks lipids typical of fungal membranes (e.g., ergosterol).

Plant EV markers can be identified using any approaches known in the art that enable identification of small molecules (e.g., mass spectroscopy, mass spectrometry), lipids (e.g., mass spectroscopy, mass spectrometry), proteins (e.g., mass spectroscopy, immunoblotting), or nucleic acids (e.g., PCR analysis). In some instances, a PMP composition described herein includes a detectable amount, e.g., a predetermined threshold amount, of a plant EV marker described herein.

C. Loading of Agents

The PMPs can be modified to include a heterologous plant-modifying agent, such as those described herein. The PMPs can carry or associate with such agents by a variety of means to enable delivery of the agent to a target plant, e.g., by encapsulating the agent, incorporation of the component in the lipid bilayer structure, or association of the component (e.g., by conjugation) with the surface of the lipid bilayer structure of the PMP.

The heterologous plant-modifying agent can be incorporated or loaded into or onto the PMPs by any methods known in the art that allow association, directly or indirectly, between the PMP and agent. Heterologous plant-modifying agents can be incorporated into the PMPs by an in vivo method (e.g., in planta, e.g., through production of PMPs from a transgenic plant that includes the heterologous agent), or in vitro (e.g., in tissue culture, or in cell culture), or both in vivo and in vitro methods.

In instances where the PMPs are loaded with a heterologous plant-modifying agent in vivo, the PMPs may be produced using EVs, or a segments or portions thereof, or an extract containing EVs that has been loaded in planta. In planta methods include expression of the heterologous plant-modifying agent in a plant that has been genetically modified to express the heterologous plant-modifying agent for loading into EVs. In some instances, the heterologous plant-modifying agent is exogenous to the plant. Alternatively, the heterologous plant-modifying agent may be naturally found in the plant, but engineered to be expressed at an elevated level relative to level of that found in a non-genetically modified plant.

In some instances, the PMPs can be loaded in vitro. The substance may be loaded onto or into (e.g., may be encapsulated by) the PMPs using, but not limited to, physical, chemical, and/or biological methods (e.g., in tissue culture or in cell culture). For example, the heterologous plant-modifying agent may be introduced into PMPs by one or more of electroporation, sonication, passive diffusion, stirring, lipid extraction, or extrusion. Loaded PMPs can be assessed to confirm the presence or level of the loaded agent using a variety of methods, such as HPLC (e.g., to assess small molecules); immunoblotting (e.g., to assess proteins); and quantitative PCR (e.g., to assess nucleotides). However, it should be appreciated by those skilled in the art that the loading of a substance of interest into PMPs is not limited to the above-illustrated methods.

In some instances, the heterologous plant-modifying agent can be conjugated to the PMP, in which the heterologous plant-modifying agent is connected or joined, indirectly or directly, to the PMP. For instance, one or more plant-modifying agents can be chemically-linked to a PMP, such that the one or more plant-modifying agents are joined (e.g., by covalent or ionic bonds) directly to the lipid bilayer of the PMP. In some instances, the conjugation of various plant-modifying agents to the PMPs can be achieved by first mixing the one or more heterologous plant-modifying agents with an appropriate cross-linking agent (e.g., N-ethylcarbodiimide ("EDC"), which is generally utilized as a carboxyl activating agent for amide bonding with primary amines and also reacts with phosphate groups) in a suitable solvent. After a period of incubation sufficient to allow the heterologous plant-modifying agent to attach to the cross-linking agent, the cross-linking agent/heterologous plant-modifying agent mixture can then be combined with the PMPs and, after another period of incubation, subjected to a sucrose gradient (e.g., and 8, 30, 45, and 60% sucrose gradient) to separate the free heterologous plant-modifying agent and free PMPs from the plant-modifying agents conjugated to the PMPs. As part of combining the mixture with a sucrose gradient, and an accompanying centrifugation step, the PMPs conjugated to the plant-modifying agents are then seen as a band in the sucrose gradient, such that the conjugated PMPs can then be collected, washed, and dissolved in a suitable solution for use as described herein.

In some instances, the PMPs are stably associated with the heterologous plant-modifying agent prior to and following delivery of the PMP, e.g., to a plant. In other instances, the PMPs are associated with the heterologous plant-modifying agent such that the heterologous plant-modifying agent becomes dissociated from the PMP following delivery of the PMP, e.g., to a plant.

The PMPs can be further modified with other components (e.g., lipids, e.g., sterols, e.g., cholesterol; or small molecules) to further alter the functional and structural characteristics of the PMP. For example, the PMPs can be further modified with stabilizing molecules that increase the stability of the PMP (e.g., for at least one day at room temperature, and/or stable for at least one week at 4° C.).

The PMPs can be loaded with various concentrations of the heterologous plant-modifying agent, depending on the particular agent or use. For example, in some instances, the PMPs are loaded such that the plant-modifying composition disclosed herein includes about 0.001, 0.01, 0.1, 1.0, 2, 3, 4, 5, 6, 7, 8, 9, 10, 15, 20, 30, 40, 50, 60, 70, 80, 90, or 95 (or any range between about 0.001 and 95) or more wt % of a plant-modifying agent. In some instances, the PMPs are loaded such that the plant-modifying composition includes about 95, 90, 80, 70, 60, 50, 40, 30, 20, 15, 10, 9, 8, 7, 6, 5, 4, 3, 2, 1.0, 0.1, 0.01, 0.001 (or any range between about 95 and 0.001) or less wt % of a plant-modifying agent. For example, the plant-modifying composition can include about 0.001 to about 0.01 wt %, about 0.01 to about 0.1 wt %, about 0.1 to about 1 wt %, about 1 to about 5 wt %, or about 5 to about 10 wt %, about 10 to about 20 wt % of the plant-modifying agent. In some instances, the PMPs can be loaded with about 1, 5, 10, 50, 100, 200, or 500, 1,000, 2,000 (or any range between about 1 and 2,000) or more µg/ml of a plant-modifying agent. In some instances, the PMPs can be loaded with about 2,000, 1,000, 500, 200, 100, 50, 10, 5, 1 (or any range between about 2,000 and 1) or less µg/ml of a plant-modifying agent.

in some instances, the PMPs are loaded such that the plant-modifying composition disclosed herein includes at least 0.001 wt %, at least 0.01 wt %, at least 0.1 wt %, at least 1.0 wt %, at least 2 wt %, at least 3 wt %, at least 4 wt %, at least 5 wt %, at least 6 wt %, at least 7 wt %, at least 8 wt %, at least 9 wt %, at least 10 wt %, at least 15 wt %, at least 20 wt %, at least 30 wt %, at least 40 wt %, at least 50 wt %, at least 60 wt %, at least 70 wt %, at least 80 wt %, at least 90 wt %, or at least 95 wt % of a plant-modifying agent. In some instances, the PMPs can be loaded with at least 1 µg/ml, at least 5 µg/ml, at least 10 µg/ml, at least 50 µg/ml, at least 100 µg/ml, at least 200 µg/ml, at least 500 µg/ml, at least 1,000 µg/ml, at least 2,000 µg/ml of a plant-modifying agent.

Examples of particular plant-modifying agents that can be loaded into the PMPs are further outlined in the section entitled "Heterologous Plant-Modifying Agents."

D. Formulations

To allow ease of application, handling, transportation, storage, and activity, the plant-modifying compositions can be formulated with other substances such as agriculturally acceptable carriers. The plant-modifying composition can be formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions.

Plant-modifying compositions can be applied as aqueous suspensions or emulsions prepared from concentrated formulations of such agents. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the plant-modifying composition, a carrier, and surfactants. The carrier is usually selected from among the attapulgite clays, the montmorillonite clays, the diatomaceous earths, or the purified silicates. Effective surfactants, including from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates can comprise a suitable concentration of PMPs and/or plant-modifying agents, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble plant-modifying compositions dispersed in an aqueous carrier at a concentration in the range from about 5% to about 50% by weight. Suspensions are prepared by finely grinding the active agent and vigorously mixing it into a carrier comprised of water and surfactants. Ingredients, such as inorganic salts and synthetic or natural gums may also be added, to increase the density and viscosity of the aqueous carrier.

Plant-modifying compositions may also be applied as granular compositions that are particularly useful for applications to the soil. Granular compositions usually contain from about 0.5% to about 10% by weight of the plant-modifying composition, dispersed in a carrier that comprises clay or a similar substance. Such compositions are usually prepared by dissolving the formulation in a suitable solvent and applying it to a granular carrier which has been preformed to the appropriate particle size, in the range of from about 0.5 to about 3 mm. Such compositions may also be formulated by making a dough or paste of the carrier and compound and crushing and drying to obtain the desired granular particle size.

Dusts containing the present compositions are prepared by intimately mixing the plant-modifying composition in powdered form with a suitable dusty agricultural carrier, such as kaolin clay, ground volcanic rock, and the like. Dusts can suitably contain from about 1% to about 10% of the packets. They can be applied as a seed dressing or as a foliage application with a dust blower machine.

It is equally practical to apply the present formulation in the form of a solution in an appropriate organic solvent, usually petroleum oil, such as the spray oils, which are widely used in agricultural chemistry.

Plant-modifying composition can also be applied in the form of an aerosol composition. In such compositions the packets are dissolved or dispersed in a carrier, which is a pressure-generating propellant mixture. The aerosol composition is packaged in a container from which the mixture is dispensed through an atomizing valve.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer including: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007. For ease of use, this embodiment will be referred to as "OIWE."

Additionally, generally, when the molecules disclosed above are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO (ethylene oxide-propylene oxide) block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the plant-modifying composition on the target. The types of surfactants used for bioenhancement depend generally on the nature and mode of action of the plant-modifying composition. However, they are often non-ionics such as: alkyl ethoxylates; linear aliphatic alcohol ethoxylates; aliphatic amine ethoxylates.

A carrier or diluent in an agricultural formulation is a material added to the plant-modifying composition to give a product of the required strength. Carriers are usually materials with high absorptive capacities, while diluents are usually materials with low absorptive capacities. Carriers and diluents are used in the formulation of dusts, wettable powders, granules, and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of plant-modifying compositions when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions, and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol, and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g., plant and animal sources. Specific examples are: vegetable oils, seed oils, and esters thereof, also alkoxylated alkyl polyglucosides.

In some instances, the plant-modifying composition can be freeze-dried or lyophilized. See U.S. Pat. No. 4,311,712. The plant-modifying composition can later be reconstituted on contact with water or another liquid. Other components can be added to the lyophilized or reconstituted, for example, other plant-modifying agents, agriculturally acceptable carriers, or other materials in accordance with the formulations described herein.

Other optional features of the composition include carriers or delivery vehicles that protect the plant-modifying composition against UV and/or acidic conditions. In some instances, the delivery vehicle contains a pH buffer. In some instances, the composition is formulated to have a pH in the range of about 4.5 to about 9.0, including for example pH ranges of about any one of 5.0 to about 8.0, about 6.5 to about 7.5, or about 6.5 to about 7.0.

For further information on agricultural formulations, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

II. Plant-Modification Methods

The plant-modifying compositions described herein are useful in a variety of methods. The present methods involve delivering the plant-modifying compositions described herein to a plant, such as those described herein. The compositions and related methods can be used to modify a plant or a plant part (e.g., leaves, roots, flowers, fruits, or seeds) to increase the fitness of the plants. The details of each of these methods are described further below.

A. Delivery to a Plant

Provided herein are methods of delivering a plant-modifying composition to a plant (e.g., such as those disclosed in the section entitled "Plants"). Included are methods for delivering a plant-modifying composition to a plant by contacting the plant, or part thereof, with a plant-modifying composition. The methods are useful for modifying the plant to increase the fitness of a plant.

In one aspect, provided herein is a method of increasing the fitness of a plant, the method including delivering to the plant the plant-modifying composition described herein (e.g., in an effective amount and duration) to increase the fitness of the plant relative to an untreated plant (e.g., a plant that has not been delivered the plant-modifying composition).

An increase in the fitness of the plant as a consequence of delivery of a plant-modifying composition can manifest in a number of ways, e.g., thereby resulting in a better production of the plant, for example, an improved yield, improved vigor of the plant or quality of the harvested product from the plant, an improvement in pre- or post-harvest traits deemed desirable for agriculture or horticulture (e.g., taste, appearance, shelf life), or for an improvement of traits that otherwise benefit humans (e.g., decreased allergen production). An improved yield of a plant relates to an increase in the yield of a product (e.g., as measured by plant biomass, grain, seed or fruit yield, protein content, carbohydrate or oil content or leaf area) of the plant by a measurable amount over the yield of the same product of the plant produced under the same conditions, but without the application of the instant compositions or compared with application of conventional plant-modifying agents (e.g., plant-modifying agents delivered without PMPs). For example, yield can be increased by at least about 0.5%, about 1%, about 2%, about 3%, about 4%, about 5%, about 10%, about 20%, about 30%, about 40%, about 50%, about 60%, about 70%, about 80%, about 90%, about 100%, or more than 100%. In some instances, the method is effective to increase yield by about 2×-fold, 5×-fold, 10×-fold, 25×-fold, 50×-fold, 75×-fold, 100×-fold, or more than 100×-fold relative to an untreated plant. Yield can be expressed in terms of an amount by weight or volume of the plant or a product of the plant on some basis. The basis can be expressed in terms of time, growing area, weight of plants produced, or amount of a raw material used. For example, such methods may increase the yield of plant tissues including, but not limited to: seeds, fruits, kernels, bolls, tubers, roots, and leaves.

An increase in the fitness of a plant as a consequence of delivery of a plant-modifying composition can also be measured by other means, such as an increase or improvement of the vigor rating, the stand (the number of plants per unit of area), plant height, stalk circumference, stalk length, leaf number, leaf size, plant canopy, visual appearance (such as greener leaf color), root rating, emergence, protein content, increased tillering, bigger leaves, more leaves, less dead basal leaves, stronger tillers, less fertilizer needed, less seeds needed, more productive tillers, earlier flowering, early grain or seed maturity, less plant verse (lodging), increased shoot growth, earlier germination, or any combination of these factors, by a measurable or noticeable amount over the same factor of the plant produced under the same conditions, but without the administration of the instant compositions or with application of conventional plant-modifying agents (e.g., plant-modifying agents delivered without PMPs).

Accordingly, provided herein is a method of modifying a plant, the method including delivering to the plant an effective amount of any of the plant-modifying compositions provided herein, wherein the method modifies the plant and thereby introduces or increases a beneficial trait in the plant (e.g., by about 1%, 2%, 5%, 10%, 20%, 30%, 40%, 50%, 60%, 70%, 80%, 90%, 100%, or more than 100%) relative to an untreated plant. In particular, the method may increase the fitness of the plant (e.g., by about 1%, 2%, 5%, 10%, 20%, 30%, 40%, 50%, 60%, 70%, 80%, 90%, 100%, or more than 100%) relative to an untreated plant.

In some instances, the increase in plant fitness is an increase (e.g., by about 1%, 2%, 5%, 10%, 20%, 30%, 40%, 50%, 60%, 70%, 80%, 90%, 100%, or more than 100%) in disease resistance, drought tolerance, heat tolerance, cold tolerance, salt tolerance, metal tolerance, herbicide tolerance, chemical tolerance, water use efficiency, nitrogen utilization, resistance to nitrogen stress, nitrogen fixation, pest resistance, herbivore resistance, pathogen resistance, yield, yield under water-limited conditions, vigor, growth, photosynthetic capability, nutrition, protein content, carbohydrate content, oil content, biomass, shoot length, root length, root architecture, seed weight, or amount of harvestable produce.

In some instances, the increase in fitness is an increase (e.g., by about 1%, 2%, 5%, 10%, 20%, 30%, 40%, 50%, 60%, 70%, 80%, 90%, 100%, or more than 100%) in development, growth, yield, resistance to abiotic stressors, or resistance to biotic stressors. An abiotic stress refers to an environmental stress condition that a plant or a plant part is subjected to that includes, e.g., drought stress, salt stress, heat stress, cold stress, and low nutrient stress. A biotic stress refers to an environmental stress condition that a plant or plant part is subjected to that includes, e.g. nematode stress, insect herbivory stress, fungal pathogen stress, bacterial pathogen stress, or viral pathogen stress. The stress may be temporary, e.g. several hours, several days, several months, or permanent, e.g. for the life of the plant.

In some instances, the increase in plant fitness is an increase (e.g., by about 1%, 2%, 5%, 10%, 20%, 30%, 40%, 50%, 60%, 70%, 80%, 90%, 100%, or more than 100%) in quality of products harvested from the plant. For example, the increase in plant fitness may be an improvement in commercially favorable features (e.g., taste or appearance) of a product harvested from the plant. In other instances, the increase in plant fitness is an increase in shelf-life of a product harvested from the plant (e.g., by about 1%, 2%, 5%, 10%, 20%, 30%, 40%, 50%, 60%, 70%, 80%, 90%, 100%, or more than 100%).

Alternatively, the increase in fitness may be an alteration of a trait that is beneficial to human or animal health, such as a reduction in allergen production. For example, the increase in fitness may be a decrease (e.g., by about 1%, 2%, 5%, 10%, 20%, 30%, 40%, 50%, 60%, 70%, 80%, 90%, 100%, or more than 100%) in production of an allergen (e.g., pollen) that stimulates an immune response in an animal (e.g., human).

The modification of the plant (e.g., increase in fitness) may arise from modification of one or more plant parts. For example, the plant can be modified by contacting leaf, seed, pollen, root, fruit, shoot, flower, cells, protoplasts, or tissue (e.g., meristematic tissue) of the plant. As such, in another aspect, provided herein is a method of increasing the fitness of a plant, the method including contacting pollen of the plant with an effective amount of any of the plant-modifying compositions herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In yet another aspect, provided herein is a method of increasing the fitness of a plant, the method including contacting a seed of the plant with an effective amount of any of the plant-modifying compositions disclosed herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method including contacting a protoplast of the plant with an effective amount of any of the plant-modifying compositions herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In a further aspect, provided herein is a method of increasing the fitness of a plant, the method including contacting a plant cell of the plant with an effective amount of any of the plant-modifying compositions herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method of increasing the fitness of a plant, the method including contacting meristematic tissue of the plant with an effective amount of any of the plant-modifying compositions herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method of increasing the fitness of a plant, the method including contacting an embryo of the plant with an effective amount of any of the plant-modifying compositions herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

B. Application Methods

A plant described herein can be exposed to any of the compositions described herein in any suitable manner that permits delivering or administering the composition to the plant. The plant-modifying composition may be delivered either alone or in combination with other active (e.g., fertilizing agents) or inactive substances and may be applied by, for example, spraying, injection (e.g. microinjection), through plants, pouring, dipping, in the form of concentrated liquids, gels, solutions, suspensions, sprays, powders, pellets, briquettes, bricks and the like, formulated to deliver an effective concentration of the plant-modifying composition. Amounts and locations for application of the compositions described herein are generally determined by the habitat of the plant, the lifecycle stage at which the plant can be targeted by the plant-modifying composition, the site where the application is to be made, and the physical and functional characteristics of the plant-modifying composition.

In some instances, the composition is sprayed directly onto a plant e.g., crops, by e.g., backpack spraying, aerial spraying, crop spraying/dusting etc. In instances where the plant-modifying composition is delivered to a plant, the plant receiving the plant-modifying composition may be at any stage of plant growth. For example, formulated plant-modifying compositions can be applied as a seed-coating or root treatment in early stages of plant growth or as a total plant treatment at later stages of the crop cycle. In some instances, the plant-modifying composition may be applied as a topical agent to a plant.

Further, the plant-modifying composition may be applied (e.g., in the soil in which a plant grows, or in the water that is used to water the plant) as a systemic agent that is absorbed and distributed through the tissues of a plant. In some instances, plants or food organisms may be genetically transformed to express the plant-modifying composition.

Delayed or continuous release can also be accomplished by coating the plant-modifying composition or a composition with the plant-modifying composition(s) with a dissolvable or bioerodable coating layer, such as gelatin, which coating dissolves or erodes in the environment of use, to then make the plant-modifying composition available, or by dispersing the agent in a dissolvable or erodable matrix. Such continuous release and/or dispensing means devices may be advantageously employed to consistently maintain an effective concentration of one or more of the plant-modifying compositions described herein.

In some instances, the plant-modifying composition is delivered to a part of the plant, e.g., a leaf, seed, pollen, root, fruit, shoot, or flower, or a tissue, cell, or protoplast thereof. In some instances, the plant-modifying composition is delivered to a cell of the plant. In some instances, the plant-modifying composition is delivered to a protoplast of the plant. In some instances, the plant-modifying composition is delivered to a tissue of the plant. For example, the composition may be delivered to meristematic tissue of the plant (e.g., apical meristem, lateral meristem, or intercalary meristem). In some instances, the composition is delivered to permanent tissue of the plant (e.g., simple tissues (e.g., parenchyma, collenchyma, or sclerenchyma) or complex permanent tissue (e.g., xylem or phloem)). In some instances, the composition is delivered to a plant embryo.

In some instances, the plant-modifying composition may be recommended for field application as an amount of PMPs per hectare (g/ha or kg/ha) or the amount of active ingredient (e.g., plant-modifying agent) or acid equivalent per hectare (kg a.i./ha or g a.i./ha). In some instances, a lower amount of plant-modifying agent in the present compositions may be required to be applied to soil, plant media, seeds plant tissue, or plants to achieve the same results as where the plant-modifying agent is applied in a composition lacking PMPs. For example, the amount of plant-modifying agent may be applied at levels about 2, 3, 4, 5, 6, 7, 8, 9, 10, 15, 20, 30, 50, or 100-fold (or any range between about 2 and about 100-fold, for example about 2- to 10-fold; about 5- to 15-fold, about 10- to 20-fold; about 10- to 50-fold) less than the same plant-modifying agent applied in a non-PMP composition, e.g., direct application of the same plant-modifying agent without PMPs. Plant-modifying compositions of the invention can be applied at a variety of amounts per hectare, for example at about 0.0001, 0.001, 0.005, 0.01, 0.1, 1, 2, 10, 100, 1,000, 2,000, 5,000 (or any range between about 0.0001 and 5,000) kg/ha. For example, about 0.0001 to about 0.01, about 0.01 to about 10, about 10 to about 1,000, about 1,000 to about 5,000 kg/ha.

III. Plants

A variety of plants can be delivered to or treated with a plant-modifying composition described herein. Plants that can be delivered a plant-modifying composition (i.e., "treated") in accordance with the present methods include whole plants and parts thereof, including, but not limited to, shoot vegetative organs/structures (e.g., leaves, stems and tubers), roots, flowers and floral organs/structures (e.g., bracts, sepals, petals, stamens, carpels, anthers and ovules), seed (including embryo, endosperm, cotyledons, and seed coat) and fruit (the mature ovary), plant tissue (e.g., vascular tissue, ground tissue, and the like) and cells (e.g., guard cells, egg cells, and the like), and progeny of same. Plant parts can further refer parts of the plant such as the shoot, root, stem, seeds, stipules, leaves, petals, flowers, ovules, bracts, branches, petioles, internodes, bark, pubescence, tillers, rhizomes, fronds, blades, pollen, stamen, and the like.

The class of plants that can be treated in a method disclosed herein includes the class of higher and lower plants, including angiosperms (monocotyledonous and dicotyledonous plants), gymnosperms, ferns, horsetails, psilophytes, lycophytes, bryophytes, and algae (e.g., multicellular or unicellular algae). Plants that can be treated in accordance with the present methods further include any vascular plant, for example monocotyledons or dicotyledons or gymnosperms, including, but not limited to alfalfa, apple, *Arabidopsis*, banana, barley, canola, castor bean, chrysanthemum, clover, cocoa, coffee, cotton, cottonseed, corn, crambe, cranberry, cucumber, dendrobium, dioscorea, eucalyptus, fescue, flax, gladiolus, liliacea, linseed, millet, muskmelon, mustard, oat, oil palm, oilseed rape, papaya, peanut, pineapple, ornamental plants, *Phaseolus*, potato, rapeseed, rice, rye, ryegrass, safflower, sesame, *Ssorghum*, soybean, sugarbeet, sugarcane, sunflower, strawberry, tobacco, tomato, turfgrass, wheat and vegetable crops such as lettuce, celery, broccoli, cauliflower, cucurbits; fruit and nut trees, such as apple, pear, peach, orange, grapefruit, lemon, lime, almond, pecan, walnut, hazel; vines, such as grapes (e.g., a vineyard), kiwi, hops; fruit shrubs and brambles, such as raspberry, blackberry, gooseberry; forest trees, such as ash, pine, fir, maple, oak, chestnut, popular; with alfalfa, canola, castor bean, corn, cotton, crambe, flax, linseed, mustard, oil palm, oilseed rape, peanut, potato, rice, safflower, sesame, soybean, sugarbeet, sunflower, tobacco, tomato, and wheat. Plants that can be treated in accordance with the methods of the present invention include any crop plant, for example, forage crop, oilseed crop, grain crop, fruit crop, vegetable crop, fiber crop, spice crop, nut crop, turf crop, sugar crop, beverage crop, and forest crop. In certain instances, the crop plant that is treated in the method is a soybean plant. In other certain instances, the crop plant is wheat. In certain instances, the crop plant is corn. In certain instances, the crop plant is cotton. In certain instances, the crop plant is alfalfa. In certain instances, the crop plant is sugarbeet. In certain instances, the crop plant is rice. In certain instances, the crop plant is potato. In certain instances, the crop plant is tomato.

In certain instances, the plant is a crop. Examples of such crop plants include, but are not limited to, monocotyledonous and dicotyledonous plants including, but not limited to, fodder or forage legumes, ornamental plants, food crops, trees, or shrubs selected from Acer spp., *Allium* spp., *Amaranthus* spp., *Ananas comosus*, *Apium graveolens*, *Arachis* spp, *Asparagus officinalis*, *Beta vulgaris*, *Brassica* spp. (e.g., *Brassica napus*, *Brassica rapa* ssp. (canola, oilseed rape, turnip rape), *Camellia sinensis*, *Canna indica*, *Cannabis saliva*, *Capsicum* spp., *Castanea* spp., *Cichorium endivia*, *Citrullus lanatus*, *Citrus* spp., *Cocos* spp., *Coffea* spp., *Coriandrum sativum*, *Corylus* spp., *Crataegus* spp., *Cucurbita* spp., *Cucumis* spp., *Daucus carota*, *Fagus* spp., *Ficus carica*, *Fragaria* spp., *Ginkgo biloba*, *Glycine* spp. (e.g., *Glycine max*, *Soja hispida* or *Soja max*), *Gossypium hirsutum*, *Helianthus* spp. (e.g., *Helianthus annuus*), *Hibiscus* spp., *Hordeum* spp. (e.g., *Hordeum vulgare*), *Ipomoea batatas*, *Juglans* spp., *Lactuca sativa*, *Linum usitatissimum*, *Litchi chinensis*, *Lotus* spp., *Luffa acutangula*, *Lupinus* spp., *Lycopersicon* spp. (e.g., *Lycopersicon esculenturn*, *Lycopersicon lycopersicum*, *Lycopersicon pyriforme*), *Malus* spp., *Medicago sativa*, *Mentha* spp., *Miscanthus sinensis*, *Morus nigra*, *Musa* spp., *Nicotiana* spp., *Olea* spp., *Oryza* spp. (e.g., *Oryza sativa*, *Oryza latifolia*), *Panicum miliaceum*, *Panicum virgatum*, *Passiflora edulis*, *Petroselinum crispum*, *Phaseolus* spp., *Pinus* spp., *Pistacia vera*, *Pisum* spp., *Poa* spp., *Populus* spp., *Prunus* spp., *Pyrus communis*, *Quercus* spp., *Raphanus sativus*, *Rheum rhabarbarum*, *Ribes* spp., *Ricinus communis*, *Rubus* spp., *Saccharum* spp., *Salix* sp., *Sambucus* spp., *Secale cereale*, *Sesamum* spp., *Sinapis* spp., *Solanum* spp. (e.g., *Solanum tuberosum*, *Solanum integrifolium* or *Solanum lycopersicum*), *Sorghum bicolor*, *Sorghum halepense*, *Spinacia* spp., *Tamarindus indica*, *Theobroma cacao*, *Trifolium* spp., *Triticosecale rimpaui*, *Triticum* spp. (e.g., *Triticum aestivum*, *Triticum durum*, *Triticum turgidum*, *Triticum hybernum*, *Triticum macha*, *Triticum sativum* or *Triticum vulgare*), *Vaccinium* spp., *Vicia* spp., *Vigna* spp., *Viola odorata*, *Vitis* spp., and *Zea mays*. In certain embodiments, the crop plant is rice, oilseed rape, canola, soybean, corn (maize), cotton, sugarcane, alfalfa, *Ssorghum*, or wheat.

In certain instance, the compositions and methods can be used to treat post-harvest plants or plant parts, food, or feed products. In some instances, the food or feed product is a non-plant food or feed product (e.g., a product edible for humans, veterinary animals, or livestock (e.g., mushrooms)).

The plant or plant part for use in the present invention include plants of any stage of plant development. In certain instances, the delivery can occur during the stages of germination, seedling growth, vegetative growth, and reproductive growth. In certain instances, delivery to the plant occurs during vegetative and reproductive growth stages. In some instances, the composition is delivered to pollen of the plant. In some instances, the composition is delivered to a seed of the plant. In some instances, the composition is delivered to a protoplast of the plant. In some instances, the composition is delivered to a tissue of the plant. For example, the composition may be delivered to meristematic tissue of the plant (e.g., apical meristem, lateral meristem, or intercalary meristem). In some instances, the composition is delivered to permanent tissue of the plant (e.g., simple tissues (e.g., parenchyma, collenchyma, or sclerenchyma) or complex permanent tissue (e.g., xylem or phloem)). In some instances, the composition is delivered to a plant embryo. In some instances, the composition is delivered to a plant cell. The stages of vegetative and reproductive growth are also referred to herein as "adult" or "mature" plants.

In instances where the composition is delivered to a plant part, the plant part may be modified by the plant-modifying agent. Alternatively, the plant-modifying agent may be distributed to other parts of the plant that are subsequently modified by the plant-modifying agent.

IV. Heterologous Plant-Modifying Agents

The plant-modifying compositions described herein include one or more heterologous plant-modifying agents. For example, the PMPs may encapsulate the heterologous plant-modifying agent. Alternatively or additionally, the heterologous plant-modifying agent can be embedded on or conjugated to the surface of the PMP.

In some instances, the plant-modifying agent can include a peptide or a nucleic acid. The plant-modifying agent may be an agent that increases the fitness of a variety of plants or can be one that targets one or more specific plants (e.g., a specific species or genera of plants). Additionally, in some instances, the plant-modifying compositions include two or more (e.g., 2, 3, 4, 5, 6, 7, 8, 9, 10, or more than 10) different plant-modifying agents. In some instances, the heterologous plant-modifying agent comprises a ribonucleoprotein (RNP), e.g., comprises one or more RNA molecules associated with one or more RNA-binding proteins.

Further, in some instances, the heterologous plant-modifying agent (e.g., an agent including a nucleic acid molecule or peptide) can be modified. For example, the modification can be a chemical modification, e.g., conjugation to a marker, e.g., fluorescent marker or a radioactive marker. In other examples, the modification can include conjugation or operational linkage to a moiety that enhances the stability, delivery, targeting, bioavailability, or half-life of the agent, e.g., a lipid, a glycan, a polymer (e.g., PEG), a cation moiety.

Examples of heterologous plant-modifying agents (e.g., peptides or nucleic acids) that can be used in the presently disclosed plant-modifying compositions and methods are outlined below.

A. Polypeptides

The plant-modifying compositions (e.g., PMPs) described herein may include a heterologous polypeptide. In some instances, the plant-modifying compositions described herein includes a polypeptide or functional fragments or derivative thereof that modifies a plant (e.g., e.g., increases the fitness of the plant). For example, the polypeptide can increase the fitness of a plant. A plant-modifying composition including a polypeptide as described herein can be contacted with a plant in an amount and for a time sufficient to: (a) reach a target level (e.g., a predetermined or threshold level) of polypeptide concentration; and (b) modify the plant (e.g., increase the fitness of the plant).

Examples of polypeptides that can be used herein can include an enzyme (e.g., a metabolic recombinase, a helicase, an integrase, a RNAse, a DNAse, or an ubiquitination protein), a pore-forming protein, a signaling ligand, a cell penetrating peptide, a transcription factor, a receptor, an antibody, a nanobody, a gene editing protein (e.g., CRISPR-Cas system, TALEN, or zinc finger), riboprotein, a protein aptamer, or a chaperone.

Polypeptides included herein may include naturally occurring polypeptides or recombinantly produced variants. In some instances, the polypeptide may be a functional fragments or variants thereof (e.g., an enzymatically active fragment or variant thereof). For example, the polypeptide may be a functionally active variant of any of the polypeptides described herein with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a polypeptide described herein or a naturally occurring polypeptide. In some instances, the polypeptide may have at least 50% (e.g., at least 50%, 60%, 70%, 80%, 90%, 95%, 97%, 99%, or greater) identity to a protein of interest.

The polypeptides described herein may be formulated in a composition for any of the uses described herein. The compositions disclosed herein may include any number or type (e.g., classes) of polypeptides, such as at least about any one of 1 polypeptide, 2, 3, 4, 5, 10, 15, 20, or more polypeptides. A suitable concentration of each polypeptide in the composition depends on factors such as efficacy, stability of the polypeptide, number of distinct polypeptides in the composition, the formulation, and methods of application of the composition. In some instances, each polypeptide in a liquid composition is from about 0.1 ng/mL to about 100 mg/mL. In some instances, each polypeptide in a solid composition is from about 0.1 ng/g to about 100 mg/g.

Methods of making a polypeptide are routine in the art. See, in general, Smales & James (Eds.), *Therapeutic Proteins: Methods and Protocols (Methods in Molecular Biology)*, Humana Press (2005); and Crommelin, Sindelar & Meibohm (Eds.), *Pharmaceutical Biotechnology: Fundamentals and Applications*, Springer (2013).

Methods for producing a polypeptide involve expression in plant cells, although recombinant proteins can also be produced using insect cells, yeast, bacteria, mammalian cells, or other cells under the control of appropriate promoters. Mammalian expression vectors may comprise nontranscribed elements such as an origin of replication, a suitable promoter and enhancer, and other 5' or 3' flanking nontranscribed sequences, and 5' or 3' nontranslated sequences such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Appropriate cloning and expression vectors for use with bacterial, fungal, yeast, and mammalian cellular hosts are described in Green & Sambrook, *Molecular Cloning: A Laboratory Manual (Fourth Edition)*, Cold Spring Harbor Laboratory Press (2012).

Various mammalian cell culture systems can be employed to express and manufacture a recombinant polypeptide agent. Examples of mammalian expression systems include CHO cells, COS cells, HeLA and BHK cell lines. Processes of host cell culture for production of protein therapeutics are described in, e.g., Zhou and Kantardjieff (Eds.), *Mammalian Cell Cultures for Biologics Manufacturing (Advances in Biochemical Engineering/Biotechnology)*, Springer (2014). Purification of proteins is described in Franks, *Protein Biotechnology: Isolation, Characterization, and Stabilization*, Humana Press (2013); and in Cutler, *Protein Purification Protocols (Methods in Molecular Biology)*, Humana Press (2010). Formulation of protein therapeutics is described in Meyer (Ed.), *Therapeutic Protein Drug Products: Practical Approaches to formulation in the Laboratory, Manufacturing, and the Clinic*, Woodhead Publishing Series (2012).

In some instances, the plant-modifying composition includes an antibody or antigen binding fragment thereof. For example, an agent described herein may be an antibody that blocks or potentiates activity and/or function of a component of the plant. The antibody may act as an antagonist or agonist of a polypeptide (e.g., enzyme or cell receptor) in the plant. The making and use of antibodies against a target antigen is known in the art. See, for example, Zhiqiang An (Ed.), *Therapeutic Monoclonal Antibodies: From Bench to Clinic*, 1st Edition, Wiley, 2009 and also Greenfield (Ed.), *Antibodies: A Laboratory Manual*, 2nd Edition, Cold Spring Harbor Laboratory Press, 2013, for methods of making recombinant antibodies, including antibody engineering, use of degenerate oligonucleotides, 5'-RACE, phage display, and mutagenesis; antibody testing and characterization; antibody pharmacokinetics and pharmacodynamics; antibody purification and storage; and screening and labeling techniques.

B. Nucleic Acids

In some instances, the PMPs described herein include a heterologous nucleic acid. Numerous nucleic acids are useful in the plant-modifying compositions and methods described herein. The plant-modifying compositions disclosed herein may include any number or type (e.g., classes) of nucleic acids (e.g., DNA molecule or RNA molecule, e.g., mRNA, guide RNA (gRNA), or inhibitory RNA molecule (e.g., siRNA, shRNA, or miRNA), or a hybrid DNA-RNA molecule), such as at least about 1 class or variant of a nucleic acid, 2, 3, 4, 5, 10, 15, 20, or more classes or variants of nucleic acids. A suitable concentration of each nucleic acid in the composition depends on factors such as efficacy, stability of the nucleic acid, number of distinct nucleic acids, the formulation, and methods of application of the composition. Examples of nucleic acids useful herein include an antisense RNA, a Dicer substrate small interfering RNA (dsiRNA), a short interfering RNA (siRNA), a short hairpin (shRNA), a microRNA (miRNA), an (asymmetric interfering RNA) aiRNA, a peptide nucleic acid (PNA), a morpholino, a locked nucleic acid (LNA), a piwi-interacting RNA (piRNA), a ribozyme, a deoxyribozymes (DNAzyme), an aptamer (DNA, RNA), a circular RNA (circRNA), a guide RNA (gRNA), or a DNA molecule. The nucleic acid can be associated with other factors (e.g., polypeptides) in any way known in the art to ensure the nucleic acids are stable e.g., nuclease resistant. For example, the nucleic acids may be nuclease-resistant when complexed with proteins.

A plant-modifying composition including a nucleic acid as described herein can be contacted with a plant in an amount and for a time sufficient to: (a) reach a target level (e.g., a predetermined or threshold level) of nucleic acid concentration; and (b) modify the plant (e.g., increase the fitness of the plant).

(a) Nucleic Acid Encoding Peptides

In some instances, the plant-modifying composition includes a nucleic acid encoding a polypeptide. Nucleic acids encoding a polypeptide may have a length from about 10 to about 50,000 nucleotides (nts), about 25 to about 100 nts, about 50 to about 150 nts, about 100 to about 200 nts, about 150 to about 250 nts, about 200 to about 300 nts, about 250 to about 350 nts, about 300 to about 500 nts, about 10 to about 1000 nts, about 50 to about 1000 nts, about 100 to about 1000 nts, about 1000 to about 2000 nts, about 2000 to about 3000 nts, about 3000 to about 4000 nts, about 4000 to about 5000 nts, about 5000 to about 6000 nts, about 6000 to about 7000 nts, about 7000 to about 8000 nts, about 8000 to about 9000 nts, about 9000 to about 10,000 nts, about 10,000 to about 15,000 nts, about 10,000 to about 20,000 nts, about 10,000 to about 25,000 nts, about 10,000 to about 30,000 nts, about 10,000 to about 40,000 nts, about 10,000 to about 45,000 nts, about 10,000 to about 50,000 nts, or any range therebetween.

The plant-modifying composition may also include functionally active variants of a nucleic acid sequence of interest. In some instances, the variant of the nucleic acids has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a nucleic acid of interest. In some instances, the invention includes a functionally active polypeptide encoded by a nucleic acid variant as described herein. In some instances, the functionally active polypeptide encoded by the nucleic acid variant has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire amino acid sequence, to a sequence of a polypeptide of interest or the naturally derived polypeptide sequence.

Certain methods for expressing a nucleic acid encoding a protein may involve expression in cells, including insect, yeast, plant, bacteria, or other cells under the control of appropriate promoters. Expression vectors may include non-transcribed elements, such as an origin of replication, a suitable promoter and enhancer, and other 5' or 3' flanking nontranscribed sequences, and 5' or 3' nontranslated sequences such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Appropriate cloning and expression vectors for use with bacterial, fungal, yeast, and mammalian cellular hosts are described in Green et al., *Molecular Cloning: A Laboratory Manual*, Fourth Edition, Cold Spring Harbor Laboratory Press, 2012.

Genetic modification using recombinant methods is generally known in the art. A nucleic acid sequence coding for a desired gene can be obtained using recombinant methods known in the art, such as, for example by screening libraries from cells expressing the gene, by deriving the gene from a vector known to include the same, or by isolating directly from cells and tissues containing the same, using standard techniques. Alternatively, a gene of interest can be produced synthetically, rather than cloned.

Expression of natural or synthetic nucleic acids is typically achieved by operably linking a nucleic acid encoding the gene of interest to a promoter, and incorporating the construct into an expression vector. Expression vectors can be suitable for replication and expression in bacteria. Expression vectors can also be suitable for replication and integration in eukaryotes. Typical cloning vectors contain transcription and translation terminators, initiation sequences, and promoters useful for expression of the desired nucleic acid sequence.

Additional promoter elements, e.g., enhancers, regulate the frequency of transcriptional initiation. Typically, these are located in the region 30-110 basepairs (bp) upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Alternatively, the promoter may be an inducible promoter. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

The expression vector to be introduced can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes may be used for identifying potentially transformed cells and for evaluating the functionality of regulatory sequences. In general, a reporter gene is a gene that is not present in or expressed by the recipient source and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., *FEBS Letters* 479:79-82, 2000). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some instances, an organism may be genetically modified to alter expression of one or more proteins. Expression of the one or more proteins may be modified for a specific time, e.g., development or differentiation state of the organism. In one instances, the invention includes a composition to alter expression of one or more proteins, e.g., proteins that affect activity, structure, or function. Expression of the one or more proteins may be restricted to a specific location(s) or widespread throughout the organism.

(b) Synthetic mRNA

The plant-modifying composition may include a synthetic mRNA molecule, e.g., a synthetic mRNA molecule encoding a polypeptide. The synthetic mRNA molecule can be modified, e.g., chemically. The mRNA molecule can be chemically synthesized or transcribed in vitro. The mRNA molecule can be disposed on a plasmid, e.g., a viral vector, bacterial vector, or eukaryotic expression vector. In some examples, the mRNA molecule can be delivered to cells by transfection, electroporation, or transduction (e.g., adenoviral or lentiviral transduction).

In some instances, the modified RNA agent of interest described herein has modified nucleosides or nucleotides. Such modifications are known and are described, e.g., in WO 2012/019168. Additional modifications are described, e.g., in WO 2015/038892; WO 2015/038892; WO 2015/089511; WO 2015/196130; WO 2015/196118 and WO 2015/196128 A2.

In some instances, the modified RNA encoding a polypeptide of interest has one or more terminal modification, e.g., a 5' cap structure and/or a poly-A tail (e.g., of between 100-200 nucleotides in length). The 5' cap structure may be selected from the group consisting of CapO, CapI, ARCA, inosine, NI-methyl-guanosine, 2'fluoro-guanosine, 7-deaza-guanosine, 8-oxo-guanosine, 2-amino-guanosine, LNA-guanosine, and 2-azido-guanosine. In some cases, the modified RNAs also contain a 5' UTR including at least one Kozak sequence, and a 3' UTR. Such modifications are known and are described, e.g., in WO 2012/135805 and WO 2013/052523. Additional terminal modifications are described, e.g., in WO 2014/164253 and WO 2016/011306, WO 2012/045075, and WO 2014/093924. Chimeric enzymes for synthesizing capped RNA molecules (e.g., modified mRNA) which may include at least one chemical modification are described in WO 2014/028429.

In some instances, a modified mRNA may be cyclized, or concatemerized, to generate a translation competent molecule to assist interactions between poly-A binding proteins and 5'-end binding proteins. The mechanism of cyclization or concatemerization may occur through at least 3 different routes: 1) chemical, 2) enzymatic, and 3) ribozyme catalyzed. The newly formed 5'-/3'-linkage may be intramolecular or intermolecular. Such modifications are described, e.g., in WO 2013/151736.

Methods of making and purifying modified RNAs are known and disclosed in the art. For example, modified RNAs are made using only in vitro transcription (IVT) enzymatic synthesis. Methods of making IVT polynucleotides are known in the art and are described in WO 2013/151666, WO 2013/151668, WO 2013/151663, WO 2013/151669, WO 2013/151670, WO 2013/151664, WO 2013/151665, WO 2013/151671, WO 2013/151672, WO 2013/151667 and WO 2013/151736. Methods of purification include purifying an RNA transcript including a polyA tail by contacting the sample with a surface linked to a plurality of thymidines or derivatives thereof and/or a plurality of uracils or derivatives thereof (polyT/U) under conditions such that the RNA transcript binds to the surface and eluting the purified RNA transcript from the surface (WO 2014/152031); using ion (e.g., anion) exchange chromatography that allows for separation of longer RNAs up to 10,000 nucleotides in length via a scalable method (WO 2014/144767); and subjecting a modified mRNA sample to DNAse treatment (WO 2014/152030).

Formulations of modified RNAs are known and are described, e.g., in WO 2013/090648. For example, the formulation may be, but is not limited to, nanoparticles, poly(lactic-co-glycolic acid)(PLGA) microspheres, lipidoids, lipoplex, liposome, polymers, carbohydrates (including simple sugars), cationic lipids, fibrin gel, fibrin hydrogel, fibrin glue, fibrin sealant, fibrinogen, thrombin, rapidly eliminated lipid nanoparticles (reLNPs) and combinations thereof.

Modified RNAs encoding polypeptides in the fields of human disease, antibodies, viruses, and a variety of in vivo settings are known and are disclosed in for example, Table 6 of International Publication Nos. WO 2013/151666, WO 2013/151668, WO 2013/151663, WO 2013/151669, WO 2013/151670, WO 2013/151664, WO 2013/151665, WO 2013/151736; Tables 6 and 7 International Publication No. WO 2013/151672; Tables 6, 178 and 179 of International Publication No. WO 2013/151671; Tables 6, 185 and 186 of International Publication No WO 2013/151667. Any of the foregoing may be synthesized as an IVT polynucleotide, chimeric polynucleotide or a circular polynucleotide, and each may include one or more modified nucleotides or terminal modifications.

(c) Inhibitory RNA

In some instances, the plant-modifying composition includes an inhibitory RNA molecule, e.g., that acts via the RNA interference (RNAi) pathway. In some instances, the inhibitory RNA molecule decreases the level of gene expression in a plant and/or decreases the level of a protein in the plant. In some instances, the inhibitory RNA molecule inhibits expression of a plant gene. For example, an inhibitory RNA molecule may include a short interfering RNA, short hairpin RNA, and/or a microRNA that targets a gene in the plant. Certain RNA molecules can inhibit gene expression through the biological process of RNA interference (RNAi). RNAi molecules include RNA or RNA-like structures typically containing 15-50 base pairs (such as about 18-25 base pairs) and having a nucleobase sequence identical (complementary) or nearly identical (substantially complementary) to a coding sequence in an expressed target gene within the cell. RNAi molecules include, but are not limited to: Dicer substrate small interfering RNAs (dsiRNAs), short interfering RNAs (siRNAs), double-strand RNAs (dsRNA), short hairpin RNAs (shRNA), meroduplexes, dicer substrates, and multivalent RNA interference (U.S. Pat. Nos. 8,084,599 8,349,809, 8,513,207 and 9,200,276). A shRNA is a RNA molecule including a hairpin turn that decreases expression of target genes via RNAi. shRNAs can be delivered to cells in the form of plasmids, e.g., viral or bacterial vectors, e.g., by transfection, electroporation, or transduction). A microRNA is a non-coding RNA molecule that typically has a length of about 22 nucleotides. MiRNAs bind to target sites on mRNA molecules and silence the mRNA, e.g., by causing cleavage of the mRNA, destabilization of the mRNA, or inhibition of translation of the mRNA. In some instances, the inhibitory RNA molecule decreases the level and/or activity of a negative regulator of function. In other instances, the inhibitor RNA molecule decreases the level and/or activity of an inhibitor of a positive regulator of function. The inhibitory RNA molecule can be chemically synthesized or transcribed in vitro.

In some instances, the nucleic acid is a DNA, a RNA, or a PNA. In some instances, the RNA is an inhibitory RNA. In some instances, the inhibitory RNA inhibits gene expression in a plant. In some instances, the nucleic acid is an mRNA, a modified mRNA, or a DNA molecule that, in the plant, increases expression of an enzyme (e.g., a metabolic recombinase, a helicase, an integrase, a RNAse, a DNAse, or an ubiquitination protein), a pore-forming protein, a signaling ligand, a cell penetrating peptide, a transcription factor, a receptor, an antibody, a nanobody, a gene editing protein (e.g., CRISPR-Cas system, TALEN, or zinc finger), riboprotein, a protein aptamer, or a chaperone. In some instances, the nucleic acid is an mRNA, a modified mRNA, or a DNA molecule that increases the expression of an enzyme (e.g., a metabolic enzyme, a recombinase enzyme, a helicase enzyme, an integrase enzyme, a RNAse enzyme, a DNAse enzyme, or an ubiquitination protein), a pore-forming protein, a signaling ligand, a cell penetrating peptide, a transcription factor, a receptor, an antibody, a nanobody, a gene editing protein (e.g., a CRISPR-Cas system, a TALEN, or a zinc finger), a riboprotein, a protein aptamer, or a chaperone. In some instances, the increase in expression in the plant is an increase in expression of about 5%, 10%, 15%, 20%, 30%, 40%, 50%, 60%, 70%, 80%, 90%, 100%, or more than 100% relative to a reference level (e.g., the expression in an untreated plant). In some instances, the increase in expression in the plant is an increase in expression of about 2× fold, about 4× fold, about 5× fold, about 10× fold, about 20× fold, about 25× fold, about 50× fold, about 75× fold, or about 100× fold or more, relative to a reference level (e.g., the expression in an untreated plant).

In some instances, the nucleic acid is an antisense RNA, a siRNA, a shRNA, a miRNA, an aiRNA, a PNA, a morpholino, a LNA, a piRNA, a ribozyme, a DNAzyme, an aptamer (DNA, RNA), a circRNA, a gRNA, or a DNA molecules (e.g., an antisense polynucleotide) to reduces, in the plant, expression of, e.g., an enzyme (a metabolic enzyme, a recombinase enzyme, a helicase enzyme, an integrase enzyme, a RNAse enzyme, a DNAse enzyme, a polymerase enzyme, a ubiquitination protein, a superoxide management enzyme, or an energy production enzyme), a transcription factor, a secretory protein, a structural factor (actin, kinesin, or tubulin), a riboprotein, a protein aptamer, a chaperone, a receptor, a signaling ligand, or a transporter. In some instances, the decrease in expression in the plant is a decrease in expression of about 5%, 10%, 15%, 20%, 30%, 40%, 50%, 60%, 70%, 80%, 90%, 100%, or more than 100% relative to a reference level (e.g., the expression in an untreated plant). In some instances, the decrease in expression in the plant is a decrease in expression of about 2× fold, about 4× fold, about 5× fold, about 10× fold, about 20× fold, about 25× fold, about 50× fold, about 75× fold, or about 100× fold or more, relative to a reference level (e.g., the expression in an untreated plant).

RNAi molecules include a sequence substantially complementary, or fully complementary, to all or a fragment of a target gene. RNAi molecules may complement sequences at the boundary between introns and exons to prevent the maturation of newly-generated nuclear RNA transcripts of specific genes into mRNA for transcription. RNAi molecules complementary to specific genes can hybridize with the mRNA for a target gene and prevent its translation. The antisense molecule can be DNA, RNA, or a derivative or hybrid thereof. Examples of such derivative molecules include, but are not limited to, peptide nucleic acid (PNA) and phosphorothioate-based molecules such as deoxyribonucleic guanidine (DNG) or ribonucleic guanidine (RNG).

RNAi molecules can be provided as ready-to-use RNA synthesized in vitro or as an antisense gene transfected into cells which will yield RNAi molecules upon transcription. Hybridization with mRNA results in degradation of the hybridized molecule by RNAse H and/or inhibition of the formation of translation complexes. Both result in a failure to produce the product of the original gene.

The length of the RNAi molecule that hybridizes to the transcript of interest may be around 10 nucleotides, between about 15 or 30 nucleotides, or about 15, 16, 17, 18, 19, 20, 21, 22, 23, 24, 25, 26, 27, 28, 29, 30 or more nucleotides. The degree of identity of the antisense sequence to the targeted transcript may be at least 75%, at least 80%, at least 85%, at least 90%, or at least 95.

RNAi molecules may also include overhangs, i.e., typically unpaired, overhanging nucleotides which are not directly involved in the double helical structure normally formed by the core sequences of the herein defined pair of sense strand and antisense strand. RNAi molecules may contain 3' and/or 5' overhangs of about 1-5 bases independently on each of the sense strands and antisense strands. In some instances, both the sense strand and the antisense strand contain 3' and 5' overhangs. In some instances, one or more of the 3' overhang nucleotides of one strand base pairs with one or more 5' overhang nucleotides of the other strand. In other instances, the one or more of the 3' overhang nucleotides of one strand base do not pair with the one or more 5' overhang nucleotides of the other strand. The sense and antisense strands of an RNAi molecule may or may not contain the same number of nucleotide bases. The antisense and sense strands may form a duplex wherein the 5' end only has a blunt end, the 3' end only has a blunt end, both the 5' and 3' ends are blunt ended, or neither the 5' end nor the 3' end are blunt ended. In another instance, one or more of the nucleotides in the overhang contains a thiophosphate, phosphorothioate, deoxynucleotide inverted (3' to 3' linked) nucleotide or is a modified ribonucleotide or deoxynucleotide.

Small interfering RNA (siRNA) molecules include a nucleotide sequence that is identical to about 15 to about 25 contiguous nucleotides of the target mRNA. In some instances, the siRNA sequence commences with the dinucleotide AA, includes a GC-content of about 30-70% (about 30-60%, about 40-60%, or about 45%-55%), and does not have a high percentage identity to any nucleotide sequence other than the target in the genome in which it is to be introduced, for example as determined by standard BLAST search.

siRNAs and shRNAs resemble intermediates in the processing pathway of the endogenous microRNA (miRNA) genes (Bartel, *Cell* 116:281-297, 2004). In some instances, siRNAs can function as miRNAs and vice versa (Zeng et al., *Mol. Cell* 9:1327-1333, 2002; Doench et al., *Genes Dev.* 17:438-442, 2003). Exogenous siRNAs downregulate mRNAs with seed complementarity to the siRNA (Birmingham et al., *Nat. Methods* 3:199-204, 2006). Multiple target sites within a 3' UTR give stronger downregulation (Doench et al., *Genes Dev.* 17:438-442, 2003).

Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al., *Nat. Methods* 3(9):670-676, 2006; Reynolds et al., *Nat. Biotechnol.* 22(3): 326-330, 2004; Khvorova et al., *Nat. Struct. Biol.* 10(9): 708-712, 2003; Schwarz et al., *Cell* 115(2):199-208, 2003; Ui-Tei et al., *Nucleic Acids Res.* 32(3):936-948, 2004; Heale et al., *Nucleic Acids Res.* 33(3):e30, 2005; Chalk et al., *Biochem. Biophys. Res. Commun.* 319(1):264-274, 2004; and Amarzguioui et al., *Biochem. Biophys. Res. Commun.* 316(4):1050-1058, 2004).

The RNAi molecule modulates expression of RNA encoded by a gene. Because multiple genes can share some degree of sequence homology with each other, in some instances, the RNAi molecule can be designed to target a class of genes with sufficient sequence homology. In some instances, the RNAi molecule can contain a sequence that has complementarity to sequences that are shared amongst different gene targets or are unique for a specific gene target. In some instances, the RNAi molecule can be designed to target conserved regions of an RNA sequence having homology between several genes thereby targeting several genes in a gene family (e.g., different gene isoforms, splice variants, mutant genes, etc.). In some instances, the RNAi molecule can be designed to target a sequence that is unique to a specific RNA sequence of a single gene.

An inhibitory RNA molecule can be modified, e.g., to contain modified nucleotides, e.g., 2'-fluoro, 2'-o-methyl, 2'-deoxy, unlocked nucleic acid, 2'-hydroxy, phosphorothioate, 2'-thiouridine, 4'-thiouridine, 2'-deoxyuridine. Without being bound by theory, it is believed that such modifications can increase nuclease resistance and/or serum stability, or decrease immunogenicity.

In some instances, the RNAi molecule is linked to a delivery polymer via a physiologically labile bond or linker. The physiologically labile linker is selected such that it undergoes a chemical transformation (e.g., cleavage) when present in certain physiological conditions, (e.g., disulfide bond cleaved in the reducing environment of the cell cytoplasm). Release of the molecule from the polymer, by cleavage of the physiologically labile linkage, facilitates interaction of the molecule with the appropriate cellular components for activity.

The RNAi molecule-polymer conjugate may be formed by covalently linking the molecule to the polymer. The polymer is polymerized or modified such that it contains a reactive group A. The RNAi molecule is also polymerized or modified such that it contains a reactive group B. Reactive groups A and B are chosen such that they can be linked via a reversible covalent linkage using methods known in the art.

Conjugation of the RNAi molecule to the polymer can be performed in the presence of an excess of polymer. Because the RNAi molecule and the polymer may be of opposite charge during conjugation, the presence of excess polymer can reduce or eliminate aggregation of the conjugate. Alternatively, an excess of a carrier polymer, such as a polycation, can be used. The excess polymer can be removed from the conjugated polymer prior to administration of the conjugate. Alternatively, the excess polymer can be co-administered with the conjugate.

The making and use of inhibitory agents based on non-coding RNA such as ribozymes, RNAse P, siRNAs, and miRNAs are also known in the art, for example, as described in Sioud, *RNA Therapeutics: Function, Design, and Delivery (Methods in Molecular Biology)*. Humana Press (2010).

(d) Gene Editing

The plant-modifying compositions described herein may include a component of a gene editing system. For example, the agent may introduce an alteration (e.g., insertion, deletion (e.g., knockout), translocation, inversion, single point mutation, or other mutation) in a gene in the plant. Exemplary gene editing systems include the zinc finger nucleases (ZFNs), Transcription Activator-Like Effector-based Nucleases (TALEN), and the clustered regulatory interspaced short palindromic repeat (CRISPR) system. ZFNs, TALENs, and CRISPR-based methods are described, e.g., in Gaj et al., *Trends Biotechnol.* 31(7):397-405, 2013.

In a typical CRISPR/Cas system, an endonuclease is directed to a target nucleotide sequence (e.g., a site in the genome that is to be sequence-edited) by sequence-specific, non-coding guide RNAs that target single- or double-stranded DNA sequences. Three classes (I-III) of CRISPR systems have been identified. The class II CRISPR systems use a single Cas endonuclease (rather than multiple Cas proteins). One class II CRISPR system includes a type II Cas endonuclease such as Cas9, a CRISPR RNA (crRNA), and a trans-activating crRNA (tracrRNA). The crRNA contains a guide RNA, i.e., typically an about 20-nucleotide RNA sequence that corresponds to a target DNA sequence. The crRNA also contains a region that binds to the tracrRNA to form a partially double-stranded structure which is cleaved by RNase III, resulting in a crRNA/tracrRNA hybrid. The RNAs serve as guides to direct Cas proteins to silence specific DNA/RNA sequences, depending on the spacer sequence. See, e.g., Horvath et al., *Science* 327:167-170, 2010; Makarova et al., *Biology Direct* 1:7, 2006; Pennisi, *Science* 341:833-836, 2013. The target DNA sequence must generally be adjacent to a protospacer adjacent motif (PAM) that is specific for a given Cas endonuclease; however, PAM sequences appear throughout a given genome. CRISPR endonucleases identified from various prokaryotic species have unique PAM sequence requirements; examples of PAM sequences include 5'-NGG (SEQ ID NO: 1) (*Streptococcus pyogenes*), 5'-NNAGAA (SEQ ID NO: 2) (*Streptococcus thermophilus* CRISPR1), 5'-NGGNG (SEQ ID NO: 3) (*Streptococcus thermophilus* CRISPR3), and 5'-NNNGATT (SEQ ID NO: 4) (*Neisseria meningitidis*). Some endonucleases, e.g., Cas9 endonucleases, are associated with G-rich PAM sites, e.g., 5'-NGG (SEQ ID NO: 1), and perform blunt-end cleaving of the target DNA at a location 3 nucleotides upstream from (5' from) the PAM site. Another class II CRISPR system includes the type V endonuclease Cpf1, which is smaller than Cas9; examples include AsCpf1 (from *Acidaminococcus* sp.) and LbCpf1 (from Lachnospiraceae sp.). Cpf1-associated CRISPR arrays are processed into mature crRNAs without the requirement of a tracrRNA; in other words a Cpf1 system requires only the Cpf1 nuclease and a crRNA to cleave the target DNA sequence. Cpf1 endonucleases, are associated with T-rich PAM sites, e.g., 5'-TTN (SEQ ID NO: 5). Cpf1 can also recognize a 5'-CTA (SEQ ID NO: 6) PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e.g., Zetsche et al., *Cell* 163:759-771, 2015.

For the purposes of gene editing, CRISPR arrays can be designed to contain one or multiple guide RNA sequences corresponding to a desired target DNA sequence; see, for example, Cong et al., *Science* 339:819-823, 2013; Ran et al., *Nature Protocols* 8:2281-2308, 2013. At least about 16 or 17 nucleotides of gRNA sequence are required by Cas9 for DNA cleavage to occur; for Cpf1 at least about 16 nucleotides of gRNA sequence is needed to achieve detectable DNA cleavage. In practice, guide RNA sequences are generally designed to have a length of between 17-24 nucleotides (e.g., 19, 20, or 21 nucleotides) and complementarity to the targeted gene or nucleic acid sequence. Custom gRNA generators and algorithms are available commercially for use in the design of effective guide RNAs. Gene editing has also been achieved using a chimeric single guide RNA (sgRNA), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNAs have also been demonstrated to be effective in genome editing; see, for example, Hendel et al., *Nature Biotechnol.* 985-991, 2015. In some instances, the heterologous plant-modifying agent comprises a ribonucleoprotein complex (RNP) comprising one or more RNA molecules, e.g., a gRNA or a sgRNA, and one or more RNA-binding proteins, e.g., an endonuclease, e.g., a Cas endonuclease (e.g., a Cas9 endonuclease).

Whereas wild-type Cas9 generates double-strand breaks (DSBs) at specific DNA sequences targeted by a gRNA, a number of CRISPR endonucleases having modified functionalities are available, for example: a nickase version of Cas9 generates only a single-strand break; a catalytically inactive Cas9 (dCas9) does not cut the target DNA but interferes with transcription by steric hindrance. dCas9 can further be fused with an effector to repress (CRISPRi) or activate (CRISPRa) expression of a target gene. For example, Cas9 can be fused to a transcriptional repressor (e.g., a KRAB domain) or a transcriptional activator (e.g., a dCas9-VP64 fusion). A catalytically inactive Cas9 (dCas9) fused to FokI nuclease (dCas9-FokI) can be used to generate DSBs at target sequences homologous to two gRNAs. See, e.g., the numerous CRISPR/Cas9 plasmids disclosed in and publicly available from the Addgene repository (Addgene, 75 Sidney St., Suite 550A, Cambridge, MA 02139; addgene.org/crispr/). A double nickase Cas9 that introduces two separate double-strand breaks, each directed by a separate guide RNA, is described as achieving more accurate genome editing by Ran et al., *Cell* 154:1380-1389, 2013.

CRISPR technology for editing the genes of eukaryotes is disclosed in US Patent Application Publications US 2016/0138008 A1 and US 2015/0344912 A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1.

In some instances, the desired genome modification involves homologous recombination, wherein one or more double-stranded DNA breaks in the target nucleotide sequence is generated by the RNA-guided nuclease and guide RNA(s), followed by repair of the break(s) using a homologous recombination mechanism (homology-directed repair). In such instances, a donor template that encodes the desired nucleotide sequence to be inserted or knocked-in at the double-stranded break is provided to the cell or subject; examples of suitable templates include single-stranded DNA templates and double-stranded DNA templates (e.g., linked to the polypeptide described herein). In general, a donor template encoding a nucleotide change over a region of less than about 50 nucleotides is provided in the form of single-stranded DNA; larger donor templates (e.g., more than 100 nucleotides) are often provided as double-stranded DNA plasmids. In some instances, the donor template is provided to the cell or subject in a quantity that is sufficient to achieve the desired homology-directed repair but that does not persist in the cell or subject after a given period of time (e.g., after one or more cell division cycles). In some instances, a donor template has a core nucleotide sequence that differs from the target nucleotide sequence (e.g., a homologous endogenous genomic region) by at least 1, at least 5, at least 10, at least 20, at least 30, at least 40, at least 50, or more nucleotides. This core sequence is flanked by homology arms or regions of high sequence identity with the targeted nucleotide sequence; in some instances, the regions of high identity include at least 10, at least 50, at least 100, at least 150, at least 200, at least 300, at least 400, at least 500, at least 600, at least 750, or at least 1000 nucleotides on each side of the core sequence. In some instances where the donor template is in the form of a single-stranded DNA, the core sequence is flanked by homology arms including at least 10, at least 20, at least 30, at least 40, at least 50, at least 60, at least 70, at least 80, or at least 100 nucleotides on each side of the core sequence. In instances, where the donor template is in the form of a double-stranded DNA, the core sequence is flanked by homology arms including at least 500, at least 600, at least 700, at least 800, at least 900, or at least 1000 nucleotides on each side of the core sequence. In one instance, two separate double-strand breaks are introduced into the cell or subject's target nucleotide sequence with a double nickase Cas9 (see Ran et al., *Cell* 154:1380-1389, 2013), followed by delivery of the donor template.

In some instances, the composition includes a gRNA and a targeted nuclease, e.g., a Cas9, e.g., a wild type Cas9, a nickase Cas9 (e.g., Cas9 D10A), a dead Cas9 (dCas9), eSpCas9, Cpf1, C2C1, or C2C3, or a nucleic acid encoding such a nuclease. The choice of nuclease and gRNA(s) is determined by whether the targeted mutation is a deletion, substitution, or addition of nucleotides, e.g., a deletion, substitution, or addition of nucleotides to a targeted sequence. Fusions of a catalytically inactive endonuclease e.g., a dead Cas9 (dCas9, e.g., D10A; H840A) tethered with all or a portion of (e.g., biologically active portion of) an (one or more) effector domain create chimeric proteins that can be linked to the polypeptide to guide the composition to specific DNA sites by one or more RNA sequences (sgRNA) to modulate activity and/or expression of one or more target nucleic acids sequences. In some instances, the gRNA and the targeted nuclease are provided as a ribonucleoprotein complex (RNP).

In instances, the agent includes a guide RNA (gRNA) for use in a CRISPR system for gene editing. In some instances, the agent includes a zinc finger nuclease (ZFN), or a mRNA encoding a ZFN, that targets (e.g., cleaves) a nucleic acid sequence (e.g., DNA sequence) of a gene in the plant. In some instances, the agent includes a TALEN, or an mRNA encoding a TALEN, that targets (e.g., cleaves) a nucleic acid sequence (e.g., DNA sequence) in a gene in the plant.

For example, the gRNA can be used in a CRISPR system to engineer an alteration in a gene in the plant. In other examples, the ZFN and/or TALEN can be used to engineer an alteration in a gene in the plant. Exemplary alterations include insertions, deletions (e.g., knockouts), translocations, inversions, single point mutations, or other mutations. The alteration can be introduced in the gene in a cell, e.g., in vitro, ex vivo, or in vivo. In some examples, the alteration increases the level and/or activity of a gene in the plant. In other examples, the alteration decreases the level and/or activity of (e.g., knocks down or knocks out) a gene in the plant. In yet another example, the alteration corrects a defect (e.g., a mutation causing a defect), in a gene in the plant.

In some instances, the CRISPR system is used to edit (e.g., to add or delete a base pair) a target gene in the plant. In other instances, the CRISPR system is used to introduce a premature stop codon, e.g., thereby decreasing the expression of a target gene. In yet other instances, the CRISPR system is used to turn off a target gene in a reversible manner, e.g., similarly to RNA interference. In some instances, the CRISPR system is used to direct Cas to a promoter of a gene, thereby blocking an RNA polymerase sterically.

In some instances, a CRISPR system can be generated to edit a gene in the plant, using technology described in, e.g., U.S. Publication No. 20140068797, Cong, *Science* 339: 819-823, 2013; Tsai, *Nature Biotechnol.* 32:6 569-576, 2014; U.S. Pat. Nos. 8,871,445; 8,865,406; 8,795,965; 8,771,945; and 8,697,359.

In some instances, the CRISPR interference (CRISPRi) technique can be used for transcriptional repression of specific genes in the plant. In CRISPRi, an engineered Cas9 protein (e.g., nuclease-null dCas9, or dCas9 fusion protein, e.g., dCas9-KRAB or dCas9-SID4X fusion) can pair with a sequence specific guide RNA (sgRNA). The Cas9-gRNA complex can block RNA polymerase, thereby interfering with transcription elongation. The complex can also block transcription initiation by interfering with transcription factor binding. The CRISPRi method is specific with minimal off-target effects and is multiplexable, e.g., can simultaneously repress more than one gene (e.g., using multiple gRNAs). Also, the CRISPRi method permits reversible gene repression.

In some instances, CRISPR-mediated gene activation (CRISPRa) can be used for transcriptional activation of a gene in the plant. In the CRISPRa technique, dCas9 fusion proteins recruit transcriptional activators. For example, dCas9 can be fused to polypeptides (e.g., activation domains) such as VP64 or the p65 activation domain (p65D) and used with sgRNA (e.g., a single sgRNA or multiple sgRNAs), to activate a gene or genes in the plant. Multiple activators can be recruited by using multiple sgRNAs—this can increase activation efficiency. A variety of activation domains and single or multiple activation domains can be used. In addition to engineering dCas9 to recruit activators, sgRNAs can also be engineered to recruit activators. For example, RNA aptamers can be incorporated into a sgRNA to recruit proteins (e.g., activation domains) such as VP64. In some examples, the synergistic activation mediator (SAM) system can be used for transcriptional activation. In SAM, MS2 aptamers are added to the sgRNA. MS2 recruits the MS2 coat protein (MCP) fused to p65AD and heat shock factor 1 (HSF1).

The CRISPRi and CRISPRa techniques are described in greater detail, e.g., in Dominguez et al., *Nat. Rev. Mol. Cell Biol.* 17:5-15, 2016, incorporated herein by reference. In addition, dCas9-mediated epigenetic modifications and simultaneous activation and repression using CRISPR systems, as described in Dominguez et al., can be used to modulate a gene in the plant.

V. Kits

The present invention also provides a kit for the modification of plants, where the kit includes a container having a plant modifying composition described herein. The kit may further include instructional material for applying or delivering (e.g., to a plant) the p plant modifying composition to modify a plant in accordance with a method of the present invention. The skilled artisan will appreciate that the instructions for applying the plant modifying composition in the methods of the present invention can be any form of instruction. Such instructions include, but are not limited to, written instruction material (such as, a label, a booklet, a pamphlet), oral instructional material (such as on an audio cassette or CD) or video instructions (such as on a video tape or DVD).

EXAMPLES

The following are examples of the methods of the invention. It is understood that various other embodiments may be practiced, given the general description provided above.

TABLE of Contents (Examples):

| | |
|---|---|
| Example 1. | Isolation of Plant Messenger Packs from Plants. |
| Example 2. | Production of purified Plant Messenger Packs (PMPs). |
| Example 3. | Plant Messenger Pack characterization. |
| Example 4. | Characterization of Plant Messenger Pack stability. |
| Example 5. | Loading PMPs with cargo. |
| Example 6. | Modification of a plant by PMP-mediated plasmid delivery in planta. |
| Example 7. | Modification of a plant by PMP-mediated short nucleic acid delivery. |
| Example 8. | Modification of a plant by PMP-mediated plasmid delivery to protoplasts. |
| Example 9. | PMP production from blended fruit juice using ultracentrifugation and sucrose gradient purification. |
| Example 10. | PMP production from mesh-pressed fruit juice using ultracentrifugation and sucrose gradient purification. |
| Example 11. | PMP production using Ultracentrifugation and Size Exclusion Chromatography. |
| Example 12. | Scaled PMP production using Tangential Flow Filtration and Size Exclusion Chromatography combined with EDTA/Dialysis to reduce contaminants. |
| Example 13. | PMP production from plant cell culture medium. |
| Example 14. | Uptake of PMPs by plant cells. |
| Example 15. | Uptake of PMPs in plants. |
| Example 16. | Treatment of Arabidopsis thaliana seedlings with DOX-loaded grapefruit PMPs. |
| Example 17. | Uptake of pectinase-treated PMPs by alfalfa sprouts. |
| Example 18. | Modification of PMPs using cationic lipids. |
| Example 19. | Modification of a plant by PMP-mediated gRNA delivery. |

Example 1: Isolation of Plant Messenger Packs from Plants

This example describes the isolation of crude plant messenger packs (PMPs) from various plant sources, including the leaf apoplast, seed apoplast, root, fruit, vegetable, pollen, phloem, xylem sap and plant cell culture medium.

Experimental Design:

a) PMP Isolation from the Apoplast of *Arabidopsis thaliana* Leaves

Arabidopsis (*Arabidopsis thaliana* Col-0) seeds are surface sterilized with 50% bleach and plated on 0.53 Murashige and Skoog medium containing 0.8% agar. The seeds are vernalized for 2 d at 4° C. before being moved to short-day conditions (9-h days, 22° C., 150 $\mu Em^{-2}$). After 1 week, the seedlings are transferred to Pro-Mix PGX. Plants are grown for 4-6 weeks before harvest.

PMPs are isolated from the apoplastic wash of 4-6-week old *Arabidopsis* rosettes, as described by Rutter and Innes, *Plant Physiol.* 173(1): 728-741, 2017. Briefly, whole rosettes are harvested at the root and vacuum infiltrated with vesicle isolation buffer (20 mM MES, 2 mM CaCl2), and 0.1 M NaCl, pH6). Infiltrated plants are carefully blotted to remove excess fluid, placed inside 30-mL syringes, and centrifuged in 50 mL conical tubes at 700 g for 20 min at 2° C. to collect the apoplast extracellular fluid containing EVs. Next, the apoplast extracellular fluid is filtered through a 0.85 μm filter to remove large particles, and PMPs are purified as described in Example 2.

b) PMP Isolation from the Apoplast of Sunflower Seeds

Intact sunflower seeds (*H. annuus* L.), and are imbibed in water for 2 hours, peeled to remove the pericarp, and the apoplastic extracellular fluid is extracted by a modified vacuum infiltration-centrifugation procedure, adapted from Regente et al, *FEBS Letters.* 583: 3363-3366, 2009. Briefly, seeds are immersed in vesicle isolation buffer (20 mM MES, 2 mM CaCl2), and 0.1 M NaCl, pH6) and subjected to three vacuum pulses of 10 s, separated by 30 s intervals at a pressure of 45 kPa. The infiltrated seeds are recovered, dried on filter paper, placed in fritted glass filters and centrifuged for 20 min at 400 g at 4° C. The apoplast extracellular fluid is recovered, filtered through a 0.85 μm filter to remove large particles, and PMPs are purified as described in Example 2.

c) PMP Isolation from Ginger Roots

Fresh ginger (*Zingiber officinale*) rhizome roots are purchased from a local supplier and washed 3× with PBS. A total of 200 grams of washed roots is ground in a mixer (Osterizer 12-speed blender) at the highest speed for 10 min (pause 1 min for every 1 min of blending), and PMPs are isolated as described in Zhuang et al., *J Extracellular Vesicles.* 4(1):28713, 2015. Briefly, ginger juice is sequentially centrifuged at 1,000 g for 10 min, 3,000 g for 20 min and 10,000 g for 40 min to remove large particles from the PMP-containing supernatant. PMPs are purified as described in Example 2.

d) PMP Isolation from Grapefruit Juice

Fresh grapefruits (*Citrus* x *paradisi*) are purchased from a local supplier, their skins are removed, and the fruit is manually pressed, or ground in a mixer (Osterizer 12-speed blender) at the highest speed for 10 min (pause 1 min for every minute of blending) to collect the juice, as described by Wang et al., *Molecular Therapy.* 22(3): 522-534, 2014 with minor modifications. Briefly, juice/juice pulp is sequentially centrifuged at 1,000 g for 10 min, 3,000 g for 20 min, and 10,000 g for 40 min to remove large particles from the PMP-containing supernatant. PMPs are purified as described in Example 2.

e) PMP Isolation from Broccoli Heads

Broccoli (*Brassica oleracea* var. *italica*) PMPs are isolated as previously described (Deng et al., *Molecular Therapy,* 25(7): 1641-1654, 2017). Briefly, fresh broccoli is purchased from a local supplier, washed three times with PBS, and ground in a mixer (Osterizer 12-speed blender) at the highest speed for 10 min (pause 1 min for every minute of blending). Broccoli juice is then sequentially centrifuged at 1,000 g for 10 min, 3,000 g for 20 min, and 10,000 g for 40 min to remove large particles from the PMP-containing supernatant. PMPs are purified as described in Example 2.

f) PMP Isolation from Olive Pollen

Olive (*Olea europaea*) pollen EVs are isolated as previously described in Prado et al., *Molecular Plant.* 7(3):573-577, 2014. Briefly, olive pollen (0.1 g) is hydrated in a humid chamber at room temperature for 30 min before transferring to petri dishes (15 cm in diameter) containing 20 ml germination medium: 10% sucrose, 0.03% $Ca(NO_3)_2$, 0.01% $KNO_3$, 0.02% $MgSO_4$, and 0.03% $H_3BO_3$. Pollen is germinated at 30° C. in the dark for 16 h. Pollen grains are considered germinated only when the tube is longer than the diameter of the pollen grain. Cultured medium containing PMPs is collected and cleared of pollen debris by two successive filtrations on 0.85 um filters by centrifugation. PMPs are purified as described in Example 2.

g) PMP Isolation from *Arabidopsis* Phloem Sap

Arabidopsis (*Arabidopsis thaliana* Col-0) seeds are surface sterilized with 50% bleach and plated on 0.53 Murashige and Skoog medium containing 0.8% agar. The seeds are vernalized for 2 d at 4° C. before being moved to short-day conditions (9-h days, 22° C., 150 $\mu Em^{-2}$). After 1 week, the seedlings are transferred to Pro-Mix PGX. Plants are grown for 4-6 weeks before harvest.

Phloem sap from 4-6-week old *Arabidopsis* rosette leaves is collected as described by Tetyuk et al., *JoVE*. 80, 2013. Briefly, leaves are cut at the base of the petiole, stacked, and placed in a reaction tube containing 20 mM K2-EDTA for one hour in the dark to prevent sealing of the wound. Leaves are gently removed from the container, washed thoroughly with distilled water to remove all EDTA, put in a clean tube, and phloem sap is collected for 5-8 hours in the dark. Leaves are discarded, phloem sap is filtered through a 0.85 pm filter to remove large particles, and PMPs are purified as described in Example 2.

h) PMP Isolation from Tomato Plant Xylem Sap

Tomato (*Solanum lycopersicum*) seeds are planted in a single pot in an organic-rich soil, such as Sunshine Mix (Sun Gro Horticulture, Agawam, MA) and maintained in a greenhouse between 22° C. and 28° C. About two weeks after germination, at the two true-leaf stage, the seedlings are transplanted individually into pots (10 cm diameter and 17 cm deep) filled with sterile sandy soil containing 90% sand and 10% organic mix. Plants are maintained in a greenhouse at 22-28° C. for four weeks.

Xylem sap from 4-week old tomato plants is collected as described by Kohlen et al., *Plant Physiology*. 155(2):974-987, 2011. Briefly, tomato plants are decapitated above the hypocotyl, and a plastic ring is placed around the stem. The accumulating xylem sap is collected for 90 min after decapitation. Xylem sap is filtered through a 0.85 µm filter to remove large particles, and PMPs are purified as described in Example 2.

i) PMP Isolation from Tobacco BY-2 Cell Culture Medium

Tobacco BY-2 (*Nicotiana tabacum* L cv. Bright Yellow 2) cells are cultured in the dark at 26° C., on a shaker at 180 rpm in MS (Murashige and Skoog, 1962) BY-2 cultivation medium (pH 5.8) comprised MS salts (Duchefa, Haarlem, Netherlands, at #M0221) supplemented with 30 g/L sucrose, 2.0 mg/L potassium dihydrogen phosphate, 0.1 g/L myo-inositol, 0.2 mg/L 2,4-dichlorophenoxyacetic acid, and 1 mg/L thiamine HCl. The BY-2 cells are subcultured weekly by transferring 5% (v/v) of a 7-day-old cell culture into 100 mL fresh liquid medium. After 72-96 hours, BY-2 cultured medium is collected and centrifuged at 300 g at 4° C. for 10 minutes to remove cells. The supernatant containing PMPs is collected and cleared of debris by filtration on 0.85 um filter. PMPs are purified as described in Example 2.

Example 2: Production of Purified Plant Messenger Packs (PMPs)

This example describes the production of purified PMPs from crude PMP fractions as described in Example 1, using ultrafiltration combined with size-exclusion chromatography, a density gradient (iodixanol or sucrose), and the removal of aggregates by precipitation or size-exclusion chromatography.

Experimental Design:

a) Production of Purified Grapefruit PMPs Using Ultrafiltration Combined with Size-Exclusion Chromatography The crude grapefruit PMP fraction from Example 1a is concentrated using 100-kDA molecular weight cut-off (MWCO) Amicon spin filter (Merck Millipore). Subsequently, the concentrated crude PMP solution is loaded onto a PURE-EV size exclusion chromatography column (HansaBioMed Life Sciences Ltd) and isolated according to the manufacturer's instructions. The purified PMP-containing fractions are pooled after elution. Optionally, PMPs can be further concentrated using a 100-kDa MWCO Amicon spin filter, or by Tangential Flow Filtration (TFF). The purified PMPs are analyzed as described in Example 3.

b) Production of Purified *Arabidopsis* Apoplast PMPs Using an Iodixanol Gradient Crude *Arabidopsis* leaf apoplast PMPs are isolated as described in Example 1a, and purified PMPs are produced by using an iodixanol gradient as described in Rutter and Innes, *Plant Physiol*. 173(1): 728-741, 2017. To prepare discontinuous iodixanol gradients (OptiPrep; Sigma-Aldrich), solutions of 40% (v/v), 20% (v/v), 10% (v/v), and 5% (v/v) iodixanol are created by diluting an aqueous 60% OptiPrep stock solution in vesicle isolation buffer (VIB; 20 mM MES, 2 mM CaCl2), and 0.1 M NaCl, pH6). The gradient is formed by layering 3 ml of 40% solution, 3 mL of 20% solution, 3 mL of 10% solution, and 2 mL of 5% solution. The crude apoplast PMP solution from Example 1a is centrifuged at 40,000 g for 60 min at 4° C. The pellet is resuspended in 0.5 ml of VIB and layered on top of the gradient. Centrifugation is performed at 100,000 g for 17 h at 4° C. The first 4.5 ml at the top of the gradient is discarded, and subsequently 3 volumes of 0.7 ml that contain the apoplast PMPs are collected, brought up to 3.5 mL with VIB and centrifuged at 100,000 g for 60 min at 4° C. The pellets are washed with 3.5 ml of VIB and repelleted using the same centrifugation conditions. The purified PMP pellets are combined for subsequent analysis, as described in Example 3.

c) Production of Purified Grapefruit PMPs Using a Sucrose Gradient

Crude grapefruit juice PMPs are isolated as described in Example 1d, centrifuged at 150,000 g for 90 min, and the PMP-containing pellet is resuspended in 1 ml PBS as described (Mu et al., *Molecular Nutrition & Food Research*. 58(7):1561-1573, 2014). The resuspended pellet is transferred to a sucrose step gradient (8%/15%/30%/45%/60%) and centrifuged at 150,000 g for 120 min to produce purified PMPs. Purified grapefruit PMPs are harvested from the 30%/45% interface, and subsequently analyzed, as described in Example 3.

d) Removal of Aggregates from Grapefruit PMPs

In order to remove protein aggregates from produced grapefruit PMPs as described in Example 1d or purified PMPs from Example 2a-c, an additional purification step can be included. The produced PMP solution is taken through a range of pHs to precipitate protein aggregates in solution. The pH is adjusted to 3, 5, 7, 9, or 11 with the addition of sodium hydroxide or hydrochloric acid. pH is measured using a calibrated pH probe. Once the solution is at the specified pH, it is filtered to remove particulates. Alternatively, the isolated PMP solution can be flocculated using the addition of charged polymers, such as Polymin-P or Praestol 2640. Briefly, 2-5 g per L of Polymin-P or Praestol 2640 is added to the solution and mixed with an impeller. The solution is then filtered to remove particulates. Alternatively, aggregates are solubilized by increasing salt concentration. NaCl is added to the PMP solution until it is at 1 mol/L. The solution is then filtered to purify the PMPs. Alternatively, aggregates are solubilized by increasing the temperature. The isolated PMP mixture is heated under mixing until it has reached a uniform temperature of 50° C. for 5 minutes. The PMP mixture is then filtered to isolate the PMPs. Alternatively, soluble contaminants from PMP solutions are separated by size-exclusion chromatography column according to standard procedures, where PMPs elute in the first fractions, whereas proteins and ribonucleoproteins and some lipoproteins are eluted later. The efficiency of protein aggregate removal is determined by measuring and comparing the protein concentration before and after removal of protein aggregates via BCA/Bradford protein quantification. The produced PMPs are analyzed as described in Example 3.

Example 3: Plant Messenger Pack Characterization

This example describes the characterization of PMPs produced as described in Example 1 or Example 2.
Experimental Design:
a) Determining PMP Concentration PMP particle concentration is determined by Nanoparticle Tracking Analysis (NTA) using a Malvern NanoSight, or by Tunable Resistive Pulse Sensing (TRPS) using an iZon qNano, following the manufacturer's instructions. The protein concentration of purified PMPs is determined by using the DC Protein assay (Bio-Rad). The lipid concentration of purified PMPs is determined using a fluorescent lipophilic dye, such as DiOC6 (ICN Biomedicals) as described by Rutter and Innes, *Plant Physiol.* 173(1): 728-741, 2017. Briefly, purified PMP pellets from Example 2 are resuspended in 100 ml of 10 mM DiOC6 (ICN Biomedicals) diluted with MES buffer (20 mM MES, pH 6) plus 1% plant protease inhibitor cocktail (Sigma-Aldrich) and 2 mM 2,29-dipyridyl disulfide. The resuspended PMPs are incubated at 37° C. for 10 min, washed with 3 mL of MES buffer, repelleted (40,000 g, 60 min, at 4° C.), and resuspended in fresh MES buffer. DiOC6 Fluorescence Intensity is Measured at 485 nm Excitation and 535 nm Emission.
b) Biophysical and molecular characterization of PMPs PMPs are characterized by electron and cryo-electron microscopy on a JEOL 1010 transmission electron microscope, following the protocol from Wu et al., *Analyst.* 140(2):386-406, 2015. The size and zeta potential of the PMPs are also measured using a Malvern Zetasizer or iZon qNano, following the manufacturer's instructions. Lipids are isolated from PMPs using chloroform extraction and characterized with LC-MS/MS as demonstrated in Xiao et al. *Plant Cell.* 22(10): 3193-3205, 2010. Glycosyl inositol phosphorylceramides (GIPCs) lipids are extracted and purified as described by Cacas et al., *Plant Physiology.* 170: 367-384, 2016, and analyzed by LC-MS/MS as described above. Total RNA, DNA, and protein are characterized using Quant-It kits from Thermo Fisher according to instructions. Proteins on the PMPs are characterized by LC-MS/MS following the protocol in Rutter and Innes, *Plant Physiol.* 173(1): 728-741, 2017. RNA and DNA are extracted using Trizol, prepared into libraries with the TruSeq Total RNA with Ribo-Zero Plant kit and the Nextera Mate Pair Library Prep Kit from Illumina, and sequenced on an Illumina MiSeq following manufacturer's instructions.

Example 4: Characterization of Plant Messenger Pack Stability

This example describes measuring the stability of PMPs under a wide variety of storage and physiological conditions.
Experimental Design:

PMPs produced as described in Examples 1 and 2 are subjected to various conditions. PMPs are suspended in water, 5% sucrose, or PBS and left for 1, 7, 30, and 180 days at −20° C., 4° C., 20° C., and 37° C. PMPs are also suspended in water and dried using a rotary evaporator system and left for 1, 7, and 30, and 180 days at 4° C., 20° C., and 37° C. PMPs are also suspended in water or 5% sucrose solution, flash-frozen in liquid nitrogen and lyophilized. After 1, 7, 30, and 180 days, dried and lyophilized PMPs are then resuspended in water. The previous three experiments with conditions at temperatures above 0° C. are also exposed to an artificial sunlight simulator in order to determine content stability in simulated outdoor UV conditions. PMPs are also subjected to temperatures of 37° C., 40° C., 45° C., 50° C., and 55° C. for 1, 6, and 24 hours in buffered solutions with a pH of 1, 3, 5, 7, and 9 with or without the addition of 1 unit of trypsin or in other simulated gastric fluids.

After each of these treatments, PMPs are bought back to 20° C., neutralized to pH 7.4, and characterized using some or all of the methods described in Example 3.

Example 5. Loading PMPs with Cargo

This example describes methods of loading PMPs with small molecules, proteins, and nucleic acids.
a) Loading Small Molecules into PMPs PMPs are produced as described in Example 1 and Example 2. To load small molecules into PMPs, PMPs are placed in PBS solution with the small molecule either in solid form or solubilized. The solution is left for 1 hour at 22 C, according to the protocol in Sun, Mol. Ther., 2010. Alternatively, the solution is sonicated to induce poration and diffusion into the exosomes according to the protocol from Wang et al, Nature Comm., 2013. Alternatively, PMPs are electroporated according to the protocol from Wahlgren et al, Nucl. Acids. Res. 2012.

Alternatively, PMP lipids are isolated by adding 3.75 ml 2:1 (v/v) MeOH:CHCl3 to 1 ml of PMPs in PBS and are vortexed. CHCl3 (1.25 ml) and ddH2O (1.25 ml) are added sequentially and vortexed. The mixture is then centrifuged at 2,000 r.p.m. for 10 min at 22° C. in glass tubes to separate the mixture into two phases (aqueous phase and organic phase). The organic phase sample containing the PMP lipids is dried by heating under nitrogen (2 psi). To produce small molecule-loaded PMPs, the isolated PMP lipids are mixed with the small molecule solution and passed through a lipid extruder according to the protocol from Haney et al, J Contr. Rel., 2015.

Before use, the loaded PMPs are purified using methods as described in Example 2 to remove unbound small molecules. Loaded PMPs are characterized as described in Example 3, and their stability is tested as described in Example 4.
b) Loading Proteins or Peptides into PMPs PMPs are produced as described in Example 1 and Example 2. To load proteins or peptides into PMPs, PMPs are placed in solution with the protein or peptide in PBS. If the protein or peptide is insoluble, pH is adjusted until it is soluble. If the protein or peptide is still insoluble, the insoluble protein or peptide is used. The solution is then sonicated to induce poration and diffusion into the PMPs according to the protocol from Wang et al, Nature Comm., 2013. Alternatively, PMPs are electroporated according to the protocol from Wahlgren et al, Nucl. Acids. Res. 2012.

Alternatively, PMP lipids are isolated by adding 3.75 ml 2:1 (v/v) MeOH:CHCl3 to 1 ml of PMPs in PBS and are vortexed. CHCl3 (1.25 ml) and ddH2O (1.25 ml) are added sequentially and vortexed. The mixture is then centrifuged at 2,000 r.p.m. for 10 min at 22° C. in glass tubes to separate the mixture into two phases (aqueous phase and organic phase). The organic phase sample containing the PMP lipids is dried by heating under nitrogen (2 psi). To produce small molecule-loaded PMPs, the isolated PMP lipids are mixed with the small molecule solution and passed through a lipid extruder according to the protocol from Haney et al, J Contr. Rel., 2015.

Before use, the loaded PMPs are purified using the methods as described in Example 2 to remove unbound peptides and protein. Loaded PMPs are characterized as described in Example 3, and their stability is tested as described in Example 4. To measure loading of the protein or peptide, the Pierce Quantitative Colorimetric Peptide Assay is used on a small sample of the loaded and unloaded PMPs.

c) Loading Nucleic Acids into PMPs

PMPs are produced as described in Example 1 and Example 2. To load nucleic acids into PMPs, PMPs are placed in solution with the nucleic acid in PBS. The solution is then sonicated to induce poration and diffusion into the PMPs according to the protocol from Wang et al, Nature Comm., 2013. Alternatively, PMPs are electroporated according to the protocol from Wahlgren et al, Nucl. Acids. Res. 2012.

Alternatively, PMP lipids are isolated by adding 3.75 ml 2:1 (v/v) MeOH:CHCl3 to 1 ml of PMPs in PBS and are vortexed. CHCl3 (1.25 ml) and ddH2O (1.25 ml) are added sequentially and vortexed. The mixture is then centrifuged at 2,000 r.p.m. for 10 min at 22° C. in glass tubes to separate the mixture into two phases (aqueous phase and organic phase). The organic phase sample containing the PMP lipids is dried by heating under nitrogen (2 psi). To produce small molecule-loaded PMPs, the isolated PMP lipids are mixed with the small molecule solution and passed through a lipid extruder according to the protocol from Haney et al, J Contr. Rel., 2015.

Before use, the PMPs are purified using the methods as described in Example 2 to remove unbound nucleic acids. Loaded PMPs are characterized as described in Example 3, and their stability is tested as described in Example 4. Nucleic acids that are loaded in the PMPs are quantified using either a Quant-It assay from Thermo Fisher following manufacturer's instructions, or fluorescence is quantified with a plate reader if the nucleic acids are fluorescently labeled.

Example 6: Modification of a Plant by PMP-Mediated Plasmid Delivery in Planta

This example describes the loading and functional delivery of plasmid-loaded PMPs in planta, to affect the fitness of a plant. This example further demonstrates that plasmid-loaded PMPs are stable and retain their activity over a range of processing and environmental conditions.

In this example, cotton is used as a model plant, grapefruit PMPs as model PMP, and the pCambia1303 GUSA:mGFP5 reporter expression vector is used as a model plasmid.

Therapeutic Design:

The grapefruit PMP solution is formulated with an equivalent dose of 0, 0.5 µg/ml, 1 µg/ml, 5 µg/ml, 10 µg/ml and 20 µg/ml of plasmid in sterile water.

Experimental Protocol:

Loading of Grapefruit PMPs with a GUSA:mGFPS Reporter Plasmid

PMPs are produced from grapefruit as described in Example 1 and Example 2. To show functional plasmid delivery by PMPs, grapefruit PMPs are loaded with the pCambia1303 reporter plasmid (12,361 bp; purchased from Marker Gene Technologies) that expresses fusion gusA: mgfp5 reporter genes driven by a double-enhancer version of the CaMV35S promoter and terminated by the CaMV35S polyA signal. Upon transcription, both GUSA and mGFP5 are transcribed and can be detected. pCambia1303 plasmid is loaded into PMP by methods described in Example 5.

Encapsulation of plasmid into PMPs is determined by PCR analysis. Total genomic DNA is isolated from the loaded-PMPs using standard procedures. For PCR analysis, 50 ng of total DNA is added to a 10 µl PCR containing 5 µl RedTaq Readymix (Sigma Aldrich) and 0.1 µM of each primer pair for the amplification of the mgfp5gene: 5'-AAG GAG AAG AAC TTT TCA CTG GAG-3' (SEQ ID NO: 7) and 5'-AGT TCA TCC ATG CCA TGT GTA-3' (SEQ ID NO: 8). PCR amplification is performed in a thermal cycler with an initial denaturation at 95° C. for 1 min, followed by 30 cycles at 95° C. for 1 min, 55° C. for 1 min, 68° C. for 1 min and a final extension of 68° C. for 10 min. PCR products are separated on a 1.0% agarose gel using electrophoresis and imaged. The gel is scored for the presence and intensity of the mgfp5 product (≈700 bp), compared to know quantities of the pCambia1303 plasmid. PMPs loaded with plasmid are formulated in water to a concentration that delivers an equivalent of a plasmid dose of 0, 0.5 µg/ml, 1 µg/ml, 5 µg/ml, 10 µg/ml and 20 µg/ml plasmid in sterile water, and an equivalent concentration of unloaded PMPs is used as a control. The stability of plasmid-loaded PMPs is measures as described in Example 4.

Functional Delivery of Grapefruit PMPs Loaded with a GUSA:mGFPS Reporter Plasmid in Cotton Plants Cotton seeds (*Gossypium hirsutum* and *Gossypium raimondii*) are obtained through the US National Plant Germplasm System. Sterilized seeds are wrapped in moist absorbent cotton, placed in Petri dishes and placed in a growth chamber at 25° C., 150 µE m$^{-2}$ S$^{-1}$ light intensity, with a 14 hour light/10 hour dark photoperiod for 3 days to germinate. The seedlings are grown in sterile culture vessels with Hoagland's nutrient solution (Sigma Aldrich) under long-day conditions (16/8 h light/dark photoperiod) with 26/20° C. day/night temperatures. After 4 days, seedlings with fully expanded cotyledons (before the first true leaf appeared) are used for PMP treatments.

Seven-day-old cotton seedlings are transferred onto 0.5× Murashige and Skoog (MS) mineral salts (Sigma Aldrich) with 1×MS vitamins (Sigma Aldrich) pH 5.6-5.8, with 0.8% (w/v) agarose and are treated with an effective dose of 0, 0.5 µg/ml, 1 µg/ml, 5 µg/ml, 10 µg/ml and 20 µg/ml plasmid in sterile water (ddH2O), and an equivalent concentration of unloaded PMPs is used as a control, by spraying the whole seedling with 1 ml solution per plant, with 3 plants per group. Alternatively, prior to PMP treatment the underside of cotyledons of cotton plant is punched with a 25 G needle without piercing through the cotyledons. The PMP solutions (for this application formulated in VIB medium (20 mM MES, 2 mM CaCl2), and 0.1 M NaCl, pH6) are hand infiltrated from the underside of cotyledons through the wounding sites using a 1 mL needleless syringe. Alternatively, 4 day-old seedlings are maintained under hydroponic growth conditions, and plasmid-loaded PMP formulations are added to the growth medium to determine root uptake by PMPs. All plants are transferred to a growth chamber and kept under long-day conditions (16 h/8 h light/dark photoperiod) with light intensity of 90 µmol m$^{-2}$ s$^{-1}$ and 26/20° C. day/night temperatures.

After 1, 2, 3, 5, 8 and 14 days, the expression of GFP and GUS is determined to assess the functional delivery of the plasmid-loaded PMPs into plant cells. Total protein is extracted from 100 mg fresh cotton leaves (methods) and plant protease inhibitors are added. Western blot for GFP (Abcam ab1218), is performed using an actin (Abcam ab197345) loading control. The relative GFP expression normalized to actin, is compared between the plasmid-loaded PMP treatments, formulations and controls. In addition, prior to protein isolation, cotton plants are examined for GFP expression by fluorescent microscopy (EVOS2 FL).

Histochemical localization of GUS activity in the plasmid-loaded PMP treated plants and controls is analyzed after incubating of the plants in X-gluc buffer (50 mM sodium phosphate buffer, pH 7.0, 10 mM EDTA, 0.1% Triton X-100, 0.5 mM potassium ferrocyanide and 2 mg/ml 5-bromo-4-chloro-3-indolyl glucuronide (X-gluc) at 37 C for 12 h. Bright field images are collected using a dissection microscope.

pCambia1303 plasmid-loaded grapefruit PMPs functionally deliver their cargo to plant cells, and successfully transcribe the reporter proteins encoded in the plasmid.

Example 7: Modification of a Plant by PMP-Mediated Short Nucleic Acid Delivery

This example describes the loading and functional delivery of short nucleic acids-loaded PMPs in planta, to affect the fitness of a plant. This example further demonstrates that short nucleic acid-loaded PMPs are stable and retain their activity over a range of processing and environmental conditions. In this example, cotton is used as a model plant, grapefruit PMPs as model PMP, and amiRNA against Cla1 is used as a model dsRNA.

Therapeutic Design:

The grapefruit PMP solution is formulated with an effective dose of 0 (negative control), 1, 5, 10 and 20 ng/µl dsRNA in sterile water.

Experimental Protocol:
Loading of Grapefruit PMPs with CLA1 dsRNA

To demonstrate cellular uptake by PMPs in planta, grapefruit PMPs are loaded with artificial miRNAs (amiRNAs, designed using P-SAMS (p-sama.carringtonlab.org)) or custom dicer substrate siRNA (DsiRNA, designed by IDT) targeting the cotton photosynthesis gene GrCLA1 (1-deoxy-D-xylulose-5-phosphate synthase). GrCLA1 is a homolog gene of *Arabidopsis* Cloroplastos alterados 1 gene (AtCLA1), which loss-of-function results in an albino phenotype on true leaves, providing a visual marker for silencing efficiency. Oligonucleotides are obtained from IDT.

PMPs are produced from grapefruit as described in Example 1 and Example 2. To determine the PMP uptake, grapefruit PMPs are loaded with GrCLA1-amiRNA or GrCLA1-DsiRNA duplexes (Table 1), as described in Example 5. amiRNA or DsiRNA encapsulation of PMPs is measured using the Quant-It RiboGreen RNA assay kit, or using a control fluorescent dye labeled amiRNA or DsiRNA (IDT). To determine the PMP effect of CLA1-amiRNA/DsiRNA-loaded PMPs versus unloaded PMPs, cotton seedlings are treated and analyzed for CLA1 gene silencing. PMPs loaded with amiRNA or DsiRNA (collectively referred to as dsRNA) are formulated in water to a concentration that delivers an equivalent of an effective dsRNA dose of 0, 1, 5, 10 and 20 ng/μl in sterile water, and an equivalent concentration of unloaded PMPs is delivered as control. The stability is the dsRNA-loaded PMPs is measures as described in Example 4.

Functional Delivery of Grapefruit PMPs Loaded with dsRNA Targeting CLA1 in Cotton Plants Cotton seeds (*Gossypium hirsutum* and *Gossypium raimondii*) are obtained through the US National Plant Germplasm System. Sterilized seeds are wrapped in moist absorbent cotton, placed in Petri dishes and placed in a growth chamber at 25° C., 150 μE $m^{-2}$ $S^{-1}$ light intensity, with a 14 hour light/10 hour dark photoperiod for 3 days to germinate. The seedlings are grown in sterile culture vessels with Hoagland's nutrient solution (Sigma Aldrich) under long-day conditions (16/8 h light/dark photoperiod) with 26/20° C. day/night temperatures. After 4 days, seedlings with fully expanded cotyledons (before the first true leaf appeared) are used for PMP treatments.

Seven-day-old cotton seedlings are transferred onto 0.5× Murashige and Skoog (MS) mineral salts (Sigma Aldrich) with 1×MS vitamins (Sigma Aldrich) pH 5.6-5.8, with 0.8% (w/v) agarose and are treated with an effective dose of 0 (ddH2O), 1, 5, 10 and 20 ng/μl GrCLA1 dsRNA-loaded PMPs and an equivalent PMP particle concentration of unmodified grapefruit PMPs by spraying the whole seedling, 1 ml solution per plant, with 3 plants per group. Alternatively, prior to PMP treatment the underside of cotyledons of cotton plant is punched with a 25 G needle without piercing through the cotyledons. The PMP solutions are hand infiltrated from the underside of cotyledons through the wounding sites using a 1 mL needleless syringe. Plants are transferred to a growth chamber and kept under long-day conditions (16 h/8 h light/dark photoperiod) with light intensity of 90 μmol $m^{-2}$ $s^{-1}$ and 26/20° C. day/night temperatures.

After 2, 5, 8 and 14 days, the gene silencing efficiency of the CLA1 dsRNA is examined by the expression level of endogenous CLA1 mRNA using quantitative reverse transcription polymerase chain reaction (qRT-PCR). Total RNA is extracted from 100 mg fresh cotton leaves using Trizol reagent according to the manufacturer's instructions (Invitrogen) and treated extensively with RNase-free DNase I (Promega). First-strand cDNA is synthesized from 2 μg total RNA with the SuperScript™ First-Strand Synthesis system (Invitrogen). To estimate the levels of CLA1 transcripts qRT-PCR is performed using SYBR Green Real-Time PCR Master Mix (Thermo Scientific) with primers: GrCLA1q1_F 5'-CCAGGTGGGGCTTATGCATC-3' (SEQ ID NO: 9), GrCLA1q1_R 5'-CCACACCAAGGCTTGAACCC-3' (SEQ ID NO: 10), and GrCLA1 q2_F 5'-GGCCGGATTCACGAAACGGT-3' (SEQ ID NO: 11), GrCLA1q2_R 5'-CGTCGAGATTGGCAGTTGGC-3' (SEQ ID NO: 12), and 18 s RNA_F 5'-TCTGCCCTATCAACTTTCGATGGTA-3' (SEQ ID NO: 13), 18 s RNA_R 5'-AATTTGCGCGCCTGCTGCCTTCCTT-3' (SEQ ID NO: 7), using the following program: (a) 95 C for 5 min; (b) 40 cycles of 94 C for 30 s, 55 C for 30 s; and 72 C for 30 s. The 18S rRNA gene is used as internal control to normalize the results. The CLA1 knock down efficiency in cotton after treatment with CLA1-dsRNA-loaded PMPs compared to unmodified PMPs and water controls is determined by calculating the ΔΔCt value, comparing the normalized CLA1 expression after treatment with dsRNA-loaded PMPs, with normalized CLA1 expression after treatment with unmodified PMPs.

Additionally, the gene silencing efficiency of CLA1 dsRNA is examined by phenotypic photobleaching analysis. Leaves of treated and untreated cotton plants are photographed and ImageJ software is used to determine the percentage gene silencing, which is reflected by white photobleaching on the leaf versus the control leaf green color. Three leaves per plants are assayed to quantify the effect of photobleaching, and the gene silencing efficiency of CLA1-dsRNA-loaded PMPs versus controls are assessed.

CLA1-dsRNA-loaded PMPs are functionally delivered in planta and induce CLA1 gene silencing and photobleaching phenotype compared to unmodified PMPs and water controls.

TABLE 1

GrCLA1-amiRNA and GrCLA1-DsiRNA

| Species | Gene name | Reference sequence | Type | Name | dsRNA (5'-3') | dsRNA* (5'-3') |
|---|---|---|---|---|---|---|
| Gossypium hirsutum | GhCLA1 | CotAD_74769_BGI-AD1_v1.0 | amiRNA | amiRNA_GhCL-1 | UGGCAACAAUAUUUUUGUCUC (SEQ ID NO: 15) | GACAAAAGAUUGUUGCCACA (SEQ ID NO: 16) |
| Gossypium hirsutum | GhCLA1 | CotAD_74769_BGI-AD1_v1.0 | amiRNA | amiRNA_GhCL-2 | UUAGUACCCUGCCUUUGCCAU (SEQ ID NO: 17) | GGCAAAGGAAGGGUACUAACA (SEQ ID NO: 18) |
| Gossypium hirsutum | GhCLA1 | CotAD_74769_BGI-AD1_v1.0 | amiRNA | amiRNA_GhCL-3 | UACUUCGUGUGACUUUGCCAC (SEQ ID NO: 19) | GGCAAAGUAACACGAAGUACA (SEQ ID NO: 20) |
| Gossypium raimondii | GrCLA1 | XM_012600276 | amiRNA | amiRNA_GrCL-1 | UGGCAACAAUAUUUUUGUCUC (SEQ ID NO: 21) | GACAAAAGAUUGUUGCCACA (SEQ ID NO: 22) |
| Gossypium raimondii | GrCLA1 | XM_012600276 | amiRNA | amiRNA_GrCL-2 | UCAGUACCCUGCCUUUGCCAU (SEQ ID NO: 23) | GGCAAAGGAAGGGUACUGACA (SEQ ID NO: 24) |
| Gossypium raimondii | GrCLA1 | XM_012600276 | amiRNA | amiRNA_GrCL-3 | UACUUCGUGUGACUUUGCCAC (SEQ ID NO: 25) | GGCAAAGUAACACGAAGUACA (SEQ ID NO: 26) |
| Gossypium hirsutum | GhCLA1 | GALV01059036 | amiRNA | amiRNA_GhCL-4 | UUAGUGGCCAUCAACAGGCCG (SEQ ID NO: 27) | GCCUGUUGCUGGCCACUAACA (SEQ ID NO: 28) |
| Gossypium hirsutum | GhCLA1 | GALV01059036 | amiRNA | amiRNA_GhCL-5 | UAUCGAUGUUAGUGGCCACCU (SEQ ID NO:29) | GUGGCCACGAACAUCGAUACA (SEQ ID NO: 30) |
| Gossypium hirsutum | GhCLA1 | GALV01059036 | amiRNA | amiRNA_GhCL-6 | UACCGGUACCCGUUGUUUCAC (SEQ ID NO: 31) | GAAACAACGGGUACCGGUACA (SEQ ID NO: 32) |
| Gossypium raimondii | GrCLA1 | XM_012600276 | DsiRNA | DsiRNA_GrCL-1 | CAGUCCACUUAGUAUCAUCAUCAAG (SEQ ID NO: 33) | CUUGAUGAUGAUACUAAGUGGACUGUG (SEQ ID NO: 34) |
| Gossypium raimondii | GrCLA1 | XM_012600276 | DsiRNA | DsiRNA_GrCL-2 | GUCCACUUAGUAUCAUCAUCAAGCA (SEQ ID NO: 35) | UGCUUGAUGAUGAUACUAAGUGGACUG (SEQ ID NO: 36) |
| Gossypium raimondii | GrCLA1 | XM_012600276 | DsiRNA | DsiRNA_GrCL-3 | AGUCCACUUAGUAUCAUCAUCAAGO (SEQ ID NO: 37) | GCUUGAUGAUGAUACUAAGUGGACUGU (SEQ ID NO: 38) |
| Gossypium raimondii | GrCLA1 | XM_012600276 | DsiRNA | DsiRNA_GrCL-4 | AAUCUUUCAUUGAUUGGAUAGCCTT (SEQ ID NO: 39) | AAGGCUAUCCAAUCAAUGAAAGAUUUA (SEQ ID NO: 40) |
| Gossypium raimondii | GrCLA1 | XM_012600276 | DsiRNA | DsiRNA_GrCL-5 | CAACAACCUUACGAGUAAUAUCACA (SEQ ID NO: 41) | UGUGAUAUUACUCGUAAGGUUGUGGG (SEQ ID NO: 42) |
| Gossypium hirsutum | GhCLA1 | GALV01059036 | DsiRNA | DsiRNA_GhCL-1 | CAUCGAUGAUUUAGUUUCUAUUCUC (SEQ ID NO: 43) | GAGAAUAGAAACUAAAUCAUCGAUGUU (SEQ ID NO: 44) |
| Gossypium hirsutum | GhCLA1 | GALV01059036 | DsiRNA | DsiRNA_GhCL-2 | UCGAUGAUUUAGUUUCUAUUCUCAA (SEQ ID NO: 45) | UUGAGAAUAGAAACUAAAUCAUCGAUG (SEQ ID NO: 46) |
| Gossypium hirsutum | GhCLA1 | GALV01059036 | DsiRNA | DsiRNA_GhCL-3 | AUCGAUGAUUUAGUUUCUAUUCUCA (SEQ ID NO: 47) | UGAGAAUAGAAACUAAAUCAUCGAUGU (SEQ ID NO: 48) |
| Gossypium hirsutum | GhCLA1 | GALV01059036 | DsiRNA | DsiRNA_GhCL-4 | CGAUGAUUUAGUUUCUAUUCUCAAA (SEQ ID NO: 49) | UUUGAGAAUAGAAACUAAAUCAUCGAU (SEQ ID NO: 50) |

TABLE 1-continued

GrCLA1-amiRNA and GrCLA1-DsiRNA

| Species | Gene name | Reference sequence | Type | Name | dsRNA (5'-3') | dsRNA* (5'-3') |
|---|---|---|---|---|---|---|
| Gossypium hirsutum | GhCLA1 | GALV010590 36 | DsiRNA | DsiRNA_GhCL-5 | GAUAUGAUUGUUAU UCUUAAUGACA (SEQ ID NO: 51) | UGUCAUUAAGAAUAAC AAUCAUAUCAG (SEQ ID NO: 52) |

Example 8: Modification of a Plant by PMP-Mediated Plasmid Delivery to Protoplasts This example describes the loading and functional delivery of plasmid-loaded PMPs to protoplasts, to affect the fitness of a plant. This example further demonstrates that plasmid-loaded PMPs are stable and retain their activity over a range of processing and environmental conditions.

In this example, soybean protoplasts are used as a model protoplast, BY-2 PMPs as model PMP, and the pCambia1303 GUSA:mGFP5 reporter expression vector is used as a model plasmid.

Therapeutic Design:

The BY-2 PMP solution is formulated with an equivalent dose of 0, 0.5 µg/ml, 1 µg/ml, 5 µg/ml, 10 µg/ml and 20 µg/ml of plasmid in sterile water.

Experimental Protocol:

Loading of BY-2 PMPs with a GUSA:mGFP5 Reporter Plasmid

PMPs are produced from the BY-2 cell line as described in Example 1 and Example 2. To show functional plasmid delivery by PMPs, BY-2 PMPs are loaded with the pCambia1303 reporter plasmid (12,361 bp; purchased from Marker Gene Technologies) that expresses fusion gusA: mgfp5 reporter genes driven by a double-enhancer version of the CaMV35S promoter and terminated by the CaMV35S polyA signal. Upon transcription, both GUSA and mGFP5 are transcribed and can be detected. pCambia1303 plasmid is loaded into PMP by methods described in Example 5.

Encapsulation of plasmid into PMPs is determined by PCR analysis. Total genomic DNA is isolated from the loaded-PMPs using standard procedures. For PCR analysis, 50 ng of total DNA is added to a 10 µl PCR containing 5 µl RedTaq Readymix (Sigma Aldrich) and 0.1 µM of each primer pair for the amplification of the mgfp5gene: 5'-AAG GAG AAG AAC TTT TCA CTG GAG-3' (SEQ ID NO: 7) and 5'-AGT TCA TCC ATG CCA TGT GTA-3' (SEQ ID NO: 8). PCR amplification is performed in a thermal cycler with an initial denaturation at 95° C. for 1 min, followed by 30 cycles at 95° C. for 1 min, 55° C. for 1 min, 68° C. for 1 min and a final extension of 68° C. for 10 min. PCR products are separated on a 1.0% agarose gel using electrophoresis and imaged. The gel is scored for the presence and intensity of the mgfp5 product (≈700 bp), compared to know quantities of the pCambia1303 plasmid. PMPs loaded with plasmid are formulated in water to a concentration that delivers an equivalent of a plasmid dose of 0, 0.5 µg/ml, 1 µg/ml, 5 µg/ml, 10 µg/ml and 20 µg/ml plasmid in sterile water, and an equivalent concentration of unloaded PMPs is used as a control. The stability of plasmid-loaded PMPs is measures as described in Example 4.

Isolation of Soybean Protoplasts

Soybean seeds (*Glycine max* (L.) Merr.) are obtained through the US National Plant Germplasm System. 5-10 soybean seeds (Williams 82) are sown in a 13 cm pot in a grow chamber under long-day conditions (16 h light at 1,500 µmol m$^{-2}$ s$^{-1}$) at 25 C on the custom soil mix for Soybean (the 1:1:1 ratio of soil, perlite and torpedo sand). Protoplasts are isolated as described by Wu and Hanzawa, 2018 *J. Vis. Exp.* (131), e57258. Briefly, newly expanded unifoliate leaves are cut from 10-day old soybean seedlings. With a fresh razor blade, the midrib is removed from the unifoliate leaf and the remains are cut into 0.5-1 mm strips. Using a pair of forceps, the leaf strips are transferred immediately and gently into 10 mL of freshly prepared enzyme solution (MES, pH 5.7 20 mM, 2% (w/v) Cellulase CELF, 0.1% (w/v) Pectolyase Y-23, 0.75M Mannitol, 0.2 mM CaCl2), 0.1% (w/v) BSA, 0.5 mM DTT) in a 15 mL tube. Vacuum infiltrate the leaf strips for 15 min at room temperature, and incubate the leaf strips in the enzyme solution with gentle agitation (40 rpm) under low light for 4-6 h at room temperature. 10 mL of enzyme/protoplast solution is transferred to a 50 mL tube by gently pouring and 10 mL of W5 solution (2 mM MES pH 5.7, 154 mM NaCl, 125 mM CaCl2), 5 mM KCl) is added at room temperature to stop the digestion. The enzyme/protoplasts solution is poured on a clean 75 µm nylon mesh placed on top of a 50 mL tube to remove the undigested leaf tissues. The flow-through enzyme/protoplasts solution is centrifuged at 100×g in the 50 mL tube for 1-2 min at room temperature and the supernatant is removed without disturbing the protoplast pellet. Resuspended protoplasts are diluted to a concentration of 2×10$^5$ cells/ml in chilled W5 solution at 4° C. by counting protoplast number on a hemacytometer. After washing, protoplasts are resuspended in MMG solution (4 mM MES pH 5.7, 400 mM Mannitol, 15 mM MgCl2) at a concentration of 2×10$^5$ cells/ml at room temperature.

Functional Delivery of BY-2 PMPs Loaded with a GUSA: mGFP5 Reporter Plasmid in Soybean Protoplasts 100 µL of protoplasts containing 2×10$^4$ protoplasts at 2×10$^5$ cells/mL) are transferred to a 24-well flat bottom plate. Protoplasts are treated with an effective dose of 0, 0.5 µg/ml, 1 µg/ml, 5 µg/ml, 10 µg/ml and 20 µg/ml plasmid in sterile water (ddH2O), and an equivalent concentration of unloaded PMPs is used as a control. If more than 100 ul PMP solution need to be added, PMPs are formulated in MMG solution and seeded in triplicate per time point.

After 2 hrs, 4 hrs, 6 hrs, 1 d, 2 d, and 3 d, the expression of GFP and GUS is determined to assess the functional delivery of the plasmid-loaded PMPs into soybean protoplasts. Samples are washed 5×10 minutes with medium as described above. Total protein is extracted from one whole well of treated protoplasts and western blot is performed for GFP (Abcam ab1218), using an actin (Abcam ab197345) loading control. The relative GFP expression normalized to actin, is compared between the plasmid-loaded PMP treatments, formulations and controls.

In addition, 10 µL of washed protoplasts are put onto a glass slide and examined for GFP expression by fluorescent microscopy (EVOS2 FL).

Histochemical localization of GUS activity in the plasmid-loaded PMP treated protoplasts and controls is analyzed after incubating of the protoplasts in X-gluc buffer (50 mM sodium phosphate buffer, pH 7.0, 10 mM EDTA, 0.1% Triton X-100, 0.5 mM potassium ferrocyanide and 2 mg/ml 5-bromo-4-chloro-3-indolyl glucuronide (X-gluc) at 37 C for 12 h. Bright field images are collected using an EVOS2 FL. pCambia1303 plasmid-loaded BY-2 PMPs functionally deliver their cargo to protoplasts, and successfully transcribe the reporter proteins encoded in the plasmid.

Example 9: PMP Production from Blended Fruit Juice Using Ultracentrifugation and Sucrose Gradient Purification This example describes production of PMPs from fruit by blending the fruit and using a combination of sequential centrifugation to remove debris, ultracentrifugation to pellet crude PMPs, and using a sucrose density gradient to purify PMPs. In this example, grapefruit was used as a model fruit.
a) Production of Grapefruit PMPs by Ultracentrifugation and Sucrose Density Gradient Purification A workflow for grapefruit PMP production using a blender, ultracentrifugation and sucrose gradient purification is shown in FIG. 1A. One red grapefruit was purchased from a local Whole Foods Market®, and the albedo, flavedo, and segment membranes were removed to collect juice sacs, which were homogenized using a blender at maximum speed for 10 minutes. One hundred mL juice was diluted 5× with PBS, followed by subsequent centrifugation at 1000×g for 10 minutes, 3000×g for 20 minutes, and 10,000×g for 40 minutes to remove large debris. 28 mL of cleared juice was ultracentrifuged on a Sorvall™ MX 120 Plus Micro-Ultracentrifuge at 150,000×g for 90 minutes at 4° C. using a S50-ST (4×7 mL) swing bucket rotor to obtain a crude PMP pellet which was resuspended in PBS pH 7.4. Next, a sucrose gradient was prepared in Tris-HCL pH7.2, crude PMPs were layered on top of the sucrose gradient (from top to bottom: 8, 15. 30. 45 and 60% sucrose), and spun down by ultracentrifugation at 150,000×g for 120 minutes at 4° C. using a S50-ST (4×7 mL) swing bucket rotor. One mL fractions were collected and PMPs were isolated at the 30-45% interface. The fractions were washed with PBS by ultracentrifugation at 150,000×g for 120 minutes at 4° C. and pellets were dissolved in a minimal amount of PBS.

Figure 1B:
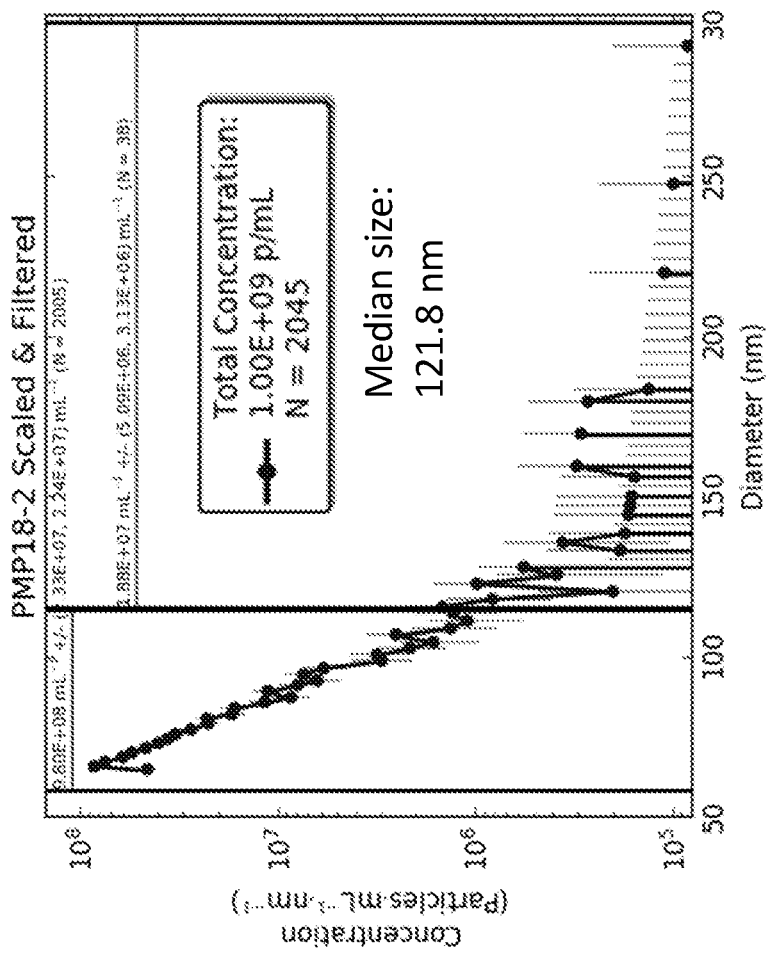
FIG. 1B is a plot of the PMP particle distribution measured by the Spectradyne NCS1.

PMP concentration (1×10$^9$ PMPs/mL) and median PMP size (121.8 nm) were determined using a Spectradyne nCS1™ particle analyzer, using a TS-400 cartridge (FIG. 1B). The zeta potential was determined using a Malvern Zetasizer Ultra and was −11.5+/−0.357 mV.

This example demonstrates that grapefruit PMPs can be isolated using ultracentrifugation combined with sucrose gradient purification methods. However, this method induced severe gelling of the samples at all PMP production steps and in the final PMP solution.

Figure 2:
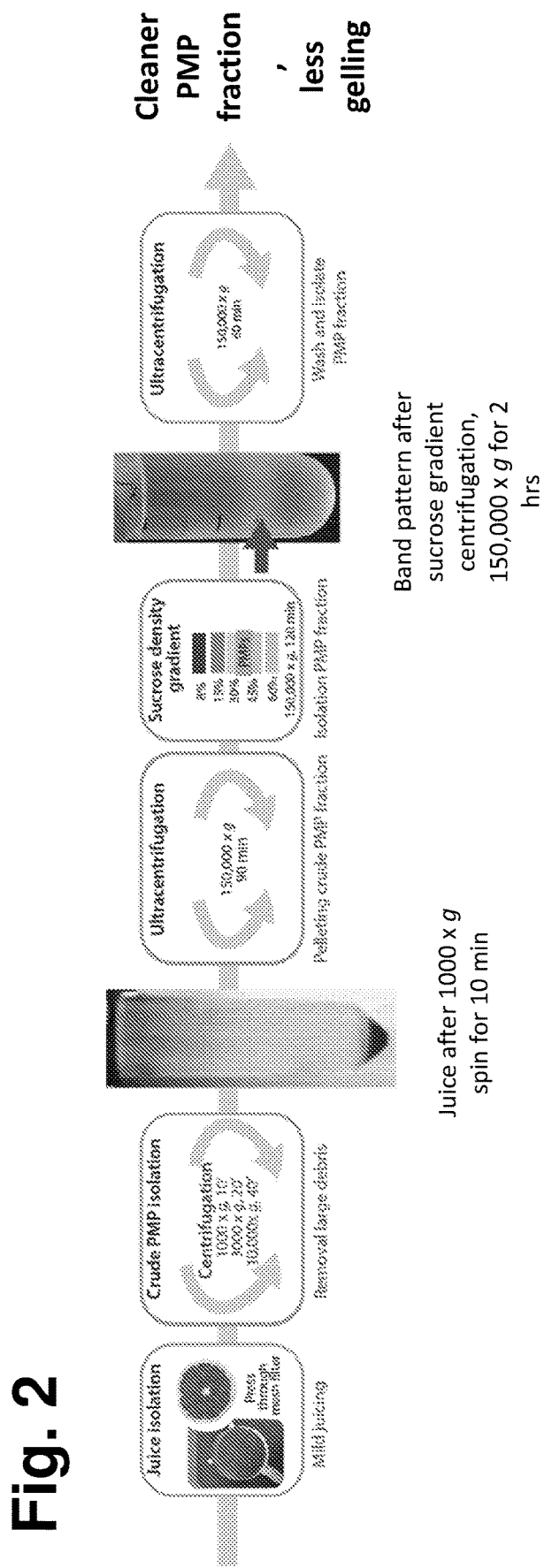
FIG. 2 is a schematic diagram showing a protocol for grapefruit PMP production using a mild juicing step involving use of a mesh filter, followed by ultracentrifugation and sucrose gradient purification. Images are included of the grapefruit juice after centrifugation at 1000×g for 10 min and the sucrose gradient band pattern after ultracentrifugation at 150,000×g for 2 hours.

Example 10: PMP Production from Mesh-Pressed Fruit Juice Using Ultracentrifugation and Sucrose Gradient Purification This example describes reduction of cell wall and cell membrane contaminants during the PMP production process by using a milder juicing process (mesh strainer). In this example, grapefruit was used as a model fruit.
a) Mild Juicing Reduces Gelling During PMP Production from Grapefruit PMPs Juice sacs were isolated from a red grapefruit as described in Example 9. To reduce gelling during PMP production, instead of using a destructive blending method, juice sacs were gently pressed against a tea strainer mesh to collect the juice and to reduce cell wall and cell membrane contaminants. After differential centrifugation, the juice was more clear than after using a blender, and one clean PMP-containing sucrose band at the 30-45% intersection was observed after sucrose density gradient centrifugation (FIG. 2). There was overall less gelling during and after PMP production.

Our data shows that use of a mild juicing step reduces gelling caused by contaminants during PMP production when compared to a method comprising blending.

Figure 3A:
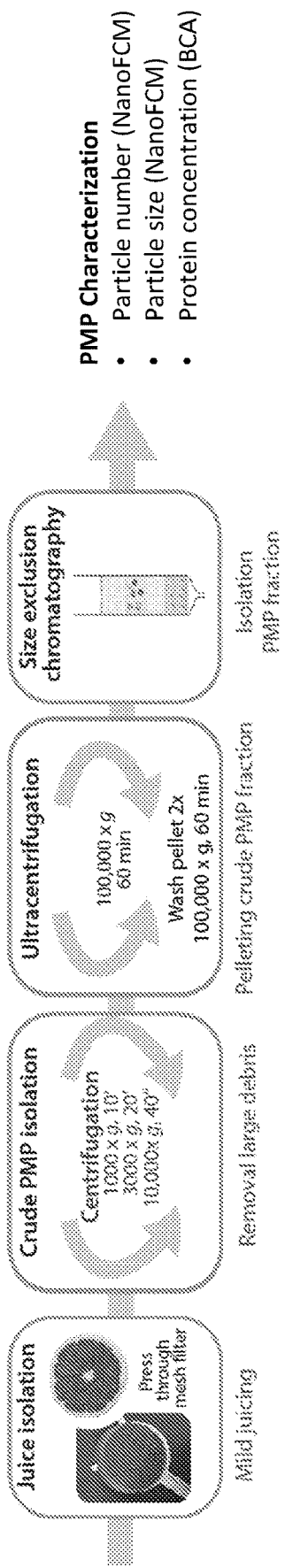
FIG. 3A is a schematic diagram showing a protocol for grapefruit PMP production using ultracentrifugation, followed by size exclusion chromatography (SEC) to isolate the PMP-containing fractions. The eluted SEC fractions are analyzed for particle concentration (NanoFCM), median particle size (NanoFCM), and protein concentration (BCA).
Figure 3B:
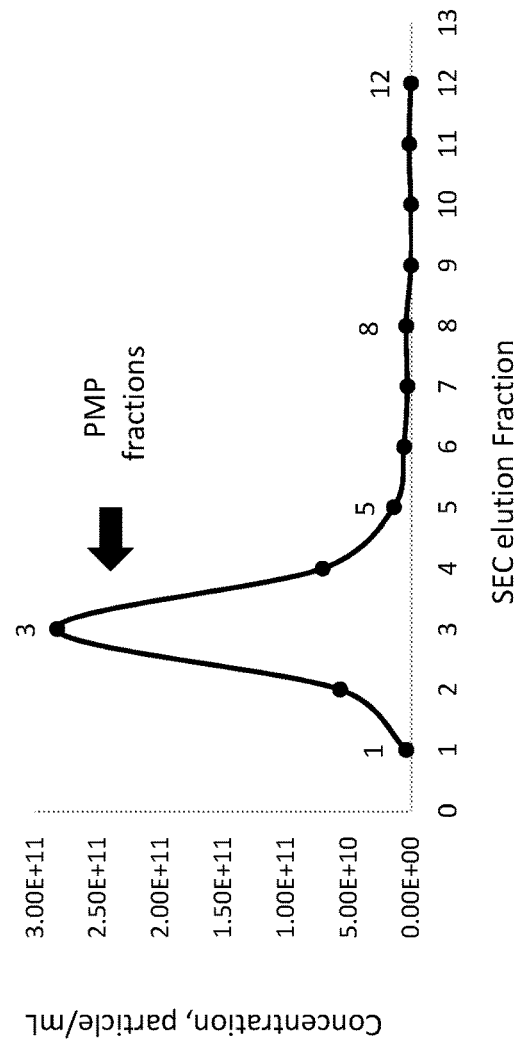
FIG. 3B is a graph showing particle concentration per mL in eluted size exclusion chromatography (SEC) fractions (NanoFCM). The fractions containing the majority of PMPs ("PMP fraction") are indicated with an arrow. PMPs are eluted in fractions 2-4.

Example 11: PMP Production Using Ultracentrifugation and Size Exclusion Chromatography This example describes the production of PMPs from fruits by using Ultracentrifugation (UC) and Size Exclusion Chromatography (SEC). In this example, grapefruit is used as a model fruit.
a) Production of Grapefruit PMPs Using UC and SEC Juice sacs were isolated from a red grapefruit, as described in Example 9a, and were gently pressed against a tea strainer mesh to collect 28 ml juice. The workflow for grapefruit PMP production using UC and SEC is depicted in FIG. 3A. Briefly, juice was subjected to differential centrifugation at 1000×g for 10 minutes, 3000×g for 20 minutes, and 10,000×g for 40 minutes to remove large debris. 28 ml of cleared juice was ultracentrifuged on a Sorvall™ MX 120 Plus Micro-Ultracentrifuge at 100,000×g for 60 minutes at 4° C. using a S50-ST (4×7 mL) swing bucket rotor to obtain a crude PMP pellet which was resuspended in MES buffer (20 mM MES, NaCl, pH 6). After washing the pellets twice with MES buffer, the final pellet was resuspended in 1 ml PBS, pH 7.4. Next, we used size exclusion chromatography to elute the PMP-containing fractions. SEC elution fractions were analyzed by nano-flow cytometry using a NanoFCM to determine PMP size and concentration using concentration and size standards provided by the manufacturer. In addition, absorbance at 280 nm (SpectraMax®) and protein concentration (Pierce™ BCA assay, ThermoFisher) were determined on SEC fractions to identify in which fractions PMPs are eluted (FIGS. 3B-3D). SEC fractions 2-4 were identified as the PMP-containing fractions. Analysis of earlier- and later-eluting fractions indicated that SEC fraction 3 is the main PMP-containing fraction, with a concentration of 2.83×10$^{11}$ PMPs/mL (57.2% of all particles in the 50-120 nm size range), with a median size of 83.6 nm+/−14.2 nm (SD). While the late elution fractions 8-13 had a very low concentration of particles as shown by NanoFCM, protein contaminants were detected in these fractions by BCA analysis.

Our data shows that TFF and SEC can be used to isolate purified PMPs from late-eluting contaminants, and that a combination of the analysis methods used here can identify PMP fractions from late-eluting contaminants.

Example 12: Scaled PMP Production Using Tangential Flow Filtration and Size Exclusion Chromatography Combined with EDTA/Dialysis to Reduce Contaminants This example describes the scaled production of PMPs from fruits by using Tangential Flow Filtration (TFF) and Size Exclusion Chromatography (SEC), combined with an EDTA incubation to reduce the formation of pectin macromolecules, and overnight dialysis to reduce contaminants. In this example, grapefruit is used as a model fruit.

a) Production of Grapefruit PMPs Using TFF and SEC

Figure 4A:
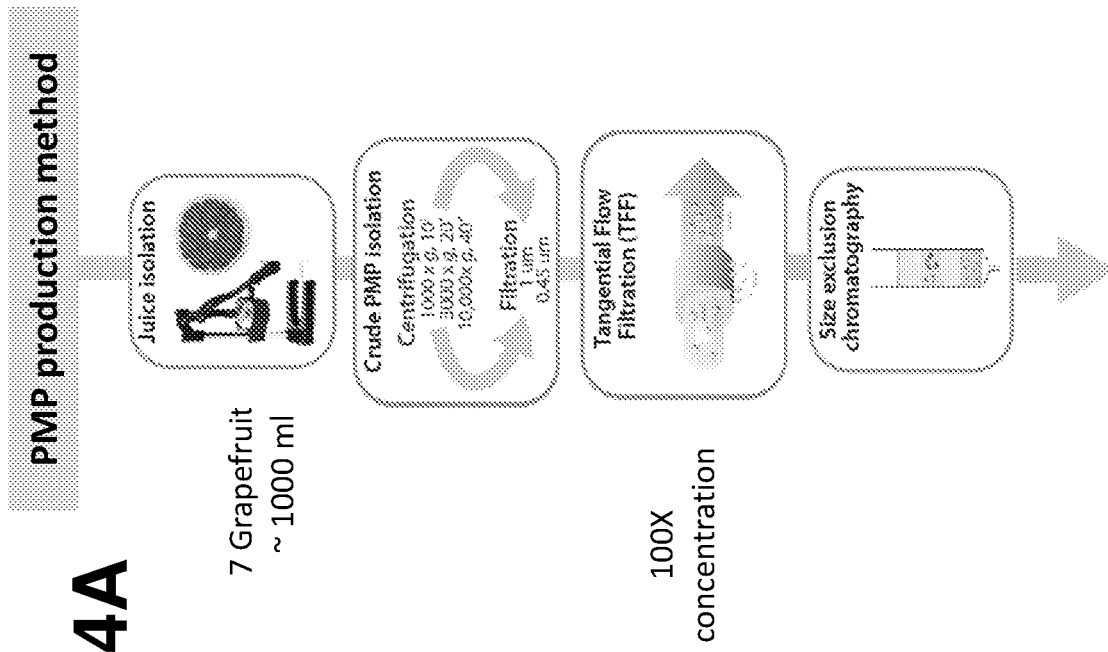
FIG. 4A is a schematic diagram showing a protocol for scaled PMP production from 1 liter of grapefruit juice (~7 grapefruits) using a juice press, followed by differential centrifugation to remove large debris, 100× concentration of the juice using TFF, and size exclusion chromatography (SEC) to isolate the PMP containing fractions. The SEC elution fractions are analyzed for particle concentration (NanoFCM), median particle size (NanoFCM) and protein concentration (BCA).
Figure 4B:
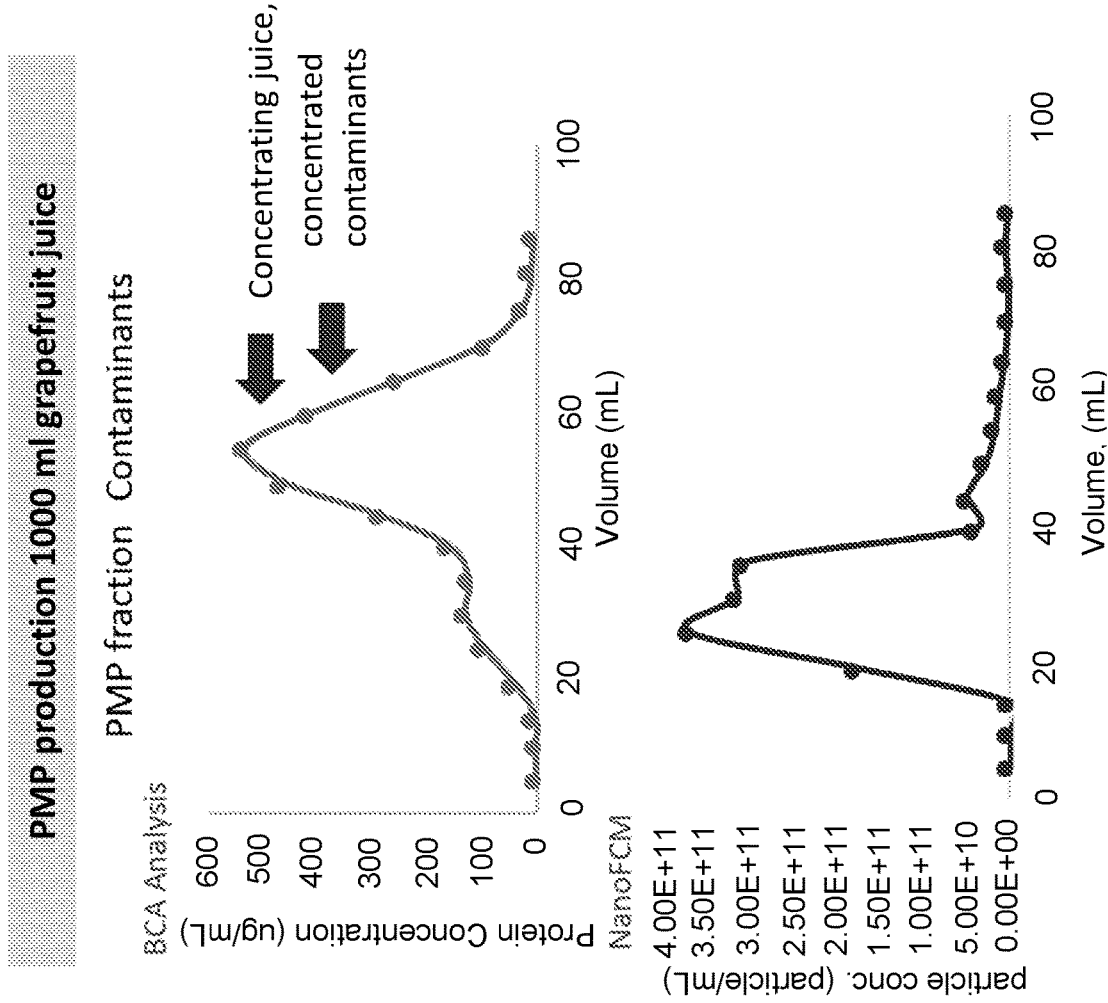
FIG. 4B is a pair of graphs showing protein concentration (BCA assay, top panel) and particle concentration (NanoFCM, bottom panel) of SEC eluate volume (ml) from a scaled starting material of 1000 ml of grapefruit juice, showing a high amount of contaminants in the late SEC elution volumes.

Red grapefruits were obtained from a local Whole Foods Market®, and 1000 ml juice was isolated using a juice press. The workflow for grapefruit PMP production using TFF and SEC is depicted in FIG. 4A. Juice was subjected to differential centrifugation at 1000×g for 10 minutes, 3000×g for 20 minutes, and 10,000×g for 40 minutes to remove large debris. Cleared grapefruit juice was concentrated and washed once using a TFF (5 nm pore size) to 2 mL (100×). Next, we used size exclusion chromatography to elute the PMP-containing fractions. SEC elution fractions were analyzed by nano-flow cytometry using a NanoFCM to determine PMP concentration using concentration and size standards provided by the manufacturer. In addition, protein concentration (Pierce™ BCA assay, ThermoFisher) was determined for SEC fractions to identify the fractions in which PMPs are eluted. The scaled production from 1 liter of juice (100× concentrated) also concentrated a high amount of contaminants in the late SEC fractions as can be detected by BCA assay (FIG. 4B, top panel). The overall total PMP yield (FIG. 4B, bottom panel) was lower in the scaled production when compared to single grapefruit isolations, which may indicate loss of PMPs.

b) Reducing Contaminants by EDTA Incubation and Dialysis

Figure 4C:
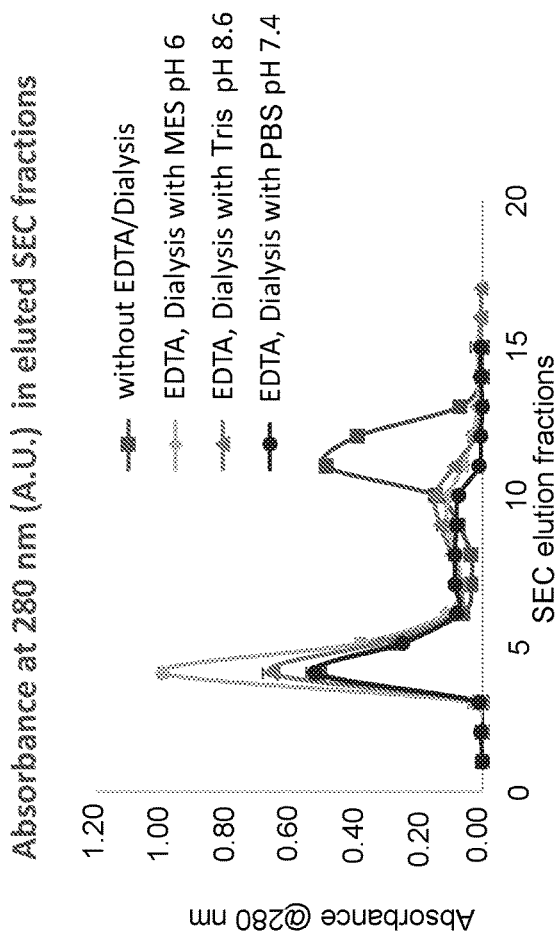
FIG. 4C is a graph showing that incubation of the crude grapefruit PMP fraction with a final concentration of 50 mM EDTA, pH 7.15 followed by overnight dialysis using a 300 kDa membrane, successfully removed contaminants present in the late SEC elution fractions, as shown by absorbance at 280 nm. There was no difference in the dialysis buffers used (PBS without calcium/magnesium pH 7.4, MES pH 6, Tris pH 8.6).
Figure 4D:
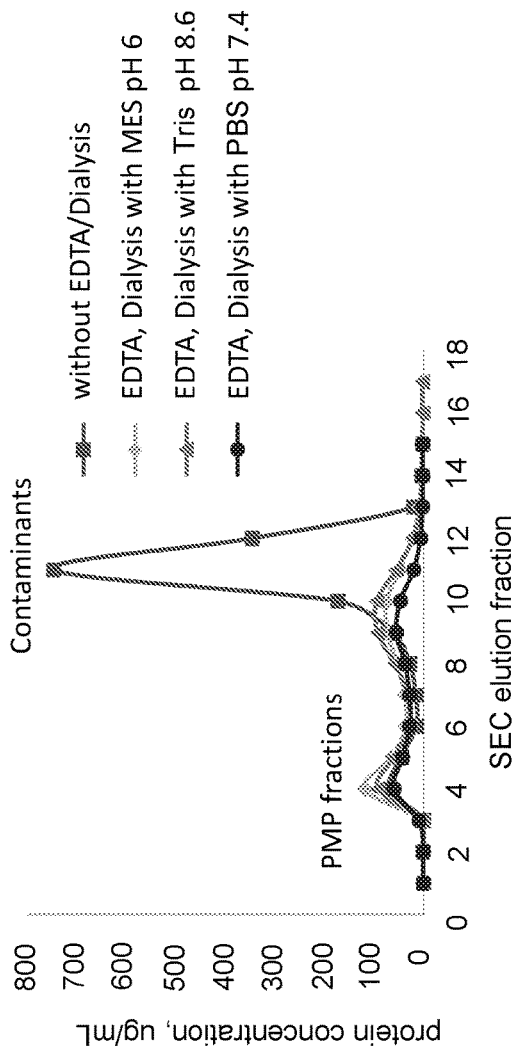
FIG. 4D is a graph showing that incubation of the crude grapefruit PMP fraction with a final concentration of 50 mM EDTA, pH 7.15, followed by overnight dialysis using a 300 kDa membrane, successfully removed contaminants present in the late elution fractions after SEC, as shown by BCA protein analysis, which, besides detecting protein, is sensitive to the presence of sugars and pectins. There was no difference in the dialysis buffers used (PBS without calcium/magnesium pH 7.4, MES pH 6, Tris pH 8.6).

Red grapefruits were obtained from a local Whole Foods Market®, and 800 ml juice was isolated using a juice press. Juice was subjected to differential centrifugation at 1000×g for 10 minutes, 3000×g for 20 minutes, and 10,000×g for 40 minutes to remove large debris, and filtered through a 1 μm and 0.45 μm filter to remove large particles. Cleared grapefruit juice was split into 4 different treatment groups containing 125 ml juice each. Treatment Group 1 was processed as described in Example 12a, concentrated and washed (PBS) to a final concentration of 63×, and subjected to SEC. Prior to TFF, 475 ml juice was incubated with a final concentration of 50 mM EDTA, pH 7.15 for 1.5 hrs at RT to chelate iron and reduce the formation of pectin macromolecules. Afterwards, juice was split in three treatment groups that underwent TFF concentration with either a PBS (without calcium/magnesium) pH 7.4, MES pH 6, or Tris pH 8.6 wash to a final juice concentration of 63×. Next, samples were dialyzed in the same wash buffer overnight at 4° C. using a 300 kDa membrane and subjected to SEC. Compared to the high contaminant peak in the late elution fractions of the TFF only control, EDTA incubation followed by overnight dialysis strongly reduced contaminants, as shown by absorbance at 280 nm (FIG. 4C) and BCA protein analysis (FIG. 4D), which is sensitive to the presence of sugars and pectins. There was no difference in the dialysis buffers used (PBS without calcium/magnesium pH 7.4, MES pH 6, Tris pH 8.6).

Our data indicates that incubation with EDTA followed by dialysis reduces the amount of co-purified contaminants, facilitating scaled PMP production.

Example 13: PMP Production from Plant Cell Culture Medium

This example describes the production of PMPs from plant cell culture. In this example, the *Zea mays* Black Mexican Sweet (BMS) cell line is used as a model plant cell line.

a) Production of *Zea mays* BMS Cell Line PMPs

The *Zea mays* Black Mexican sweet (BMS) cell line was purchased from the ABRC and was grown in Murashige and Skoog basal medium pH 5.8, containing 4.3 g/L Murashige and Skoog Basal Salt Mixture (Sigma M5524), 2% sucrose (S0389, Millipore Sigma), 1×MS vitamin solution (M3900, Millipore Sigma), 2 mg/L 2,4-dichlorophenoxyacetic acid (D7299, Millipore Sigma) and 250 ug/L thiamine HCL (V-014, Millipore Sigma), at 24° C. with agitation (110 rpm), and was passaged 20% volume/volume every 7 days.

Figure 5D:
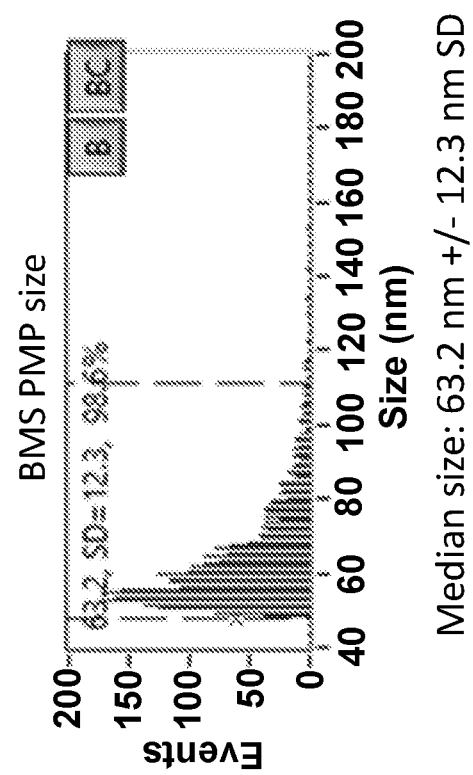
FIG. 5D is a scatter plot showing particles in the combined BMS PMP-containing SEC fractions as measured by nano-flow cytometry (NanoFCM). PMP concentration (particles/ml) was determined using a bead standard according to NanoFCM's instructions.
Figure 5E:
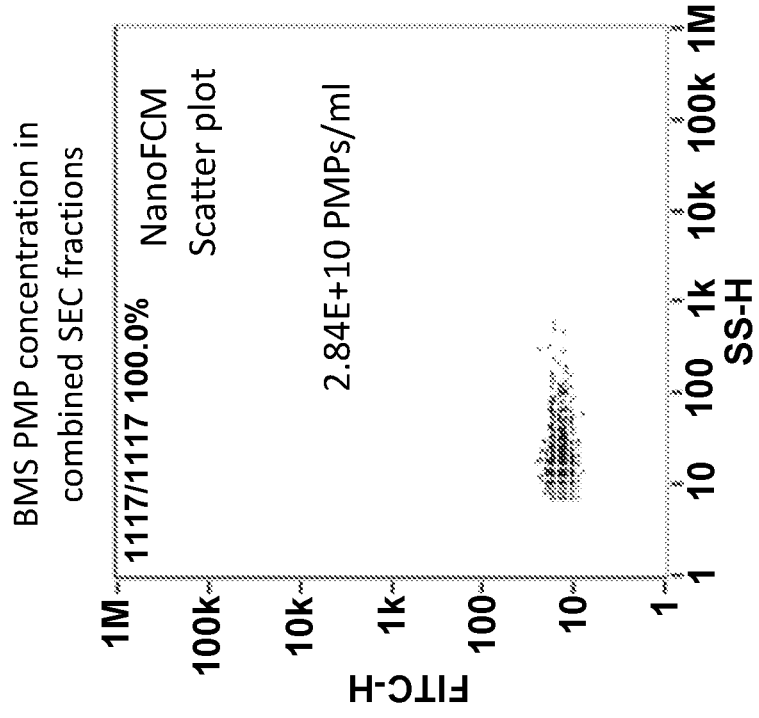
FIG. 5E is a graph showing the size distribution of BMS PMPs (nm) for the gated particles (background subtracted) of FIG. 5D. Median PMP size (nm) was determined using Exo bead standards according to NanoFCM's instructions.

Three days after passaging, 160 ml BMS cells was collected and spun down at 500×g for 5 min to remove cells, and 10,000×g for 40 min to remove large debris. Medium was passed through a 0.45 am filter to remove large particles, and filtered medium was concentrated and washed (100 ml MES buffer, 20 mM MES, 100 mM NaCL, pH 6) by TFF (5 nm pore size) to 4 mL (40×). Next, we used size exclusion chromatography to elute the PMP-containing fractions, which were analyzed by NanoFCM for PMP concentration, by absorbance at 280 nm (SpectraMax®), and by a protein concentration assay (Pierce™ BCA assay, ThermoFisher) to verify the PMP-containing fractions and late fractions containing contaminants (FIGS. 5A-5C). SEC fractions 4-6 contained purified PMPs (fractions 9-13 contained contaminants), and were pooled together. The final PMP concentration ($2.84\times10^{10}$ PMPs/ml) and median PMP size (63.2 nm+/−12.3 nm SD) in the combined PMP containing fractions were determined by NanoFCM, using concentration and size standards provided by the manufacturer (FIGS. 5D-5E).

These data show that PMPs can be isolated, purified, and concentrated from plant liquid culture media.

Example 14: Uptake of PMPs by Plant Cells

This example describes the ability of PMPs to associate with and be taken up by plant cells. In this example, lemon PMPs are used as a model PMP, and soy, wheat and corn cell lines are used as model plant cells.

a) Production of Grapefruit PMPs Using TFF Combined with SEC

Red organic grapefruits (Florida) were obtained from a local Whole Foods Market®. One liter of grapefruit juice was collected using a juice press, and was subsequently centrifuged at 3000×g for 20 minutes, followed by 10,000×g for 40 minutes to remove large debris. Next, 500 mM EDTA pH 8.6 was added to a final concentration of 50 mM EDTA, pH 7, and the solution was incubated for 30 minutes to chelate calcium and prevent the formation of pectin macromolecules. Subsequently the juice was passaged through 11 μm, 1 μm and 0.45 μm filters to remove large particles. Filtered juice was concentrated and washed (500 ml PBS) by Tangential Flow Filtration (TFF) (pore size 5 nm) to 400 ml (2.5×) and dialyzed overnight in PBS pH 7.4 (with one medium exchange) using a 300 kDa dialysis membrane to remove contaminants. Subsequently, the dialyzed juice was further concentrated by TFF to a final concentration of 50 ml (20×). Next, we used size exclusion chromatography to elute the PMP-containing fractions, which were analyzed by absorbance at 280 nm (SpectraMax®) and a protein concentration assay (Pierce™ BCA assay, ThermoFisher) to verify the PMP-containing fractions and late fractions containing contaminants. SEC fractions 4-6 contained purified PMPs (fractions 8-14 contained contaminants), were pooled together, and were filter sterilized by sequential filtration using 0.8 μm, 0.45 μm and 0.22 μm syringe filters. The final PMP concentration ($1.32\times10^{11}$ PMPs/mL) and median PMP size (71.9 nm+/−14.5 nm) in the combined sterilized PMP-containing fractions were determined by NanoFCM using concentration and size standards provided by the manufacturer.

b) Production of Lemon PMPs Using TFF Combined with SEC

Lemons were obtained from a local Whole Foods Market®. One liter of lemon juice was collected using a juice press, and was subsequently centrifuged at 3000 g for 20 minutes, followed by 10,000 g for 40 minutes to remove large debris. Next, 500 mM EDTA pH 8.6 was added to a final concentration of 50 mM EDTA, pH 7, and the solution was incubated for 30 minutes to chelate calcium and prevent the formation of pectin macromolecules. Subsequently the juice was passaged through a coffee filter, 1 μm and 0.45 μm filters to remove large particles. Filtered juice was concentrated by Tangential Flow Filtration (TFF) (5 nm pore size) to 400 ml (2.5× concentrated) and dialyzed overnight in PBS pH 7.4 using a 300 kDa dialysis membrane to remove contaminants. Subsequently, the dialyzed juice was further concentrated by TFF to a final concentration of 50 ml (20×). Next, we used size exclusion chromatography to elute the PMP-containing fractions, which were analyzed by absorbance at 280 nm (SpectraMax®) and a protein concentration assay (Pierce™ BCA assay, ThermoFisher) to verify the PMP-containing fractions and late fractions containing contaminants. SEC fractions 4-6 contained purified PMPs (fractions 8-14 contained contaminants), were pooled together, and were filter sterilized by sequential filtration using 0.8 μm, 0.45 μm and 0.22 μm syringe filters. The final PMP concentration ($2.7 \times 10^{11}$ PMPs/mL) and median PMP size (70.7 nm+/−15.8 nm) in the combined sterilized PMP-containing fractions were determined by NanoFCM, using concentration and size standards provided by the manufacturer.

c) Labeling of Lemon PMPs with Alexa Fluor 488 NHS Ester

Figure 6A:
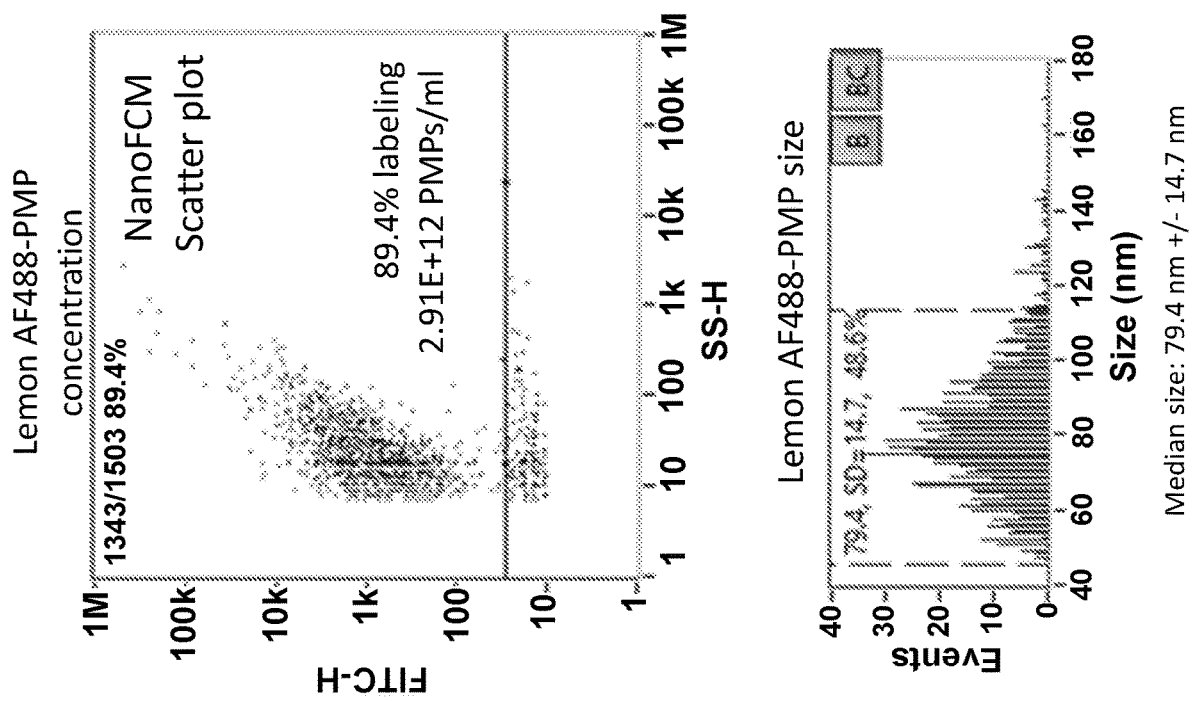
FIG. 6A is a scatter plot and a graph showing particle size in AF488-labeled lemon PMPs as measured by nanoflow cytometry (NanoFCM). The top panel is a scatter plot showing AF488-labeled lemon PMPs. Particles were gated on the FITC fluorescence signal, relative to unlabeled particles and background signal. The labeling efficiency was 89.4% as determined by the number of fluorescent particles relative to the total number of particles detected. The final AF488-PMP concentration ($2.91 \times 10^{12}$ PMPs/ml) was determined from the number of fluorescent particles and using a bead standard with a known concentration according to NanoFCM's instructions. The bottom panel is a size (nm) distribution graph of 488-labeled lemon PMPs. The median PMP size was determined using Exo bead standards according to NanoFCM's instructions. The median lemon AF488-PMPs size was 79.4 nm+/−14.7 nm (SD).

Lemon PMPs were produced as described in Example 14b. PMPs were labeled with the Alexa Fluor 488® NHS Ester (Life Technologies, covalent membrane dye (AF488)). Briefly, AF488 was dissolved in DMSO to a final concentration of 10 mg/ml, 200 ul of PMPs (1.53E+13 PMPs/ml) were mixed with 5 ul dye, incubated for 1 h at room temperature on a shaker, and labeled PMPs were washed 2-3 times by ultracentrifuge at 100,000×g for 1 hr at 4° C. Pellets were resuspended with 1.5 ml UltraPure water. To control for the presence of potential dye aggregates, a dye-only control sample was prepared according to the same procedure, adding 200 ul of UltraPure water instead of PMPs. The final AF488-labeled PMP pellet and AF488 dye-only control were resuspended in a minimal amount of UltraPure water and characterized by NanoFCM. The final concentration of lemon 488-labeled PMPs was $2.91 \times 10^{12}$ PMPs/ml with a median AF488-PMP size of 79.4 nm+/−14.7 nm and a labeling efficiency of 89.4% (FIG. 6A).

d) Uptake of AF488-Labeled Lemon PMPs by Plant Cells

Plant cell lines were purchased from the Deutsche Sammlung von Mikroorganismen und Zellkulturen (DSMZ) (*Glycine max*, #PC-1026; *Triticum aestivum*, #PC-998) and ABRC (*Zea mays*, Black Mexican sweet (BMS), and were grown in baffled vented 250 mL flasks in the dark, at 24° C. with agitation (110 rpm). *Glycine max* and *Triticum aestivum* were grown in 3.2 g/L Gamborg's B-5 Basal Medium with Minimal Organics supplemented (G5893, Millipore Sigma) pH 5.5, supplemented with 2% sucrose, and 2 mg/L 2,4-dichlorophenoxyacetic acid (2,4D) (D7299, Millipore Sigma) according to the supplier's instructions. BMS cells were grown in Murashige and Skoog basal medium pH 5.8, containing 4.3 g/L Murashige and Skoog Basal Salt Mixture (Sigma M5524), 2% sucrose (S0389, Millipore Sigma), 1×MS vitamin solution (M3900, Millipore Sigma), 2 mg/L 2,4-dichlorophenoxyacetic acid (D7299, Millipore Sigma) and 250 ug/L thiamine HCL (V-014, Millipore Sigma).

For treatment with AF488-PMPs, 5 mL of the cell suspensions was taken to determine the percent Pack Cell Volume (PCV). The PCV is defined as the volume of cells divided by the total volume of the cell culture aliquot, and expressed as a percentage. Cells were centrifuged for 5 min at 3900 rpm, and the volume of the cell pellet was determined. The % PCV for BMS, *Glycine max*, and *Triticum aestivum* were 20%, 15%, and 18%, respectively. For the uptake experiment, the % PCV of the cultures was adjusted to 2%, by diluting cells in their appropriate medium. Next, 125 μl of the plant cell suspensions was added to a 24 well plate, and duplicate samples were treated with 125 μl MES buffer (200 mM MES+10 mM NaCl, pH6) alone (negative control), AF488 dye only (dye only control) or a final concentration of $1 \times 10^{12}$ AF488-PMPs/mL diluted in MES buffer to 125 μl. Cells were incubated for 2 hours at 24° C. in the dark, washed three times with 1 mL MES buffer to remove AF488-PMPs or free dye that had not been taken up, and resuspended in 300 μL of MES buffer for imaging on an epifluorescence microscope (EVOS FL Auto 2, Invitrogen). Compared to the AF488 dye only control which had no detectable fluorescence, a variable fluorescent signal could be detected in all plant cell lines, indicating PMP uptake (FIG. 6B). *Triticum aestivum* cells displayed the strongest fluorescence signal, indicating that out of the three plant cell lines tested, they had the highest uptake of AF488-labeled lemon PMPs.

Our data shows that PMPs can be taken up by plant cells in vitro.

Example 15: Uptake of PMPs in Plants

This example describes the uptake and systemic transport of PMPs in planta. In this example, grapefruit, lemon and *Arabidopsis thaliana* seedling PMPs are used as model PMPs, and *Arabidopsis* seedlings and alfalfa sprouts are used as model plants.

a) Labeling of Lemon and Grapefruit PMPs with DyLight 800 NHS Ester

Grapefruit and lemon PMPs were produced as described in Examples 14a and 14b. PMPs were labeled with the DyLight 800 NHS Ester (Life Technologies, #46421) covalent membrane dye (DyL800). Briefly, Dyl800 was dissolved in DMSO to a final concentration of 10 mg/ml, 200 μl of PMPs were mixed with 5 μl dye, incubated for 1 h at room temperature on a shaker, and labeled PMPs were washed 2-3 times by ultracentrifugation at 100,000×g for 1 hr at 4° C. and pellets were resuspended with 1.5 ml UltraPure water. To control for the presence of potential dye aggregates, a dye-only control sample was prepared according to the same procedure, adding 200 μl of UltraPure water instead of PMPs. The final DyL800-labeled PMP pellet and DyL800 dye-only control were resuspended in a minimal amount of UltraPure water and characterized by NanoFCM. The final concentration of grapefruit DyL800-labeled PMPs was $4.44 \times 10^{12}$ PMPs/ml, and of lemon DyL800-labeled PMPs was $5.18 \times 10^{12}$ PMPs/ml. The labeling efficiency could not be determined using the NanoFCM, as it cannot detect infrared.

b) Germination and Growth of *Arabidopsis thaliana* Seedlings

Wild type *Arabidopsis thaliana* Col-0 seeds were obtained from the ABRC and were surface sterilized with 70% ethanol, incubation with 50% bleach/0.1% triton X-100 for 10 minutes, and 4 sterile ddH2O washes to remove the bleach solution. Seeds were stratified for 1 d at 4° C. in the dark. Approximately 250 seeds were germinated per 100 cm² plate (pre-coated with 0.5% fetal calf serum in water), containing 20 mL 0.5×MS medium (2.15 g/L Murashige and Skoog salts, 1% sucrose, pH 5.8), sealed with 3M surgical tape and grown in an incubator with a photoperiod of 16 h light at 23° C./8 h dark at 21° C.

c) Uptake of DyL800-Labeled Grapefruit, Lemon and Ats PMPs by *Arabidopsis thaliana* and Alfalfa To assess whether PMPs can be taken up and transported systemically in planta, *Arabidopsis* seedlings were germinated in liquid culture as described in Example 15b on top of a mesh filter, to allow the roots to grow through the mesh, and to allow partial exposure of At seedlings to a PMP solution. Alfalfa sprouts were obtained from a local supermarket. 9 day-old *Arabidopsis* seedlings and Alfalfa sprouts were treated with a 0.5 ml solution of water (negative control), DyL800 dye only (dye control) DyL800-labeled grapefruit PMPs ($1.6 \times 10^{10}$ PMPs/ml), or lemon ($5.1 \times 10^{10}$ PMPs/ml) PMPs in 0.5×MS medium by partial root exposure (At seedlings in a mesh floating in a PMP solution, or in Alfalfa sprouts by partial root exposure in a 1.5 ml Eppendorf tube) for 22 or 24 hours, respectively, at 23° C. Plants where then washed 3 times in MS medium and imaged using an Odyssey® CLx infrared imager (Li-Cor).

Compared to the negative (some autofluorescence in Alfalfa sprout leaves) and dye only control, all PMP sources showed a fluorescence signal (white is high fluorescent signal, black is no signal) in both *Arabidopsis* seedlings and Alfalfa sprouts, indicating that PMPs are taken up by both plants (FIG. 7). The presence of fluorescence signal in *Arabidopsis* leaves or Alfalfa stem areas that were not exposed to the PMP solution indicates active transport of the PMPs in planta. As the DyL800 treatment concentrations were not normalized in this experiment, it is not possible to assess source/target uptake efficiency differences.

Our data indicate that PMPs derived from various plant sources can be taken up and transported in planta.

Example 16: Treatment of *Arabidopsis thaliana* Seedlings with DOX-Loaded Grapefruit PMPs This example describes the loading of PMPs with a small molecule with the purpose of decreasing the fitness of a plant. In this example, doxorubicin is used as a model small molecule, and *Arabidopsis thaliana* is used as a model plant. Doxorubicin is a cytotoxic anthracycline antibiotic isolated from cultures of *Streptomyces peucetius* var. *caesius*. Doxorubicin interacts with DNA by intercalation and inhibits both DNA replication and RNA transcription. Doxorubicin has been shown to be cytotoxic in plants (Culiarez-Mac et al, *Plant Growth Regulation*, (5): 155-164, 1987.

Effective and safe herbicides are necessary to prevent major crop yield loss due to weeds, while protecting the environment from the toxic side-effects of herbicide overuse.

a) Production of Grapefruit PMPs Using TFF Combined with SEC

Red organic grapefruits were obtained from a local Whole Foods Market®. Four liters of grapefruit juice were collected using a juice press, pH adjusted to pH4 with NaOH, incubated with 1 U/ml pectinase (Sigma, 17389) to remove pectin contaminants, and subsequently centrifuged at 3,000 g for 20 minutes, followed by 10,000 g for 40 minutes to remove large debris. Next, the processed juice was incubated with 500 mM EDTA pH8.6, to a final concentration of 50 mM EDTA, pH7.7 for 30 minutes to chelate calcium and prevent the formation of pectin macromolecules. Subsequently, the EDTA-treated juice was passaged through an 11 µm, 1 µm and 0.45 µm filter to remove large particles. Filtered juice was washed and concentrated by Tangential Flow Filtration (TFF) using a 300 kDa TFF. Juice was concentrated 5×, followed by a 6 volume exchange wash with PBS, and further filtrated to a final concentration 198 mL (20×). Next, we used size exclusion chromatography to elute the PMP-containing fractions, which were analyzed by absorbance at 280 nm (SpectraMax®) and protein concentration (Pierce™ BCA assay, ThermoFisher) to verify the PMP-containing fractions and late fractions containing contaminants. SEC fractions 3-7 contained purified PMPs (fractions 9-12 contained contaminants), were pooled together, were filter sterilized by sequential filtration using 0.8 µm, 0.45 µm and 0.22 µm syringe filters, and were concentrated further by pelleting PMPs for 1.5 hrs at 40,000×g and resuspending the pellet in 4 ml UltraPure™ DNase/RNase-Free Distilled Water (ThermoFisher, 10977023). Final PMP concentration ($7.56 \times 10^{12}$ PMPs/ml) and average PMP size (70.3 nm+/−12.4 nm SD) were determined by NanoFCM, using concentration and size standards provided by the manufacturer. The produced grapefruit PMPs were used for loading doxorubicin.

b) Loading of Doxorubicin in Grapefruit PMPs

Grapefruit PMPs produced in Example 16a were used for loading doxorubicin (DOX). A stock solution of doxorubicin (Sigma PHR1789) was prepared at a concentration of 10 mg/mL in UltraPure water and filter sterilized (0.22 µm). Sterile grapefruit PMPs (3 mL at particle concentration of $7.56 \times 10^{12}$ PMPs/ml) were mixed with the 1.29 mL of DOX solution. The final DOX concentration in the mixture was 3 mg/mL. The mixture was sonicated for 20 min in a sonication bath (Branson 2800) with temperature rising to 40° C. and kept an additional 15 minutes in the bath without sonication. The mixture was agitated for 4 hours at 24° C., 100 rpm, in the dark. Next, the mixture was extruded using Avanti Mini Extruder (Avanti Lipids). To reduce the number of lipid bilayers and overall particle size, the DOX-loaded PMPs were extruded in a decreasing stepwise fashion: 800 nm, 400 nm and 200 nm. The extruded sample was filter sterilized by subsequent passage through a 0.8 µm and 0.45 µm filter (Millipore, diameter 13 mm) in a TC hood. To remove unloaded or weakly-bound DOX, the sample was purified using an ultracentrifugation approach. Specifically, the sample was spun down at 100,000×g for 1 h at 4° C. in 1.5 mL ultracentrifuge tubes. The supernatant was collected for further analysis and stored at 4° C. The pellet was resuspended in sterile water and ultracentrifuged under the same conditions. This step was repeated four times. The final pellet was resuspended in sterile UltraPure water and kept at 4° C. until further use.

Next, the concentration of particles and the loading capacity of PMPs was determined. The total number of PMPs in the sample ($4.76 \times 10^{12}$ PMP/ml) and the median particle size (72.8 nm+/−21 nm SD) were determined using a NanoFCM. The DOX concentration was assessed by fluorescence intensity measurement (Ex/Em=485/550 nm) using a SpectraMax® spectrophotometer. A calibration curve of free DOX from 0 to 50 ug/mL was prepared in sterile water. To dissociate DOX-loaded PMPs and DOX complexes (π-π stacking), samples and standards were incubated with 1% SDS at 37° C. for 45 min prior to fluorescence measurements. The loading capacity (pg DOX per 1000 particles) was calculated as the concentration of DOX (pg/ml) divided by the total number of PMPs (PMPs/ml). The PMP-DOX loading capacity was 1.2 pg DOX per 1000 PMPs. However, it should be noted that the loading efficiency (the % of DOX-loaded PMPs compared to the total number of PMPs) could not be assessed as the DOX fluorescence spectrum could not be detected on the NanoFCM.

c) Treatment of *Arabidopsis thaliana* Seedlings with Doxorubicin-Loaded PMPs

Grapefruit PMPs were produced and loaded with doxorubicin as described in Examples 16a and 16b. Wild type *Arabidopsis thaliana* Col-0 seeds were obtained from the ABRC, surface sterilized with 50% bleach, stratified for 1-3 d at 4° C., and germinated on half-strength (0.5×) Murashige and Skoog (MS) medium supplemented with 0.5% sucrose, 2.5 mM MES, pH 5.6, containing 0.8% agar, with a photoperiod of 16 h light 23° C./8 h dark 21° C.

To test whether PMPs can deliver a small molecule cargo in planta, 7-day old *Arabidopsis thaliana* seedlings were transferred to 0.5× liquid MS medium in a 24 well plate (1 seedling per well), and treated with free DOX or DOX-loaded PMPs with an encapsulated DOX dose of 0 (negative control), 25 µM, 50 µM and 100 µM. The plate was covered with aluminum foil and incubated for 24 hours. DOX-containing medium was removed, the seedlings were washed two times with ½×MS medium, and fresh medium was added. Seedlings were incubated for an additional 3 days under a normal photoperiod (16 h light 23° C./8 h dark 21° C.). Next, seedlings were removed from the plate and towel-dried for imaging and cytotoxicity was assessed by analyzing leaf vigor, leaf color and root length. Cytotoxicity is defined by shortening of the roots, loss of leaf vigor, and leaf discoloration (yellow instead of green) when compared to an untreated seedling control. Compared to free DOX that only showed cytotoxicity at 100 µM DOX (root shortening and leaf discoloration), PMPs loaded with DOX were cytotoxic at 50 µM and 100 µM DOX. 50 µM PMP-DOX treated seedlings showed severe leaf yellowing with reduced leaf vigor, and shortening of the roots. Our data indicates that PMPs can be loaded with and can deliver a small molecule in planta, and that PMPs loaded with doxorubicin are twice as efficient in inducing a cytotoxic response than free doxorubicin.

Example 17. Uptake of Pectinase-Treated PMPs by Alfalfa Sprouts

This example describes that the removal of pectins during the PMP production process does not impact their in planta uptake and systemic transport. In this example, lemon PMPs were used as model PMPs, and Alfalfa sprouts were used as model plant.

a) Production of Lemon PMPs with or without the Addition of Pectinase

Lemons were obtained from a local Whole Foods Market®. Lemon juice (1260 ml) was collected using a juice press, and split into two fractions. 630 ml was untreated, and 630 ml was pH adjusted to pH4 with NaOH and incubated with 6 U/ml pectinase (Sigma, 17389) for 1.45 hrs at room temperature. Pectinase treated and untreated juice was subsequently centrifuged at 3000 g for 20 minutes, followed by 10,000 g for 40 minutes to remove large debris. Next, the processed juice was incubated with 500 mM EDTA pH8.6, to a final concentration of 50 mM EDTA, pH 7.19-7.25, for 30 minutes at room temperature to chelate calcium and prevent the formation of pectin macromolecules. Subsequently, the EDTA-treated juice was passaged through an 11 µm, 1 µm and 0.45 um filter to remove large particles. Filtered juice was washed (260 ml PBS during TFF procedure) and concentrated ~1.6× to a total volume of 400 ml by Tangential Flow Filtration (TFF), and dialyzed overnight in PBS, pH 7.4 using a 300 kDa dialysis membrane. Subsequently, the dialyzed juice was further concentrated by TFF to a final concentration of 30 ml (~21×). Next, we used size exclusion chromatography to elute the PMP-containing fractions, and analyzed the 280 nm absorbance (SpectraMax) to determine the PMP-containing fractions from late elution fractions containing contaminants. SEC fractions 4-6 (no pectinase treatment) and SEC fractions 4-7 (with pectinase treatment) containing purified PMPs were pooled together in the individual treatment groups. Pooled SEC fractions were dialyzed o/n in PBS, pH 7.4 using a 300 kDa dialysis membrane. Samples were sterilized by sequential filtration using 0.85 um, 0.4 um and 0.22 um syringe filters, and concentrated further by pelleting PMPs for 1.5 hrs at 40,000×g and finally the pellet is resuspended in Ultrapure water. The final PMP concentration for untreated lemon PMPs was $1.24 \times 10^{12}$ PMPs/ml and median PMP size was 129 nm+/−12 nm SD; for pectinase-treated lemon PMPs the final concentration was $2.2610^{12}$ PMPs/ml and median PMP size was 130 nm+/−11 nm (SD), as determined by nano-flow cytometry (NanoFCM) using concentration and size standards provided by the manufacturer.

b) Labeling of Lemon PMPs with DyLight 800 NHS Ester

Pectinase treated and untreated lemon PMPs were labeled with the DyLight 800 NHS Ester (Life Technologies, #46421) covalent membrane dye (DyL800). Briefly, DyL800 was dissolved in DMSO to a final concentration of 10 mg/ml, 200 ul of PMPs were mixed with 5 ul dye, incubated for 1 h at room temperature on a shaker, and labeled PMPs were washed 2-3 times by ultracentrifugation at 100,000×g for 1 hr at 4° C. and pellets were resuspended with 1.5 ml UltraPure water. To control for the presence of potential dye aggregates, a dye-only control sample was prepared according to the same procedure, adding 200 ul of UltraPure water instead of PMPs. The final DyL800-labeled PMP pellet and DyL800 dye-only control were resuspended in a minimal amount of UltraPure water and characterized by NanoFCM. The final concentration of non-pectinase treated Dyl800-labeled lemon PMPs was $3.2 \times 10^{12}$ PMPs/ml, and of pectinase treated DyL800-labeled was $5.57 \times 10^{12}$ PMPs/ml. The labeling efficiency could not be determined using the nanoFCM, as it cannot detect infrared.

c) Treatment of Alfalfa Sprouts with Pectinase Treated and Untreated DyL800-PMPs To assess whether the removal of pectin during PMP production impacts PMP uptake, Alfalfa sprouts were obtained from a local supermarket, were treated with pectinase-treated and untreated DyLight800-Lemon PMPs, water (negative control), DyLight800 nm dye only (dye aggregate control) in half-strength Murashige and Skoog (MS), supplemented with 0.5% sucrose and 2.5 mM MES, pH 5.6 for 21 hours at 23° C. (FIG. 8A). Seedlings where then washed 3 times in MS medium, and imaged using an Odyssey infrared imager. There was no difference in uptake and transport of PMPs produced with or without pectinase treatment (FIG. 8B).

Example 18: Modification of PMPs Using Cationic Lipids

This example demonstrates the ability to modify surface charge, increase the cargo loading capacity, and increase the cellular uptake of PMPs in plant cells, by modification of PMPs with cationic lipids. In this example, DOTAP (1,2-dioleoyl-3-trimethylammonium-propane) and DC-Cholesterol (3β-[N—(N',N'-dimethylaminoethane)-carbamoyl] cholesterol) are used as model cationic lipids, grapefruit and lemon PMPs as model PMPs, siRNA/Trans-activating CRISPR RNA (TracrRNA) as a model negatively charged payload, and *Zea mays* (corn) Black Mexican sweet (BMS) as a model plant cell line.

Experimental Protocol:

a) Production of Lemon/Grapefruit PMPs

Red organic grapefruits or yellow organic lemons were obtained from a local grocery store. Six liters of grapefruit juice were collected using a juice press, pH adjusted to pH 4 with NaOH, incubated with 1 U/mL pectinase (Sigma, 17389) to remove pectin contaminants, and subsequently centrifuged at 3,000 g for 20 minutes, followed by 10,000 g for 40 minutes to remove large debris. Next, the processed juice was incubated with 500 mM EDTA pH 8.6 to a final concentration of 50 mM EDTA, pH 7.7 for 30 minutes to chelate calcium and prevent the formation of pectin macromolecules. Subsequently, the EDTA-treated juice was passed through an 11 µm, 1 µm and 0.45 µm filter to remove large particles. Filtered juice was washed and concentrated by Tangential Flow Filtration (TFF) using a 300 kDa TFF. Juice was concentrated 10×, followed by diafiltration into 10 diavolumes of PBS, and further concentrated to a final concentration 120 mL (50×). Next, we used size exclusion chromatography (SEC) to elute the PMP-containing fractions, which were analyzed by absorbance at 280 (SpectraMax®) and protein concentration (Pierce™ BCA Protein Assay) to verify the PMP-containing fractions and late fractions containing contaminants. SEC fractions 3-7 contained purified PMPs (fractions 9-12 contained contaminants) and were pooled together, filter sterilized by sequential filtration using 0.8 µm, 0.45 µm and 0.22 µm syringe filters, and concentrated further by pelleting PMPs for 1.5 hrs at 40,000×g and resuspending the pellet in 4 mL UltraPure™ DNase/RNase-Free Distilled Water (ThermoFisher, 10977023). Final PMP concentration ($7.56 \times 10^{12}$ PMPs/mL) and PMP size (70.3 nm+/−12.4 nm SD) were determined by NanoFCM, using concentration and size standards provided by the manufacturer. The produced grapefruit (GF) or lemon (LM) PMPs were used for lipid extraction using the Bligh-Dyer method, as described below.

b) Modification of PMPs with Cationic Lipids

Figure 11:
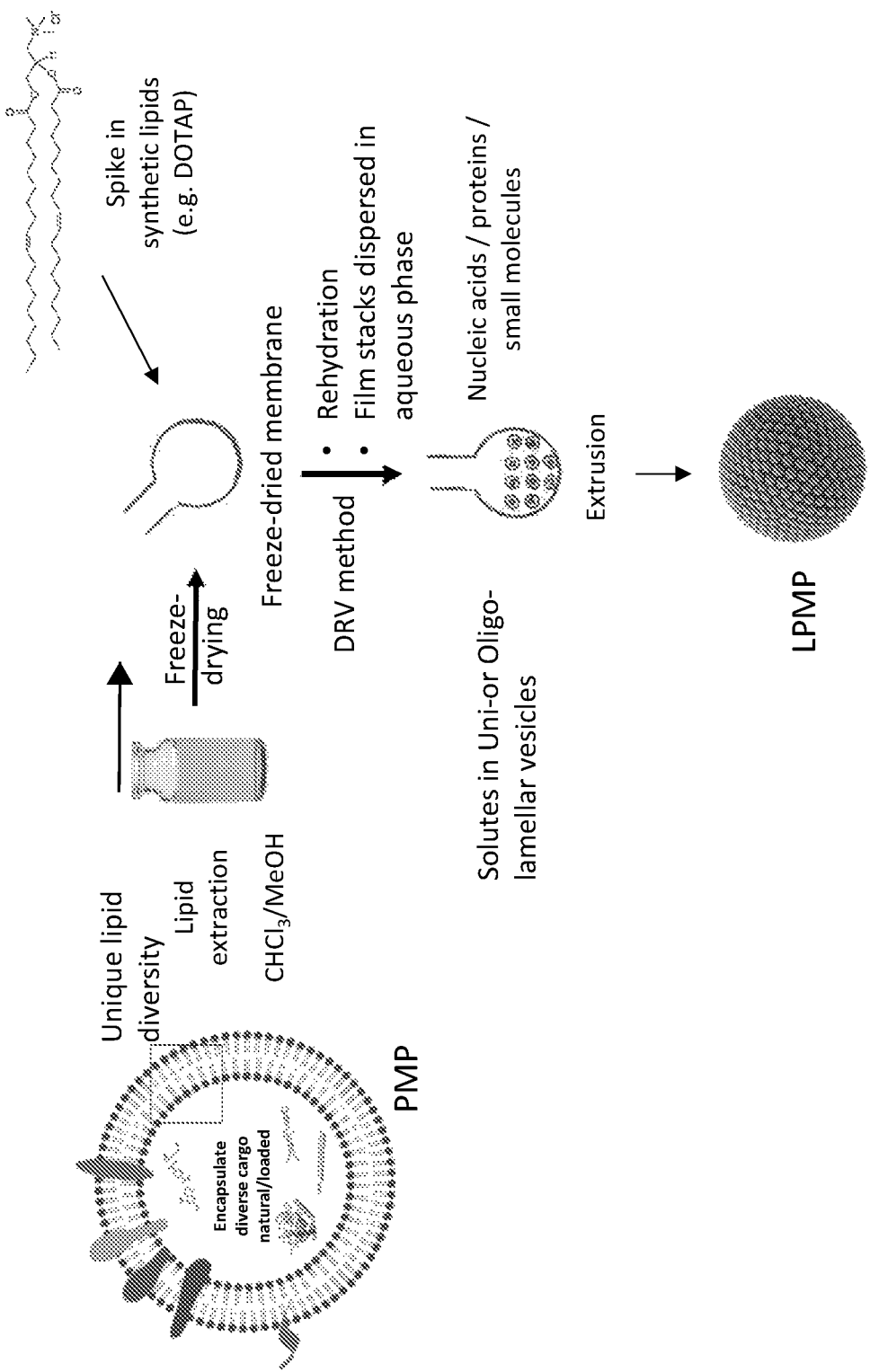
FIG. 11 is a schematic diagram showing a workflow for preparation of lipid reconstituted PMPs (LPMP) from grapefruit and lemon PMPs.

To prepare lipid reconstituted PMPs (LPMP), total lipid extraction from a concentrated solution of grapefruit or lemon PMPs was performed using the Bligh-Dyer method (Bligh and Dyer, *J Biolchem Physiol*, 37: 911-917, 1959). Briefly, 1 mL of concentrated PMPs ($10^{12}$-$10^{13}$ PMPs/mL) was mixed with a 3.5 mL chloroform:methanol mixture (1:2, v/v) and vortexed well. Then 1.25 mL chloroform was added and vortexed, followed by agitating with 1.25 mL sterile water. Finally, the mixture was centrifuged at 300 g for 5 minutes at RT. The bottom organic phase containing lipids was recovered and dried out using a TurboVap® system (Biotage®). To modify the lipid composition of natural LPMPs, synthetic cationic lipids (DOTAP, DC-Cholesterol) were dissolved in chloroform:methanol (9:1) and added to the PMP extracted lipids to amount to 25% or 40% (w/w) of the total lipid, followed by vigorous mixing. Dried lipid film was prepared by evaporation of the solvent with a stream of inert gas (e.g., nitrogen) or by evaporation using the TurboVap® system (FIG. 11). To prepare reconstituted PMPs from extracted lipids, water or buffer (e.g., PBS) was added to the dried lipid film and was left for 1 h at RT to hydrate.

Figure 12:
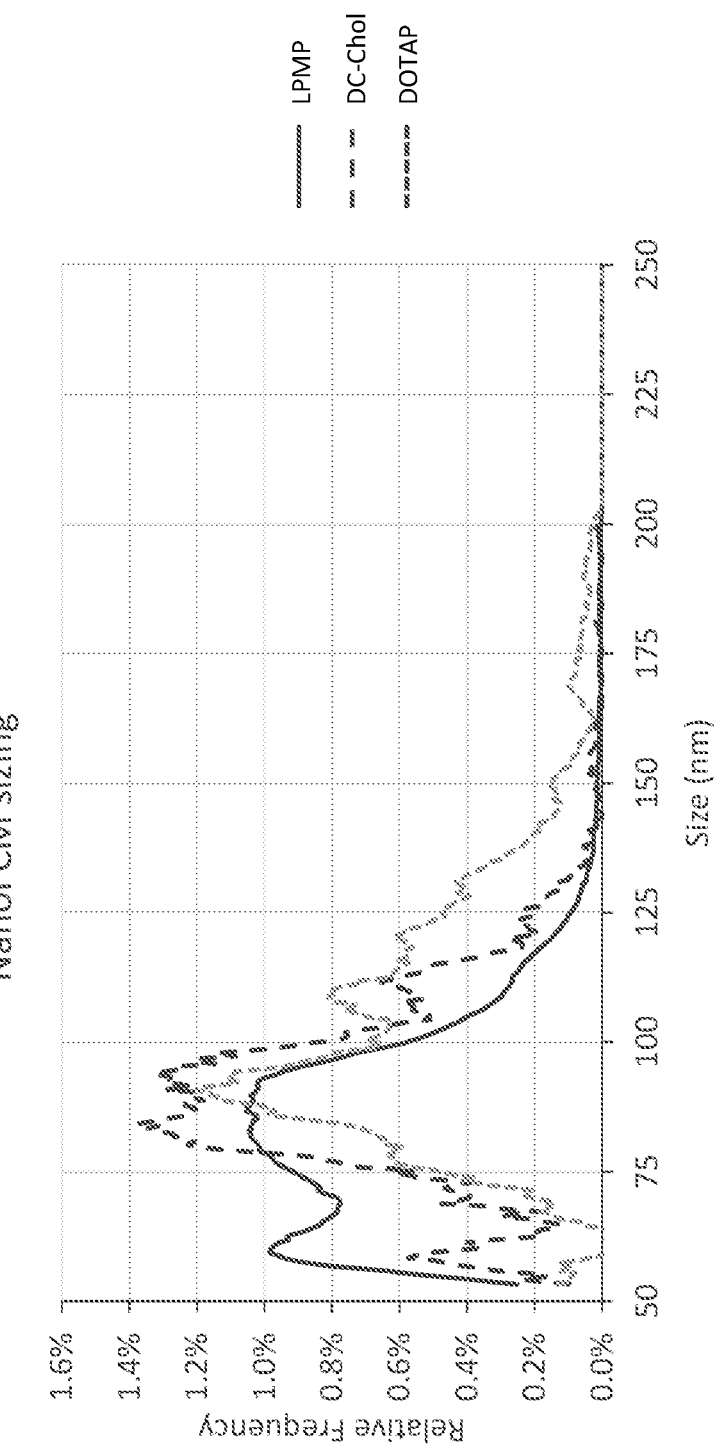
FIG. 12 is a graph showing the relative frequency of particles of a given size (nm) in LPMPs; LPMPs with added DC-cholesterol (DC-Chol); and LPMPs with added DOTAP (DOTAP). Data were acquired by NanoFCM using concentration and size standards provided by the manufacturer.
Figure 14A:
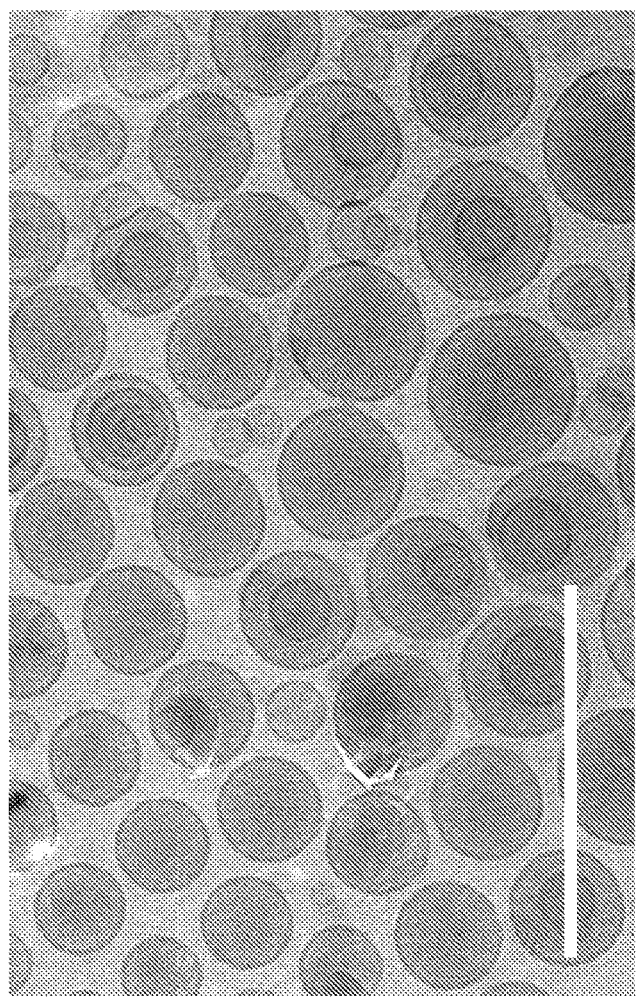
FIG. 14A is a cryo-electron micrograph showing LPMPs reconstructed from extracted lemon lipids. Scale bar: 500 nm.
Figure 14B:
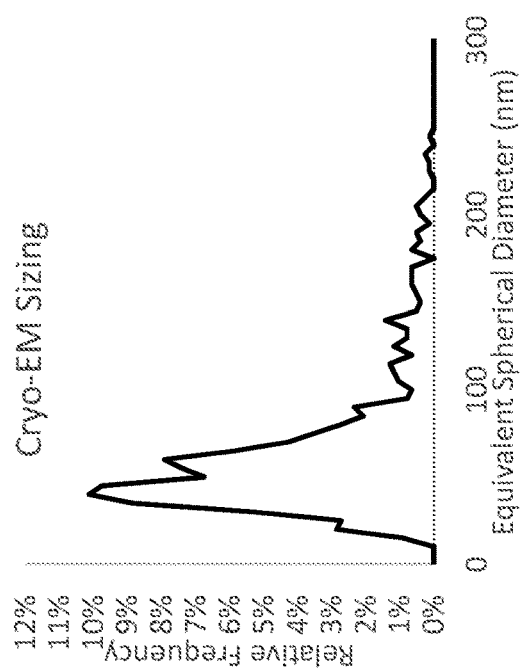
FIG. 14B is a graph showing the relative frequency of particles of a given equivalent spherical diameter (nm) in LPMPs reconstructed from extracted lemon lipids, as measured using cryo-electron microscopy.

Formed lipid particles were subjected to 10 freeze-thaw cycles or sonication (Branson 2800 sonication bath, 10 min, RT). Then, to reduce the number of lipid bilayers and overall particle size, the lipid PMPs were extruded through 0.8 µm, 0.4 µm and 0.2 µm polycarbonate filters using a Mini Extruder (Avanti® Polar Lipids) (FIG. 11). If concentrated LPMP was required, the samples were concentrated by ultracentrifugation at 100,000×g for 30 min at 4° C. The final pellet was resuspended in sterile UltraPure water or PBS and kept at 4° C. until further use. Final LPMP concentration and median LPMP size (ranging from 89-104 nm) were determined by NanoFCM, using concentration and size standards provided by the manufacturer. The surface charge (zeta potential) was measured by dynamic light scattering using a Zetasizer (Malvern Panalytical). The range of LPMP size and concentrations was 83±19 nm and $1.7 \times 10^{12}$ LPMPs/mL for LM LPMPs, 106±25 nm and $6.54 \times 10^{10}$ LPMPs/mL for DOTAP-modified LPMPs, and 91±17 nm and $3.08 \times 10^{11}$ LPMPs/mL for DC-Cholesterol-modified PMPs (FIG. 12). Modification of lipid reconstituted PMPs with the cationic lipids DOTAP and DC-Cholesterol changed the surface charge of LPMPs: with increasing cationic lipid content, the surface charge of LPMPs increased (FIG. 13A). Analysis of Cryo-EM images of LPMPs reconstructed from extracted lemon lipids confirmed the sphericity of LPMPs and particle size distribution (68.7±23 nm (SD)) (FIGS. 14A and 14B).

c) Loading of Cationic Lipid-Modified PMPs with Negatively Charged Cargo

To load siRNA/TracrRNA, GF or LM extracted lipids were supplemented with cationic lipids and dried out as described above. siRNA/TracrRNA dissolved in a nuclease free water or Duplex Buffer (IDT®) was added to the dried lipid film at 1.5 nmol per 1 mg of PMP lipids and was left for 1 h at RT to hydrate. Formed lipid particles were subjected to 10 freeze-thaw cycles and extruded through 0.8 µm, 0.4 µm and 0.2 µm polycarbonate filters using a Mini Extruder (Avanti® Polar Lipids) (FIG. 11). Loaded PMPs were dialyzed over night against PBS in a dialysis device (Spectrum®) with a 100 kDa MWCO membrane and then sterilized using 0.2 µm Polyethersulfone (PES) filters. Additionally, samples were purified and concentrated using ultracentrifugation. Loaded PMPs were centrifuged for 30 min at 100,000×g at 4° C., supernatant was removed, and the pellet was resuspended in 1 mL PBS and concentrated at 100,000×g for 30 min. The resulting pellet was resuspended in water (for cellular uptake by plant cells). Size of the RNA-loaded LPMPs and number of particles were assessed by NanoFCM: the mean size and particle concentration were 89±15 nm and $1.54 \times 10^{12}$ LPMPs/mL for unmodified LPMPs, 104±25 nm and $2.54 \times 10^{11}$ LPMPs/mL for DC-Chol, and 100±30 nm and $9.7 \times 10^{11}$ LPMPs/mL for DOTAP. RNA loading was determined by Quant-iT™ RiboGreen™ assay or by measurement of fluorescent intensity of labeled cargo (siRNA labeled with Alexa Fluor 555 or TracrRNA labeled with ATTO 550). The morphology and size of the unmodified LPMPs was also analyzed by Cryogenic Electron microscopy (Cryo-EM) (FIGS. 14A and 14B). The RiboGreen™ assay was performed according to the manufacturer's protocol in the presence of heparin (5 mg/mL) and 1% Triton-X100 to lyse PMPs and release encapsulated cargo. Modification of LPMPs with the cationic lipids DOTAP and DC-Cholesterol changed the surface charge of LPMPs and increased loading of negatively charged cargo (e.g. RNA), as compared to LPMPs without cationic lipids (FIGS. 4A-4D).

d) Increased Delivery of RNA to Plant Cells by DC-Cholesterol-Modified PMPs

*Zea mays*, Black Mexican sweet (BMS) cells were purchased from the *Arabidopsis* Biological Resource Center (ABRC). BMS cells were grown in Murashige and Skoog basal medium pH 5.8, containing 4.3 g/L Murashige and Skoog Basal Salt Mixture (Sigma M5524), 2% sucrose (S0389, Millipore Sigma), 2 mg/L 2,4-dichlorophenoxy-acetic acid (D7299, Millipore Sigma), 250 µg/L thiamine HCL (V-014, Millipore Sigma) and a 1×MS vitamin mix solution in ddH2O. The 1× vitamin mix solution contained niacin (N0761-100G, Millipore Sigma), Pyroxidine hydrochloride (P6280-25G, Millipore Sigma), D-pantothenic acid hemicalcium salt (P5155-100G, Millipore Sigma), L-Asparagine (A4159-25G, Millipore Sigma), and Myo-inositol (17508-100G, Millipore Sigma) at respective final concentrations of 1.3 mg/L, 250 µg/L, 250 µg/L, 130 mg/L, and 200 mg/L. Cells were grown in 1 L vented conical sterile flasks, in dark conditions at 24° C. with agitation (110 rpm).

Figure 15:
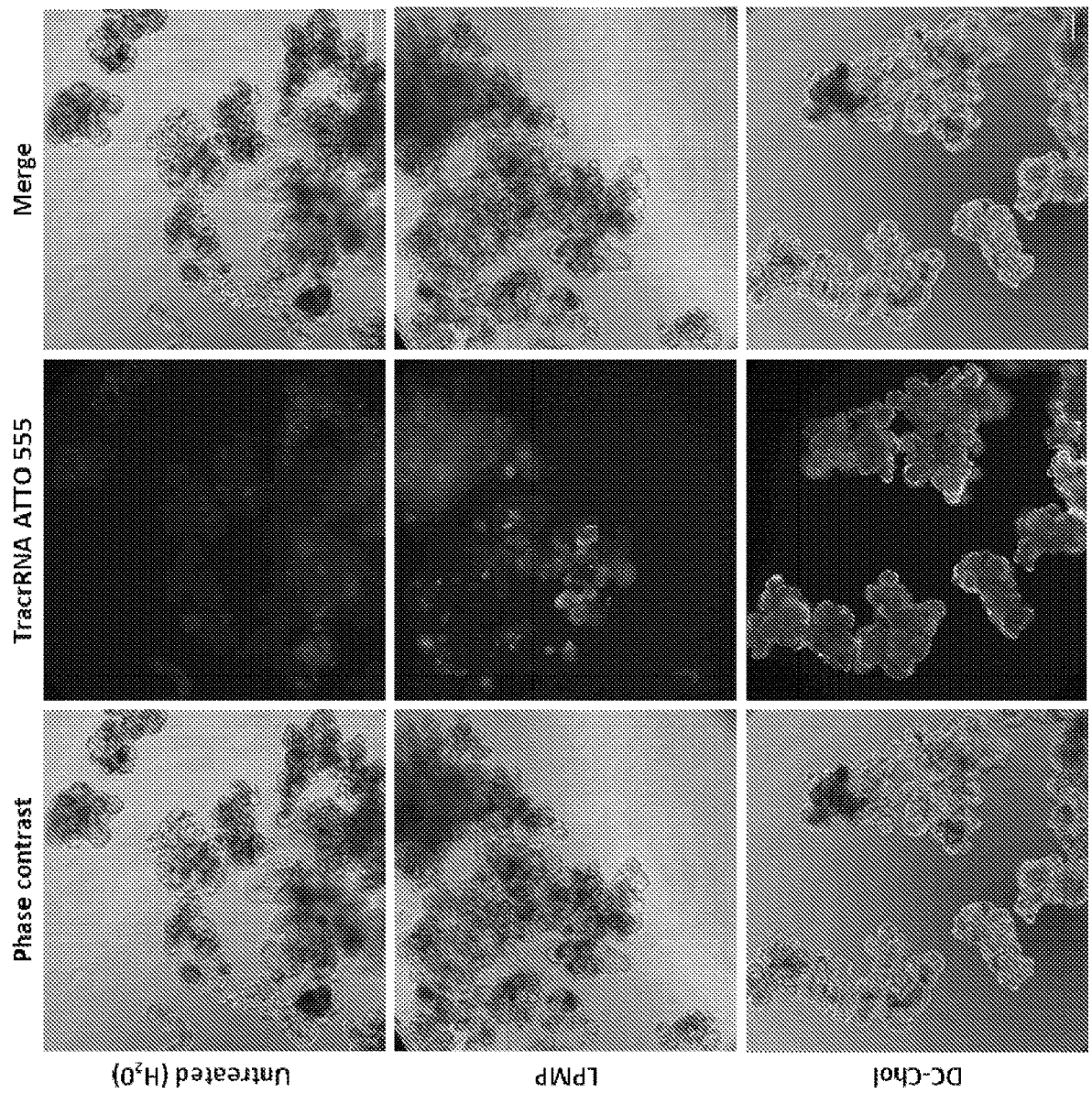
FIG. 15 is a set of photomicrographs showing phase contrast (left column), ATTO 550 fluorescence (center column), and merged views of maize Black Mexican Sweet (BMS) cells treated with LPMPs not comprising added lipids (center row) and LPMPs comprising 40% DC-cholesterol (DC-Chol). Cells that were treated with only $H_2O$ are provided as a negative control (top panels). Uptake of LPMPs or LPMPs modified with DC-Cholesterol by a cell is indicated by the presence of the TracrRNA ATTO 550 signal in the cell. Scale bar: 100 μm.

For BMS cells treatments, 10 mL of the cell suspensions was taken to determine the percent Pack Cell Volume (PCV). The PCV is defined as the volume of cells divided by the total volume of the cell culture aliquot and is expressed as a percentage. Cells were centrifuged for 5 min at 3900 rpm, and the volume of the cell pellet was determined. The % PCV for BMS was 20%. For the uptake experiment, the % PCV of the cultures was adjusted to 4% by diluting cells in the medium as described above. LPMPs and LPMPs modified with DC-Cholesterol were loaded with TracrRNA labeled with ATTO 550 as described above, sterilized, and resuspended in sterile water. The mean size and concentration of the particles were analyzed by NanoFCM and were 104±25 nm and $2.54 \times 10^{11}$ LPMPs/mL for DC-Chol and 89±15 nm and $1.54 \times 10^{12}$ LPMPs/mL for unmodified LPMPs. The amount of TracrRNA ATTO 550 (IDT) in samples was quantified by Quant-iT™ RiboGreen®. 50 µL of both LPMPs and LPMP modified with DC-Cholesterol containing 433 ng of TracrRNA was added to an aliquot of 450 µL of plant cell suspension in a 24-well plate in duplicate. 50 µl of ultrapure sterile water was added to the cells and was used as a negative control. Cells were incubated for 3 hours at 24° C. in the dark and were washed three times with 1 mL ultrapure sterile water to remove particles that had not been taken up by cells. Cells were resuspended in 500 µL of ultrapure sterile water for imaging on an epifluorescence microscope (Olympus IX83). Compared to the negative control (ultrapure sterile water), which had no detectable fluorescence, a variable fluorescent signal could be detected in plant cells treated with LPMPs and LPMPs modified with DC-Cholesterol (FIG. 15). LPMPs modified with DC-Cholesterol displayed the strongest fluorescence signal, indicating this PMP modification had the highest delivery of TracrRNA to plant cells. Our data shows that modification of LPMPs with the cationic lipid DC-Cholesterol improved lemon LPMP uptake by plant cells in vitro.

Example 19: Modification of a Plant by PMP-Mediated gRNA Delivery

This example demonstrates the loading and functional delivery of short nucleic acids in planta to affect gene expression. This example further demonstrates that short nucleic acid-loaded PMPs are stable and retain their activity inside the plant. In this example, transgenic dCas9-SunTag-VP64 *Arabidopsis thaliana* is used as model plant, grapefruit PMPs are used as a model PMP, and guide RNAs (gRNAs) against the FLOWERING WAGENINGEN (FWA) gene are used as model short nucleic acids (approx. 35 kDa).

a) Uptake of Lipid Reconstituted PMPs by Intact Plants

We previously demonstrated that natural PMPs from lemon and grapefruit can be taken up by intact plant roots, including *Arabidopsis thaliana* (Example 15). In this example, we demonstrate that lipid reconstituted PMPs (LPMPs) can likewise be taken up by *Arabidopsis* roots. Lipids were extracted from natural lemon (LM) and grapefruit (GF) PMPs and reconstructed as described in Example 18. The LPMPs obtained thusly were labeled with the near-infrared fluorescent lipophilic dye 1,1'-dioctadecyl-3, 3,3',3'-tetramethylindotricarbocyanine iodide (DiR) (Thermo Fisher). Note that 3 µL of DiR stock solution (5 mg/mL) was added to 1 mg of PMP lipids extracted from grapefruit and lemon. Dried lipid film was prepared as described in Example 18, followed by sonication (10 min, RT, Branson 2800 sonication bath) and extrusion through 0.8 µm, 0.4 µm, and 0.2 µm polycarbonate filters using a Mini Extruder (Avanti Polar Lipids). Unbound dye was removed using Zeba™ Spin Desalting Columns (40 kDa MWCO, Thermo Fisher Scientific) equilibrated with water. DiR-labeled PMPs were concentrated on Amicon® Ultra-0.5 Centrifugal Filter Unit (molecular weight cutoff (MWCO) 100 kDa).

The washed and sterile-filtered preparations of DiR-labeled LPMPs were diluted 1:5 with liquid ½ MS medium (Murashige & Skoog basal salt mixture (Sigma) 2.15 g/L, sucrose 10 g/L, MES (Sigma) 0.5 g/L, pH 5.8 adjusted with KOH), and 100 µL was aliquoted into sterile 1.5 mL Eppendorf tubes. Two week-old *Arabidopsis* seedlings (Col-0 wild-type) were transferred into the prepared Eppendorf tubes using sterile forceps. Care was taken that only the bottom third of the root was submerged. For each treatment (untreated control, DiR control, LM-LPMP-DiR, GF-LPMP-DiR), five seedlings were used in individual tubes. Tubes were sealed, covered with aluminum foil, and placed in a plant growth incubator for 48 hrs. Seedlings were then washed twice with water containing 1% Triton X-100 (Sigma) and once with water only. Seedlings were towel-dried and placed on an iBright 1500 imaging system (Thermo Fisher) for imaging at 750 nm (wavelength of DiR dye). Enhanced fluorescent signal in plants treated with LM-LPMP-DiR and GF-LPMP-DiR compared with controls was observed (FIGS. 9A and 9B), indicating uptake of the LPMPs by plants.

b) Modification and Loading of PMPs with gRNA

Modification and loading of PMPs used in this example are described in Example 18. Natural lemon PMPs were used as the lipid source, and two different formulations were used: (1) unmodified LPMPs and (2) LPMPs with added DC-Cholesterol (DC-Chol-LPMPs). The guide RNAs (gRNAs) used in this example were obtained from Integrated DNA Technologies (IDT). To form a functional gRNA duplex, Alt-R® CRISPR-Cas9 crRNA XT (23 bp) sequences targeting the *Arabidopsis* gene FLOWERING WAGENINGEN (FWA) (At4 g25530) were annealed to the universal Alt-R® CRISPR-Cas9 tracrRNA (67 bp) following the manufacturer's instructions. Two different crRNA sequences were used: FWA-g4 5'-ACGGAAAGATGTATGGGCTT-3' (SEQ ID NO: 53) and FWA-g17 5'-AAAACTAGGCCATC-CATGGA-3' (Papikian et al., *Nat Commun*, 10: Article number 729, 2019) (SEQ ID NO: 54). gRNA duplex 4 and 17 (SEQ ID NOs: 53 and 54) were mixed in equimolar amounts and loaded into LPMPs as described in Example 18. Loaded LPMP preparations were sterilized (0.2 um sterile filters), washed using an ultracentrifugation approach (100,000 g, 30 min, 4° C.), and resuspended in 150 µL sterile water after ultracentrifugation. Concentration and median size of particles were assessed by NanoFCM and RNA loading quantified using the Quant-iT™ RiboGreen™ RNA Assay Kit (Thermo Fisher) as described in Example 18 (Table 2).

TABLE 2

Concentration and median size of gRNA-loaded and tracrRNA-loaded PMPs

| Sample | Particle number (P/ml) | Mean size (nm) | SD size (nm) | RNA content (ng/ul) |
|---|---|---|---|---|
| LPMP-gRNA | 1.11E+12 | 88.5 | 21.4 | 11.21 |
| DC-Chol-gRNA | 1.17E+12 | 105.0 | 23.6 | 487.17 |
| DC-Chol-tracrRNA | 1.37E+12 | 103.7 | 22.6 | 379.81 | c) Functional Delivery of Lemon PMPs Loaded with gRNA Targeting FWA in dCas9-SunTag-VP64 *Arabidopsis thaliana*

For this example, we took advantage of the dCas9-SunTag-VP64 system in transgenic *Arabidopsis thaliana* (Papikian et al., *Nat Commun*, 10: Article number 729, 2019). In this system, which consists of two modules, a deactivated Cas9 endonuclease (dCas9) is fused to GCN4 peptide repeats and the transcriptional activator VP64 is fused to a single chain variable fragment GCN4 antibody, allowing multiple copies of VP64 to associate with a single dCas9 protein. By supplying gRNAs corresponding to the promoter sequence of a gene of interest (in this case, FWA), this dCas9-SunTag-VP64 (referred to as SunTag from here on) system can be used as a 'homing device' to activate gene expression. Transgenic seeds of SunTag *Arabidopsis thaliana* plants (Papikian et al., *Nat Commun*, 10: Article number 729, 2019) were obtained from the *Arabidopsis* Biological Resource Center (ABRC). Seeds were sterilized as follows: 70% ethanol for 1 min, 50% household bleach with 0.1% Triton X-100 (Sigma) for 10 min, washed three times with sterile deionized water. Sterilized seeds were resuspended in sterile 0.1% agarose and stratified at 4° C. for three days in the dark. Seeds were then placed on ½ MS plates (Murashige & Skoog basal salt mixture (Sigma) 2.15 g/L, sucrose 10 g/L, MES (Sigma) 0.5 g/L, phytoagar (Duchefa) 5 g/L, pH 5.8 adjusted with KOH) supplemented with 35 mg/L Hygromycin B (GoldBio) to select SunTag-positive seedlings among the segregating T2 population. Plates were sealed with medical tape (3M) and placed in a plant growth incubator with light for 6 hrs to stimulate germination. Plates were then covered with aluminum foil for 48 hrs, unwrapped, and the seedlings grown for three days under normal growth conditions (16 hr light, 23° C./21° C. day/night). Seedlings resistant to Hygromycin B showed a typical etiolated phenotype (elongated hypocotyl relative to non-resistant seedlings; non-resistant seedlings died). This selection protocol was previously described by Harrison et al., *Plant Methods*, 2: Article number 19, 2006.

Resistant seedlings (eight per treatment, pooled) were picked from plates with sterile forceps and placed into sterile 2 mL Eppendorf tubes containing 200 µL liquid ½ MS medium and 50 µL LPMPs modified with cationic or ionizable lipids containing between 19-27 µg of gRNA and unmodified LPMPs containing 0.6 µg of gRNA. Treatments were (1) LPMP-gRNA, (2) DC-Chol-LPMP-gRNA, (3) DC-Chol-LPMP-tracrRNA, and (4) gRNA only (27 ug). Care was taken to submerge roots in the medium and leave the cotyledons floating on the surface. Eight seedlings were used per treatment. Sealed tubes were placed in a plant growth incubator for 24 or 48 hrs to allow time for the PMPs to be taken up by the plant roots, to migrate through the plant, and to deliver their gRNA cargo into plant cells, and for the gRNA to be incorporated into the dCas9-SunTag-VP64 complex and activate expression of the FWA gene, which is not expressed in seedlings (Fujimoto et al., *PLoS Genet.*, 4: e1000048, 2008). Following the prescribed incubation time, the seedlings were removed from the PMP-containing solution, rinsed once in UltraPure water (Thermo Fisher), towel-dried, and frozen in liquid nitrogen.

Figure 10A:
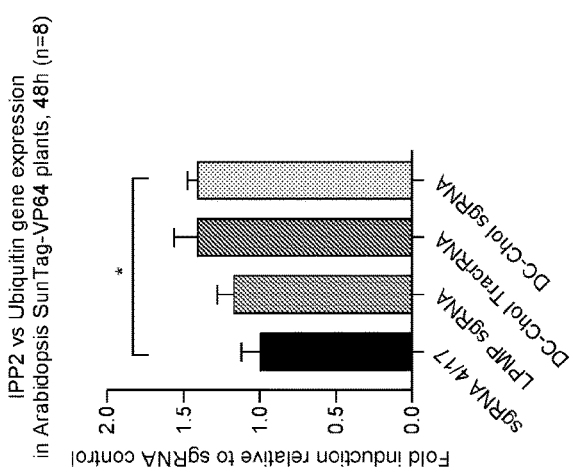
FIG. 10A is a bar graph showing RT-qPCR gene expression analysis of FLOWERING WAGENINGEN (FWA) relative to ubiquitin (UBI) in *Arabidopsis thaliana* dCas9-SunTag-VP64 plants treated for 48 h with LPMPs loaded with an equimolar amount of FWA-gRNA 4 and 17 (LPMP sgRNA) and LPMPs with added DC-cholesterol loaded with an equimolar amount of FWA-gRNA 4 and 17 (DC-Chol sgRNA). Plants treated with an equivalent amount of duplexed FWA-gRNA 4/17 mix (sgRNA4/17) and LPMPs with added DC-cholesterol loaded with only a tracrRNA (no gRNA) (DC-Chol tracrRNA) are provided as controls. Data are presented as mean±SD. * $p<0.05$, one-way ANOVA with Sidak post-hoc test.
Figure 10B:
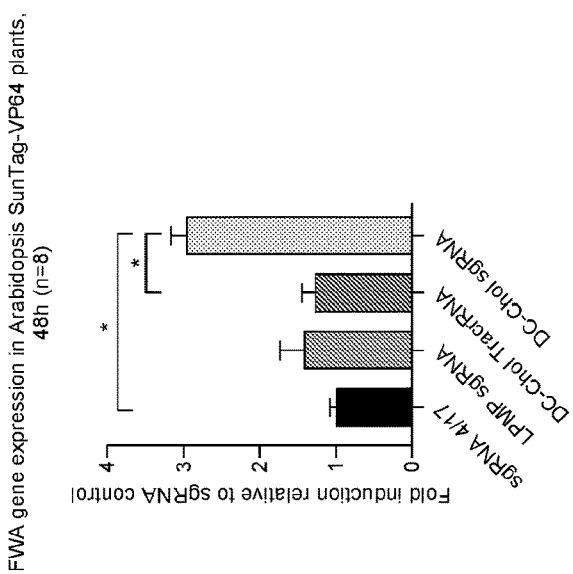
FIG. 10B is a bar graph showing fold induction of FWA in *Arabidopsis thaliana* dCas9-SunTag-VP64 plants treated for 48 h with LPMPs loaded with an equimolar amount of FWA-gRNA 4 and 17 (LPMP sgRNA) and LPMPs with added DC-cholesterol loaded with an equimolar amount of FWA-gRNA 4 and 17 (DC-Chol sgRNA) relative to a duplexed FWA-gRNA 4/17 mix (sgRNA4/17) control, as measured using RT-qPCR gene expression analysis. Data are presented as mean±SD. * $p<0.05$, one-way ANOVA with Sidak post-hoc test.
Figure 10C:
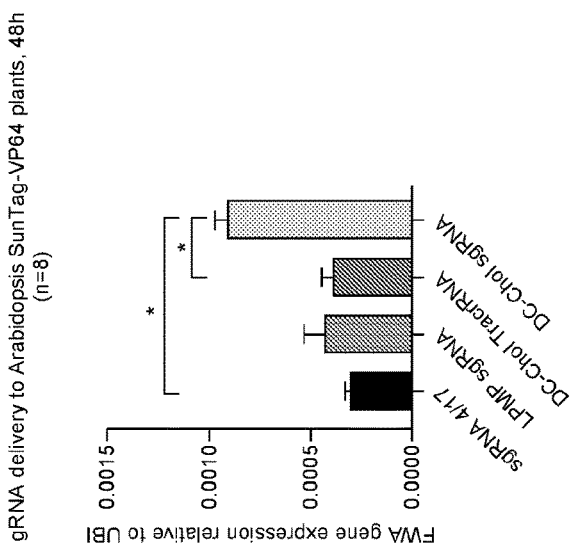
FIG. 10C is a bar graph showing fold induction of ATISOPENTENYL DIPHOSPHE ISOMERASE 2 (IPP2) in *Arabidopsis thaliana* dCas9-SunTag-VP64 plants treated for 48 h with LPMPs loaded with an equimolar amount of FWA-gRNA 4 and 17 (LPMP sgRNA) and LPMPs with added DC-cholesterol loaded with an equimolar amount of FWA-gRNA 4 and 17 (DC-Chol sgRNA) relative to a duplexed FWA-gRNA 4/17 mix (sgRNA4/17) control, as measured using RT-qPCR gene expression analysis. Data are presented as mean±SD. * p<0.05, one-way ANOVA with Sidak post-hoc test.

To determine activation of FWA gene expression, mRNA transcript levels were assayed using reverse transcription quantitative PCR (RT-qPCR). Frozen seedlings were ground in the tubes using plastic pestles, and total RNA was extracted using the RNeasy® Plant Mini Kit (Qiagen) following the manufacturer's instructions. Purified RNA was eluted from the columns using 40 µL RNase-free water (Qiagen). Genomic DNA was removed from RNA preparations using the DNase I, Amplification Grade kit (Sigma) following the manufacturer's instructions. cDNA synthesis was performed using the Invitrogen SuperScript™ III First-Strand Synthesis SuperMix (Thermo Fisher) and Oligo(dT) primers following the manufacturer's instructions. To detect expression of the FWA gene (At4 g25530), quantitative PCR was performed using the Luna® Universal qPCR Master Mix (NEB) following the manufacturer's instructions on an Applied Biosystems™ QuantStudio™ 7 Flex Real-Time PCR System (Thermo Fisher). Primers used for the qPCR experiment were previously published (Cabanillas et al., *Plant Cell*, 30: 2594-2615, 2018; Papikian et al., *Nat Commun*, 10: Article number 729, 2019): FWA_F 5'-TTAGATC-CAAAGGAGTATCAAAG-3' (SEQ ID NO; 55), FWA_R 5'-CTTTGGTACCAGCGGAGA-3' (SEQ ID NO: 56), IPP2_F 5'-GTATGAGTTGCTTCTCCAGCAAAG-3' (SEQ ID NO: 57), IPP2_R 5'-GAGGATGGCTGCAACAAGTGT-3' (SEQ ID NO: 58), Ubiquitin_F 5'-CCTACCTTT-GAGGGGCTTCT-3' (SEQ ID NO: 59), Ubiquitin_R 5'-GAAGTCGTGAGACAGCGTTG-3' (SEQ ID NO: 60). qPCR was performed using the following program: (a) 95° C. for 60 s; (b) 40 cycles of 95° C. for 15 s, 60° C. for 30 s. A ubiquitin gene (At2 g36060) was used to normalize the results. ATISOPENTENYL DIPHOSPHE ISOMERASE 2 (IPP2) (At3 g02780) was used as an internal control. Activation of FWA gene expression in the different treatments was determined by calculating the normalized ΔΔCt values (FIGS. 10A-10C). Plants exposed for 48 hrs to DC-Cholesterol modified LPMPs loaded with equimolar amount of gRNA 4 and 17 showed 3-fold increase in the expression of the FWA gene as compared to gRNA control (FIG. 101B). DC-Chol LPMPs with tracrRNA control did not induce FWA expression (FIGS. 10A and 101B). No significant difference in the expression of IPP2 (housekeeping gene) was found between the DC-Chol and tracrRNA control (FIG. 10C).

OTHER EMBODIMENTS

Some embodiments of the invention are within the following numbered paragraphs.

1. A plant-modifying composition comprising a plurality of plant messenger packs (PMPs), wherein the PMPs comprise a plant-modifying agent.

2. The plant-modifying composition of paragraph 1, wherein the PMPs in the composition are at a concentration effective to modify a plant trait, wherein the modification increases the fitness of the plant.

3. A plant-modifying composition comprising a plurality of plant messenger packs (PMPs), wherein the PMPs comprise a plant-modifying agent and the PMPs in the composition are at a concentration effective to modify a plant trait, wherein the modification increases the fitness of the plant.

4. The plant-modifying composition of paragraph 2 or 3, wherein the increase in fitness is an increase in development, growth, yield, resistance to abiotic stressors, or resistance to biotic stressors.

5. The plant-modifying composition of paragraph 2 or 3, wherein the increase in plant fitness is an increase in disease resistance, drought tolerance, heat tolerance, cold tolerance, salt tolerance, metal tolerance, herbicide tolerance, chemical tolerance, water use efficiency, nitrogen utilization, resistance to nitrogen stress, nitrogen fixation, pest resistance, herbivore resistance, pathogen resistance, yield, yield under water-limited conditions, vigor, growth, photosynthetic capability, nutrition, protein content, carbohydrate content, oil content, biomass, shoot length, root length, root architecture, seed weight, or amount of harvestable produce.

6. The plant-modifying composition of paragraph 2 or 3, wherein the increase in plant fitness is an increase in the quality of products harvested from the plant.

7. The plant-modifying composition of paragraph 6, wherein the increase in plant fitness is an improvement in taste, appearance, or shelf-life of a product harvested from the plant.

8. The plant-modifying composition of paragraph 2 or 3, wherein the increase in fitness is a decrease in production of an allergen that stimulates an immune response in an animal.

9. The plant-modifying composition of any one of paragraphs 1-8, wherein the plant-modifying agent is a heterologous nucleic acid.

10. A plant-modifying composition comprising a plurality of plant messenger packs (PMPs), wherein the PMPs comprise a heterologous nucleic acid and the PMPs in the composition are at an effective concentration to increase plant fitness.

11. The plant-modifying composition of paragraph 9 or 10, wherein the heterologous nucleic acid is a DNA, an RNA, a PNA, or a hybrid DNA-RNA molecule.

12. The plant-modifying composition of paragraph 11, wherein the RNA is a messenger RNA (mRNA), a guide RNA (gRNA), or an inhibitory RNA.

13. The plant-modifying composition of paragraph 12, wherein the inhibitory RNA is RNAi, shRNA, or miRNA.

14. The plant-modifying composition of paragraph 12 or 13, wherein the inhibitory RNA inhibits expression of a gene in a plant.

15. The plant-modifying composition of paragraph 9 or 10, wherein the nucleic acid is an mRNA, a modified mRNA, or a DNA molecule that, in the plant, increases expression of an enzyme, a pore-forming protein, a signaling ligand, a cell penetrating peptide, a transcription factor, a receptor, an antibody, a nanobody, a gene editing protein, a riboprotein, a protein aptamer, or a chaperone.

16. The plant-modifying composition of paragraph 9 or 10, wherein the nucleic acid is an antisense a RNA, a siRNA, a shRNA, a miRNA, an aiRNA, a PNA, a morpholino, a LNA, a piRNA, a ribozyme, a DNAzyme, an aptamer, a circRNA, a gRNA, or a DNA molecule that, in the plant, decreases expression of an enzyme, a transcription factor, a secretory protein, a structural factor, a riboprotein, a protein aptamer, a chaperone, a receptor, a signaling ligand, or a transporter.

17. The plant-modifying composition of paragraph 9 or 10, wherein the heterologous nucleic acid is a non-integrating construct that expresses a nucleic acid in the plant.

18. The plant-modifying composition of paragraph 9 or 10, wherein the heterologous nucleic acid is an integrating construct that expresses a nucleic acid in the plant.

19. The plant-modifying composition of any one of paragraphs 1-8, wherein the plant-modifying agent is a heterologous peptide.

20. A plant-modifying composition comprising a plurality of plant messenger packs (PMPs), wherein the PMPs comprise a heterologous peptide and the PMPs in the composition are at a concentration effective to increase plant fitness.

21. The plant-modifying composition of paragraph 19 or 20, wherein the peptide is an enzyme, pore-forming protein, signaling ligand, cell penetrating peptide, transcription factor, receptor, antibody, nanobody, gene editing protein, riboprotein, a protein aptamer, or chaperone.

22. The plant-modifying composition of paragraph 19 or 20, wherein the peptide decreases expression of a gene in the plant.

23. The plant-modifying composition of paragraph 19 or 20, wherein the peptide increases expression of a gene in the plant.

24. The plant-modifying composition of any one of paragraphs 1-23, wherein the PMPs comprise two or more different plant-modifying agents.

25. The plant-modifying composition of paragraph 24, wherein the two or more different plant-modifying agents comprise a heterologous nucleic acid and a heterologous peptide.

26. The plant-modifying composition of any one of paragraphs 1-25, wherein the plant-modifying agent is encapsulated by the PMPs.

27. The plant-modifying composition of any one of paragraphs 1-25, wherein the plant-modifying agent is embedded on the surface of the PMPs.

28. The plant-modifying composition of any one of paragraphs 1-25, wherein the plant-modifying agent is conjugated to the surface of the PMPs.

29. The plant-modifying composition of any one of paragraphs 1-28, wherein the plant-modifying agent is non-pesticidal.

30. The plant-modifying composition of any one of paragraphs 1-29, wherein the composition is stable for at least one day at room temperature and/or stable for at least one week at 4° C.

31. The plant-modifying composition of any one of paragraphs 1-29, wherein the PMPs are stable for at least 24 hours, 48 hours, seven days, or 30 days.

32. The plant-modifying composition of paragraph 31, wherein the PMPs are stable at a temperature of at least 4° C., 20° C., 24° C., or 37° C.

33. The plant-modifying composition of any one of paragraphs 1-32, wherein the PMPs in the composition are at a concentration of at least 1, 10, 50, 100, or 250 μg PMP protein/ml.

34. The plant-modifying composition of any one of paragraphs 1-33, wherein the PMPs comprise a purified plant extracellular vesicle (EV), or a segment or extract thereof.

35. The plant-modifying composition of paragraph 34, wherein the plant EV is a modified plant extracellular vesicle (EV).

36. The plant-modifying composition of any one of paragraphs 1-35, wherein the plant is an agricultural or horticultural plant.

37. The plant-modifying composition of paragraph 36, wherein the agricultural plant is a soy plant, a wheat plant, or a corn plant.

38. The plant-modifying composition of any one of paragraphs 1-37, wherein the composition is formulated for delivery to a plant.

39. The plant-modifying composition of paragraph 38, wherein the composition is formulated for delivery to a leaf, seed, root, fruit, shoot, or flower of the plant.

40. The plant-modifying composition of any one of paragraphs 1-39, wherein the composition comprises an agriculturally acceptable carrier.

41. The plant-modifying composition of any one of paragraphs 1-40, wherein the composition is formulated to stabilize the PMPs.

42. The plant-modifying composition of any one of paragraphs 1-41, wherein the composition is formulated as a liquid, a solid, an aerosol, a paste, a gel, or a gas composition.

43. A plant-modifying composition comprising a plurality of PMPs, wherein the PMPs are produced by a process which comprises the steps of:
  (a) providing an initial sample from a plant, or a part thereof, wherein the plant or part thereof comprises EVs;
  (b) isolating a crude PMP fraction from the initial sample, wherein the crude PMP fraction has a decreased level of at least one contaminant or undesired component from the plant or part thereof relative to the level in the initial sample;
  (c) purifying the crude PMP fraction, thereby producing a plurality of pure PMPs, wherein the plurality of pure PMPs have a decreased level of at least one contaminant or undesired component from the plant or part thereof relative to the level in the crude EV fraction;
  (d) loading the plurality of pure PMPs with a plant-modifying agent; and
  (e) formulating the PMPs of step (d) for delivery to a plant.

44. A plant comprising the plant-modifying composition of any one of paragraphs 1-43.

45. A method of delivering a plant-modifying composition to a plant comprising contacting the plant with the composition of any one of paragraphs 1-43.

46. A method of increasing the fitness of a plant, the method comprising delivering to the plant an effective amount of the plant-modifying composition of any one of paragraphs 1-43, wherein the method increases the fitness of the plant relative to an untreated plant.

47. The method of paragraph 45 or 46, wherein the plant-modifying composition is delivered to a leaf, seed, root, fruit, shoot, flower, or portion thereof.

48. A method of increasing the fitness of a plant, the method comprising contacting a seed of the plant with an effective amount of the plant-modifying composition of any one of paragraphs 1-43, wherein the method increases the fitness of the plant relative to an untreated plant.

49. A method of increasing the fitness of a plant, the method comprising contacting meristematic tissue of the plant with an effective amount of the plant-modifying composition of any one of paragraphs 1-43, wherein the method increases the fitness of the plant relative to an untreated plant.

50. A method of increasing the fitness of a plant, the method comprising contacting an embryo of the plant with an effective amount of the plant-modifying composition of any one of paragraphs 1-43, wherein the method increases the fitness of the plant relative to an untreated plant.

51. A method of increasing the fitness of a plant, the method comprising contacting a protoplast of the plant with an effective amount of the plant-modifying composition of any one of paragraphs 1-43, wherein the method increases the fitness of the plant relative to an untreated plant.

52. A method of increasing the fitness of a plant, the method comprising contacting a plant cell of the plant with an effective amount of the plant-modifying composition of any one of paragraphs 1-43, wherein the method increases the fitness of the plant relative to an untreated plant.

53. The method of any one of paragraphs 46-52, wherein the increase in fitness is an increase in development, growth, yield, resistance to abiotic stressors, or resistance to biotic stressors.

54. The method of paragraph 46-52, wherein the increase in plant fitness is an increase in disease resistance, drought tolerance, heat tolerance, cold tolerance, salt tolerance, metal tolerance, herbicide tolerance, chemical tolerance, water use efficiency, nitrogen utilization, resistance to nitrogen stress, nitrogen fixation, pest resistance, herbivore resistance, pathogen resistance, yield, yield under water-limited conditions, vigor, growth, photosynthetic capability, nutrition, protein content, carbohydrate content, oil content, biomass, shoot length, root length, root architecture, seed weight, or amount of harvestable produce.

55. The method of paragraph 46-52, wherein the increase in plant fitness is an increase in quality of products harvested from the plant.

56. The method of paragraph 55, wherein the increase in quality is an improvement in taste, appearance, or shelf-life of a product harvested from the plant.

57. The method of paragraph 46-52, wherein the increase in fitness is a decrease in production of an allergen that stimulates an immune response in an animal.

58. The method of any one of paragraphs 45-57, wherein the plant is an agricultural or horticultural plant.

59. The method of paragraph 58, wherein the plant is a soybean plant, a wheat plant, or a corn plant.

60. The method of any one of paragraphs 45-59, wherein the plant-modifying composition is delivered as a liquid, a solid, an aerosol, a paste, a gel, or a gas.

61. The plant-modifying composition of any one of paragraphs 1-43, wherein the PMPs are lipid reconstituted PMPs (LPMPs).

62. The plant-modifying composition of paragraph 61, wherein the LPMPs comprise an exogenous cationic lipid.

63. The plant-modifying composition of paragraph 61 or 62, wherein each of the modified PMPs comprises at least 1%, 5%, 10%, 20%, 30%, 40%, 50%, 60%, 70%, 80%, 90%, or more than 90% cationic lipid.

64. The plant-modifying composition of any one of paragraphs 61-63, wherein the cationic lipid is DC-cholesterol or DOTAP.

65. A method of administering a heterologous RNA to a plant, the method comprising delivering to the plant a composition comprising a plurality of plant messenger packs (PMPs), each of the plurality comprising the heterologous RNA, wherein the composition is delivered at an effective concentration to increase plant fitness.

66. The method of paragraph 65, wherein the heterologous RNA is a guide RNA (gRNA).

67. The method of paragraph 66, wherein the gRNA is a component of a ribonucleoprotein complex (RNP), and wherein each of the plurality of PMPs comprises the RNP.

68. The method of paragraph 65, wherein the PMPs are lipid reconstituted PMPs (LPMPs).

69. The method of paragraph 65, wherein the heterologous RNA is encapsulated by the PMPs.

70. The method of paragraph 65, wherein each of the PMPs comprises a purified plant extracellular vesicle (EV).

71. The method of paragraph 65, wherein the PMPs in the composition are at a concentration effective to modify a plant trait, wherein the modification increases the fitness of the plant.

72. The method of paragraph 65, wherein the increase in plant fitness is an increase in development, growth, yield, resistance to abiotic stressors, or resistance to biotic stressors.

73. The method of paragraph 65, wherein the increase in plant fitness is a modification to flowering time.

74. The method of paragraph 65, wherein the increase in plant fitness is an increase in the quality of products harvested from the plant.

75. The method of paragraph 65, wherein the increase in plant fitness is an improvement in taste, appearance, or shelf life of a product harvested from the plant.

76. The method of paragraph 65, wherein the increase in fitness is a decrease in production of an allergen that stimulates an immune response in an animal.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Other embodiments are within the claims.

APPENDIX

Table 1: Plant EV-Markers

| Example Species | Accession No. | Protein Name |
| --- | --- | --- |
| Arabidopsis thaliana | C0LGG8 | Probable LRR receptor-like serine/threonine-protein kinase At1g53430 (EC 2.7.11.1) |
| Arabidopsis thaliana | F4HQT8 | Uncharacterized protein |
| Arabidopsis thaliana | F4HWU0 | Protein kinase superfamily protein |
| Arabidopsis thaliana | F4I082 | Bifunctional inhibitor/lipid-transfer protein/seed storage 2S albumin superfamily protein |
| Arabidopsis thaliana | F4I3M3 | Kinase with tetratricopeptide repeat domain-containing protein |
| Arabidopsis thaliana | F4IB62 | Leucine-rich repeat protein kinase family protein |
| Arabidopsis thaliana | O03042 | Ribulose bisphosphate carboxylase large chain (RuBisCO large subunit) (EC 4.1.1.39) |
| Arabidopsis thaliana | O03986 | Heat shock protein 90-4 (AtHSP90.4) (AtHsp90-4) (Heat shock protein 81-4) (Hsp81-4) |
| Arabidopsis thaliana | O04023 | Protein SRC2 homolog (AtSRC2) |
| Arabidopsis thaliana | O04309 | Jacalin-related lectin 35 (JA-responsive protein 1) (Myrosinase-binding protein-like At3g16470) |
| Arabidopsis thaliana | O04314 | PYK10-binding protein 1 (Jacalin-related lectin 30) (Jasmonic acid-induced protein) |
| Arabidopsis thaliana | O04922 | Probable glutathione peroxidase 2 (EC 1.11.1.9) |
| Arabidopsis thaliana | O22126 | Fasciclin-like arabinogalactan protein 8 (AtAGP8) |
| Arabidopsis thaliana | O23179 | Patatin-like protein 1 (AtPLP1) (EC 3.1.1.-) (Patatin-related phospholipase A IIgamma) (pPLAIIg) (Phospholipase A IVA) (AtPLAIVA) |
| Arabidopsis thaliana | O23207 | Probable NAD(P)H dehydrogenase (quinone) FQR1-like 2 (EC 1.6.5.2) |
| Arabidopsis thaliana | O23255 | Adenosylhomocysteinase 1 (AdoHcyase 1) (EC 3.3.1.1) (Protein EMBRYO DEFECTIVE 1395) (Protein HOMOLOGY-DEPENDENT GENE SILENCING 1) (S-adenosyl-L-homocysteine hydrolase 1) (SAH hydrolase 1) |
| Arabidopsis thaliana | O23482 | Oligopeptide transporter 3 (AtOPT3) |
| Arabidopsis thaliana | O23654 | V-type proton ATPase catalytic subunit A (V-ATPase subunit A) (EC 3.6.3.14) (V-ATPase 69 kDa subunit) (Vacuolar H(+)-ATPase subunit A) (Vacuolar proton pump subunit alpha) |
| Arabidopsis thaliana | O48788 | Probable inactive receptor kinase At2g26730 |
| Arabidopsis thaliana | O48963 | Phototropin-1 (EC 2.7.11.1) (Non-phototropic hypocotyl protein 1) (Root phototropism protein 1) |
| Arabidopsis thaliana | O49195 | Vegetative storage protein 1 |
| Arabidopsis thaliana | O50008 | 5-methyltetrahydropteroyltriglutamate--homocysteine methyltransferase 1 (EC 2.1.1.14) (Cobalamin-independent methionine synthase 1) (AtMS1) (Vitamin-B12-independent methionine synthase 1) |
| Arabidopsis thaliana | O64696 | Putative uncharacterized protein At2g34510 |
| Arabidopsis thaliana | O65572 | Carotenoid 9,10(9',10')-cleavage dioxygenase 1 (EC 1.14.99.n4) (AtCCD1) (Neoxanthin cleavage enzyme NC1) (AtNCED1) |
| Arabidopsis thaliana | O65660 | PLAT domain-containing protein 1 (AtPLAT1) (PLAT domain protein 1) |
| Arabidopsis thaliana | O65719 | Heat shock 70 kDa protein 3 (Heat shock cognate 70 kDa protein 3) (Heat shock cognate protein 70-3) (AtHsc70-3) (Heat shock protein 70-3) (AtHsp70-3) |
| Arabidopsis thaliana | O80517 | Uclacyanin-2 (Blue copper-binding protein II) (BCB II) (Phytocyanin 2) (Uclacyanin-II) |
| Arabidopsis thaliana | O80576 | At2g44060 (Late embryogenesis abundant protein, group 2) (Similar to late embryogenesis abundant proteins) |

APPENDIX-continued

Table 1: Plant EV-Markers

| Example Species | Accession No. | Protein Name |
| --- | --- | --- |
| Arabidopsis thaliana | O80725 | ABC transporter B family member 4 (ABC transporter ABCB.4) (AtABCB4) (Multidrug resistance protein 4) (P-glycoprotein 4) |
| Arabidopsis thaliana | O80837 | Remorin (DNA-binding protein) |
| Arabidopsis thaliana | O80852 | Glutathione S-transferase F9 (AtGSTF9) (EC 2.5.1.18) (AtGSTF7) (GST class-phi member 9) |
| Arabidopsis thaliana | O80858 | Expressed protein (Putative uncharacterized protein At2g30930) (Putative uncharacterized protein At2g30930; F7F1.14) |
| Arabidopsis thaliana | O80939 | L-type lectin-domain containing receptor kinase IV.1 (Arabidopsis thaliana lectin-receptor kinase e) (AthlecRK-e) (LecRK-IV.1) (EC 2.7.11.1) (Lectin Receptor Kinase 1) |
| Arabidopsis thaliana | O80948 | Jacalin-related lectin 23 (Myrosinase-binding protein-like At2g39330) |
| Arabidopsis thaliana | O82628 | V-type proton ATPase subunit G1 (V-ATPase subunit G1) (Vacuolar H(+)-ATPase subunit G isoform 1) (Vacuolar proton pump subunit G1) |
| Arabidopsis thaliana | P10795 | Ribulose bisphosphate carboxylase small chain 1A, chloroplastic (RuBisCO small subunit 1A) (EC 4.1.1.39) |
| Arabidopsis thaliana | P10896 | Ribulose bisphosphate carboxylase/oxygenase activase, chloroplastic (RA) (RuBisCO activase) |
| Arabidopsis thaliana | P17094 | 60S ribosomal protein L3-1 (Protein EMBRYO DEFECTIVE 2207) |
| Arabidopsis thaliana | P19456 | ATPase 2, plasma membrane-type (EC 3.6.3.6) (Proton pump 2) |
| Arabidopsis thaliana | P20649 | ATPase 1, plasma membrane-type (EC 3.6.3.6) (Proton pump 1) |
| Arabidopsis thaliana | P22953 | Probable mediator of RNA polymerase II transcription subunit 37e (Heat shock 70 kDa protein 1) (Heat shock cognate 70 kDa protein 1) (Heat shock cognate protein 70-1) (AtHsc70-1) (Heat shock protein 70-1) (AtHsp70-1) (Protein EARLY-RESPONSIVE TO DEHYDRATION 2) |
| Arabidopsis thaliana | P23586 | Sugar transport protein 1 (Glucose transporter) (Hexose transporter 1) |
| Arabidopsis thaliana | P24636 | Tubulin beta-4 chain (Beta-4-tubulin) |
| Arabidopsis thaliana | P25696 | Bifunctional enolase 2/transcriptional activator (EC 4.2.1.11) (2-phospho-D-glycerate hydro-lyase 2) (2-phosphoglycerate dehydratase 2) (LOW EXPRESSION OF OSMOTICALLY RESPONSIVE GENES 1) |
| Arabidopsis thaliana | P25856 | Glyceraldehyde-3-phosphate dehydrogenase GAPA1, chloroplastic (EC 1.2.1.13) (NADP-dependent glyceraldehydephosphate dehydrogenase A subunit 1) |
| Arabidopsis thaliana | P28186 | Ras-related protein RABE1c (AtRABE1c) (Ras-related protein Ara-3) (Ras-related protein Rab8A) (AtRab8A) |
| Arabidopsis thaliana | P30302 | Aquaporin PIP2-3 (Plasma membrane intrinsic protein 2-3) (AtPIP2;3) (Plasma membrane intrinsic protein 2c) (PIP2c) (RD28-PIP) (TMP2C) (Water stress-induced tonoplast intrinsic protein) (WSI-TIP) [Cleaved into: Aquaporin PIP2-3, N-terminally processed] |
| Arabidopsis thaliana | P31414 | Pyrophosphate-energized vacuolar membrane proton pump 1 (EC 3.6.1.1) (Pyrophosphate-energized inorganic pyrophosphatase 1) (H(+)-PPase 1) (Vacuolar proton pyrophosphatase 1) (Vacuolar proton pyrophosphatase 3) |
| Arabidopsis thaliana | P32961 | Nitrilase 1 (EC 3.5.5.1) |
| Arabidopsis thaliana | P38666 | 60S ribosomal protein L24-2 (Protein SHORT VALVE 1) |
| Arabidopsis thaliana | P39207 | Nucleoside diphosphate kinase 1 (EC 2.7.4.6) (Nucleoside diphosphate kinase I) (NDK I) (NDP kinase I) (NDPK I) |
| Arabidopsis thaliana | P42643 | 14-3-3-like protein GF14 chi (General regulatory factor 1) |
| Arabidopsis thaliana | P42737 | Beta carbonic anhydrase 2, chloroplastic (AtbCA2) (AtbetaCA2) (EC 4.2.1.1) (Beta carbonate dehydratase 2) |
| Arabidopsis thaliana | P42759 | Dehydrin ERD10 (Low-temperature-induced protein LTI45) |
| Arabidopsis thaliana | P42761 | Glutathione S-transferase F10 (AtGSTF10) (EC 2.5.1.18) (AtGSTF4) (GST class-phi member 10) (Protein EARLY RESPONSE TO DEHYDRATION 13) |
| Arabidopsis thaliana | P42763 | Dehydrin ERD14 |
| Arabidopsis thaliana | P42791 | 60S ribosomal protein L18-2 |
| Arabidopsis thaliana | P43286 | Aquaporin PIP2-1 (Plasma membrane intrinsic protein 2-1) (AtPIP2;1) (Plasma membrane intrinsic protein 2a) (PIP2a) [Cleaved into: Aquaporin PIP2-1, N-terminally processed] |
| Arabidopsis thaliana | P46286 | 60S ribosomal protein L8-1 (60S ribosomal protein L2) (Protein EMBRYO DEFECTIVE 2296) |
| Arabidopsis thaliana | P46422 | Glutathione S-transferase F2 (AtGSTF2) (EC 2.5.1.18) (24 kDa auxin-binding protein) (AtPM24) (GST class-phi member 2) |

APPENDIX-continued

Table 1: Plant EV-Markers

| Example Species | Accession No. | Protein Name |
|---|---|---|
| *Arabidopsis thaliana* | P47998 | Cysteine synthase 1 (EC 2.5.1.47) (At.OAS.5-8) (Beta-substituted Ala synthase 1;1) (ARAth-Bsas1;1) (CSase A) (AtCS-A) (Cys-3A) (O-acetylserine (thiol)-lyase 1) (OAS-TL A) (O-acetylserine sulfhydrylase) (Protein ONSET OF LEAF DEATH 3) |
| *Arabidopsis thaliana* | P48347 | 14-3-3-like protein GF14 epsilon (General regulatory factor 10) |
| *Arabidopsis thaliana* | P48491 | Triosephosphate isomerase, cytosolic (TIM) (Triose-phosphate isomerase) (EC 5.3.1.1) |
| *Arabidopsis thaliana* | P50318 | Phosphoglycerate kinase 2, chloroplastic (EC 2.7.2.3) |
| *Arabidopsis thaliana* | P53492 | Actin-7 (Actin-2) |
| *Arabidopsis thaliana* | P54144 | Ammonium transporter 1 member 1 (AtAMT1;1) |
| *Arabidopsis thaliana* | P92963 | Ras-related protein RABB1c (AtRABB1c) (Ras-related protein Rab2A) (AtRab2A) |
| *Arabidopsis thaliana* | P93004 | Aquaporin PIP2-7 (Plasma membrane intrinsic protein 2-7) (AtPIP2;7) (Plasma membrane intrinsic protein 3) (Salt stress-induced major intrinsic protein) [Cleaved into: Aquaporin PIP2-7, N-terminally processed] |
| *Arabidopsis thaliana* | P93025 | Phototropin-2 (EC 2.7.11.1) (Defective in chloroplast avoidance protein 1) (Non-phototropic hypocotyl 1-like protein 1) (AtKin7) (NPH1-like protein 1) |
| *Arabidopsis thaliana* | P93819 | Malate dehydrogenase 1, cytoplasmic (EC 1.1.1.37) (Cytosolic NAD-dependent malate dehydrogenase 1) (cNAD-MDH1) (Cytsolic malate dehydrogenase 1) (Cytosolic MDH1) |
| *Arabidopsis thaliana* | Q03250 | Glycine-rich RNA-binding protein 7 (AtGR-RBP7) (AtRBG7) (Glycine-rich protein 7) (AtGRP7) (Protein COLD, CIRCADIAN RHYTHM, AND RNA BINDING 2) (Protein CCR2) |
| *Arabidopsis thaliana* | Q05431 | L-ascorbate peroxidase 1, cytosolic (AP) (AtAPx01) (EC 1.11.1.11) |
| *Arabidopsis thaliana* | Q06611 | Aquaporin PIP1-2 (AtPIP1;2) (Plasma membrane intrinsic protein 1b) (PIP1b) (Transmembrane protein A) (AthH2) (TMP-A) |
| *Arabidopsis thaliana* | Q07488 | Blue copper protein (Blue copper-binding protein) (AtBCB) (Phytocyanin 1) (Stellacyanin) |
| *Arabidopsis thaliana* | Q0WLB5 | Clathrin heavy chain 2 |
| *Arabidopsis thaliana* | Q0WNJ6 | Clathrin heavy chain 1 |
| *Arabidopsis thaliana* | Q1ECE0 | Vesicle-associated protein 4-1 (Plant VAP homolog 4-1) (AtPVA41) (Protein MEMBRANE-ASSOCIATED MANNITOL-INDUCED) (AtMAMI) (VAMP-associated protein 4-1) |
| *Arabidopsis thaliana* | Q38882 | Phospholipase D alpha 1 (AtPLDalpha1) (PLD alpha 1) (EC 3.1.4.4) (Choline phosphatase 1) (PLDalpha) (Phosphatidylcholine-hydrolyzing phospholipase D 1) |
| *Arabidopsis thaliana* | Q38900 | Peptidyl-prolyl cis-trans isomerase CYP19-1 (PPIase CYP19-1) (EC 5.2.1.8) (Cyclophilin of 19 kDa 1) (Rotamase cyclophilin-3) |
| Arabidopsis thaliana | Q39033 | Phosphoinositide phospholipase C 2 (EC 3.1.4.11) (Phosphoinositide phospholipase PLC2) (AtPLC2) (PI-PLC2) |
| *Arabidopsis thaliana* | Q39085 | Delta(24)-sterol reductase (EC 1.3.1.72) (Cell elongation protein DIMINUTO) (Cell elongation protein Dwarf1) (Protein CABBAGE1) (Protein ENHANCED VERY-LOW-FLUENCE RESPONSE 1) |
| *Arabidopsis thaliana* | Q39228 | Sugar transport protein 4 (Hexose transporter 4) |
| *Arabidopsis thaliana* | Q39241 | Thioredoxin H5 (AtTrxh5) (Protein LOCUS OF INSENSITIVITY TO VICTORIN 1) (Thioredoxin 5) (AtTRX5) |
| *Arabidopsis thaliana* | Q39258 | V-type proton ATPase subunit E1 (V-ATPase subunit E1) (Protein EMBRYO DEFECTIVE 2448) (Vacuolar H(+)-ATPase subunit E isoform 1) (Vacuolar proton pump subunit E1) |
| *Arabidopsis thaliana* | Q42112 | 60S acidic ribosomal protein PO-2 |
| *Arabidopsis thaliana* | Q42403 | Thioredoxin H3 (AtTrxh3) (Thioredoxin 3) (AtTRX3) |
| *Arabidopsis thaliana* | Q42479 | Calcium-dependent protein kinase 3 (EC 2.7.11.1) (Calcium-dependent protein kinase isoform CDPK6) (AtCDPK6) |
| *Arabidopsis thaliana* | Q42547 | Catalase-3 (EC 1.11.1.6) |
| *Arabidopsis thaliana* | Q56WH1 | Tubulin alpha-3 chain |
| *Arabidopsis thaliana* | Q56WK6 | Patellin-1 |
| *Arabidopsis thaliana* | Q56X75 | CASP-like protein 4D2 (AtCASPL4D2) |
| *Arabidopsis thaliana* | Q56ZI2 | Patellin-2 |
| *Arabidopsis thaliana* | Q7Y208 | Glycerophosphodiester phosphodiesterase GDPDL1 (EC 3.1.4.46) (Glycerophosphodiester phosphodiesterase-like 1) (ATGDPDL1) (Glycerophosphodiesterase-like 3) (Protein SHV3-LIKE 2) |
| *Arabidopsis thaliana* | Q84VZ5 | Uncharacterized GPI-anchored protein At5g19240 |
| *Arabidopsis thaliana* | Q84WU7 | Eukaryotic aspartyl protease family protein (Putative uncharacterized protein At3g51330) |

APPENDIX-continued

Table 1: Plant EV-Markers

| Example Species | Accession No. | Protein Name |
|---|---|---|
| *Arabidopsis thaliana* | Q8GUL8 | Uncharacterized GPI-anchored protein At5g19230 |
| *Arabidopsis thaliana* | Q8GYA4 | Cysteine-rich receptor-like protein kinase 10 (Cysteine-rich RLK10) (EC 2.7.11.-) (Receptor-like protein kinase 4) |
| *Arabidopsis thaliana* | Q8GYN5 | RPM1-interacting protein 4 |
| *Arabidopsis thaliana* | Q8GZ99 | At5g49760 (Leucine-rich repeat protein kinase family protein) (Leucine-rich repeat receptor-like protein kinase) (Putative receptor protein kinase) |
| *Arabidopsis thaliana* | Q8L636 | Sodium/calcium exchanger NCL (Na(+)/Ca(2+)-exchange protein NCL) (Protein NCX-like) (AtNCL) |
| *Arabidopsis thaliana* | Q8L7S1 | At1g45200 (At1g45200/At1g45200) (Triacylglycerol lipase-like 1) |
| *Arabidopsis thaliana* | Q8LAA6 | Probable aquaporin PIP1-5 (AtPIP1;5) (Plasma membrane intrinsic protein 1d) (PIP1d) |
| *Arabidopsis thaliana* | Q8LCP6 | Endoglucanase 10 (EC 3.2.1.4) (Endo-1,4-beta glucanase 10) |
| *Arabidopsis thaliana* | Q8RWV0 | Transketolase-1, chloroplastic (TK) (EC 2.2.1.1) |
| *Arabidopsis thaliana* | Q8S8Q6 | Tetraspanin-8 |
| *Arabidopsis thaliana* | Q8VZG8 | MDIS1-interacting receptor like kinase 2 (AtMIK2) (Probable LRR receptor-like serine/threonine-protein kinase At4g08850) (EC 2.7.11.1) |
| *Arabidopsis thaliana* | Q8VZU2 | Syntaxin-132 (AtSYP132) |
| *Arabidopsis thaliana* | Q8W4E2 | V-type proton ATPase subunit B3 (V-ATPase subunit B3) (Vacuolar H(+)-ATPase subunit B isoform 3) (Vacuolar proton pump subunit B3) |
| *Arabidopsis thaliana* | Q8W4S4 | V-type proton ATPase subunit a3 (V-ATPase subunit a3) (V-type proton ATPase 95 kDa subunit a isoform 3) (V-ATPase 95 kDa isoform a3) (Vacuolar H(+)-ATPase subunit a isoform 3) (Vacuolar proton pump subunit a3) (Vacuolar proton translocating ATPase 95 kDa subunit a isoform 3) |
| *Arabidopsis thaliana* | Q93VG5 | 40S ribosomal protein S8-1 |
| *Arabidopsis thaliana* | Q93XY5 | Tetraspanin-18 (TOM2A homologous protein 2) |
| *Arabidopsis thaliana* | Q93YS4 | ABC transporter G family member 22 (ABC transporter ABCG.22) (AtABCG22) (White-brown complex homolog protein 23) (AtWBC23) |
| *Arabidopsis thaliana* | Q93Z08 | Glucan endo-1,3-beta-glucosidase 6 (EC 3.2.1.39) ((1->3)-beta-glucan endohydrolase 6) ((1->3)-beta-glucanase 6) (Beta-1,3-endoglucanase 6) (Beta-1,3-glucanase 6) |
| *Arabidopsis thaliana* | Q940M8 | 3-oxo-5-alpha-steroid 4-dehydrogenase (DUF1295) (At1g73650/F25P22_7) |
| *Arabidopsis thaliana* | Q944A7 | Probable serine/threonine-protein kinase At4g35230 (EC 2.7.11.1) |
| *Arabidopsis thaliana* | Q944G5 | Protein NRT1/PTR FAMILY 2.10 (AtNPF2.10) (Protein GLUCOSINOLATE TRANSPORTER-1) |
| *Arabidopsis thaliana* | Q94AZ2 | Sugar transport protein 13 (Hexose transporter 13) (Multicopy suppressor of snf4 deficiency protein 1) |
| *Arabidopsis thaliana* | Q94BT2 | Auxin-induced in root cultures protein 12 |
| *Arabidopsis thaliana* | Q94CE4 | Beta carbonic anhydrase 4 (AtbCA4) (AtbetaCA4) (EC 4.2.1.1) (Beta carbonate dehydratase 4) |
| *Arabidopsis thaliana* | Q94KI8 | Two pore calcium channel protein 1 (Calcium channel protein 1) (AtCCH1) (Fatty acid oxygenation up-regulated protein 2) (Voltage-dependent calcium channel protein TPC1) (AtTPC1) |
| *Arabidopsis thaliana* | Q96262 | Plasma membrane-associated cation-binding protein 1 (AtPCAP1) (Microtubule-destabilizing protein 25) |
| *Arabidopsis thaliana* | Q9C5Y0 | Phospholipase D delta (AtPLDdelta) (PLD delta) (EC 3.1.4.4) |
| *Arabidopsis thaliana* | Q9C7F7 | Non-specific lipid transfer protein GPI-anchored 1 (AtLTPG-1) (Protein LTP-GPI-ANCHORED 1) |
| *Arabidopsis thaliana* | Q9C821 | Proline-rich receptor-like protein kinase PERK15 (EC 2.7.11.1) (Proline-rich extensin-like receptor kinase 15) (AtPERK15) |
| *Arabidopsis thaliana* | Q9C8G5 | CSC1-like protein ERD4 (Protein EARLY-RESPONSIVE TO DEHYDRATION STRESS 4) |
| *Arabidopsis thaliana* | Q9C9C5 | 60S ribosomal protein L6-3 |
| *Arabidopsis thaliana* | Q9CAR7 | Hypersensitive-induced response protein 2 (AtHIR2) |
| *Arabidopsis thaliana* | Q9FFH6 | Fasciclin-like arabinogalactan protein 13 |
| *Arabidopsis thaliana* | Q9FGT8 | Temperature-induced lipocalin-1 (AtTIL1) |
| *Arabidopsis thaliana* | Q9FJ62 | Glycerophosphodiester phosphodiesterase GDPDL4 (EC 3.1.4.46) (Glycerophosphodiester phosphodiesterase-like 4) (ATGDPDL4) (Glycerophosphodiesterase-like 1) (Protein SHV3-LIKE 1) |
| *Arabidopsis thaliana* | Q9FK68 | Ras-related protein RABA1c (AtRABA1c) |
| *Arabidopsis thaliana* | Q9FKS8 | Lysine histidine transporter 1 |
| *Arabidopsis thaliana* | Q9FM65 | Fasciclin-like arabinogalactan protein 1 |
| *Arabidopsis thaliana* | Q9FNH6 | NDR1/HIN1-like protein 3 |
| *Arabidopsis thaliana* | Q9FRL3 | Sugar transporter ERD6-like 6 |

APPENDIX-continued

Table 1: Plant EV-Markers

| Example Species | Accession No. | Protein Name |
|---|---|---|
| *Arabidopsis thaliana* | Q9FWR4 | Glutathione S-transferase DHAR1, mitochondrial (EC 2.5.1.18) (Chloride intracellular channel homolog 1) (CLIC homolog 1) (Glutathione-dependent dehydroascorbate reductase 1) (AtDHAR1) (GSH-dependent dehydroascorbate reductase 1) (mtDHAR) |
| *Arabidopsis thaliana* | Q9FX54 | Glyceraldehyde-3-phosphate dehydrogenase GAPC2, cytosolic (EC 1.2.1.12) (NAD-dependent glyceraldehydephosphate dehydrogenase C subunit 2) |
| *Arabidopsis thaliana* | Q9LE22 | Probable calcium-binding protein CML27 (Calmodulin-like protein 27) |
| *Arabidopsis thaliana* | Q9LEX1 | At3g61050 (CaLB protein) (Calcium-dependent lipid-binding (CaLB domain) family protein) |
| *Arabidopsis thaliana* | Q9LF79 | Calcium-transporting ATPase 8, plasma membrane-type (EC 3.6.3.8) (Ca(2+)-ATPase isoform 8) |
| *Arabidopsis thaliana* | Q9LJG3 | GDSL esterase/lipase ESM1 (EC 3.1.1.-) (Extracellular lipase ESM1) (Protein EPITHIOSPECIFIER MODIFIER 1) (AtESM1) |
| *Arabidopsis thaliana* | Q9LJI5 | V-type proton ATPase subunit d1 (V-ATPase subunit d1) (Vacuolar H(+)-ATPase subunit d isoform 1) (Vacuolar proton pump subunit d1) |
| *Arabidopsis thaliana* | Q9LME4 | Probable protein phosphatase 2C 9 (AtPP2C09) (EC 3.1.3.16) (Phytochrome-associated protein phosphatase 2C) (PAPP2C) |
| *Arabidopsis thaliana* | Q9LNP3 | At1g17620/F11A6_23 (F1L3.32) (Late embryogenesis abundant (LEA) hydroxyproline-rich glycoprotein family) (Putative uncharacterized protein At1g17620) |
| *Arabidopsis thaliana* | Q9LNW1 | Ras-related protein RABA2b (AtRABA2b) |
| *Arabidopsis thaliana* | Q9LQU2 | Protein PLANT CADMIUM RESISTANCE 1 (AtPCR1) |
| *Arabidopsis thaliana* | Q9LQU4 | Protein PLANT CADMIUM RESISTANCE 2 (AtPCR2) |
| *Arabidopsis thaliana* | Q9LR30 | Glutamate--glyoxylate aminotransferase 1 (AtGGT2) (EC 2.6.1.4) (Alanine aminotransferase GGT1) (EC 2.6.1.2) (Alanine--glyoxylate aminotransferase GGT1) (EC 2.6.1.44) (Alanine-2-oxoglutarate aminotransferase 1) (EC 2.6.1.-) |
| *Arabidopsis thaliana* | Q9LSI9 | Inactive LRR receptor-like serine/threonine-protein kinase BIR2 (Protein BAK1-INTERACTING RECEPTOR-LIKE KINASE 2) |
| *Arabidopsis thaliana* | Q9LSQ5 | NAD(P)H dehydrogenase (quinone) FQR1 (EC 1.6.5.2) (Flavodoxin-like quinone reductase 1) |
| *Arabidopsis thaliana* | Q9LUT0 | Protein kinase superfamily protein (Putative uncharacterized protein At3g17410) (Serine/threonine protein kinase-like protein) |
| *Arabidopsis thaliana* | Q9LV48 | Proline-rich receptor-like protein kinase PERK1 (EC 2.7.11.1) (Proline-rich extensin-like receptor kinase 1) (AtPERK1) |
| *Arabidopsis thaliana* | Q9LX65 | V-type proton ATPase subunit H (V-ATPase subunit H) (Vacuolar H(+)-ATPase subunit H) (Vacuolar proton pump subunit H) |
| *Arabidopsis thaliana* | Q9LYG3 | NADP-dependent malic enzyme 2 (AtNADP-ME2) (NADP-malic enzyme 2) (EC 1.1.1.40) |
| *Arabidopsis thaliana* | Q9M0B8 | Glucan endo-1,3-beta-glucosidase 5 (EC 3.2.1.39) ((1->3)-beta-glucan endohydrolase 5) ((1->3)-beta-glucanase 5) (Beta-1,3-endoglucanase 5) (Beta-1,3-glucanase 5) |
| *Arabidopsis thaliana* | Q9M2D8 | Uncharacterized protein At3g61260 |
| *Arabidopsis thaliana* | Q9M386 | Late embryogenesis abundant (LEA) hydroxyproline-rich glycoprotein family (Putative uncharacterized protein At3g54200) (Putative uncharacterized protein F24B22.160) |
| *Arabidopsis thaliana* | Q9M390 | Protein NRT1/PTR FAMILY 8.1 (AtNPF8.1) (Peptide transporter PTR1) |
| *Arabidopsis thaliana* | Q9M5P2 | Secretory carrier-associated membrane protein 3 (AtSC3) (Secretory carrier membrane protein 3) |
| *Arabidopsis thaliana* | Q9M8T0 | Probable inactive receptor kinase At3g02880 |
| *Arabidopsis thaliana* | Q9SDS7 | V-type proton ATPase subunit C (V-ATPase subunit C) (Vacuolar H(+)-ATPase subunit C) (Vacuolar proton pump subunit C) |
| *Arabidopsis thaliana* | Q9SEL6 | Vesicle transport v-SNARE 11 (AtVTI11) (Protein SHOOT GRAVITROPISM 4) (Vesicle soluble NSF attachment protein receptor VTI1a) (AtVTI1a) (Vesicle transport v-SNARE protein VTI1a) |
| *Arabidopsis thaliana* | Q9SF29 | Syntaxin-71 (AtSYP71) |
| *Arabidopsis thaliana* | Q9SF85 | Adenosine kinase 1 (AK 1) (EC 2.7.1.20) (Adenosine 5'-phosphotransferase 1) |
| Arabidopsis thaliana | Q9SIE7 | PLAT domain-containing protein 2 (AtPLAT2) (PLAT domain protein 2) |
| *Arabidopsis thaliana* | Q9SIM4 | 60S ribosomal protein L14-1 |
| *Arabidopsis thaliana* | Q9SIU8 | Probable protein phosphatase 2C 20 (AtPP2C20) (EC 3.1.3.16) (AtPPC3;1.2) |

APPENDIX-continued

Table 1: Plant EV-Markers

| Example Species | Accession No. | Protein Name |
|---|---|---|
| *Arabidopsis thaliana* | Q9SJ81 | Fasciclin-like arabinogalactan protein 7 |
| *Arabidopsis thaliana* | Q9SKB2 | Leucine-rich repeat receptor-like serine/threonine/tyrosine-protein kinase SOBIR1 (EC 2.7.10.1) (EC 2.7.11.1) (Protein EVERSHED) (Protein SUPPRESSOR OF BIR1-1) |
| *Arabidopsis thaliana* | Q9SKR2 | Synaptotagmin-1 (NTMC2T1.1) (Synaptotagmin A) |
| *Arabidopsis thaliana* | Q9SLF7 | 60S acidic ribosomal protein P2-2 |
| *Arabidopsis thaliana* | Q9SPE6 | Alpha-soluble NSF attachment protein 2 (Alpha-SNAP2) (N-ethylmaleimide-sensitive factor attachment protein alpha 2) |
| *Arabidopsis thaliana* | Q9SRH6 | Hypersensitive-induced response protein 3 (AtHIR3) |
| *Arabidopsis thaliana* | Q9SRY5 | Glutathione S-transferase F7 (EC 2.5.1.18) (AtGSTF8) (GST class-phi member 7) (Glutathione S-transferase 11) |
| *Arabidopsis thaliana* | Q9SRZ6 | Cytosolic isocitrate dehydrogenase [NADP] (EC 1.1.1.42) |
| *Arabidopsis thaliana* | Q9SSK5 | MLP-like protein 43 |
| *Arabidopsis thaliana* | Q9SU13 | Fasciclin-like arabinogalactan protein 2 |
| *Arabidopsis thaliana* | Q9SU40 | Monocopper oxidase-like protein SKU5 (Skewed roots) |
| *Arabidopsis thaliana* | Q9SUR6 | Cystine lyase CORI3 (EC 4.4.1.35) (Protein CORONATINE INDUCED 3) (Protein JASMONIC ACID RESPONSIVE 2) (Tyrosine aminotransferase CORI3) |
| *Arabidopsis thaliana* | Q9SVC2 | Syntaxin-122 (AtSYP122) (Synt4) |
| *Arabidopsis thaliana* | Q9SVF0 | Putative uncharacterized protein AT4g38350 (Putative uncharacterized protein F22113.120) |
| *Arabidopsis thaliana* | Q9SW40 | Major facilitator superfamily protein (Putative uncharacterized protein AT4g34950) (Putative uncharacterized protein T11/11.190) |
| *Arabidopsis thaliana* | Q9SYT0 | Annexin D1 (AnnAt1) (Annexin A1) |
| *Arabidopsis thaliana* | Q9SZ11 | Glycerophosphodiester phosphodiesterase GDPDL3 (EC 3.1.4.46) (Glycerophosphodiester phosphodiesterase-like 3) (ATGDPDL3) (Glycerophosphodiesterase-like 2) (Protein MUTANT ROOT HAIR 5) (Protein SHAVEN 3) |
| *Arabidopsis thaliana* | Q9SZN1 | V-type proton ATPase subunit B2 (V-ATPase subunit B2) (Vacuolar H(+)-ATPase subunit B isoform 2) (Vacuolar proton pump subunit B2) |
| *Arabidopsis thaliana* | Q9SZP6 | AT4g38690/F20M13_250 (PLC-like phosphodiesterases superfamily protein) (Putative uncharacterized protein AT4g38690) (Putative uncharacterized protein F20M13.250) |
| *Arabidopsis thaliana* | Q9SZR1 | Calcium-transporting ATPase 10, plasma membrane-type (EC 3.6.3.8) (Ca(2+)-ATPase isoform 10) |
| *Arabidopsis thaliana* | Q9T053 | Phospholipase D gamma 1 (AtPLDgamma1) (PLD gamma 1) (EC 3.1.4.4) (Choline phosphatase) (Lecithinase D) (Lipophosphodiesterase II) |
| *Arabidopsis thaliana* | Q9T076 | Early nodulin-like protein 2 (Phytocyanin-like protein) |
| *Arabidopsis thaliana* | Q9T0A0 | Long chain acyl-CoA synthetase 4 (EC 6.2.1.3) |
| *Arabidopsis thaliana* | Q9T0G4 | Putative uncharacterized protein AT4g10060 (Putative uncharacterized protein T5L19.190) |
| *Arabidopsis thaliana* | Q9XEE2 | Annexin D2 (AnnAt2) |
| *Arabidopsis thaliana* | Q9XGM1 | V-type proton ATPase subunit D (V-ATPase subunit D) (Vacuolar H(+)-ATPase subunit D) (Vacuolar proton pump subunit D) |
| *Arabidopsis thaliana* | Q9XI93 | At1g13930/F16A14.27 (F16A14.14) (F7A19.2 protein) (Oleosin-B3-like protein) |
| *Arabidopsis thaliana* | Q9XIE2 | ABC transporter G family member 36 (ABC transporter ABCG.36) (AtABCG36) (Pleiotropic drug resistance protein 8) (Protein PENETRATION 3) |
| *Arabidopsis thaliana* | Q9ZPZ4 | Putative uncharacterized protein (Putative uncharacterized protein At1g09310) (T31J12.3 protein) |
| *Arabidopsis thaliana* | Q9ZQX4 | V-type proton ATPase subunit F (V-ATPase subunit F) (V-ATPase 14 kDa subunit) (Vacuolar H(+)-ATPase subunit F) (Vacuolar proton pump subunit F) |
| *Arabidopsis thaliana* | Q9ZSA2 | Calcium-dependent protein kinase 21 (EC 2.7.11.1) |
| *Arabidopsis thaliana* | Q9ZSD4 | Syntaxin-121 (AtSYP121) (Syntaxin-related protein At-Syr1) |
| *Arabidopsis thaliana* | Q9ZV07 | Probable aquaporin PIP2-6 (Plasma membrane intrinsic protein 2-6) (AtPIP2;6) (Plasma membrane intrinsic protein 2e) (PIP2e) [Cleaved into: Probable aquaporin PIP2-6, N-terminally processed] |
| *Arabidopsis thaliana* | Q9ZVF3 | MLP-like protein 328 |
| *Arabidopsis thaliana* | Q9ZWA8 | Fasciclin-like arabinogalactan protein 9 |
| *Arabidopsis thaliana* | Q9ZSD4 | SYR1, Syntaxin Related Protein 1, also known as SYP121, PENETRATION1/PEN1 (Protein PENETRATION 1) |
| *Citrus lemon* | A1ECK0 | Putative glutaredoxin |
| *Citrus lemon* | A9YVC9 | Pyrophosphate--fructose 6-phosphate 1-phosphotransferase subunit beta (PFP) (EC 2.7.1.90) (6-phosphofructokinase, pyrophosphate dependent) (PPi-PFK) (Pyrophosphate-dependent 6-phosphofructose-1-kinase) |

APPENDIX-continued

Table 1: Plant EV-Markers

| Example Species | Accession No. | Protein Name |
|---|---|---|
| *Citrus lemon* | B2YGY1 | Glycosyltransferase (EC 2.4.1.-) |
| *Citrus lemon* | B6DZD3 | Glutathione S-transferase Tau2 (Glutathione transferase Tau2) |
| *Citrus lemon* | C3VIC2 | Translation elongation factor |
| *Citrus lemon* | C8CPS0 | Importin subunit alpha |
| *Citrus lemon* | D3JWB5 | Flavanone 3-hydroxylase |
| *Citrus lemon* | E0ADY2 | Putative caffeic acid O-methyltransferase |
| *Citrus lemon* | E5DK62 | ATP synthase subunit alpha (Fragment) |
| *Citrus lemon* | E9M5S3 | Putative L-galactose-1-phosphate phosphatase |
| *Citrus lemon* | F1CGQ9 | Heat shock protein 90 |
| *Citrus lemon* | F8WL79 | Aminopeptidase (EC 3.4.11.-) |
| *Citrus lemon* | F8WL86 | Heat shock protein |
| *Citrus lemon* | K9JG59 | Abscisic acid stress ripening-related protein |
| *Citrus lemon* | Q000W4 | Fe(III)-chelate reductase |
| Citrus lemon | Q39538 | Heat shock protein (Fragment) |
| *Citrus lemon* | Q5UEN6 | Putative signal recognition particle protein |
| *Citrus lemon* | Q8GV08 | Dehydrin |
| *Citrus lemon* | Q8L893 | Cytosolic phosphoglucomutase (Fragment) |
| *Citrus lemon* | Q8S990 | Polygalacturonase-inhibiting protein |
| *Citrus lemon* | Q8W3U6 | Polygalacturonase-inhibitor protein |
| *Citrus lemon* | Q93XL8 | Dehydrin COR15 |
| *Citrus lemon* | Q941Q1 | Non-symbiotic hemoglobin class 1 |
| *Citrus lemon* | Q9MBF3 | Glycine-rich RNA-binding protein |
| *Citrus lemon* | Q9SP55 | V-type proton ATPase subunit G (V-ATPase subunit G) (Vacuolar proton pump subunit G) |
| *Citrus lemon* | Q9THJ8 | Ribulose bisphosphate carboxylase large chain (EC 4.1.1.39) (Fragment) |
| *Citrus lemon* | Q9ZST2 | Pyrophosphate--fructose 6-phosphate 1-phosphotransferase subunit alpha (PFP) (6-phosphofructokinase, pyrophosphate dependent) (PPi-PFK) (Pyrophosphate-dependent 6-phosphofructose-1-kinase) |
| *Citrus lemon* | Q9ZWH6 | Polygalacturonase inhibitor |
| *Citrus lemon* | S5DXI9 | Nucleocapsid protein |
| *Citrus lemon* | S5NFC6 | GTP cyclohydrolase |
| *Citrus lemon* | V4RG42 | Uncharacterized protein |
| *Citrus lemon* | V4RGP4 | Uncharacterized protein |
| *Citrus lemon* | V4RHN8 | Uncharacterized protein |
| *Citrus lemon* | V4RJ07 | Uncharacterized protein |
| *Citrus lemon* | V4RJK9 | Adenosylhomocysteinase (EC 3.3.1.1) |
| *Citrus lemon* | V4RJM1 | Uncharacterized protein |
| *Citrus lemon* | V4RJX1 | 40S ribosomal protein S6 |
| *Citrus lemon* | V4RLB2 | Uncharacterized protein |
| *Citrus lemon* | V4RMX8 | Uncharacterized protein |
| *Citrus lemon* | V4RNA5 | Uncharacterized protein |
| *Citrus lemon* | V4RP81 | Glycosyltransferase (EC 2.4.1.-) |
| *Citrus lemon* | V4RPZ5 | Adenylyl cyclase-associated protein |
| *Citrus lemon* | V4RTN9 | Histone H4 |
| *Citrus lemon* | V4RUZ4 | Phosphoserine aminotransferase (EC 2.6.1.52) |
| *Citrus lemon* | V4RVF6 | Uncharacterized protein |
| *Citrus lemon* | V4RXD4 | Uncharacterized protein |
| *Citrus lemon* | V4RXG2 | Uncharacterized protein |
| *Citrus lemon* | V4RYA0 | Uncharacterized protein |
| *Citrus lemon* | V4RYE3 | Uncharacterized protein |
| *Citrus lemon* | V4RYH3 | Uncharacterized protein |
| *Citrus lemon* | V4RYX8 | Uncharacterized protein |
| *Citrus lemon* | V4RZ12 | Coatomer subunit beta' |
| *Citrus lemon* | V4RZ89 | Uncharacterized protein |
| *Citrus lemon* | V4RZE3 | Uncharacterized protein |
| *Citrus lemon* | V4RZF3 | 1,2-dihydroxy-3-keto-5-methylthiopentene dioxygenase (EC 1.13.11.54) (Acireductone dioxygenase (Fe(2+)-requiring)) (ARD) (Fe-ARD) |
| *Citrus lemon* | V4RZM7 | Uncharacterized protein |
| *Citrus lemon* | V4RZX6 | Uncharacterized protein |
| *Citrus lemon* | V4S1V0 | Uncharacterized protein |
| *Citrus lemon* | V4S2B6 | Uncharacterized protein |
| *Citrus lemon* | V4S2N1 | Uncharacterized protein |
| *Citrus lemon* | V4S2S5 | Uncharacterized protein (Fragment) |
| *Citrus lemon* | V4S346 | Uncharacterized protein |
| *Citrus lemon* | V4S3T8 | Uncharacterized protein |
| *Citrus lemon* | V4S409 | Cyanate hydratase (Cyanase) (EC 4.2.1.104) (Cyanate hydrolase) (Cyanate lyase) |
| *Citrus lemon* | V4S4E4 | Histone H2B |
| *Citrus lemon* | V4S4F6 | Flavin-containing monooxygenase (EC 1.-.-.-) |
| *Citrus lemon* | V4S4J1 | Uncharacterized protein |
| *Citrus lemon* | V4S4K9 | Uncharacterized protein |
| *Citrus lemon* | V4S535 | Proteasome subunit alpha type (EC 3.4.25.1) |

APPENDIX-continued

Table 1: Plant EV-Markers

| Example Species | Accession No. | Protein Name |
|---|---|---|
| *Citrus lemon* | V4S5A8 | Isocitrate dehydrogenase [NADP] (EC 1.1.1.42) |
| *Citrus lemon* | V4S5G8 | Uncharacterized protein |
| *Citrus lemon* | V4S5I6 | Uncharacterized protein |
| *Citrus lemon* | V4S5N4 | Uncharacterized protein (Fragment) |
| *Citrus lemon* | V4S5Q3 | Uncharacterized protein |
| *Citrus lemon* | V4S5X8 | Uncharacterized protein |
| *Citrus lemon* | V4S5Y1 | Uncharacterized protein |
| *Citrus lemon* | V4S6P4 | Calcium-transporting ATPase (EC 3.6.3.8) |
| *Citrus lemon* | V4S6W0 | Uncharacterized protein |
| *Citrus lemon* | V4S6W7 | Uncharacterized protein (Fragment) |
| *Citrus lemon* | V4S6Y4 | Uncharacterized protein |
| *Citrus lemon* | V4S7I3 | Ribosomal protein L19 |
| *Citrus lemon* | V4S7U0 | Uncharacterized protein |
| *Citrus lemon* | V4S7U5 | Uncharacterized protein |
| *Citrus lemon* | V4S7W4 | Pyruvate kinase (EC 2.7.1.40) |
| *Citrus lemon* | V4S885 | Uncharacterized protein |
| *Citrus lemon* | V4S8T3 | Peptidyl-prolyl cis-trans isomerase (PPIase) (EC 5.2.1.8) |
| *Citrus lemon* | V4S920 | Uncharacterized protein |
| *Citrus lemon* | V4S999 | Uncharacterized protein |
| *Citrus lemon* | V4S9G5 | Phosphoglycerate kinase (EC 2.7.2.3) |
| *Citrus lemon* | V4S9Q6 | Beta-amylase (EC 3.2.1.2) |
| *Citrus lemon* | V4SA44 | Serine/threonine-protein phosphatase (EC 3.1.3.16) |
| *Citrus lemon* | V4SAE0 | Alpha-1,4 glucan phosphorylase (EC 2.4.1.1) |
| *Citrus lemon* | V4SAF6 | Uncharacterized protein |
| *Citrus lemon* | V4SAI9 | Eukaryotic translation initiation factor 3 subunit M (eIF3m) |
| *Citrus lemon* | V4SAJ5 | Ribosomal protein |
| *Citrus lemon* | V4SAR3 | Uncharacterized protein |
| *Citrus lemon* | V4SB37 | Uncharacterized protein |
| *Citrus lemon* | V4SBI0 | Elongation factor 1-alpha |
| *Citrus lemon* | V4SBI8 | D-3-phosphoglycerate dehydrogenase (EC 1.1.1.95) |
| *Citrus lemon* | V4SBL9 | Polyadenylate-binding protein (PABP) |
| *Citrus lemon* | V4SBR1 | S-formylglutathione hydrolase (EC 3.1.2.12) |
| *Citrus lemon* | V4SBR6 | Uncharacterized protein |
| *Citrus lemon* | V4SCG7 | Uncharacterized protein |
| *Citrus lemon* | V4SCJ2 | Uncharacterized protein |
| *Citrus lemon* | V4SCQ6 | Peptidyl-prolyl cis-trans isomerase (PPIase) (EC 5.2.1.8) |
| *Citrus lemon* | V4SDJ8 | Uncharacterized protein |
| *Citrus lemon* | V4SE41 | Protein DETOXIFICATION (Multidrug and toxic compound extrusion protein) |
| *Citrus lemon* | V4SE90 | Uncharacterized protein |
| *Citrus lemon* | V4SED1 | Succinate dehydrogenase [ubiquinone] flavoprotein subunit, mitochondrial (EC 1.3.5.1) |
| *Citrus lemon* | V4SEI1 | Uncharacterized protein |
| *Citrus lemon* | V4SEN9 | Uncharacterized protein |
| *Citrus lemon* | V4SEX8 | Uncharacterized protein |
| *Citrus lemon* | V4SF31 | Uncharacterized protein |
| *Citrus lemon* | V4SF69 | 40S ribosomal protein S24 |
| *Citrus lemon* | V4SF76 | Cysteine synthase (EC 2.5.1.47) |
| *Citrus lemon* | V4SFK3 | Uncharacterized protein |
| *Citrus lemon* | V4SFL4 | Uncharacterized protein |
| *Citrus lemon* | V4SFW2 | Uncharacterized protein |
| *Citrus lemon* | V4SGC9 | Uncharacterized protein |
| *Citrus lemon* | V4SGJ4 | Uncharacterized protein |
| *Citrus lemon* | V4SGN4 | Uncharacterized protein |
| *Citrus lemon* | V4SGV6 | Uncharacterized protein |
| *Citrus lemon* | V4SGV7 | Uncharacterized protein |
| *Citrus lemon* | V4SHH1 | Plasma membrane ATPase (EC 3.6.3.6) (Fragment) |
| *Citrus lemon* | V4SHI2 | Uncharacterized protein |
| *Citrus lemon* | V4SHJ3 | Uncharacterized protein |
| *Citrus lemon* | V4SI86 | Uncharacterized protein |
| *Citrus lemon* | V4SI88 | Uncharacterized protein |
| *Citrus lemon* | V4SIA2 | Uncharacterized protein |
| *Citrus lemon* | V4SIC1 | Phospholipase D (EC 3.1.4.4) |
| *Citrus lemon* | V4SJ14 | Uncharacterized protein |
| *Citrus lemon* | V4SJ48 | Uncharacterized protein |
| *Citrus lemon* | V4SJ69 | Uncharacterized protein |
| *Citrus lemon* | V4SJD9 | Uncharacterized protein |
| *Citrus lemon* | V4SJS7 | Uncharacterized protein |
| *Citrus lemon* | V4SJT5 | Uncharacterized protein |
| Citrus lemon | V4SKA2 | Uncharacterized protein |
| *Citrus lemon* | V4SKG4 | Glucose-6-phosphate isomerase (EC 5.3.1.9) |
| *Citrus lemon* | V4SKJ1 | Uncharacterized protein |
| *Citrus lemon* | V4SL90 | Uncharacterized protein |
| *Citrus lemon* | V4SLC6 | Proteasome subunit beta type (EC 3.4.25.1) |
| *Citrus lemon* | V4SLI7 | Uncharacterized protein |
| *Citrus lemon* | V4SLQ6 | Uncharacterized protein |

APPENDIX-continued

Table 1: Plant EV-Markers

| Example Species | Accession No. | Protein Name |
|---|---|---|
| *Citrus lemon* | V4SMD8 | Uncharacterized protein |
| *Citrus lemon* | V4SMN7 | Uncharacterized protein |
| *Citrus lemon* | V4SMV5 | Uncharacterized protein |
| *Citrus lemon* | V4SN00 | Uncharacterized protein |
| *Citrus lemon* | V4SNA9 | Uncharacterized protein |
| *Citrus lemon* | V4SNC1 | Uncharacterized protein |
| *Citrus lemon* | V4SNC4 | Aconitate hydratase (Aconitase) (EC 4.2.1.3) |
| *Citrus lemon* | V4SNZ3 | Uncharacterized protein |
| *Citrus lemon* | V4SP86 | Uncharacterized protein |
| *Citrus lemon* | V4SPM1 | 40S ribosomal protein S12 |
| *Citrus lemon* | V4SPW4 | 40S ribosomal protein S4 |
| *Citrus lemon* | V4SQ71 | Uncharacterized protein |
| *Citrus lemon* | V4SQ89 | Uncharacterized protein |
| *Citrus lemon* | V4SQ92 | Uncharacterized protein |
| *Citrus lemon* | V4SQC7 | Peroxidase (EC 1.11.1.7) |
| *Citrus lemon* | V4SQG3 | Uncharacterized protein |
| *Citrus lemon* | V4SR15 | Uncharacterized protein |
| *Citrus lemon* | V4SRN3 | Transmembrane 9 superfamily member |
| *Citrus lemon* | V4SS09 | Uncharacterized protein |
| *Citrus lemon* | V4SS11 | Uncharacterized protein |
| *Citrus lemon* | V4SS50 | Uncharacterized protein |
| *Citrus lemon* | V4SSB6 | Uncharacterized protein |
| *Citrus lemon* | V4SSB8 | Proteasome subunit alpha type (EC 3.4.25.1) |
| *Citrus lemon* | V4SSL7 | Uncharacterized protein |
| *Citrus lemon* | V4SSQ1 | Uncharacterized protein |
| *Citrus lemon* | V4SST6 | Uncharacterized protein |
| *Citrus lemon* | V4SSW9 | Uncharacterized protein |
| *Citrus lemon* | V4SSX5 | Uncharacterized protein |
| *Citrus lemon* | V4SU82 | Uncharacterized protein |
| *Citrus lemon* | V4SUD3 | Uncharacterized protein |
| *Citrus lemon* | V4SUL7 | Uncharacterized protein |
| *Citrus lemon* | V4SUP3 | Uncharacterized protein |
| *Citrus lemon* | V4SUT4 | UDP-glucose 6-dehydrogenase (EC 1.1.1.22) |
| *Citrus lemon* | V4SUY5 | Uncharacterized protein |
| *Citrus lemon* | V4SV60 | Serine/threonine-protein phosphatase (EC 3.1.3.16) |
| *Citrus lemon* | V4SV61 | Uncharacterized protein |
| *Citrus lemon* | V4SVI5 | Proteasome subunit alpha type (EC 3.4.25.1) |
| *Citrus lemon* | V4SVI6 | Uncharacterized protein |
| *Citrus lemon* | V4SW04 | Uncharacterized protein (Fragment) |
| *Citrus lemon* | V4SWD9 | Uncharacterized protein |
| *Citrus lemon* | V4SWJ0 | 40S ribosomal protein S3a |
| *Citrus lemon* | V4SWQ9 | Uncharacterized protein |
| *Citrus lemon* | V4SWR9 | Uncharacterized protein |
| *Citrus lemon* | V4SWU9 | Fructose-bisphosphate aldolase (EC 4.1.2.13) |
| *Citrus lemon* | V4SX11 | Uncharacterized protein |
| *Citrus lemon* | V4SX99 | Uncharacterized protein |
| *Citrus lemon* | V4SXC7 | Proteasome subunit alpha type (EC 3.4.25.1) |
| *Citrus lemon* | V4SXQ5 | Uncharacterized protein |
| *Citrus lemon* | V4SXW1 | Beta-adaptin-like protein |
| *Citrus lemon* | V4SXY9 | Uncharacterized protein |
| *Citrus lemon* | V4SY74 | Uncharacterized protein |
| *Citrus lemon* | V4SY90 | Uncharacterized protein |
| *Citrus lemon* | V4SY93 | Uncharacterized protein |
| *Citrus lemon* | V4SYH9 | Uncharacterized protein |
| *Citrus lemon* | V4SYK6 | Uncharacterized protein |
| *Citrus lemon* | V4SZ03 | Uncharacterized protein |
| *Citrus lemon* | V4SZ73 | Uncharacterized protein |
| *Citrus lemon* | V4SZI9 | Uncharacterized protein |
| *Citrus lemon* | V4SZX7 | Uncharacterized protein |
| *Citrus lemon* | V4T057 | Ribosomal protein L15 |
| *Citrus lemon* | V4T0V5 | Eukaryotic translation initiation factor 3 subunit A (eIF3a) (Eukaryotic translation initiation factor 3 subunit 10) |
| *Citrus lemon* | V4T0Y1 | Uncharacterized protein |
| *Citrus lemon* | V4T1Q6 | Uncharacterized protein |
| *Citrus lemon* | V4T1U7 | Uncharacterized protein |
| *Citrus lemon* | V4T2D9 | Uncharacterized protein |
| *Citrus lemon* | V4T2M6 | Tubulin beta chain |
| *Citrus lemon* | V4T3G2 | Uncharacterized protein |
| *Citrus lemon* | V4T3P3 | 6-phosphogluconate dehydrogenase, decarboxylating (EC 1.1.1.44) |
| *Citrus lemon* | V4T3V9 | Uncharacterized protein |
| *Citrus lemon* | V4T3Y6 | Uncharacterized protein |
| *Citrus lemon* | V4T4H3 | Uncharacterized protein |
| *Citrus lemon* | V4T4I7 | Uncharacterized protein |
| *Citrus lemon* | V4T4M7 | Superoxide dismutase [Cu—Zn] (EC 1.15.1.1) |
| *Citrus lemon* | V4T539 | Uncharacterized protein |

APPENDIX-continued

Table 1: Plant EV-Markers

| Example Species | Accession No. | Protein Name |
|---|---|---|
| Citrus lemon | V4T541 | Uncharacterized protein |
| Citrus lemon | V4T576 | Uncharacterized protein |
| Citrus lemon | V4T5E1 | Uncharacterized protein |
| Citrus lemon | V4T5I3 | Uncharacterized protein |
| Citrus lemon | V4T5W7 | Uncharacterized protein |
| Citrus lemon | V4T6T5 | 60S acidic ribosomal protein P0 |
| Citrus lemon | V4T722 | Uncharacterized protein |
| Citrus lemon | V4T785 | Uncharacterized protein |
| Citrus lemon | V4T7E2 | Uncharacterized protein |
| Citrus lemon | V4T7I7 | Uncharacterized protein |
| Citrus lemon | V4T7N0 | Proteasome subunit beta type (EC 3.4.25.1) |
| Citrus lemon | V4T7N4 | Uncharacterized protein |
| Citrus lemon | V4T7T2 | Uncharacterized protein |
| Citrus lemon | V4T7W5 | Uncharacterized protein |
| Citrus lemon | V4T825 | Uncharacterized protein |
| Citrus lemon | V4T846 | Uncharacterized protein |
| Citrus lemon | V4T8E9 | S-acyltransferase (EC 2.3.1.225) (Palmitoyltransferase) |
| Citrus lemon | V4T8G2 | Uncharacterized protein |
| Citrus lemon | V4T8G9 | Chorismate synthase (EC 4.2.3.5) |
| Citrus lemon | V4T8Y6 | Uncharacterized protein |
| Citrus lemon | V4T8Y8 | Uncharacterized protein |
| Citrus lemon | V4T939 | Carboxypeptidase (EC 3.4.16.-) |
| Citrus lemon | V4T957 | Uncharacterized protein |
| Citrus lemon | V4T998 | Uncharacterized protein |
| Citrus lemon | V4T9B9 | Uncharacterized protein |
| Citrus lemon | V4T9Y7 | Uncharacterized protein |
| Citrus lemon | V4TA70 | Uncharacterized protein |
| Citrus lemon | V4TAF6 | Uncharacterized protein |
| Citrus lemon | V4TB09 | Uncharacterized protein |
| Citrus lemon | V4TB32 | Uncharacterized protein |
| Citrus lemon | V4TB89 | Uncharacterized protein |
| Citrus lemon | V4TBN7 | Phosphoinositide phospholipase C (EC 3.1.4.11) |
| Citrus lemon | V4TBQ3 | Uncharacterized protein |
| Citrus lemon | V4TBS4 | Uncharacterized protein |
| Citrus lemon | V4TBU3 | Uncharacterized protein |
| Citrus lemon | V4TCA6 | Uncharacterized protein |
| Citrus lemon | V4TCL3 | Uncharacterized protein |
| Citrus lemon | V4TCS5 | Pectate lyase (EC 4.2.2.2) |
| Citrus lemon | V4TD99 | Uncharacterized protein |
| Citrus lemon | V4TDB5 | Uncharacterized protein |
| Citrus lemon | V4TDI2 | Uncharacterized protein |
| Citrus lemon | V4TDY3 | Serine/threonine-protein kinase (EC 2.7.11.1) |
| Citrus lemon | V4TE72 | Uncharacterized protein |
| Citrus lemon | V4TE95 | Uncharacterized protein |
| Citrus lemon | V4TEC0 | Uncharacterized protein |
| Citrus lemon | V4TED8 | Uncharacterized protein |
| Citrus lemon | V4TES4 | Uncharacterized protein |
| Citrus lemon | V4TEY9 | Uncharacterized protein |
| Citrus lemon | V4TF24 | Proteasome subunit alpha type (EC 3.4.25.1) |
| Citrus lemon | V4TF52 | Uricase (EC 1.7.3.3) (Urate oxidase) |
| Citrus lemon | V4TFV8 | Catalase (EC 1.11.1.6) |
| Citrus lemon | V4TGU1 | Uncharacterized protein |
| Citrus lemon | V4TH28 | Uncharacterized protein |
| Citrus lemon | V4TH78 | Reticulon-like protein |
| Citrus lemon | V4THM9 | Uncharacterized protein |
| Citrus lemon | V4TIU2 | Ribulose-phosphate 3-epimerase (EC 5.1.3.1) |
| Citrus lemon | V4TIW6 | Uncharacterized protein |
| Citrus lemon | V4TIY6 | Uncharacterized protein |
| Citrus lemon | V4TIZ5 | Uncharacterized protein |
| Citrus lemon | V4TJ75 | Uncharacterized protein |
| Citrus lemon | V4TJC3 | Uncharacterized protein |
| Citrus lemon | V4TJQ9 | Uncharacterized protein |
| Citrus lemon | V4TK29 | NEDD8-activating enzyme E1 regulatory subunit |
| Citrus lemon | V4TL04 | Uncharacterized protein |
| Citrus lemon | V4TLL5 | Uncharacterized protein |
| Citrus lemon | V4TLP6 | Uncharacterized protein |
| Citrus lemon | V4TM00 | Uncharacterized protein |
| Citrus lemon | V4TM19 | Uncharacterized protein |
| Citrus lemon | V4TMB7 | Uncharacterized protein (Fragment) |
| Citrus lemon | V4TMD1 | Uncharacterized protein |
| Citrus lemon | V4TMD6 | Uncharacterized protein |
| Citrus lemon | V4TMV4 | Uncharacterized protein |
| Citrus lemon | V4TN30 | Uncharacterized protein |
| Citrus lemon | V4TN38 | Uncharacterized protein |
| Citrus lemon | V4TNY8 | Uncharacterized protein |
| Citrus lemon | V4TP87 | Carbonic anhydrase (EC 4.2.1.1) (Carbonate dehydratase) |

APPENDIX-continued

Table 1: Plant EV-Markers

| Example Species | Accession No. | Protein Name |
|---|---|---|
| Citrus lemon | V4TPM1 | Homoserine dehydrogenase (HDH) (EC 1.1.1.3) |
| Citrus lemon | V4TQB6 | Uncharacterized protein |
| Citrus lemon | V4TQM7 | Uncharacterized protein |
| Citrus lemon | V4TQR2 | Uncharacterized protein |
| Citrus lemon | V4TQV9 | Uncharacterized protein |
| Citrus lemon | V4TS21 | Proteasome subunit beta type (EC 3.4.25.1) |
| Citrus lemon | V4TS28 | Annexin |
| Citrus lemon | V4TSD8 | Uncharacterized protein (Fragment) |
| Citrus lemon | V4TSF8 | Uncharacterized protein |
| Citrus lemon | V4TSI9 | Uncharacterized protein |
| Citrus lemon | V4TT89 | Uncharacterized protein |
| Citrus lemon | V4TTA0 | Uncharacterized protein |
| Citrus lemon | V4TTR8 | Uncharacterized protein |
| Citrus lemon | V4TTV4 | Uncharacterized protein |
| Citrus lemon | V4TTZ7 | Uncharacterized protein |
| Citrus lemon | V4TU54 | Uncharacterized protein |
| Citrus lemon | V4TVB6 | Uncharacterized protein |
| Citrus lemon | V4TVG1 | Eukaryotic translation initiation factor 5A (eIF-5A) |
| Citrus lemon | V4TVJ4 | Profilin |
| Citrus lemon | V4TVM6 | Uncharacterized protein |
| Citrus lemon | V4TVM9 | Uncharacterized protein |
| Citrus lemon | V4TVP7 | Uncharacterized protein |
| Citrus lemon | V4TVT8 | Uncharacterized protein |
| Citrus lemon | V4TW14 | Uncharacterized protein |
| Citrus lemon | V4TWG9 | T-complex protein 1 subunit delta |
| Citrus lemon | V4TWU1 | Probable bifunctional methylthioribulose-1-phosphate dehydratase/enolase-phosphatase E1 [Includes: Enolase-phosphatase E1 (EC 3.1.3.77) (2,3-diketo-5-methylthio-1-phosphopentane phosphatase); Methylthioribulose-1-phosphate dehydratase (MTRu-1-P dehydratase) (EC 4.2.1.109)] |
| Citrus lemon | V4TWX8 | Uncharacterized protein |
| Citrus lemon | V4TXH0 | Glutamate decarboxylase (EC 4.1.1.15) |
| Citrus lemon | V4TXK9 | Uncharacterized protein |
| Citrus lemon | V4TXU9 | Thiamine thiazole synthase, chloroplastic (Thiazole biosynthetic enzyme) |
| Citrus lemon | V4TY40 | Uncharacterized protein |
| Citrus lemon | V4TYJ6 | Uncharacterized protein |
| Citrus lemon | V4TYP5 | 60S ribosomal protein L13 |
| Citrus lemon | V4TYP6 | Uncharacterized protein |
| Citrus lemon | V4TYR6 | Uncharacterized protein |
| Citrus lemon | V4TYZ8 | Tubulin alpha chain |
| Citrus lemon | V4TZ91 | Guanosine nucleotide diphosphate dissociation inhibitor |
| Citrus lemon | V4TZA8 | Uncharacterized protein |
| Citrus lemon | V4TZJ1 | Uncharacterized protein |
| Citrus lemon | V4TZK5 | Uncharacterized protein |
| Citrus lemon | V4TZP2 | Uncharacterized protein |
| Citrus lemon | V4TZT8 | Uncharacterized protein |
| Citrus lemon | V4TZU3 | Mitogen-activated protein kinase (EC 2.7.11.24) |
| Citrus lemon | V4TZU5 | Dihydrolipoyl dehydrogenase (EC 1.8.1.4) |
| Citrus lemon | V4TZZ0 | Uncharacterized protein |
| Citrus lemon | V4U003 | Eukaryotic translation initiation factor 3 subunit K (eIF3k) (eIF-3 p25) |
| Citrus lemon | V4U068 | Uncharacterized protein |
| Citrus lemon | V4U088 | Uncharacterized protein |
| Citrus lemon | V4U0J7 | Uncharacterized protein |
| Citrus lemon | V4U133 | Uncharacterized protein |
| Citrus lemon | V4U1A8 | Uncharacterized protein |
| Citrus lemon | V4U1K1 | Xylose isomerase (EC 5.3.1.5) |
| Citrus lemon | V4U1M1 | Uncharacterized protein |
| Citrus lemon | V4U1V0 | Uncharacterized protein |
| Citrus lemon | V4U1X7 | Uncharacterized protein |
| Citrus lemon | V4U1X9 | Proteasome subunit beta type (EC 3.4.25.1) |
| Citrus lemon | V4U251 | Uncharacterized protein |
| Citrus lemon | V4U283 | Uncharacterized protein |
| Citrus lemon | V4U2E4 | Uncharacterized protein |
| Citrus lemon | V4U2F7 | Uncharacterized protein |
| Citrus lemon | V4U2H8 | Uncharacterized protein |
| Citrus lemon | V4U2L0 | Malate dehydrogenase (EC 1.1.1.37) |
| Citrus lemon | V4U2L2 | Uncharacterized protein |
| Citrus lemon | V4U2W4 | V-type proton ATPase subunit C |
| Citrus lemon | V4U3L2 | Uncharacterized protein |
| Citrus lemon | V4U3W8 | Uncharacterized protein |
| Citrus lemon | V4U412 | Uncharacterized protein |
| Citrus lemon | V4U4K2 | Uncharacterized protein |
| Citrus lemon | V4U4M4 | Uncharacterized protein |

APPENDIX-continued

Table 1: Plant EV-Markers

| Example Species | Accession No. | Protein Name |
|---|---|---|
| Citrus lemon | V4U4N5 | Eukaryotic translation initiation factor 6 (eIF-6) |
| Citrus lemon | V4U4S9 | Uncharacterized protein |
| Citrus lemon | V4U4X3 | Serine hydroxymethyltransferase (EC 2.1.2.1) |
| Citrus lemon | V4U4Z9 | Uncharacterized protein |
| Citrus lemon | V4U500 | Uncharacterized protein |
| Citrus lemon | V4U5B0 | Eukaryotic translation initiation factor 3 subunit E (eIF3e) (Eukaryotic translation initiation factor 3 subunit 6) |
| Citrus lemon | V4U5B8 | Glutathione peroxidase |
| Citrus lemon | V4U5R5 | Citrate synthase |
| Citrus lemon | V4U5Y8 | Uncharacterized protein |
| Citrus lemon | V4U6I5 | ATP synthase subunit beta (EC 3.6.3.14) |
| Citrus lemon | V4U6Q8 | Uncharacterized protein |
| Citrus lemon | V4U706 | Uncharacterized protein |
| Citrus lemon | V4U717 | Uncharacterized protein |
| Citrus lemon | V4U726 | Uncharacterized protein |
| Citrus lemon | V4U729 | Uncharacterized protein |
| Citrus lemon | V4U734 | Serine/threonine-protein phosphatase (EC 3.1.3.16) |
| Citrus lemon | V4U7G7 | Uncharacterized protein |
| Citrus lemon | V4U7H5 | Uncharacterized protein |
| Citrus lemon | V4U7R1 | Potassium transporter |
| Citrus lemon | V4U7R7 | Mitogen-activated protein kinase (EC 2.7.11.24) |
| Citrus lemon | V4U833 | Malic enzyme |
| Citrus lemon | V4U840 | Uncharacterized protein |
| Citrus lemon | V4U8C3 | Uncharacterized protein |
| Citrus lemon | V4U8J1 | 3-phosphoshikimate 1-carboxyvinyltransferase (EC 2.5.1.19) |
| Citrus lemon | V4U8J8 | T-complex protein 1 subunit gamma |
| Citrus lemon | V4U995 | Uncharacterized protein |
| Citrus lemon | V4U999 | Uncharacterized protein |
| Citrus lemon | V4U9C7 | Eukaryotic translation initiation factor 3 subunit D (eIF3d) (Eukaryotic translation initiation factor 3 subunit 7) (eIF-3-zeta) |
| Citrus lemon | V4U9G8 | Proline iminopeptidase (EC 3.4.11.5) |
| Citrus lemon | V4U9L1 | Uncharacterized protein |
| Citrus lemon | V4UA63 | Phytochrome |
| Citrus lemon | V4UAC8 | Uncharacterized protein |
| Citrus lemon | V4UAR4 | Uncharacterized protein |
| Citrus lemon | V4UB30 | Uncharacterized protein |
| Citrus lemon | V4UBK8 | V-type proton ATPase subunit a |
| Citrus lemon | V4UBL3 | Coatomer subunit alpha |
| Citrus lemon | V4UBL5 | Uncharacterized protein (Fragment) |
| Citrus lemon | V4UBM0 | Uncharacterized protein |
| Citrus lemon | V4UBZ8 | Aspartate aminotransferase (EC 2.6.1.1) |
| Citrus lemon | V4UC72 | Uncharacterized protein |
| Citrus lemon | V4UC97 | Beta-glucosidase (EC 3.2.1.21) |
| Citrus lemon | V4UCE2 | Uncharacterized protein |
| Citrus lemon | V4UCT9 | Acetyl-coenzyme A synthetase (EC 6.2.1.1) |
| Citrus lemon | V4UCZ1 | Uncharacterized protein |
| Citrus lemon | V4UE34 | Uncharacterized protein |
| Citrus lemon | V4UE78 | Uncharacterized protein |
| Citrus lemon | V4UER3 | Uncharacterized protein |
| Citrus lemon | V4UET6 | Uncharacterized protein |
| Citrus lemon | V4UEZ6 | Uncharacterized protein |
| Citrus lemon | V4UFD0 | Uncharacterized protein |
| Citrus lemon | V4UFG8 | Uncharacterized protein |
| Citrus lemon | V4UFK1 | Uncharacterized protein |
| Citrus lemon | V4UG68 | Eukaryotic translation initiation factor 3 subunit I (eIF3i) |
| Citrus lemon | V4UGB0 | Uncharacterized protein |
| Citrus lemon | V4UGH4 | Uncharacterized protein |
| Citrus lemon | V4UGL9 | Uncharacterized protein |
| Citrus lemon | V4UGQ0 | Ubiquitinyl hydrolase 1 (EC 3.4.19.12) |
| Citrus lemon | V4UH00 | Uncharacterized protein |
| Citrus lemon | V4UH48 | Uncharacterized protein |
| Citrus lemon | V4UH77 | Proteasome subunit alpha type (EC 3.4.25.1) |
| Citrus lemon | V4UHD8 | Uncharacterized protein |
| Citrus lemon | V4UHD9 | Uncharacterized protein |
| Citrus lemon | V4UHF1 | Uncharacterized protein |
| Citrus lemon | V4UHZ5 | Uncharacterized protein |
| Citrus lemon | V4UI07 | 40S ribosomal protein S8 |
| Citrus lemon | V4UI34 | Eukaryotic translation initiation factor 3 subunit L (eIF3l) |
| Citrus lemon | V4UIF1 | Uncharacterized protein |
| Citrus lemon | V4UIN5 | Uncharacterized protein |
| Citrus lemon | V4UIX8 | Uncharacterized protein |
| Citrus lemon | V4UJ12 | Uncharacterized protein |
| Citrus lemon | V4UJ42 | Uncharacterized protein |
| Citrus lemon | V4UJ63 | Uncharacterized protein |
| Citrus lemon | V4UJB7 | Uncharacterized protein (Fragment) |

APPENDIX-continued

Table 1: Plant EV-Markers

| Example Species | Accession No. | Protein Name |
|---|---|---|
| Citrus lemon | V4UJC4 | Uncharacterized protein |
| Citrus lemon | V4UJX0 | Phosphotransferase (EC 2.7.1.-) |
| Citrus lemon | V4UJY5 | Uncharacterized protein |
| Citrus lemon | V4UK18 | Uncharacterized protein |
| Citrus lemon | V4UK52 | Uncharacterized protein |
| Citrus lemon | V4UKM9 | Uncharacterized protein |
| Citrus lemon | V4UKS4 | Uncharacterized protein |
| Citrus lemon | V4UKV6 | 40S ribosomal protein SA |
| Citrus lemon | V4UL30 | Pyrophosphate--fructose 6-phosphate 1-phosphotransferase subunit beta (PFP) (EC 2.7.1.90) (6-phosphofructokinase, pyrophosphate dependent) (PPi-PFK) (Pyrophosphate-dependent 6-phosphofructose-1-kinase) |
| Citrus lemon | V4UL39 | Uncharacterized protein |
| Citrus lemon | V4ULH9 | Uncharacterized protein |
| Citrus lemon | V4ULL2 | Uncharacterized protein |
| Citrus lemon | V4ULS0 | Uncharacterized protein |
| Citrus lemon | V4UMU7 | Uncharacterized protein |
| Citrus lemon | V4UN36 | Uncharacterized protein |
| Citrus lemon | V4UNT5 | Uncharacterized protein |
| Citrus lemon | V4UNW1 | Uncharacterized protein |
| Citrus lemon | V4UP89 | Uncharacterized protein |
| Citrus lemon | V4UPE4 | Uncharacterized protein |
| Citrus lemon | V4UPF7 | Uncharacterized protein |
| Citrus lemon | V4UPK0 | Uncharacterized protein |
| Citrus lemon | V4UPX5 | Uncharacterized protein |
| Citrus lemon | V4UQ58 | Uncharacterized protein |
| Citrus lemon | V4UQF6 | Uncharacterized protein |
| Citrus lemon | V4UR21 | Uncharacterized protein |
| Citrus lemon | V4UR80 | Uncharacterized protein |
| Citrus lemon | V4URK3 | Uncharacterized protein |
| Citrus lemon | V4URT3 | Uncharacterized protein |
| Citrus lemon | V4US96 | Uncharacterized protein |
| Citrus lemon | V4USQ8 | Uncharacterized protein |
| Citrus lemon | V4UT16 | Uncharacterized protein |
| Citrus lemon | V4UTC6 | Uncharacterized protein |
| Citrus lemon | V4UTC8 | Uncharacterized protein |
| Citrus lemon | V4UTP6 | Uncharacterized protein |
| Citrus lemon | V4UTY0 | Proteasome subunit alpha type (EC 3.4.25.1) |
| Citrus lemon | V4UU96 | Uncharacterized protein |
| Citrus lemon | V4UUB6 | Uncharacterized protein |
| Citrus lemon | V4UUJ9 | Aminopeptidase (EC 3.4.11.-) |
| Citrus lemon | V4UUK6 | Uncharacterized protein |
| Citrus lemon | V4UV09 | Uncharacterized protein |
| Citrus lemon | V4UV83 | Lysine--tRNA ligase (EC 6.1.1.6) (Lysyl-tRNA synthetase) |
| Citrus lemon | V4UVJ5 | Diacylglycerol kinase (DAG kinase) (EC 2.7.1.107) |
| Citrus lemon | V4UW03 | Uncharacterized protein |
| Citrus lemon | V4UW04 | Uncharacterized protein |
| Citrus lemon | V4UWR1 | Uncharacterized protein |
| Citrus lemon | V4UWV8 | Uncharacterized protein |
| Citrus lemon | V4UX36 | Uncharacterized protein |
| Citrus lemon | V4V003 | Uncharacterized protein |
| Citrus lemon | V4V0J0 | 40S ribosomal protein S26 |
| Citrus lemon | V4V1P8 | Uncharacterized protein |
| Citrus lemon | V4V4V0 | Uncharacterized protein |
| Citrus lemon | V4V5T8 | Ubiquitin-fold modifier 1 |
| Citrus lemon | V4V600 | Uncharacterized protein |
| Citrus lemon | V4V622 | Aldehyde dehydrogenase |
| Citrus lemon | V4V6W1 | Uncharacterized protein |
| Citrus lemon | V4V6Z2 | Uncharacterized protein |
| Citrus lemon | V4V738 | Uncharacterized protein |
| Citrus lemon | V4V8H5 | Vacuolar protein sorting-associated protein 35 |
| Citrus lemon | V4V9P6 | Eukaryotic translation initiation factor 3 subunit F (eIF3f) (eIF-3-epsilon) |
| Citrus lemon | V4V9V7 | Clathrin heavy chain |
| Citrus lemon | V4V9X3 | Uncharacterized protein |
| Citrus lemon | V4VAA3 | Superoxide dismutase (EC 1.15.1.1) |
| Citrus lemon | V4VAF3 | Uncharacterized protein |
| Citrus lemon | V4VBQ0 | Uncharacterized protein (Fragment) |
| Citrus lemon | V4VCL1 | Proteasome subunit beta type (EC 3.4.25.1) |
| Citrus lemon | V4VCZ9 | Uncharacterized protein |
| Citrus lemon | V4VDK1 | Peptidylprolyl isomerase (EC 5.2.1.8) |
| Citrus lemon | V4VEA1 | Uncharacterized protein |
| Citrus lemon | V4VEB3 | Alanine--tRNA ligase (EC 6.1.1.7) (Alanyl-tRNA synthetase) (AlaRS) |
| Citrus lemon | V4VEE3 | Glutamine synthetase (EC 6.3.1.2) |
| Citrus lemon | V4VFM3 | Uncharacterized protein |

APPENDIX-continued

Table 1: Plant EV-Markers

| Example Species | Accession No. | Protein Name |
|---|---|---|
| Citrus lemon | V4VFN5 | Proteasome subunit beta type (EC 3.4.25.1) |
| Citrus lemon | V4VGD6 | Uncharacterized protein |
| Citrus lemon | V4VGL9 | Uncharacterized protein |
| Citrus lemon | V4VHI6 | Uncharacterized protein |
| Citrus lemon | V4VIP4 | Uncharacterized protein |
| Citrus lemon | V4VJT4 | Uncharacterized protein |
| Citrus lemon | V4VK14 | Uncharacterized protein |
| Citrus lemon | V4VKI5 | Protein-L-isoaspartate O-methyltransferase (EC 2.1.1.77) |
| Citrus lemon | V4VKP2 | Glyceraldehyde-3-phosphate dehydrogenase (EC 1.2.1.-) |
| Citrus lemon | V4VL73 | Acyl-coenzyme A oxidase |
| Citrus lemon | V4VLL7 | Uncharacterized protein |
| Citrus lemon | V4VN43 | Uncharacterized protein (Fragment) |
| Citrus lemon | V4VQH3 | Methylenetetrahydrofolate reductase (EC 1.5.1.20) |
| Citrus lemon | V4VTC9 | Uncharacterized protein (Fragment) |
| Citrus lemon | V4VTT4 | Uncharacterized protein |
| Citrus lemon | V4VTY7 | Uncharacterized protein |
| Citrus lemon | V4VU14 | Uncharacterized protein |
| Citrus lemon | V4VU32 | Uncharacterized protein |
| Citrus lemon | V4VUK6 | S-(hydroxymethyl)glutathione dehydrogenase (EC 1.1.1.284) |
| Citrus lemon | V4VVR8 | Uncharacterized protein |
| Citrus lemon | V4VXE2 | Uncharacterized protein |
| Citrus lemon | V4VY37 | Phosphomannomutase (EC 5.4.2.8) |
| Citrus lemon | V4VYC0 | Uncharacterized protein |
| Citrus lemon | V4VYV1 | Uncharacterized protein |
| Citrus lemon | V4VZ80 | Uncharacterized protein |
| Citrus lemon | V4VZJ7 | Uncharacterized protein |
| Citrus lemon | V4W2P2 | Alpha-mannosidase (EC 3.2.1.-) |
| Citrus lemon | V4W2Z9 | Chloride channel protein |
| Citrus lemon | V4W378 | Uncharacterized protein |
| Citrus lemon | V4W4G3 | Uncharacterized protein |
| Citrus lemon | V4W5F1 | Uncharacterized protein |
| Citrus lemon | V4W5N8 | Uncharacterized protein |
| Citrus lemon | V4W5U2 | Uncharacterized protein |
| Citrus lemon | V4W6G1 | Uncharacterized protein |
| Citrus lemon | V4W730 | Uncharacterized protein |
| Citrus lemon | V4W7J4 | Obg-like ATPase 1 |
| Citrus lemon | V4W7L5 | Uncharacterized protein |
| Citrus lemon | V4W8C5 | Uncharacterized protein |
| Citrus lemon | V4W8C9 | Uncharacterized protein |
| Citrus lemon | V4W8D3 | Uncharacterized protein |
| Citrus lemon | V4W951 | Uncharacterized protein |
| Citrus lemon | V4W9F6 | 60S ribosomal protein L18a |
| Citrus lemon | V4W9G2 | Uncharacterized protein (Fragment) |
| Citrus lemon | V4W9L3 | Uncharacterized protein |
| Citrus lemon | V4W9Y8 | Uncharacterized protein |
| Citrus lemon | V4WAP9 | Coatomer subunit beta (Beta-coat protein) |
| Citrus lemon | V4WBK6 | Cytochrome b-c1 complex subunit 7 |
| Citrus lemon | V4WC15 | Malic enzyme |
| Citrus lemon | V4WC19 | Uncharacterized protein |
| Citrus lemon | V4WC74 | Uncharacterized protein |
| Citrus lemon | V4WC86 | Serine/threonine-protein phosphatase 2A 55 kDa regulatory subunit B |
| Citrus lemon | V4WCS4 | GTP-binding nuclear protein |
| Citrus lemon | V4WD80 | Aspartate aminotransferase (EC 2.6.1.1) |
| Citrus lemon | V4WDK0 | Uncharacterized protein |
| Citrus lemon | V4WDK3 | ATP-dependent 6-phosphofructokinase (ATP-PFK) (Phosphofructokinase) (EC 2.7.1.11) (Phosphohexokinase) |
| Citrus lemon | V4WE00 | Uncharacterized protein |
| Citrus lemon | V4WEE3 | Uncharacterized protein |
| Citrus lemon | V4WEN2 | Uncharacterized protein |
| Citrus lemon | V4WG97 | Autophagy-related protein |
| Citrus lemon | V4WGV2 | Uncharacterized protein |
| Citrus lemon | V4WGW5 | Uridine kinase (EC 2.7.1.48) |
| Citrus lemon | V4WHD4 | Uncharacterized protein |
| Citrus lemon | V4WHF8 | Sucrose synthase (EC 2.4.1.13) |
| Citrus lemon | V4WHK2 | Pectinesterase (EC 3.1.1.11) |
| Citrus lemon | V4WHQ4 | Uncharacterized protein |
| Citrus lemon | V4WHT6 | Uncharacterized protein |
| Citrus lemon | V4WJ93 | Uncharacterized protein |
| Citrus lemon | V4WJA9 | Uncharacterized protein |
| Citrus lemon | V4WJB1 | Uncharacterized protein |
| Citrus lemon | V9HXG3 | Protein disulfide-isomerase (EC 5.3.4.1) |
| Citrus lemon | W8Q8K1 | Putative inorganic pyrophosphatase |
| Citrus lemon | W8QJL0 | Putative isopentenyl pyrophosphate isomerase |
| Grape | Accession Number | Identified Proteins |

APPENDIX-continued

Table 1: Plant EV-Markers

| Example Species | Accession No. | Protein Name |
|---|---|---|
| Grape | A5C5K3 (+2) | Adenosylhomocysteinase |
| Grape | Q9M6B5 | Alcohol dehydrogenase 6 |
| Grape | A3FA65 (+1) | Aquaporin PIP1;3 |
| Grape | QOMX13 (+2) | Aquaporin PIP2;2 |
| Grape | A3FA69 (+4) | Aquaporin PIP2;4 |
| Grape | A5AFS1 (+2) | Elongation factor 1-alpha |
| Grape | UPI0001985702 | elongation factor 2 |
| Grape | D7T227 | Enolase |
| Grape | D7TJ12 | Enolase |
| Grape | A5B118 (+1) | Fructose-bisphosphate aldolase |
| Grape | EOCQ39 | Glucose-6-phosphate isomerase |
| Grape | D7TW04 | Glutathione peroxidase |
| Grape | A1YW90 (+3) | Glutathione S-transferase |
| Grape | A5BEW0 | Histone H4 |
| Grape | UPI00015C9A6A | HSC70-1 (heat shock cognate 70 kDa protein 1); ATP binding isoform 1 |
| Grape | D7FBC0 (+1) | Malate dehydrogenase |
| Grape | D7TBH4 | Malic enzyme |
| Grape | A5ATB7 (+1) | Methylenetetrahydrofolate reductase |
| Grape | A5JPK7 (+1) | Monodehydroascorbate reductase |
| Grape | A5AKD8 | Peptidyl-prolyl cis-trans isomerase |
| Grape | A5BQN6 | Peptidyl-prolyl cis-trans isomerase |
| Grape | A5CAF6 | Phosphoglycerate kinase |
| Grape | Q09VU3 (+1) | Phospholipase D |
| Grape | D7SK33 | Phosphorylase |
| Grape | A5AQ89 | Profilin |
| Grape | C5DB50 (+2) | Putative 2,3-bisphosphoglycerate-independent phosphoglycerate mutase |
| Grape | D7TIZ5 | Pyruvate kinase |
| Grape | A5BV65 | Triosephosphate isomerase |
| Grapefruit | G8Z362 (+1) | (E)-beta-farnesene synthase |
| Grapefruit | Q5CD81 | (E)-beta-ocimene synthase |
| Grapefruit | D0UZK1 (+2) | 1,2 rhamnosyltransferase |
| Grapefruit | A7ISD3 | 1,6-rhamnosyltransferase |
| Grapefruit | Q80H98 | 280 kDa protein |
| Grapefruit | Q15GA4 (+2) | 286 kDa polyprotein |
| Grapefruit | D7NHW9 | 2-phospho-D-glycerate hydrolase |
| Grapefruit | D0EAL9 | 349 kDa polyprotein |
| Grapefruit | Q9DTG5 | 349-kDa polyprotein |
| Grapefruit | O22297 | Acidic cellulase |
| Grapefruit | Q8H986 | Acidic class I chitinase |
| Grapefruit | D3GQL0 | Aconitate hydratase 1 |
| Grapefruit | K7N8A0 | Actin |
| Grapefruit | A8W8Y0 | Alcohol acyl transferase |
| Grapefruit | Q84V85 | Allene oxide synthase |
| Grapefruit | F8WL79 | Aminopeptidase |
| Grapefruit | Q09MG5 | Apocytochrome f |
| Grapefruit | J7EIR8 | Ascorbate peroxidase |
| Grapefruit | B9VRH6 | Ascorbate peroxidase |
| Grapefruit | G9I820 | Auxin-response factor |
| Grapefruit | J7ICW8 | Beta-amylase |
| Grapefruit | Q8L5Q9 | Beta-galactosidase |
| Grapefruit | A7BG60 | Beta-pinene synthase |
| Grapefruit | C0KLD1 | Beta-tubulin |
| Grapefruit | Q91QZ1 | Capsid protein |
| Grapefruit | Q3SAK9 | Capsid protein |
| Grapefruit | D2U833 | Cation chloride cotransporter |
| Grapefruit | C3VPJ0 (+3) | Chalcone synthase |
| Grapefruit | D5LM39 | Chloride channel protein |
| Grapefruit | Q9M4U0 | Cinnamate 4-hydroxylase CYP73 |
| Grapefruit | Q39627 | Citrin |
| Grapefruit | G2XKD3 | Coat protein |
| Grapefruit | Q3L2I6 | Coat protein |
| Grapefruit | D5FV16 | CRT/DRE binding factor |
| Grapefruit | Q8H6S5 | CTV.2 |
| Grapefruit | Q8H6Q8 | CTV.20 |
| Grapefruit | Q8H6Q7 | CTV.22 |
| Grapefruit | Q1I1D7 | Cytochrome P450 |
| Grapefruit | Q7Y045 | Dehydrin |
| Grapefruit | F8WLD2 | DNA excision repair protein |
| Grapefruit | Q09MI8 | DNA-directed RNA polymerase subunit beta" |
| Grapefruit | D2WKC9 | Ethylene response 1 |
| Grapefruit | D2WKD2 | Ethylene response sensor 1 |
| Grapefruit | D7PVG7 | Ethylene-insensitive 3-like 1 protein |
| Grapefruit | G3CHK8 | Eukaryotic translation initiation factor 3 subunit E |
| Grapefruit | A9NJG4 (+3) | Fatty acid hydroperoxide lyase |

APPENDIX-continued

Table 1: Plant EV-Markers

| Example Species | Accession No. | Protein Name |
|---|---|---|
| Grapefruit | B8Y9B5 | F-box family protein |
| Grapefruit | Q000W4 | Fe(III)-chelate reductase |
| Grapefruit | Q6Q3H4 | Fructokinase |
| Grapefruit | F8WL95 | Gag-pol polyprotein |
| Grapefruit | Q8L5K4 | Gamma-terpinene synthase, chloroplastic |
| Grapefruit | Q9SP43 | Glucose-1-phosphate adenylyltransferase |
| Grapefruit | Q3HM93 | Glutathione S-transferase |
| Grapefruit | D0VEW6 | GRAS family transcription factor |
| Grapefruit | F8WL87 | Heat shock protein |
| Grapefruit | H9NHK0 | Hsp90 |
| Grapefruit | Q8H6R4 | Jp18 |
| Grapefruit | G3CHK6 | Leucine-rich repeat family protein |
| Grapefruit | B2YGX9 (+1) | Limonoid UDP-glucosyltransferase |
| Grapefruit | Q05KK0 | MADS-box protein |
| Grapefruit | F8WLB4 | Mechanosensitive ion channel domain-containing protein |
| Grapefruit | Q5CD82 | Monoterpene synthase |
| Grapefruit | F8WLC4 | MYB transcription factor |
| Grapefruit | A5YWA9 | NAC domain protein |
| Grapefruit | Q09MC9 | NAD(P)H-quinone oxidoreductase subunit 5, chloroplastic |
| Grapefruit | Q8H6R9 | NBS-LRR type disease resistance protein |
| Grapefruit | Q8H6S0 | NBS-LRR type disease resistance protein |
| Grapefruit | Q8H6R6 | NBS-LRR type disease resistance protein |
| Grapefruit | J9WR93 | p1a |
| Grapefruit | Q1X8V8 | P23 |
| Grapefruit | E7DSS0 (+4) | P23 |
| Grapefruit | G0Z9I6 | p27 |
| Grapefruit | I3XHN0 | p33 |
| Grapefruit | B8YDL3 | p33 protein |
| Grapefruit | B9VB22 | p33 protein |
| Grapefruit | P87587 | P346 |
| Grapefruit | B9VB56 | p349 protein |
| Grapefruit | I3RWW7 | p349 protein |
| Grapefruit | B9VB20 | p349 protein |
| Grapefruit | Q9WID7 | p349 protein |
| Grapefruit | Q2XP16 | P353 |
| Grapefruit | O04886 (+1) | Pectinesterase 1 |
| Grapefruit | F8WL74 | Peptidyl-prolyl cis-trans isomerase |
| Grapefruit | Q0ZA67 | Peroxidase |
| Grapefruit | F1CT41 | Phosphoenolpyruvate carboxylase |
| Grapefruit | B1PBV7 (+2) | Phytoene synthase |
| Grapefruit | Q9ZWQ8 | Plastid-lipid-associated protein, chloroplastic |
| Grapefruit | Q94FM1 | Pol polyprotein |
| Grapefruit | Q94FM0 | Pol polyprotein |
| Grapefruit | G9I825 | Poly C-binding protein |
| Grapefruit | O64460 (+7) | Polygalacturonase inhibitor |
| Grapefruit | I3XHM8 | Polyprotein |
| Grapefruit | C0STR9 | Polyprotein |
| Grapefruit | H6U1F0 | Polyprotein |
| Grapefruit | B8QHP8 | Polyprotein |
| Grapefruit | I3V6C0 | Polyprotein |
| Grapefruit | C0STS0 | Polyprotein |
| Grapefruit | K0FGH5 | Polyprotein |
| Grapefruit | Q3HWZ1 | Polyprotein |
| Grapefruit | F8WLA5 | PPR containing protein |
| Grapefruit | Q06652 (+1) | Probable phospholipid hydroperoxide glutathione peroxidase |
| Grapefruit | P84177 | Profilin |
| Grapefruit | Q09MB4 | Protein ycf2 |
| Grapefruit | A8C183 | PSI reaction center subunit II |
| Grapefruit | A5JVP6 | Putative 2b protein |
| Grapefruit | D0EFM2 | Putative eukaryotic translation initiation factor 1 |
| Grapefruit | Q18L98 | Putative gag-pol polyprotein |
| Grapefruit | B5AMI9 | Putative movement protein |
| Grapefruit | A1ECK5 | Putative multiple stress-responsive zinc-finger protein |
| Grapefruit | B5AMJ0 | Putative replicase polyprotein |
| Grapefruit | I7CYN5 | Putative RNA-dependent RNA polymerase |
| Grapefruit | Q8RVR2 | Putative terpene synthase |
| Grapefruit | B5TE89 | Putative uncharacterized protein |
| Grapefruit | Q8JVF3 | Putative uncharacterized protein |
| Grapefruit | F8WLB0 | Putative uncharacterized protein ORF43 |
| Grapefruit | A5JVP4 | Putative viral replicase |
| Grapefruit | M1JAW3 | Replicase |
| Grapefruit | H6VXK8 | Replicase polyprotein |
| Grapefruit | J9UF50 (+1) | Replicase protein 1a |
| Grapefruit | J9RV45 | Replicase protein 2a |
| Grapefruit | Q5EGG5 | Replicase-associated polyprotein |

APPENDIX-continued

Table 1: Plant EV-Markers

| Example Species | Accession No. | Protein Name |
|---|---|---|
| Grapefruit | G9I823 | RNA recognition motif protein 1 |
| Grapefruit | J7EPC0 | RNA-dependent RNA polymerase |
| Grapefruit | Q6DN67 | RNA-directed RNA polymerase L |
| Grapefruit | A9CQM4 | SEPALLATA1 homolog |
| Grapefruit | Q9SLS2 | Sucrose synthase |
| Grapefruit | Q9SLV8 (+1) | Sucrose synthase |
| Grapefruit | Q38JC1 | Temperature-induced lipocalin |
| Grapefruit | D0ELH6 | Tetratricopeptide domain-containing thioredoxin |
| Grapefruit | D2KU75 | Thaumatin-like protein |
| Grapefruit | C3VIC2 | Translation elongation factor |
| Grapefruit | D5LY07 | Ubiquitin/ribosomal fusion protein |
| Grapefruit | C6KI43 | UDP-glucosyltransferase family 1 protein |
| Grapefruit | A0FKR1 | Vacuolar citrate/H+ symporter |
| Grapefruit | Q944C8 | Vacuolar invertase |
| Grapefruit | Q9MB46 | V-type proton ATPase subunit E |
| Grapefruit | F8WL82 | WD-40 repeat family protein |
| *Helianthuus annuus* | HanXRQChr03g0080391 | Hsp90 |
| *Helianthuus annuus* | HanXRQChr13g0408351 | Hsp90 |
| *Helianthuus annuus* | HanXRQChr13g0408441 | Hsp90 |
| *Helianthuus annuus* | HanXRQChr14g0462551 | Hsp90 |
| *Helianthuus annuus* | HanXRQChr02g0044471 | Hsp70 |
| *Helianthuus annuus* | HanXRQChr02g0044481 | Hsp70 |
| *Helianthuus annuus* | HanXRQChr05g0132631 | Hsp70 |
| *Helianthuus annuus* | HanXRQChr05g0134631 | Hsp70 |
| *Helianthuus annuus* | HanXRQChr05g0134801 | Hsp70 |
| *Helianthuus annuus* | HanXRQChr10g0299441 | glutathione S-transferase |
| *Helianthuus annuus* | HanXRQChr16g0516291 | glutathione S-transferase |
| *Helianthuus annuus* | HanXRQChr03g0091431 | lactate/malate dehydrogenase |
| *Helianthuus annuus* | HanXRQChr13g0421951 | lactate/malate dehydrogenase |
| *Helianthuus annuus* | HanXRQChr10g0304821 | lactate/malate dehydrogenase |
| *Helianthuus annuus* | HanXRQChr12g0373491 | lactate/malate dehydrogenase |
| *Helianthuus annuus* | HanXRQChr01g0031071 | small GTPase superfamily, Rab type |
| *Helianthuus annuus* | HanXRQChr01g0031091 | small GTPase superfamily, Rab type |
| *Helianthuus annuus* | HanXRQChr02g0050791 | small GTPase superfamily, Rab type |
| *Helianthuus annuus* | HanXRQChr11g0353711 | small GTPase superfamily, Rab type |
| *Helianthuus annuus* | HanXRQChr13g0402771 | small GTPase superfamily, Rab type |
| *Helianthuus annuus* | HanXRQChr07g0190171 | isocitrate/isopropylmalate dehydrogenase |
| *Helianthuus annuus* | HanXRQChr16g0532251 | isocitrate/isopropylmalate dehydrogenase |
| *Helianthuus annuus* | HanXRQChr03g0079131 | phosphoenolpyruvate carboxylase |
| *Helianthuus annuus* | HanXRQChr15g0495261 | phosphoenolpyruvate carboxylase |
| *Helianthuus annuus* | HanXRQChr13g0388931 | phosphoenolpyruvate carboxylase |
| *Helianthuus annuus* | HanXRQChr14g0442731 | phosphoenolpyruvate carboxylase |
| *Helianthuus annuus* | HanXRQChr15g0482381 | UTP--glucose-1-phosphate uridylyltransferase |
| *Helianthuus annuus* | HanXRQChr16g0532261 | UTP--glucose-1-phosphate uridylyltransferase |
| *Helianthuus annuus* | HanXRQChr05g0135591 | tubulin |
| *Helianthuus annuus* | HanXRQChr06g0178921 | tubulin |

APPENDIX-continued

Table 1: Plant EV-Markers

| Example Species | Accession No. | Protein Name |
|---|---|---|
| Helianthuus annuus | HanXRQChr08g0237071 | tubulin |
| Helianthuus annuus | HanXRQChr11g0337991 | tubulin |
| Helianthuus annuus | HanXRQChr13g0407921 | tubulin |
| Helianthuus annuus | HanXRQChr05g0145191 | tubulin |
| Helianthuus annuus | HanXRQChr07g0187021 | tubulin |
| Helianthuus annuus | HanXRQChr07g0189811 | tubulin |
| Helianthuus annuus | HanXRQChr09g0253681 | tubulin |
| Helianthuus annuus | HanXRQChr10g0288911 | tubulin |
| Helianthuus annuus | HanXRQChr11g0322631 | tubulin |
| Helianthuus annuus | HanXRQChr12g0367231 | tubulin |
| Helianthuus annuus | HanXRQChr13g0386681 | tubulin |
| Helianthuus annuus | HanXRQChr13g0393261 | tubulin |
| Helianthuus annuus | HanXRQChr12g0371591 | ubiquitin |
| Helianthuus annuus | HanXRQChr12g0383641 | ubiquitin |
| Helianthuus annuus | HanXRQChr17g0569881 | ubiquitin |
| Helianthuus annuus | HanXRQChr06g0171511 | photosystem II HCF136, stability/assembly factor |
| Helianthuus annuus | HanXRQChr17g0544921 | photosystem II HCF136, stability/assembly factor |
| Helianthuus annuus | HanXRQChr16g0526461 | proteasome B-type subunit |
| Helianthuus annuus | HanXRQChr17g0565551 | proteasome B-type subunit |
| Helianthuus annuus | HanXRQChr05g0149801 | proteasome B-type subunit |
| Helianthuus annuus | HanXRQChr09g0241421 | proteasome B-type subunit |
| Helianthuus annuus | HanXRQChr11g0353161 | proteasome B-type subunit |
| Helianthuus annuus | HanXRQChr16g0506311 | proteinase inhibitor family 13 (Kunitz) |
| Helianthuus annuus | HanXRQChr16g0506331 | proteinase inhibitor family 13 (Kunitz) |
| Helianthuus annuus | HanXRQChr09g0265401 | metallopeptidase (M10 family) |
| Helianthuus annuus | HanXRQChr09g0265411 | metallopeptidase (M10 family) |
| Helianthuus annuus | HanXRQChr05g0154561 | ATPase, AAA-type |
| Helianthuus annuus | HanXRQChr08g0235061 | ATPase, AAA-type |
| Helianthuus annuus | HanXRQChr09g0273921 | ATPase, AAA-type |
| Helianthuus annuus | HanXRQChr16g0498881 | ATPase, AAA-type |
| Helianthuus annuus | HanXRQChr02g0058711 | oxoacid dehydrogenase acyltransferase |
| Helianthuus annuus | HanXRQChr08g0214191 | oxoacid dehydrogenase acyltransferase |
| Helianthuus annuus | HanXRQChr08g0208631 | small GTPase superfamily, SAR1-type |
| Helianthuus annuus | HanXRQChr11g0331441 | small GTPase superfamily, SAR1-type |
| Helianthuus annuus | HanXRQChr12g0371571 | small GTPase superfamily, SAR1-type |
| Helianthuus annuus | HanXRQChr12g0383571 | small GTPase superfamily, SAR1-type |
| Helianthuus annuus | HanXRQChr14g0446771 | small GTPase superfamily, SAR1-type |
| Helianthuus annuus | HanXRQChr17g0539461 | small GTPase superfamily, SAR1-type |

APPENDIX-continued

Table 1: Plant EV-Markers

| Example Species | Accession No. | Protein Name |
| --- | --- | --- |
| Helianthuus annuus | HanXRQChr17g0548271 | small GTPase superfamily, SAR1-type |
| Helianthuus annuus | HanXRQChr17g0569871 | small GTPase superfamily, SAR1-type |
| Helianthuus annuus | HanXRQChr10g0311201 | ATPase, V1 complex, subunit A |
| Helianthuus annuus | HanXRQChr12g0359711 | ATPase, V1 complex, subunit A |
| Helianthuus annuus | HanXRQChr04g0124671 | fructose-1,6-bisphosphatase |
| Helianthuus annuus | HanXRQChr06g0176631 | fructose-1,6-bisphosphatase |
| Helianthuus annuus | HanXRQCPg0579861 | photosystem II PsbD/D2, reaction centre |
| Helianthuus annuus | HanXRQChr00c0439g0574731 | photosystem II PsbD/D2, reaction centre |
| Helianthuus annuus | HanXRQChr04g0099321 | photosystem II PsbD/D2, reaction centre |
| Helianthuus annuus | HanXRQChr08g0210231 | photosystem II PsbD/D2, reaction centre |
| Helianthuus annuus | HanXRQChr11g0326671 | photosystem II PsbD/D2, reaction centre |
| Helianthuus annuus | HanXRQChr17g0549121 | photosystem II PsbD/D2, reaction centre |
| Helianthuus annuus | HanXRQCPg0579731 | photosystem II protein D1 |
| Helianthuus annuus | HanXRQChr00c0126g0571821 | photosystem II protein D1 |
| Helianthuus annuus | HanXRQChr00c0165g0572191 | photosystem II protein D1 |
| Helianthuus annuus | HanXRQChr00c0368g0574171 | photosystem II protein D1 |
| Helianthuus annuus | HanXRQChr00c0454g0574931 | photosystem II protein D1 |
| Helianthuus annuus | HanXRQChr00c0524g0575441 | photosystem II protein D1 |
| Helianthuus annuus | HanXRQChr00c0572g0575941 | photosystem II protein D1 |
| Helianthuus annuus | HanXRQChr09g0257281 | photosystem II protein D1 |
| Helianthuus annuus | HanXRQChr11g0326571 | photosystem II protein D1 |
| Helianthuus annuus | HanXRQChr11g0327051 | photosystem II protein D1 |
| Helianthuus annuus | HanXRQChr16g0503941 | photosystem II protein D1 |
| Helianthuus annuus | HanXRQCPg0580061 | photosystem II cytochrome b559 |
| Helianthuus annuus | HanXRQChr01g0020331 | photosystem II cytochrome b559 |
| Helianthuus annuus | HanXRQChr10g0283581 | photosystem II cytochrome b559 |
| Helianthuus annuus | HanXRQChr10g0284271 | photosystem II cytochrome b559 |
| Helianthuus annuus | HanXRQChr10g0289291 | photosystem II cytochrome b559 |
| Helianthuus annuus | HanXRQChr10g0318171 | photosystem II cytochrome b559 |
| Helianthuus annuus | HanXRQChr11g0326851 | photosystem II cytochrome b559 |
| Helianthuus annuus | HanXRQChr16g0529011 | photosystem II cytochrome b559 |
| Helianthuus annuus | HanXRQChr08g0219051 | chlorophyll A-B binding protein |
| Helianthuus annuus | HanXRQChr12g0370841 | chlorophyll A-B binding protein |
| Helianthuus annuus | HanXRQChr02g0053151 | chlorophyll A-B binding protein |
| Helianthuus annuus | HanXRQChr02g0053161 | chlorophyll A-B binding protein |
| Helianthuus annuus | HanXRQCPg0580051 | cytochrome f |
| Helianthuus annuus | HanXRQChr01g0020341 | cytochrome f |
| Helianthuus annuus | HanXRQChr10g0283571 | cytochrome f |

APPENDIX-continued

Table 1: Plant EV-Markers

| Example Species | Accession No. | Protein Name |
|---|---|---|
| Helianthuus annuus | HanXRQChr10g0284261 | cytochrome f |
| Helianthuus annuus | HanXRQChr10g0289281 | cytochrome f |
| Helianthuus annuus | HanXRQChr10g0318181 | cytochrome f |
| Helianthuus annuus | HanXRQChr11g0326841 | cytochrome f |
| Helianthuus annuus | HanXRQChr15g0497521 | cytochrome f |
| Helianthuus annuus | HanXRQChr06g0163851 | ribosomal protein |
| Helianthuus annuus | HanXRQChr09g0252071 | ribosomal protein |
| Helianthuus annuus | HanXRQChr12g0374041 | ribosomal protein |
| Helianthuus annuus | HanXRQChr04g0128141 | ribosomal protein |
| Helianthuus annuus | HanXRQChr05g0163131 | ribosomal protein |
| Helianthuus annuus | HanXRQChr03g0076971 | ribosomal protein |
| Helianthuus annuus | HanXRQChr05g0159851 | ribosomal protein |
| Helianthuus annuus | HanXRQChr05g0159971 | ribosomal protein |
| Helianthuus annuus | HanXRQChr11g0324631 | ribosomal protein |
| Helianthuus annuus | HanXRQChr13g0408051 | ribosomal protein |
| Helianthuus annuus | HanXRQChr03g0089331 | ribosomal protein |
| Helianthuus annuus | HanXRQChr13g0419951 | ribosomal protein |
| Helianthuus annuus | HanXRQChr15g0497041 | ribosomal protein |
| Helianthuus annuus | HanXRQChr16g0499761 | ribosomal protein |
| Helianthuus annuus | HanXRQChr04g0106961 | ribosomal protein |
| Helianthuus annuus | HanXRQChr06g0175811 | ribosomal protein |
| Helianthuus annuus | HanXRQChr04g0122771 | ribosomal protein |
| Helianthuus annuus | HanXRQChr09g0245691 | ribosomal protein |
| Helianthuus annuus | HanXRQChr16g0520021 | ribosomal protein |
| Helianthuus annuus | HanXRQChr03g0060471 | ribosomal protein |
| Helianthuus annuus | HanXRQChr14g0429531 | ribosomal protein |
| Helianthuus annuus | HanXRQChr06g0171911 | ribosomal protein |
| Helianthuus annuus | HanXRQChr15g0479091 | ribosomal protein |
| Helianthuus annuus | HanXRQChr15g0479101 | ribosomal protein |
| Helianthuus annuus | HanXRQChr17g0543641 | ribosomal protein |
| Helianthuus annuus | HanXRQChr17g0543661 | ribosomal protein |
| Helianthuus annuus | HanXRQChr04g0105831 | ribosomal protein |
| Helianthuus annuus | HanXRQChr09g0258341 | ribosomal protein |
| Helianthuus annuus | HanXRQChr10g0287141 | ribosomal protein |
| Helianthuus annuus | HanXRQChr15g0463911 | ribosomal protein |
| Helianthuus annuus | HanXRQChr03g0076171 | ribosomal protein |
| Helianthuus annuus | HanXRQChr05g0159291 | ribosomal protein |
| Helianthuus annuus | HanXRQChr13g0407551 | ribosomal protein |

APPENDIX-continued

Table 1: Plant EV-Markers

| Example Species | Accession No. | Protein Name |
|---|---|---|
| Helianthuus annuus | HanXRQChr12g0380701 | ribosomal protein |
| Helianthuus annuus | HanXRQChr15g0477271 | ribosomal protein |
| Helianthuus annuus | HanXRQChr17g0545211 | ribosomal protein |
| Helianthuus annuus | HanXRQChr17g0570741 | ribosomal protein |
| Helianthuus annuus | HanXRQChr17g0570761 | ribosomal protein |
| Helianthuus annuus | HanXRQChr02g0044021 | ribosomal protein |
| Helianthuus annuus | HanXRQChr05g0152871 | ribosomal protein |
| Helianthuus annuus | HanXRQChr01g0012781 | ribosomal protein |
| Helianthuus annuus | HanXRQChr08g0230861 | ribosomal protein |
| Helianthuus annuus | HanXRQChr13g0391831 | ribosomal protein |
| Helianthuus annuus | HanXRQChr11g0337791 | bifunctional trypsin/alpha-amylase inhibitor |
| Helianthuus annuus | HanXRQChr10g0312371 | 2-oxoacid dehydrogenase acyltransferase |
| Helianthuus annuus | HanXRQChr09g0276191 | acid phosphatase (class B) |
| Helianthuus annuus | HanXRQChr05g0142271 | aldose-1-epimerase |
| Helianthuus annuus | HanXRQChr14g0439791 | alpha-D-phosphohexomutase |
| Helianthuus annuus | HanXRQChr09g0251071 | alpha-L-fucosidase |
| Helianthuus annuus | HanXRQChr05g0147371 | annexin |
| Helianthuus annuus | HanXRQChr09g0247561 | Asp protease (Peptidase family A1) |
| Helianthuus annuus | HanXRQChr13g0409681 | berberine-bridge enzyme (S)-reticulin:oxygen oxido-reductase |
| Helianthuus annuus | HanXRQChr10g0295971 | beta-hydroxyacyl-(acyl-carrier-protein) dehydratase |
| Helianthuus annuus | HanXRQChr13g0412571 | carbohydrate esterase family 13-CE13 (pectin acylesterase-PAE) |
| Helianthuus annuus | HanXRQChr12g0360101 | carbohydrate esterase family 8-CE8 (pectin methylesterase-PME) |
| Helianthuus annuus | HanXRQChr01g0019231 | carbonic anhydrase |
| Helianthuus annuus | HanXRQChr02g0036611 | cellular retinaldehyde binding/alpha-tocopherol transport |
| Helianthuus annuus | HanXRQChr10g0313581 | chaperonin Cpn60 |
| Helianthuus annuus | HanXRQChr09g0251791 | chlathrin |
| Helianthuus annuus | HanXRQChr11g0329811 | chlorophyll A-B binding protein |
| Helianthuus annuus | HanXRQChr13g0398861 | cobalamin (vitamin B12)-independent methionine synthase |
| Helianthuus annuus | HanXRQChr10g0298981 | cyclophilin |
| Helianthuus annuus | HanXRQChr04g0103281 | Cys protease (papain family) |
| Helianthuus annuus | HanXRQChr09g0268361 | cytochrome P450 |
| Helianthuus annuus | HanXRQChr17g0535591 | dirigent protein |
| Helianthuus annuus | HanXRQChr03g0065901 | expansin |
| Helianthuus annuus | HanXRQChr11g0336761 | expressed protein (cupin domain, seed storage protein domain) |
| Helianthuus annuus | HanXRQChr10g0280931 | expressed protein (cupin domain, seed storage protein domain) |
| Helianthuus annuus | HanXRQChr10g0288971 | expressed protein (cupin domain, seed storage protein domain) |
| Helianthuus annuus | HanXRQChr12g0380361 | expressed protein (cupin domain, seed storage protein domain) |
| Helianthuus annuus | HanXRQChr09g0254381 | expressed protein (cupin domain, seed storage protein domain) |

APPENDIX-continued

Table 1: Plant EV-Markers

| Example Species | Accession No. | Protein Name |
|---|---|---|
| Helianthuus annuus | HanXRQChr04g0112711 | expressed protein (cupin domain, seed storage protein domain) |
| Helianthuus annuus | HanXRQChr07g0196131 | expressed protein (cupin domain, seed storage protein domain) |
| Helianthuus annuus | HanXRQChr10g0301281 | expressed protein (cupin domain, seed storage protein domain) |
| Helianthuus annuus | HanXRQChr10g0301931 | expressed protein (cupin domain, seed storage protein domain) |
| Helianthuus annuus | HanXRQChr13g0404461 | expressed protein (cupin domain) |
| Helianthuus annuus | HanXRQChr01g0015821 | expressed protein (DUF642) |
| Helianthuus annuus | HanXRQChr03g0065301 | expressed protein (Gnk2-homologous domain, antifungal protein of Ginkgo seeds) |
| Helianthuus annuus | HanXRQChr03g0068311 | expressed protein (LRR domains) |
| Helianthuus annuus | HanXRQChr10g0291371 | expressed protein (LRR domains) |
| Helianthuus annuus | HanXRQChr03g0075061 | fasciclin-like arabinogalactan protein (FLA) |
| Helianthuus annuus | HanXRQChr08g0221961 | ferritin |
| Helianthuus annuus | HanXRQChr09g0257521 | FMN-dependent dehydrogenase |
| Helianthuus annuus | HanXRQChr14g0441641 | fructose-bisphosphate aldolase |
| Helianthuus annuus | HanXRQChr10g0312621 | germin |
| Helianthuus annuus | HanXRQChr09g0244271 | glucose-methanol-choline oxidoreductase |
| Helianthuus annuus | HanXRQChr03g0061571 | glutamate synthase |
| Helianthuus annuus | HanXRQChr05g0144801 | glyceraldehyde 3-phosphate dehydrogenase |
| Helianthuus annuus | HanXRQChr17g0550211 | glycerophosphoryl diester phosphodiesterase |
| Helianthuus annuus | HanXRQChr06g0175391 | glycoside hydrolase family 16-GH16 (endoxyloglucan transferase) |
| Helianthuus annuus | HanXRQChr11g0351571 | glycoside hydrolase family 17-GH17 (beta-1,3-glucosidase) |
| Helianthuus annuus | HanXRQChr05g0141461 | glycoside hydrolase family 18-GH18 |
| Helianthuus annuus | HanXRQChr09g0276721 | glycoside hydrolase family 19-GH19 |
| Helianthuus annuus | HanXRQChr02g0046191 | glycoside hydrolase family 2-GH2 |
| Helianthuus annuus | HanXRQChr16g0524981 | glycoside hydrolase family 20-GH20 (N-acetyl-beta-glucosaminidase) |
| Helianthuus annuus | HanXRQChr11g0322851 | glycoside hydrolase family 27-GH27 (alpha-galactosidase/melibiase) |
| Helianthuus annuus | HanXRQChr10g0293191 | glycoside hydrolase family 3-GH3 |
| Helianthuus annuus | HanXRQChr16g0511881 | glycoside hydrolase family 31-GH31 (alpha-xylosidase) |
| Helianthuus annuus | HanXRQChr14g0461441 | glycoside hydrolase family 32-GH32 (vacuolar invertase) |
| Helianthuus annuus | HanXRQChr13g0423671 | glycoside hydrolase family 35-GH35 (beta-galactosidase) |
| Helianthuus annuus | HanXRQChr10g0319301 | glycoside hydrolase family 35-GH35 (beta-galactosidase) |
| Helianthuus annuus | HanXRQChr09g0256531 | glycoside hydrolase family 38-GH38 (alpha-mannosidase) |
| Helianthuus annuus | HanXRQChr11g0320901 | glycoside hydrolase family 5-GH5 (glucan-1,3-beta glucosidase) |
| Helianthuus annuus | HanXRQChr05g0130491 | glycoside hydrolase family 51-GH51 (alpha-arabinofuranosidase) |
| Helianthuus annuus | HanXRQChr10g0314191 | glycoside hydrolase family 79-GH79 (endo-beta-glucuronidase/heparanase |
| Helianthuus annuus | HanXRQChr13g0397411 | homologous to A. thaliana PMR5 (Powdery Mildew Resistant) (carbohydrate acylation) |
| Helianthuus annuus | HanXRQChr14g0444681 | inhibitor family 13 (Kunitz-P family) |
| Helianthuus annuus | HanXRQChr14g0445181 | lactate/malate dehydrogenase |
| Helianthuus annuus | HanXRQChr17g0564111 | lectin (D-mannose) |

APPENDIX-continued

Table 1: Plant EV-Markers

| Example Species | Accession No. | Protein Name |
| --- | --- | --- |
| Helianthuus annuus | HanXRQChr17g0558861 | lectin (PAN-2 domain) |
| Helianthuus annuus | HanXRQChr02g0039251 | lipase acylhydrolase (GDSL family) |
| Helianthuus annuus | HanXRQChr01g0000161 | lipid transfer protein/trypsin-alpha amylase inhibitor |
| Helianthuus annuus | HanXRQChr02g0047121 | mannose-binding lectin |
| Helianthuus annuus | HanXRQChr10g0303361 | mitochondrial carrier protein |
| Helianthuus annuus | HanXRQChr15g0489551 | multicopper oxidase |
| Helianthuus annuus | HanXRQChr05g0135581 | neutral/alkaline nonlysosomal ceramidase |
| Helianthuus annuus | HanXRQChr01g0017621 | nucleoside diphosphate kinase |
| Helianthuus annuus | HanXRQChr10g0295991 | peroxidase |
| Helianthuus annuus | HanXRQChr13g0398251 | peroxiredoxin |
| Helianthuus annuus | HanXRQChr11g0333171 | phosphate-induced (phi) protein 1 |
| Helianthuus annuus | HanXRQChr03g0060421 | phosphodiesterase/nucleotide pyrophosphatase/phosphate transferase |
| Helianthuus annuus | HanXRQChr03g0078011 | phosphofructokinase |
| Helianthuus annuus | HanXRQChr13g0408831 | phosphoglycerate kinase |
| Helianthuus annuus | HanXRQChr10g0286701 | phosphoglycerate mutase |
| Helianthuus annuus | HanXRQChr06g0171591 | photosystem II PsbP, oxygen evolving complex |
| Helianthuus annuus | HanXRQChr14g0434951 | plastid lipid-associated protein/fibrillin conserved domain |
| Helianthuus annuus | HanXRQChr05g0146621 | plastocyanin (blue copper binding protein) |
| Helianthuus annuus | HanXRQChr11g0330251 | polyphenol oxidase |
| Helianthuus annuus | HanXRQChr04g0094541 | proteasome A-type subunit |
| Helianthuus annuus | HanXRQChr03g0081271 | proteasome B-type subunit |
| Helianthuus annuus | HanXRQChr12g0356851 | purple acid phosphatase |
| Helianthuus annuus | HanXRQChr15g0485781 | pyridoxal phosphate-dependent transferase |
| Helianthuus annuus | HanXRQChr11g0336791 | ribosomal protein |
| Helianthuus annuus | HanXRQChr11g0330521 | ribosomal protein |
| Helianthuus annuus | HanXRQChr11g0326801 | ribulose bisphosphate carboxylase, large subunit |
| Helianthuus annuus | HanXRQChr16g0523951 | ribulose-1,5-bisphosphate carboxylase small subunit |
| Helianthuus annuus | HanXRQChr01g0022151 | S-adenosyl-L-homocysteine hydrolase |
| Helianthuus annuus | HanXRQChr14g0454811 | S-adenosylmethionine synthetase |
| Helianthuus annuus | HanXRQChr04g0109991 | SCP-like extracellular protein (PR-1) |
| Helianthuus annuus | HanXRQChr03g0072241 | Ser carboxypeptidase (Peptidase family S10) |
| Helianthuus annuus | HanXRQChr12g0377221 | Ser protease (subtilisin) (Peptidase family S8) |
| Helianthuus annuus | HanXRQChr02g0055581 | superoxide dismutase |
| Helianthuus annuus | HanXRQChr15g0493261 | thaumatin (PR5) |
| Helianthuus annuus | HanXRQChr16g0532531 | transketolase |
| Helianthuus annuus | HanXRQChr07g0197421 | translation elongation factor EFTu/EF1A |
| Helianthuus annuus | HanXRQChr06g0173951 | translationally controlled tumour protein |

What is claimed is:

1. A method of administering at least one heterologous RNA to an intact plant, the method comprising non-viral delivery to the intact plant of a composition comprising a plurality of lipid-reconstituted plant messenger packs (LPMPs), each of the plurality comprising the at least one heterologous RNA, an exogenous cationic lipid, and at least one plant protein extracellular vesicle marker, wherein the exogenous cationic lipid increases the RNA loading efficiency as compared to the loading efficiency of an LPMP not comprising the at least one heterologous cationic lipid, and wherein the composition is delivered at an effective concentration to increase plant fitness.

2. The method of claim 1, wherein the at least one heterologous RNA is a guide RNA (gRNA).

3. The method of claim 2, wherein the gRNA is a component of a ribonucleoprotein complex (RNP), and wherein each of the plurality of LPMPs comprise the RNP.

4. The method of claim 1, wherein the exogenous cationic lipid is DC-Cholesterol or DOTAP.

5. The method of claim 1, wherein the at least one heterologous RNA is encapsulated by the LPMPs.

6. The method of claim 1, wherein the LPMPs in the composition are at a concentration effective to modify a plant trait, wherein the modification increases the fitness of the plant.

7. The method of claim 1, wherein the increase in plant fitness is an increase in development, growth, yield, resistance to abiotic stressors, or resistance to biotic stressors.

8. The method of claim 1, wherein the increase in plant fitness is a modification to flowering time.

9. The method of claim 4, wherein the DC-cholesterol comprises between 20-40% of total lipids in the LPMP by weight.

10. The method of claim 4, wherein the DOTAP comprises between 25-40% of total lipids in the LPMP by weight.

11. The method of claim 1, wherein the at least one heterologous RNA is siRNA or tracrRNA.

* * * * *